US010000749B2

(12) United States Patent
Saran et al.

(10) Patent No.: US 10,000,749 B2
(45) Date of Patent: Jun. 19, 2018

(54) VALENCENE SYNTHASE POLYPEPTIDES, ENCODING NUCLEIC ACID MOLECULES AND USES THEREOF

(71) Applicant: Evolva, Inc., Lexington, KY (US)

(72) Inventors: Dayal Saran, Lexington, KY (US); Grace Eunyoung Park, Lexington, KY (US)

(73) Assignee: Evolva, Inc., Lexington, KY (US)

( * ) Notice: Subject to any disclaimer, the term of this patent is extended or adjusted under 35 U.S.C. 154(b) by 162 days.

(21) Appl. No.: 13/999,598

(22) Filed: Mar. 11, 2014

(65) Prior Publication Data

US 2015/0007368 A1 Jan. 1, 2015

Related U.S. Application Data

(60) Provisional application No. 61/852,462, filed on Mar. 14, 2013.

(51) Int. Cl.

| | |
|---|---|
| ***C12N 15/82*** | (2006.01) |
| ***C12N 9/88*** | (2006.01) |
| ***C12P 5/00*** | (2006.01) |
| ***C12P 7/26*** | (2006.01) |

(52) U.S. Cl.

CPC ........... *C12N 9/88* (2013.01); *C12N 15/8243* (2013.01); *C12P 5/007* (2013.01); *C12P 7/26* (2013.01); *C12Y 402/03073* (2013.01)

(58) Field of Classification Search

None

See application file for complete search history.

(56) References Cited

U.S. PATENT DOCUMENTS

| | | | | |
|---|---|---|---|---|
| 4,952,496 | A | 8/1990 | Studier et al. | 435/91 |
| 5,605,793 | A | 2/1997 | Stemmer | 435/6 |
| 5,811,238 | A | 9/1998 | Stemmer et al. | 435/6 |
| 5,824,774 | A | 10/1998 | Chappell | 530/350 |
| 5,830,721 | A | 11/1998 | Stemmer et al. | 435/172.1 |
| 5,834,252 | A | 11/1998 | Stemmer et al. | 435/91.1 |
| 5,837,458 | A | 11/1998 | Minshull et al. | 435/6 |
| 5,847,226 | A | 12/1998 | Muller et al. | 568/346 |
| 6,072,045 | A | 6/2000 | Chappell | 536/23.1 |
| 6,468,772 | B1 | 10/2002 | Chappell et al. | 435/183 |
| 6,495,354 | B2 | 12/2002 | Chappell et al. | 435/183 |
| 6,531,303 | B1 | 3/2003 | Millis et al. | 435/155 |
| 6,559,297 | B2 | 5/2003 | Chappell et al. | 536/23.1 |
| 6,569,656 | B2 | 5/2003 | Chappell et al. | 435/183 |
| 6,645,762 | B2 | 11/2003 | Chappell et al. | 435/325 |
| 6,689,593 | B2 | 2/2004 | Millis et al. | 435/155 |
| 6,890,752 | B2 | 5/2005 | Chappell et al. | 435/325 |
| 7,186,891 | B1 | 3/2007 | Chappell | 800/298 |
| 7,273,735 | B2 | 9/2007 | Schalk | 435/166 |
| 7,442,785 | B2 | 10/2008 | Chappell | 536/23.6 |
| 7,790,426 | B2 | 9/2010 | Schalk | 435/167 |
| 7,838,279 | B2 | 11/2010 | Millis et al. | 435/254.2 |
| 7,842,497 | B2 | 11/2010 | Millis et al. | 435/254.2 |
| 7,906,710 | B2 | 3/2011 | Karunanandaa et al. | 800/306 |
| 8,106,260 | B2 | 1/2012 | Chappell | 800/298 |
| 8,192,950 | B2 | 6/2012 | Chappell | 435/41 |
| 8,236,512 | B1 | 8/2012 | Zhao et al. | 435/7.6 |
| 8,354,504 | B2 | 1/2013 | Chappell | 530/379 |
| 8,362,309 | B2 | 1/2013 | Julien | 583/360 |
| 8,481,286 | B2 | 7/2013 | Julien | 435/69.1 |
| 8,569,025 | B2 | 10/2013 | Zulak et al. | 435/157 |
| 8,609,371 | B2 | 12/2013 | Julien | 435/69.1 |
| 8,642,815 | B2 | 2/2014 | Julien | 568/367 |
| 2004/0249219 | A1 | 12/2004 | Saucy | 568/388 |
| 2005/0019882 | A1* | 1/2005 | Bouwmeester | C12N 9/00 435/155 |
| 2005/0210549 | A1 | 9/2005 | Schalk | 800/287 |
| 2006/0218661 | A1 | 9/2006 | Chappell | 800/278 |
| 2007/0238157 | A1 | 10/2007 | Millis et al. | 435/166 |
| 2008/0213832 | A1* | 9/2008 | Schalk | C12N 9/88 435/69.1 |
| 2008/0233622 | A1 | 9/2008 | Julien | 435/148 |
| 2009/0123984 | A1 | 5/2009 | Chappell et al. | 435/166 |
| 2010/0129306 | A1 | 5/2010 | Julien | 424/65 |
| 2010/0151519 | A1 | 6/2010 | Julien | 435/69.1 |
| 2010/0151555 | A1 | 6/2010 | Julien | 435/193 |
| 2010/0216186 | A1 | 8/2010 | Chappell | 435/69.1 |
| 2011/0081703 | A1 | 4/2011 | Chappell | 435/193 |
| 2011/0189717 | A1 | 8/2011 | Ajikumar et al. | 435/29 |
| 2012/0129235 | A1 | 5/2012 | Julien | 435/166 |
| 2012/0196340 | A1 | 8/2012 | Chappell | 435/148 |

(Continued)

FOREIGN PATENT DOCUMENTS

| | | |
|---|---|---|
| EP | 0 073 657 | 12/1990 |
| EP | 1 083 233 | 8/2003 |

(Continued)

OTHER PUBLICATIONS

Takahashi et al., 2007, Biotechnol. Bioeng. 97: 170-181.*

Thornton et al., 2000, Nature Structural Biology, structural genomic supplement, Nov. 2000: 991-994.*

Guo et al., 2004, Proceedings of the National Academy of Sciences USA 101: 9205-9210.*

Keskin et al., 2004, Protein Science 13: 1043-1055.*

Huang et al., 2010, Plant Physiology 153: 1293-1310.*

Koliner et al., 2004, The Plant Cell 16: 1115-1131.*

Sharon-Asa et al., 2003, The Plant Journal 36: 664-674.*

NCBI/GenBank accession No. AF441124.1, published on Jan. 12, 2004.*

(Continued)

*Primary Examiner* — Amjad Abraham

*Assistant Examiner* — Bratislav Stankovic

(74) *Attorney, Agent, or Firm* — McDonnell Boehnen Hulbert & Berghoff LLP

(57) ABSTRACT

Provided are valencene synthase polypeptides, nucleic acid molecules encoding the valencene synthases, host cells containing the nucleic acids and methods for producing products whose production is catalyzed by the polypeptides. Also provided are methods for producing valencene and nootkatone.

29 Claims, 24 Drawing Sheets

(56) References Cited

U.S. PATENT DOCUMENTS

| | | | | |
|---|---|---|---|---|
| 2012/0246767 | A1 | 9/2012 | Amick et al. | 800/316 |
| 2013/0071877 | A1 | 3/2013 | Chappell | 435/41 |
| 2013/0236943 | A1 | 9/2013 | Julien | 435/166 |
| 2014/0073020 | A1 | 3/2014 | Park et al. | 435/131 |

FOREIGN PATENT DOCUMENTS

| | | |
|---|---|---|
| WO | WO 1997/07205 | 2/1997 |
| WO | WO 2003/025193 | 3/2003 |
| WO | WO 2004/031376 | 4/2004 |
| WO | WO 2005/021705 | 3/2005 |
| WO | WO 2011/074954 | 6/2011 |
| WO | WO 2012/177129 | 12/2012 |

OTHER PUBLICATIONS

U.S. Appl. No. 13/317,839, filed Oct. 28, 2011, 2012/0246767, Sep. 27, 2012.
U.S. Appl. No. 13/986,436, filed May 1, 2013, 2013/0236943, Sep. 12, 2013.
U.S. Appl. No. 13/987,493, filed Jul. 30, 2013.
Letter/Written Disclosure of the Information Disclosure Statement for the above-referenced application, dated May 21, 2014, 2 pages.
Allylix, "Protein engineering and chembiosynthesis to produce novel sesquiterpenoids," Presentation at BIO World Congress on Industrial Biotechnology & Bioprocessing, Washington, D.C. on Jun. 28, 2010, 19 pages.
Altschul, S., "Amino acid substitution matrices from an information theoretic perspective," J. Mol. Biol. 219(3):555-565 (1991).
Arantes et al., "The preparation and microbiological hydroxylation of the sesquiterpenoid nootkatone," J. Chem. Res. (Synopsis) 3:248 (1999).
ATCC Accession No. 28383, "*Saccharomyces cerevisiae* Hansen, teleomorph," [online][accessed on May 6, 2014] Retrieved from:<URL:atcc.org/products/all/28383.aspx [2 pages].
Ausubel et al., *Current Protocols in Molecular Biology*, vol. 2, Greene Pub. Assoc. & Wiley Interscience, Ch. 13, 138 pages (1988).
Back et al., "Expression of a plant sesquiterpene cyclase gene in *Escherichia coli*," Arch. Biochem. Biophys. 315:527-532 (1994).
Back, K. and J. Chappell, "Cloning and bacterial expression of a sesquiterpene cyclase from *Hyoscyamus muticus* and its molecular comparison to related terpene cyclases," J. Biol. Chem. 270:7375-7381 (1995).
Back, K. and J. Chappell, "Identifying functional domains within terpene cyclases using a domain-swapping strategy," Proc. Natl. Acad. Sci. U.S.A. 93:6841-6845 (1996).
Back et al., "Cloning of a sesquiterpene cyclase and its functional expression by domain swapping strategy," Mol. Cells 10:220-225 (2000).
Beier, D. and E. Young, "Characterization of a regulatory region upstream of the ADR2 locus of *S. cerevisiae*," Nature 300:724-728 (1982).
Bohlmann et al., "Plant terpenoid synthases: molecular biology and phylogenetic analysis," Proc. Natl. Acad. Sci. U.S.A. 95:4126-4133 (1998).
Brodelius et al., "Fusion of famesyldiphosphate synthase and epi-aristolochene synthase, a sesquiterpene cyclase involved in capsidiol biosynthesis in Nicotiana tabacum," Eur. J. Biochem. 269:3570-3577 (2002).
Brown et al., "Codon utilisation in the pathogenic yeast, *Candida albicans*," Nucleic Acids Res. 19(15):4298 (1991).
Calvert et al., "Germacrene A is a product of the aristolochene synthase-mediated conversion of farnesylpyrophosphate to aristolochene," J. Am. Chem. Soc. 124:11636-11641 (2002).
Cane et al., "Aristolochene biosynthesis and enzymatic cyclization of farnesyl pyrophosphate," J. Am. Chem. Soc. 111:8914-8916 (1989).
Cane, D., "Enzymatic formation of sesquiterpenes," Chem. Rev. 90:1089-1103 (1990).
Chappell, J., "Biochemistry and molecular biology of the isoprenoid biosynthetic pathway in plants," Annu. Rev. Plant Physiol. Plant Mol. Biol. 46:521-547 (1995).
Chappell et al., "Is the reaction catalyzed by 3-hydroxy-3-methylglutaryl coenzyme A reductase a rate-limiting step for isoprenoid biosynthesis in plants," Plant Physiol. 109:1337-1343 (1995).
Chappell, "The biochemistry and molecular biology of isoprenoid metabolism," Plant Physiol. 107:1-6 (1995).
Chappell, J., "The genetics and molecular genetics of terpene and sterol origami," Curr. Opin. Plant Biol. 5:151-157 (2002).
Chappell, J., "Valencene synthase—a biochemical magician and harbinger of transgenic aromas," Trends Plant Sci. 9(6):266-269 (2004).
Crameri et al., "DNA shuffling of a family of genes from diverse species accelerates directed evolution," Nature 391:288-291 (1998).
de Boer et al., "The tac promoter: a functional hybrid derived from the trp and lac promoters," Proc. Natl. Acad. Sci. U.S.A. 80:21-25 (1983).
Degenhardt et al., "Monoterpene and sesquiterpene synthases and the origin of terpene skeletal biodiversity in plants," Phytochem. 70:1621-1637 (2009).
Dolan, K., "Allylix sniffs out biotech for new fragrances," found in Forbes Magazine dated Nov. 8, 2010, Published on Oct. 21, 2010 [online][retrieved on Jun. 1, 2012] Retrieved from:<URL:forbes.com/forbes/2010/1108/technology-allylix-fragrances-flavor-carolyn-fritz-smell-test.html?partner=email [1 page].
Drawert et al., "Regioselective biotransformation of valencene in cell suspension cultures of *Citrus* sp.," Plant Cell Reports 3:37-40 (1984).
Eyal, E., "Computer modeling of the enzymatic reaction catalyzed by 5-epi-aristolochene cyclase," Masters Thesis, Department of Plant Sciences, Weizmann Institute of Science, Rehovot, Israel (Jan. 2001) [44 pages].
Fleer et al., "High-level secretion of correctly processed recombinant human interleukin-1β in *Kluyveromyces lactis*," Gene 107:285-295 (1991).
Forsburg, S., "Codon usage table for Schizosaccharomyces pombe," Yeast 10(8):1045-1047 (1994).
Fraatz et al., "Nootkatone—a biotechnological challenge," Appl. Microbiol. Biotechnol. 83(1):35-41 (2009).
Furusawa et al., "Highly efficient production of nootkatone, the grapefruit aroma from valencene, by biotransformation," Chem. Pharm. Bull. 53(11):1513-1514 (2005).
Genbank Accession No. AF441124, "Citrus sinensis valencene synthase (tps1) mRNA, complete cds," Published on Jan. 12, 2004 [retrieved on Nov. 3, 2011] [retrieved from the Internet:<URL:ncbi.nlm.nih.gov/nuccore/AF441124] [1 page].
Genbank Accession No. AY917195.1, "*Perilla frutescens* var. *frutescens* valencene synthase mRNA, complete cds," Published on Mar. 1, 2005 [online][retrieved on May 14, 2014] Retrieved from:<URL: ncbi.nlm.nih.gov/nuccore/AY917195.1 [2 pages].
Genbank Accession No. U20188.1, "Hyoscyamus muticus clone cVS1 vetispiradiene synthase mRNA, partial cds," Published on Jan. 31, 1996 [online] [retrieved on May 14, 2014] Retrieved from:<URL:ncbi.nlm.nih.gov/nuccore/U20188.1, 2 pages.
Gilbert, W. and L. Villa-Komaroff, "Useful proteins from recombinant bacteria," Scientific American 242:79-94 (1980).
Girhard et al., "Regioselective biooxidation of (+)-valencene by recombinant *E. coli* expressing CYP109B1 from Bacillus subtilis in a two-liquid-phase system," Microb. Cell Fact. 8:36, 12 pages (2009).
Greenhagen, B. and J. Chappell, "Molecular scaffolds for chemical wizardry: learning nature's rules for terpene cyclases," Proc. Natl. Acad. Sci. U.S.A. 98:13479-13491 (2001).
Greenhagen et al., "Probing sesquiterpene hydroxylase activities in a coupled assay with terpene synthases," Arch. Biochem. Biophys. 409:385-394 (2003).
Greenhagen, B., "Origins of isoprenoid diversity: A study of structure-function relationships in sesquiterpene synthases," Dissertation, College of Agriculture at the University of Kentucky, 163 pages (2003).

(56) References Cited

OTHER PUBLICATIONS

Greenhagen et al., "Identifying and manipulating structural determinates linking catalytic specificities in terpene synthases," Proc. Natl. Acad. Sci. U.S.A. 103:9826-9831 (2006).
Gribskov, M. and R. Burgess, "Sigma factors from *E. coli, B. subtilis*, phage SP01, and phage T4 are homologous proteins," Nucleic Acids Res. 14(16):6745-6763 (1986).
Hess et al., "Cooperation of glycolytic enzymes," Adv. Enzyme Reg. 7:149-167 (1969).
Hitzeman et al., "Isolation and characterization of the yeast 3-phosphoglycerokinase gene (PGK) by an immunological screening technique," J. Biol. Chem. 255:12073-12080 (1980).
Holland, M. and J. Holland, "Isolation and identification of yeast messenger ribonucleic acids coding for enolase, glyceraldehyde-3-phosphate dehydrogenase, and phosphoglycerate kinase," Biochem. 17:4900-4907 (1978).
Hunter et al., "Conversion of valencene to nootkatone," J. Food Sci. 30(5):876-878 (1965).
Jay et al., "Construction of a general vector for efficient expression of mammalian proteins in bacteria: use of a synthetic ribosome binding site," Proc. Natl. Acad. Sci. U.S.A. 78(9):5543-5548 (1981).
Joly, A. and P. Edwards, "Effect of site-directed mutagenesis of conserved aspartate and arginine residues upon farnesyl diphosphate synthase activity," J. Biol. Chem. 268:26983-26989 (1993).
Krügener et al., "A dioxygenase of Pleurotus sapidus transforms (+)-valencene regio-specifically to (+)-nootkatone via a stereo-specific allylic hydroperoxidation," Bioresource Technol. 101(2):457-462 (2010) [Epub Sep. 17, 2009].
Lesburg et al., "Crystal structure of pentalene synthase: mechanistic insights on terpenoid cyclization reaction in biology," Science 277:1820-1824 (1997).
Louzada et al., "Isolation of a terpene synthase gene from mature "Rio Red" grapefruit using differential display," Program Schedule and Abstracts for the 98th Annual International Conference of the American Society for Horticultural Science, Sacramento, CA, Jul. 22-25, 2001, HortScience 36(3):425-444 (2001).
Lucker et al., "Vitis vinifera terpenoid cyclases: functional identification of two sesquiterpene synthase cDNAs encoding (+)-valencene synthase and (−)-germacrene D synthase and expression of mono- and sesquiterpene synthases in grapevine flowers and berries," Phytochem. 65(19):2649-2659 (2004).
Martin et al., "The bouquet of grapevine (*Vitis vinifera* L. cv. Cabernet Sauvignon) flowers arises from the biosynthesis of sesquiterpene volatiles in pollen grains," Proc. Natl. Acad. Sci. U.S.A. 106(17):7245-7250 (2009).
Maruyama et al., "Molecular cloning, functional expression and characterization of (E)-β-farnesene synthase from Citrus junos," Biol. Pharm. Bull. 24(10):1171-1175 (2001).
Mathis et al., "Pre-steady-state study of recombinant sesquiterpene cyclases," Biochem. 36:8340-8348 (1997).
Mau, C. and C. West, "Cloning of casbene synthase cDNA: evidence for conserved structural features among terpenoid cyclases in plants," Proc. Natl. Acad. Sci. U.S.A. 91:8497-8501 (1994).
Mayfield et al., "Expression and assembly of a fully active antibody in algae," Proc. Natl. Acad. Sci. U.S.A. 100(2):438-442 (2003).
Muneta et al., "Large-scale production of porcine mature interleukin-18 (IL-18) in silkworms using a hybrid baculovirus expression system," J. Vet. Med. Sci. 65(2):219-223 (2003).
Needleman, S. and C. Wunsch "A general method applicable to the search for similarities in the amino acid sequence of two proteins," J Mol Biol. 48:443-453 (1970).
Newman, J. and J. Chappell, "Isoprenoid biosynthesis in plants: carbon partitioning within the cytoplasmic pathway," Crit. Rev. Biochem. Mol. Biol. 34:95-106 (1999).
Noel et al., "Structural elucidation of cisoid and transoid cyclization pathways of a sesquiterpene synthase using 2-fluorofarnesyl diphosphates," ACS Chem. Biol. 5(4):377-392 (2010).
O'Maille et al., "Biosynthetic potential of sesquiterpene synthases: alternative products of tobacco 5-epi-aristolochene synthase," Arch. Biochem. Biophys. 448:73-82 (2006).
Pala-Paul et al., "Analysis of the essential oil composition from the different parts of Eryngium glaciale Boiss. from Spain," J. of Chromatography 1094:179-182 (2005).
Park et al., "Metabolic engineering of *Saccharomyces cerevisiae* for the fermentative production of high-value terpenoid compounds," Abstract of presentation at Society for Industrial Microbiology Annual Meeting and Exhibition, Denver, CO, presented Jul. 30, 2007, 1 page.
Park et al., "Using *Saccharomyces cerevisiae* for production of terpenoid compounds for use as fragrances and flavorings," Abstract of presentation at Society for Industrial Microbiology Annual Meeting and Exhibition, San Diego, CA, presented Aug. 13, 2008, 1 page.
Pham et al., "Large-scale transient transfection of serum-free suspension-growing HEK293 EBNA1 cells: peptone additives improve cell growth and transfection efficiency," Biotechnol. Bioeng. 84(3):332-342 (2003).
Phys.org, "Substance that gives grapefruit its flavor and aroma could give insect pests the boot," found on Phys.org dated Sep. 11, 2013 [online][retrieved on Nov. 19, 2013] Retrieved from:<URL:http://phys.org/news/2013-09-substance-grapefruit-flavor-aroma-insect.html [2 pages].
Proctor, R. and T. Hohn, "Aristolochene synthase. Isolation, characterization, and bacterial expression of a sesquiterpenoid biosynthetic gene (Ari1) from Penicillium roqueforti," J. Biol. Chem. 268:4543-4548 (1993).
Quigley, K., "Allylix raises $18.2M, announces launch of new product for fragrance market," San Diego Business Journal, Published on Mar. 14, 2012 [online][retrieved on Jun. 1, 2012] Retrieved from:<URL:sdbj.com/news/2012/mar/14/allylix-raises-182m-announces-launch-new-product-f/ [1 page].
Ralston et al., "Biochemical and molecular characterization of 5-epi-aristolochene 3-hydroxylase, a putative regulatory enzyme in the biosynthesis of sesquiterpene phytoalexins in tobacco," Plant Interactions with Other Organisms. Annual Meeting of the American Society of Plant Physiologists. Madison, WI., Jun. 27-Jul. 1, 1998, Session 47:Abstract #737, Poster Presentation, 2 pages.
Ralston et al., "Cloning, heterologous expression, and fuctional characterization of 5-epi-aristolochene-1,3-dihydroxylase from tobacco (*Nicotiana tabacum*)," Arch. Biochem. Biophys. 393:222-235 (2001).
Richmond, T., "Precompiled codon-usage tables," Genome Biol. 1:241 (2000).
Russell et al., "Nucleotide sequence of the yeast alcohol dehydrogenase II gene," J. Biol. Chem. 258:2674-2682 (1982).
Salvador, J. and J. Clark, "The allylic oxidation of unsaturated steroids by tert-butyl hydroperoxide using surface functionalised silica supported metal catalysts," Green Chem. 4:352-356 (2002).
Schwartz, R. and M. Dayhoff, eds., *Atlas of Protein Sequence and Structure*, National Biomedical Research Foundation, pp. 353-358 (1979).
Sharp et al., "Codon usage patterns in *Escherichia coli, Bacillus subtilis, Saccharomyces cerevisiae, Schizosaccharomyces pombe, Drosophila melanogaster* and *Homo sapiens*; a review of the considerable within-species diversity," Nucleic Acids Res. 16(17):8207-8211 (1988).
Sharp, P. and E. Cowe, "Synonymous codon usage in *Saccharomyces cerevisiae*," Yeast 7(7):657-678 (1991).
Smith, T. and M. Waterman, "Comparison of biosequences," Advances in Applied Mathematics 2:482-489 (1981).
Starks et al., "Structural basis for cyclic terpene biosynthesis by tobacco 5-epi-aristolochene synthase," Science 277:1815-1820 (1997).
Stemmer, W., "DNA shuffling by random fragmentation and reassembly: in vitro recombination for molecular evolution," Proc. Natl. Acad. Sci. U.S.A. 91:10747-10751 (1994).
Stemmer et al., "Rapid evolution of a protein in vitro by DNA shuffling," Nature 370(6488):389-391 (1994).
Takahashi et al., "Metabolic engineering of sesquiterpene metabolism in yeast," Biotechnol. Bioeng. 97:170-181 (2007).

(56) References Cited

OTHER PUBLICATIONS

Thai et al., "Farnesol is utilized for isoprenoid biosynthesis in plant cells via farnesyl pyrophosphate formed by successive monophosphorylation reactions," Proc. Natl. Acad. Sci. U.S.A. 96:13080-13085 (1999).
Tholl, D., "Terpene synthases and the regulation, diversity and biological roles of terpene metabolism," Curr. Opin. Plant Biol. 9(3):297-304 (2006).
van den Berg et al., "Kluyveromyces as a host for heterologous gene expression: expression and secretion of prochymosin," Biotechnol. 8:135-139 (1990).
Wilson et al., "Synthesis of nootkatone from valencene," J. Agric. Food Chem. 26(6):1430-1432 (1978).
Wu et al., "Redirection of cytosolic or plastidic isoprenoid precursors elevates terpene production in plants," Nat. Biotechnol. 24:1441-1447 (2006).
Yoshioka et al., "cDNA cloning of sesquiterpene cyclase and squalene synthase, and expression of the genes in potato tuber infected with Phytophthora infestans," Plant Cell. Physiol. 40:993-998 (1999).
Genbank Accession No. GU987104 "Eleutherococcus trifoliatus alpha-copaene synthase (Cop) mRNA, complete cds," published on Apr. 1, 2012 [retrieved on Sep. 14, 2016] [retrieved from the Internet ncbi.nlm.nih.gov/nuccore/GU987104] [2 pages].
Genbank Accession No. KF294501 "Panax ginseng sesquiterpene synthase (STS) mRNA, complete cds," published on Aug. 4, 2013 [retrieved on Sep. 14, 2016] [retrieved from the Internet ncbi.nlm.nih.gov/nuccore/KF294501] [2 pages].
Nguyen et al., "De novo synthesis of high-value plant sesquiterpenoids in yeast," Methods Enzymol., 2012, 517:261-78.
Chen et al. "The family of terpene synthases in plants: a mid-size family of genes for specialized metabolism that is highly diversified throughout the kingdom," Plant J., 66:212-229 (2011).
Lee et al., "Biochemical and Genomic Characterization of Terpene Synthases in Magnolia grandiflora," Plant Physiology 147:1017-1033 (2008).
Trapp et al., "Genomic organization of plant terpene synthases and molecular evolutionary implications," Genetics 158:811-832(2001).
Wang et al., "Cloning and Comparative Studies of Seaweed Trehalose-6-Phosphate Synthase Genes," Mar. Drugs 8:2065-2079 (2010).
Genbank Accession No. AF411120.1, "Citrus x paradisi putative terpene synthase mRNA, complete cds," published on Apr. 2, 2002 [retrieved on Aug. 7, 2017] [retrieved from the internet ncbi.nlm.nih.gov/nuccore/AF411120.1] [2 pages].
Christianson, D.W., "Unearthing the roots of the terpenome." Curr. Opin. Chem. Biol. 12(2): 141-150 (2008).
Genbank Accession No. HQ652871.1, "Citrus hystrix germacrene D synthase mRNA, complete cds," published on Jun. 28, 2011 [retrieved on Aug. 7, 2017] [retrieved from the internet ncbi.nlm.nih.gov/nuccore/HQ652871.1] [2 pages].
Sharon-Asa, et al., "Citrus fruit flavor and aroma biosynthesis: isolation, functional characterization, and developmental regulation of Cstps1, a key gene in the production of the sesquiterpene aroma compound valencene." Plant J., 36(5):664-74 (2003).

* cited by examiner

FPP

Valencene (1)

Nootkatone (2)

```
EGVS (1)    MSLNVLSTSGSAPTTKSSEITRRSANYHPSLWGDKFLEYSSPDHLKNDSFTEKKHEQLKE 60
CVS (14)    --------------MSSGETFRPTADFHPSLWRNHFLKGASDFKTVDHTATQERHEALKE 46
                           .*.*  * :*::***** ::**: :*  :  :.: *:::** ***

EGVS (1)    EVKKMLVETVQKPQQQLNLINEIQRLGLSYLFEPEIEAALQEISVTYDEFCCSTDADDLH 120
CVS (14)    EVRRMITDAEDKPVQKLRLIDEVQRLGVAYHFEKEIEDAIQKLCPIYID----SNRADLH 102
            **::*:.:: :** *:*.**:*:****::* ** *** *:*::.  * :     ::  ***

EGVS (1)    NVALSFRILREHGHNVSSDVFQKFMDSNGKLKDYLVNDARGLLSLYEATHFRVHNDDKLE 180
CVS (14)    TVSLHFRLLRQQGIKISCDVFEKFKDDEGRFKSSLINDVQGMLSLYEAAYMAVRGEHILD 162
            .*:* **:**::* ::*.***:** *.:*::*. *:**.:*:******::: *:.:. *:

EGVS (1)    ELLSVTTSRLEHLKS--HVKYPLEDEISRALKHPLHKELNRLGARYYISIYEKFDSH--N 236
CVS (14)    EAIAFTTTHLKSLVAQDHVTPKLAEQINHALYRPLRKTLPRLEARYFMSMINSTSDHLYN 222
            * ::.**::*: * :  **.  * ::*.:** :**:* * ** ***::*: :. ..*  *

EGVS (1)    KLLLEFAKLDFNRLQKMYQHELAHLTRWWKDLDFTNKLPFARDRIVEGYFWILGMYFEPE 296
CVS (14)    KTLLNFAKLDFNILLELHKEELNELTKWWKDLDFTTKLPYARDRLVELYFWDLGTYFEPQ 282
            * **:******* * ::::.** .**:********.***:****:** *** ** ****:

EGVS (1)    RKDVREFLNRVFALITVVDDTYDVYGTFKELLLFTDAIERWGTSDLDQLPGYMRIIYQAL 356
CVS (14)    YAFGRKIMTQLNYILSIIDDTYDAYGTLEELSLFTEAVQRWNIEAVDMLPEYMKLIYRTL 342
                *:::.::  :::::*****.***::** ***:*::**. . :* ** **::**::*

EGVS (1)    MDVYNQMEEKLSMKADCPTYRLEFAIETVKAMFRSYLEEARWSKEHYIPSMEEYMTVALV 416
CVS (14)    LDAFNEIEEDMAKQG--RSHCVRYAKEENQKVIGAYSVQAKWFSEGYVPTIEEYMPIALT 400
            :*.:*::**.:: :.   :: :.:* *  : :: :*  :*:* .* *:*::****.:**.

EGVS (1)    SVGYKTILTNSFVGMGDIATREVFEWVFNSPLIIRASDLIARLGDDIGGHEEEQKKGDAA 476
CVS (14)    SCAYTFVITNSFLGMGDFATKEVFEWISNNPKVVKAASVICRLMDDMQGHEFEQKRGHVA 460
            * .*. ::****:****:**:*****: *.* :::*:.:*.** **: *** ***:*..*

EGVS (1)    TAIECYIKENHVTKHEAYDEFQKQIDNAWKDLNKEALR-PFPVPMTFITRVVHFTRAIHV 535
CVS (14)    SAIECYTKQHGVSKEEAIKMFEEEVANAWKDINEELMMKPTVVARPLLGTILNLARAIDF 520
            :***** *:: *:*.** . *:::: *****:*:* :  *  *. .::  :::::***..

EGVS (1)    IYADFSDGYTRSDKAIRGYITSLLVDPIPL 565
CVS (14)    IYKE-DDGYTHS-YLIKDQIASVLGDHVPF 548
            ** : .****:*   *:. *:*:* * :*:
```

FIGURE 4A

```
EGVS (1)    MSLNVLSTSGSAPTTKSSEITRRSANYHPSLWGDKFLEYSSPDHLKNDSFTEKKHEQLKE 60
CVS (15)    --------------MSSGETFRPTADFHPSLWRNHFLKGASDFKTVDHTATQERHEALKE 46
                           .*.*  * :*::***** ::**: :*  :  :.: *:::** ***

EGVS (1)    EVKKMLVETVQKPQQQLNLINEIQRLGLSYLFEPEIEAALQEISVTYDEFCCSTDADDLH 120
CVS (15)    EVRRMITDAEDKPVQKLRLIDEVQRLGVAYHFEKEIEDAILKLCPIYID----SNRADLH 102
            **::*:.:: :** *:*.**:*:****::* ** *** *: ::.  * :    ::  ***

EGVS (1)    NVALSFRILREHGHNVSSDVFQKFMDSNGKLKDYLVNDARGLLSLYEATHFRVHNDDKLE 180
CVS (15)    TVSLHFRLLRQQGIKISCDVFEKFKDDEGRFKSSLINDVQGMLSLYEAAYMAVRGEHILD 162
            .*:* **:**::* ::*.***:** *.:*::*. *:**.:*:******::: *:.:. *:

EGVS (1)    ELLSVTTSRLEHLKS--HVKYPLEDEISRALKHPLHKELNRLGARYYISIYEKFDSH--N 236
CVS (15)    EAIAFTTTHLKSLVAQDHVTPKLAEQINHALYRPLRKTLPRLEARYFMSMINSTSDHLYN 222
            * ::.**::*: * :  **.  * ::*.:** :**:* * ** ***::*: :. ..*  *

EGVS (1)    KLLLEFAKLDFNRLQKMYQHELAHLTRWWKDLDFTNKLPFARDRIVEGYFWILGMYFEPE 296
CVS (15)    KTLLNFAKLDFNILLEPHKEELNELTKWWKDLDFTTKLPYARDRLVELYFWDLGTYFEPQ 282
            * **:******* * : ::.** .**:********.***:****:** *** ** ****:

EGVS (1)    RKDVREFLNRVFALITVVDDTYDVYGTFKELLLFTDAIERWGTSDLDQLPGYMRIIYQAL 356
CVS (15)    YAFGRKIMTQLNYILSIIDDTYDAYGTLEELSLFTEAVQRWNIEAVDMLPEYMKLIYRTL 342
                *:::.::  :::::*****.***::** ***:*::**. . :* ** **::**::*

EGVS (1)    MDVYNQMEEKLSMKADCPTYRLEFAIETVKAMFRSYLEEARWSKEHYIPSMEEYMTVALV 416
CVS (15)    LDAFNEIEEDMAKQG--RSHCVRYAKEENQKVIGAYSVQAKWFSEGYVPTIEEYMPIALT 400
            :*.:*::**.:: :.   :: :.:* *  : :: :*  :*:* .* *:*::****.:**.

EGVS (1)    SVGYKTILTNSFVGMGDIATREVFEWVFNSPLIIRASDLIARLGDDIGGHEEEQKKGDAA 476
CVS (15)    SCAYTFVITNSFLGMGDFATKEVFEWISNNPKVVKAASVICRLMDDMQGHEFEQKRGHVA 460
            * .*. ::****:****:**:*****: *.* :::*:.:*.** **: *** ***:*..*

EGVS (1)    TAIECYIKENHVTKHEAYDEFQKQIDNAWKDLNKEALR-PFPVPMTFITRVVHFTRAIHV 535
CVS (15)    SAIECYTKQHGVSKEEAIKMFEEEVANAWKDIDEELMMKPTVVARPLLGTILNLARAIDF 520
            :***** *:: *:*.** . *:::: *****:::* :  *  *. .::   ::::***..

EGVS (1)    IYADFSDGYTRSDKAIRGYITSLLVDPIPL 565
CVS (15)    IYKE-DDGYTHS-YLIKDQIASVLGDHVPF 548
            ** : .****:*   *:. *:*:* * :*:
```

FIGURE 4B

```
EGVS (1)    MSLNVLSTSGSAPTTKSSEITRRSANYHPSLWGDKFLEYSSPDHLKNDSFTEKKHEQLKE 60
VVS (16)    MSTQVSASS-LAQIPQPK--NRPVANFHPNIWGDQFITYTPEDKVTR-ACKEEQIEDLKK 56
            ** :* ::*  *  .:..  .*  **:**.:***:*: *:. *::.. : .*:: *:**:

EGVS (1)    EVK-KMLVETVQKPQQQLNLINEIQRLGLSYLFEPEIEAALQEISVTYDEFCCSTDADDL 119
VVS (16)    EVKRKLTAAAVANPSQLLNFIDAVQRLGVAYHFEQEIEEALQHICNSFHD--CNDMDGDL 114
            *** *: . :* :*.* **:*: :****::* ** *** ***.*. ::.:  *.   .**

EGVS (1)    HNVALSFRILREHGHNVSSDVFQKFMDSNGKLKDYLVNDARGLLSLYEATHFRVHNDDKL 179
VVS (16)    YNIALGFRLLRQQGYTISCDIFNKFTDERGRFKEALISDVRGMLGLYEAAHLRVHGEDIL 174
            :*:**.**:**::*:.:*.*:*:** *..*::*: *:.*.**:*.****:*:***.:* *

EGVS (1)    EELLSVTTSRLEHLKSHVKYPLEDEISRALKHPLHKELNRLGARYYISIYEKFDSHNKLL 239
VVS (16)    AKALAFTTTHLKAMVESLGYHLAEQVAHALNRPIRKGLERLEARWYISVYQDEAFHDKTL 234
             : *:.**::*: : . : * * ::::**::*::*  *:** **:***:*:.   *:* *

EGVS (1)    LEFAKLDFNRLQKMYQHELAHLTRWWKDLDFTNKLPFARDRIVEGYFWILGMYFEPERKD 299
VVS (16)    LELAKLDFNLVQSLHKEELSNLARWWKELDFATKLPFARDRLVEGYFWMHGVYFEPQYLR 294
            **:****** :*.:::.**::*:****:***:.********:******: *:****:

EGVS (1)    VREFLNRVFALITVVDDTYDVYGTFKELLLFTDAIERWGTSDLDQLPGYMRIIYQALMDV 359
VVS (16)    GRRILTKVIAMTSILDDIHDAYGTPEELKLFIEAIERWDINSINQLPEYMKLCYVALLDV 354
             *.:*.:*:*: :::** :*.*** :** ** :*****. ..::*** **:: * **:**

EGVS (1)    YNQMEEKLSMKADCPTYRLEFAIETVKAMFRSYLEEARWSKEHYIPSMEEYMTVALVSVG 419
VVS (16)    YKEIEEEMEKEGNQ--YRVHYAKEVMKNQVRAYFAEAKWLHEEHVPAFEEYMRVALASSG 412
            *:::**::. :.:   **:.:* *.:*  .*:*: **:* :*.::*::**** ***.* *

EGVS (1)    YKTILTNSFVGMGDIATREVFEWVFNSPLIIRASDLIARLGDDIGGHEEEQKKGDAATAI 479
VVS (16)    YCLLATTSFVGMGEIATKEAFDWVTSDPKIMSSSNFITRLMDDIKSHKFEQKRGHVASAV 472
            *  : *.******:***:*.*:** ..* *: :*::*:** *** .*: ***:*..*:*:

EGVS (1)    ECYIKENHVTKHEAYDEFQKQIDNAWKDLNKEALRPFPVPMTFITRVVHFTRAIHVIYAD 539
VVS (16)    ECYMKQYGVSEEQVYSEFQKQIENAWLDINQECLKPTAVSMPLLARLLNLTRTMDVIYKE 532
            ***:*:  *::.:.*.******:*** *:*:*.*:* .*.*.:::*::::**::.*** :

EGVS (1)    FSDGYTRSDKAIRGYITSLLVDPIPL 565
VVS (16)    Q-DSYTHVGKVMRDNIASVFINAVI- 556
              *.**: .*.:*. *:*::::.:
```

FIGURE 4C

```
EGVS (1)      MSLNVLSTSGSAPTTKSSEITRRSANYHPSLWGDKFLEYSSPDHLKNDSFTEKKHEQLKE 60
CNVS (17)     --------------MPVKDALRRTGNHHPNLWTDDFIQSLNSPYS--DSSYHKHREILID 44
                               .:  **:.*:**.** *.*::  .. :   **  .*::* * :

EGVS (1)      EVKKMLVETVQKPQQQLN---LINEIQRLGLSYLFEPEIEAALQEISVTYDEFCCSTDAD 117
CNVS (17)     EIRDMFSNGEGDEFGVLENIWFVDVVQRLGIDRHFQEEIKTALDYI---YKFWNHDSIFG 101
              *::.*: :   .    *:   ::: :****:.  *: **::**: *   *. :  .:  .

EGVS (1)      DLHNVALSFRILREHGHNVSSDVFQKFMDSNGKLKDYLVNDARG----LLSLYEATHFRV 173
CNVS (17)     DLNMVALGFRILRLNRYVASSDVFKKFKGEEGQFSGFESSDQDAKLEMMLNLYKASELDF 161
              **: ***.***** : : .*****:** ..:*::..:  .*  .    :*.**:*:.: .

EGVS (1)      HNDDKLEELLSVTTSRLEHLKSHV------KYPLEDEISRALKHPLHKELNRLGARYYIS 227
CNVS (17)     PDEDILKEARAFASMYLKHVIKEYGDIQESKNPLLMEIEYTFKYPWRCRLPRLEAWNFIH 221
               ::* *:*  :.::  *:*: ..       * **  **. ::*:* : .* ** *  :*

EGVS (1)      IYEKFDS--------------HNKLLLEFAKLDFNRLQKMYQHELAHLTRWWKDLDFTNK 273
CNVS (17)     IMRQQDCNISLANNLYKIPKIYMKKILELAILDFNILQSQHQHEMKLISTWWKNS-SAIQ 280
              * .: *.              : * :**:* **** **. :***:  :: ***:   : :

EGVS (1)      LPFARDRIVEGYFWILGMYFEPERKDVREFLNRVFALITVVDDTYDVYGTFKELLLFTDA 333
CNVS (17)     LDFFRHRHIESYFWWASPLFEPEFSTCRINCTKLSTKMFLLDDIYDTYGTVEELKPFTTT 340
              * * *.* :*.***  .  **** .  *   .:: : : ::** **.***.:**  ** :

EGVS (1)      IERWGTSDLDQLPGYMRIIYQALMDVYNQMEEKLSMKADCPTYRLEFAIETVKAMFRSYL 393
CNVS (17)     LTRWDVSTVDNHPDYMKIAFNFSYEIYKEIASEAERKHGP--FVYKYLQSCWKSYIEAYM 398
              : **..* :*: *.**:* ::   ::*::: .: . * .   :  ::  .  *: :.:*:

EGVS (1)      EEARWSKEHYIPSMEEYMTVALVSVGYKTILTNSFVGMGDIATREVFEWVFN-SPLIIRA 452
CNVS (17)     QEAEWIASNHIPGFDEYLMNGVKSSGMRILMIHALILMDTPLSDEILEQLDIPSSKSQAL 458
              :**.*  .::**.::**:  .: * * : :: :::: *.   : *::* :   *.

EGVS (1)      SDLIARLGDDIGGHEEEQKKGDAATAIECYIKENH-VTKHEAYDEFQKQIDNAWKDLNKE 511
CNVS (17)     LSLITRLVDDVKDFEDEQAHGEMASSIECYMKDNHGSTREDALNYLKIRIESCVQELNKE 518
               .**:** **: ..*:** :*: *::****:*:**  *:.:* : :: :*:.. ::****

EGVS (1)      ALRPFPVPMTFITRVVHFTRAIHVIYADFSDGYTRSD-KAIRGYITSLLVDPIPL 565
CNVS (17)     LLEPSNMHGSFRNLYLNVGMRVIFFMLNDGDLFTHSNRKEIQDAITKFFVEPIIP 573
                    *.*  :  :* .  ::.   : .:  : .* :*:*: * *:. **.::*:**
```

FIGURE 4D

```
EGVS (1)    MSLNVLSTSGSAPTTKSSEITRRSANYHPSLWGDKFLEYSSPDHLKNDSFTEKKHEQLKE 60
V277 (31)   MSTQVSASS-LAQIPQPK--NRPVANFHPNIWGDQFITYTPEDKVTR-ACKEEQIEALKE 56
            ** :* ::*  *   .:..   .*   **:**.:***:*: *:. *::.. : .*:: * ***

EGVS (1)    EVKKMLVETVQKPQQQLNLINEIQRLGLSYLFEPEIEAALQEISVTYDEFCCSTDADDLH 120
V277 (31)   EVRRMILATGRKPIQKLRLIDEVQRLGVAYHFEKEIEDMLDHIYR-ADPYFEAHEYNDLH 115
            **::*:: * :** *:*.**:*:****::* ** ***  *:.*     * :  : : :***

EGVS (1)    NVALSFRILREHGHNVSSDVFQKFMDSNGKLKDYLVNDARGLLSLYEATHFRVHNDDKLE 180
V277 (31)   TVSLHFRLLRQQGIKISCDVFEQFKDDEGRFKSSLINDVQGMLSLYEAAYMAVRGEHILD 175
            .*:* **:**::* ::*.***::* *.:*::*. *:**.:*:******::: *:.:. *:

EGVS (1)    ELLSVTTSRLEHLKSHVKYPLEDEISRALKHPLHKELNRLGARYYISIYEKFDSHNKLLL 240
V277 (31)   EAIAFTTTHLQSAAPHLKSPLAEQINHALYRPLRKTLPRLEARYIMSVYQDEAFHNKTLL 235
            * ::.**::*:    .*:* ** ::*.:** :**:* * ** *** :*:*:.    *** **

EGVS (1)    EFAKLDFNRLQKMYQHELAHLTRWWKDLDFTNKLPFARDRIVEGYFWILGMYFEPERKDV 300
V277 (31)   NFAKLDFNILLDLHKEELNELTKWWQDLDFTTKLPYARDRLVELYFWDLGTYFESQYAFG 295
            :******* * .:::.** .**:**:*****.***:****:** *** ** ***.:

EGVS (1)    REFLNRVFALITVVDDTYDVYGTFKELLLFTDAIERWGTSDLDQLPGYMRIIYQALMDVY 360
V277 (31)   RKIMTKLNYILSIIDDTYDAYGTLEECTMFSEAVARWNIEAVDMLPDYMRIIYRTLLDTF 355
            *:::.::  :::::*****.***::*  :*::*: **. . :* **.******::*:*.:

EGVS (1)    NQMEEKLSMKADCPTYRLEFAIETVKAMFRSYLEEARWSKEHYIPSMEEYMTVALVSVGY 420
V277 (31)   NEIEEDMAKQR--RSHCVRYAKEEIQKVIGAYYVQAKWFSEGYVPTIEEYMPIALTSCAY 413
            *::**.:: :    :: :.:* * :: :: :*  :*:* .* *:*::****.:**.* .*

EGVS (1)    KTILTNSFVGMGDIATREVFEWVFNSPLIIRASDLIARLGDDIGGHEEEQKKGDAATAIE 480
V277 (31)   RFVITNSFLGMGDFATKEVFEWISGNPKVVKSASVICRLMDDMQGHEFEQKRGHVASAIE 473
            : ::****:****:**:*****: ..* :::::.:*.** **: *** ***:*..*:***

EGVS (1)    CYIKENHVTKHEAYDEFQKQIDNAWKDLNKEALRPFPVPMT-FITRVVHFTRAIHVIYAD 539
V277 (31)   CYTKQHGVSKEEAIKMFEEDVANAWKDINEELMMKPPVVARPLLGTILNLARAIDFIYKE 533
            ** *:: *:*.** . *:::: *****:*:* :    **     ::  :::::***..** :

EGVS (1)    FSDGYTRSDKAIRGYITSLLVDPIPL 565
V277 (31)   -DDGYTHS-YLIKEQIASVLGDHVPF 557
             .****:*    *:  *:*:* * :*:
```

FIGURE 4E

```
EGVS (1)      --MSLNVLSTSGSAPTTKSSEITRRSANYHPSLWGDKFLEYSSPDHLKNDSFTEKKHEQL 58
CNVS (29)     MAEMFNGNSSNDGSSCMPVKDALRRTGNHHPNLWTDDFIQSLNSPYS--DSSYHKHREIL 58
                  :*  *:...:.    .:  **:.*:**.** *.*::  .. :   **  .*::* *

EGVS (1)      KEEVKKMLVETVQKPQQQLN---LINEIQRLGLSYLFEPEIEAALQEISVTYDEFCCSTD 115
CNVS (29)     IDEIRDMFSNGEGDEFGVLENIWFVDVVQRLGIDRHFQEEIKTALDYI---YKFWNHDSI 115
               :*::.*: :   .    *:    :::  :****:.  *:  **::**: *   *.  :   .:

EGVS (1)      ADDLHNVALSFRILREHGHNVSSDVFQKFMDSNGKLKDYLVNDARG----LLSLYEATHF 171
CNVS (29)     FGDLNMVALGFRILRLNRYVASSDVFKKFKGEEGQFSGFESSDQDAKLEMMLNLYKASEL 175
               .**: ***.***** : : .*****:** ..:*::..:  .*   .    :*.**:*:.:

EGVS (1)      RVHNDDKLEELLSVTTSRLEHLKSHV------KYPLEDEISRALKHPLHKELNRLGARYY 225
CNVS (29)     DFPDEDILKEARAFASMYLKHVIKEYGDIQESKNPLLMEIEYTFKYPWRCRLPRLEAWNF 235
               . ::* *:*  :.::  *:*: ..       * **  **. ::*:* : .* ** *  :

EGVS (1)      ISIYEKFDS--------------HNKLLLEFAKLDFNRLQKMYQHELAHLTRWWKDLDFT 271
CNVS (29)     IHIMRQQDCNISLANNLYKIPKIYMKKILELAILDFNILQSQHQHEMKLISTWWKNS-SA 294
              * * .: *.               : * :**:* **** **. :***:  :: ***:   :

EGVS (1)      NKLPFARDRIVEGYFWILGMYFEPERKDVREFLNRVFALITVVDDTYDVYGTFKELLLFT 331
CNVS (29)     IQLDFFRHRHIESYFWWASPLFEPEFSTCRINCTKLSTKMFLLDDIYDTYGTVEELKPFT 354
               :*  * *.* :*.***  .  ****  .  *   .:: : : ::** **.***.:**  **

EGVS (1)      DAIERWGTSDLDQLPGYMRIIYQALMDVYNQMEEKLSMKADCPTYRLEFAIETVKAMFRS 391
CNVS (29)     TTLTRWDVSTVDNHPDYMKIAFNFSYEIYKEIASEAERKHGP--FVYKYLQSCWKSYIEA 412
               :: **..* :*: *.**:* ::    ::*::: .:  . * .   :  ::   .  *:  :.:

EGVS (1)      YLEEARWSKEHYIPSMEEYMTVALVSVGYKTILTNSFVGMGDIATREVFEWVFN-SPLII 450
CNVS (29)     YMQEAEWIASNHIPGFDEYLMNGVKSSGMRILMIHALILMDTPLSDEILEQLDIPSSKSQ 472
              *::**.*  .::**.::**:  .:  * * : :: :::: *.   : *::* :   *.

EGVS (1)      RASDLIARLGDDIGGHEEEQKKGDAATAIECYIKENH-VTKHEAYDEFQKQIDNAWKDLN 509
CNVS (29)     ALLSLITRLVDDVKDFEDEQAHGEMASSIECYMKDNHGSTREDALNYLKIRIESCVQELN 532
                 .**:** **: ..*:** :*: *::****:*:**  *:.:* : :: :*:.. ::**

EGVS (1)      KEALRPFPVPMTFITRVVHFTRAIHVIYADFSDGYTRSD-KAIRGYITSLLVDPIPL 565
CNVS (29)     KELLEPSNMHGSFRNLYLNVGMRVIFFMLNDGDLFTHSNRKEIQDAITKFFVEPIIP 589
              ** *.*  :  :*  .  ::.   :.:   : .* :*:*: * *:. **.::*:**
```

FIGURE 4F

```
EGVS (1)    MSLNVLSTSGSAPTTKSSEITRRSANYHPSLWGDKFLEYSSPDHLKNDSFTEKKHEQLKE 60
PFVS (38)   ------------MASEQAQNHRPVADFSPSLWGDQFVKYDSCPQVQKK--YSNTVDVLKK 46
                        :::.::  *  *:: ******:*::*.*  ::::.    .:. : **:

EGVS (1)    EVKKMLVETVQKPQQQLNLINEIQRLGLSYLFEPEIEAALQEISVTYDEFCCS-TDADDL 119
PFVS (38)   EVKGMITAPGTKMVDTMELIDTIERLGVSFHFQDEIEQKLQQFFDLKTDYCNDGDDAYDL 106
            *** *:. .  *  : ::**: *:***:*: *: ***  **::     ::* .  ** **

EGVS (1)    HNVALSFRILREHGHNVSSDVFQKFMDSNGKLKDYLVNDARGLLSLYEATHFRVHNDDKL 179
PFVS (38)   YTVALHFRLFRQHGYRISCDIFGRWIDGNGKFKEGLKSDGKSLLSLYEASYLRTRGETIL 166
            :.*** **::*:**:.:*.*:* :::*.***:*: * .*.:.*******:::*.:.:  *

EGVS (1)    EELLSVTTSRLEHLKSHVKYPLEDEISRALKHPLHKELNRLGARYYISIYEKFDSHNKLL 239
PFVS (38)   DEALDFAAASLKSIAPHLQSPLGKQVVHALVQPLHFGNPRIEARNFISIYEEYEGMNEAL 226
            :* *..::: *: : .*:: ** .:: :** :***    *: ** :*****:::. *: *

EGVS (1)    LEFAKLDFNRLQKMYQHELAHLTRWWKDLDFTNKLPFARDRIVEGYFWILGMYFEPERKD 299
PFVS (38)   LRLAKLDYNLLQMLHKEELHQVSRWWKDLDLITKLPYARDRVVECFFWAVGVYHEPQYSR 286
            *.:****:* ** :::.** :::*******: .***:****:** :** :*:*.**: .

EGVS (1)    VREFLNRVFALITVVDDTYDVYGTFKELLLFTDAIERWGTSDLDQLPGYMRIIYQALMDV 359
PFVS (38)   ARVMLTKTIVMTSIIDDTYDAYGTIEELDIFTEAIERWNVEETKRLPEYMKPLYKALLEL 346
            .* :*.:.:.: :::*****.***::** :**:*****...: .:** **: :*:**:::

EGVS (1)    YNQMEEKLSMKADCPTYRLEFAIETVKAMFRSYLEEARWSKEHYIPSMEEYMTVALVSVG 419
PFVS (38)  YKQFEQELEKEG--RSYVAYYAIESLKELVRSYRIEAKWFIQGYLPPYEEYLKNALITCT 404
            *:*:*::*. :.   :*   :***::* :.***  **:*  : *:*. ***:. **::

EGVS (1)    YKTILTNSFVGMGDIATREVFEWVFNSPLIIRASDLIARLGDDIGGHEEEQKKGDAATAI 479
PFVS (38)   YCYHTTTSLLGV-ESAIKENFEWLSNKPKMLVAGLLICRLIDDIATYILERGRGQVATGI 463
            *    *.*::*: : * :* ***: *.* :: *. **.** ***. :  *: :*:.**.*

EGVS (1)    ECYIKENHVTKHEAYDEFQKQIDNAWKDLNKEALRP-FPVPMTFITRVVHFTRAIHVIYA 538
PFVS (38)   ESYMKDNGATQEEPIAKIFEIATDAWKDINDECLRPSLYNSRDVLMRIFNLERIIDVTYK 523
            *.*:*:* .*:.*.  :: :   :****:*.*.*** :  .  .: *:.:: * *.* *

EGVS (1)    DFSDGYTRSDKAIRGYITSLLVDPIPL 565
PFVS (38)   GNQDRYTQPEKVLKPHIIVFFFDPILI 550
            . .* **:.:*.:: :*  ::.*** :
```

FIGURE 4G

```
EGVS (1)    MSLNVLSTSGSAPTTKSSEITRRSANYHPSLWGDKFLEYSSPDHLKNDSFTEKKHEQLKE 60
ETACS (18)  MATYLQASSGPCSTIVP-EITRRSANYHPNIWGDQFLKYNSFDLSKTDANTKEHFRQLKE 59
            *:  : ::**...*  . ***********.:***:**:*.* *  *.*: *:::..****

EGVS (1)    EVKKMLVETVQKPQQQLNLINEIQRLGLSYLFEPEIEAALQEISVTYDEFCCSTDADDLH 120
ETACS (18)  EVKKMLVDAG--PNQQLNLIDDIQRLGVAYQFEAEIDAALQRMNVIFQG-----NDDDLH 112
            *******::   *:******::*****::* **.**:****.:.* ::      : ****

EGVS (1)    NVALSFRILREHGHNVSSDVFQKFMDSNGKLKDYLVNDARGLLSLYEATHFRVHNDDKLE 180
ETACS (18)  TISLRFRLLRQHGYNVSSDVFRKFMDNNGKFKECLISDLRGVLSLYEATHFRVHGEDILE 172
            .::* **:**:**:*******:****.***:*: *:.* **:************.:* **

EGVS (1)    ELLSVTTSRLEHLKSHVKYPLEDEISRALKHPLHKELNRLGARYYISIYEKFD-SHNKLL 239
ETACS (18)  DALEFTTSHLERLKSHLKNPLAAQVIRALKCPIHKGLNRLEAKHYISIYQQEDDSHNKVL 232
            : *..***:**:****:* **  :: **** *:** **** *::*****:: * ****:*

EGVS (1)    LEFAKLDFNRLQKMYQHELAHLTRWWKDLDFTNKLPFARDRIVEGYFWILGMYFEPERKD 299
ETACS (18)  LNFAKLDFNLLQKMHQGELSHITRWWKELNFAKKLPFARDRVVECYFWILGVYFEPQYLI 292
            *:******* ****:* **:*:*****:*:*::********:** ******:****:

EGVS (1)    VREFLNRVFALITVVDDTYDVYGTFKELLLFTDAIERWGTSDLDQLPGYMRIIYQALMDV 359
ETACS (18)  ARRFLTKIIAMASVADDIYDVYGTLEELVILTDAIERWDMGALDQIPECMRVYHRALLDV 352
            .*.**.:::*: :*.** ******::**:::*******. . ***:*  **: ::**:**

EGVS (1)    YNQMEEKLSMKADCPTYRLEFAIETVKAMFRSYLEEARWSKEHYIPSMEEYMTVALVSVG 419
ETACS (18)  YTEMEEEM-AKTGRPSYRVHYAKEAYKELVRQYLAEAKWFQEDYDPTLEEYLPVALISGG 411
            *.:***::  *:. *:**:.:* *: * :.*.** **:* :*.* *::***:.***:* *

EGVS (1)    YKTILTNSFVGMGDIATREVFEWVFNSPLIIRASDLIARLGDDIGGHEEEQKKGDAATAI 479
ETACS (18)  YKMLATHSFVGMGDLATKEAFDWVSNNPLIVKASSVICRLSDDMVGHEVEHERGDVASAV 471
            ** : *:*******:**:*.*:** *.***::**.:*.**.**: *** *:::**.*:*:

EGVS (1)    ECYIKENHVTKHEAYDEFQKQIDNAWKDLNKEALRPFPVPMTFITRVVHFTRAIHVIYAD 539
ETACS (18)  ECYMKQYGVTKQEVYIEFQKQISNAWKDMNQECLHPTTVTMPLLTVIFNMTRVINLLYDE 531
            ***:*:  ***:*.* ******.*****:*:*.*:* .*.*.::* :.::**.*:::* :

EGVS (1)    FSDGYTRSDKAIRGYITSLLVDPIPL 565
ETACS (18)  -EDGYTNSNTRTKDFITSVLIDPVQI 556
             .****.*:.  :.:***:*:**: :
```

FIGURE 5A

```
EGVS (1)     MSLNVLSTS--GSAPTTKSSE---ITRRSANYHPSLWGDKFLEYSSPDHLKNDSF---TE 52
ADGDS (19)   MQLPCAQALPIPTVTTTTSIEPPHVTRRSANYHPSIWGDHFLAYSS-DAMEEEVINMEQQ 59
             *.*    .:    :..**.* *   :**********:***:** *** * :::: :    :

EGVS (1)     KKHEQLKEEVKKMLVETVQKPQQQLNLINEIQRLGLSYLFEPEIEAALQEISVTYDEFCC 112
ADGDS (19)   QRLHHLKQKVRKMLEAAAEQSSQMLNLVDKIQRLGVSYHFETEIETALRHIYKT-----C 114
             :: .:**::*:***  :.::..* ***:::*****:** **.***:**:.*  *     *

EGVS (1)     STDADDLHNVALSFRILREHGHNVSSDVFQKFMDSNGKLKDYLVNDARGLLSLYEATHFR 172
ADGDS (19)   DYHFDDLHTAALSFRLLRQQGYPVSCDMFDKFKNSKGEFQESIISDVQGMLSLYEATCLR 174
             . . ****..*****:**::*: **.*:*:** :*:*:::: ::.*.:*:******* :*

EGVS (1)     VHNDDKLEELLSVTTSRLEHLKSHVKYPLEDEISRALKHPLHKELNRLGARYYISIYEKF 232
ADGDS (19)   IHGEDILDEALAFTITQLRSALPNLSTPFKEQIIHALNQPIHKGLTRLNARSHILFFEQN 234
             :*.:* *:* *:.* ::*.    .::. *::::* :**::*:** *.**.** :* ::*:

EGVS (1)     DSHNKLLLEFAKLDFNRLQKMYQHELAHLTRWWKDLDFTNKLPFARDRIVEGYFWILGMY 292
ADGDS (19)   DCHSKDLLNFAKLDFNLLQKLHQRELCEITRWWKDLNFAKTLPFARDRMVECYFWILGVY 294
             *.*.* **:******* ***::*:**..:*******:*::.*******:** ******:*

EGVS (1)     FEPERKDVREFLNRVFALITVVDDTYDVYGTFKELLLFTDAIERWGTSDLDQLPGYMRII 352
ADGDS (19)   FEPQYLLARRMLTKVIAMISIIDDIYDVYGTLEELVLFTDAIERWEISALDQLPEYMKLC 354
             ***:    .*.:*.:*:*:*:::** ******::**:*********  * ***** **::

EGVS (1)     YQALMDVYNQMEEKLSMKADCPTYRLEFAIETVKAMFRSYLEEARWSKEHYIPSMEEYMT 412
ADGDS (19)   YQALLDVYSMIDEEMAKQG--RSYCVDYAKSSMKILVRAYFEEAKWFHQGYVPTMEEYMQ 412
             ****:***. ::*::: :.   :* :::* .::* :.*:*:***:* :: *:*:*****

EGVS (1)     VALVSVGYKTILTNSFVGMGDIATREVFEWVFNSPLIIRASDLIARLGDDIGGHEEEQKK 472
ADGDS (19)   VALVTAGYKMLATSSFVGMGDLATKEAFDWVSNDPLIVQAASVIGRLKDDIVGHKFEQKR 472
             ****:.*** : *.*******:**:*.*:** *.***::*:.:*.** *** **: ***:

EGVS (1)     GDAATAIECYIKENHVTKHEAYDEFQKQIDNAWKDLNKEALRPFPVPMTFITRVVHFTRA 532
ADGDS (19)   GHVASAVECYSKQHGTTEEEAIIELDKQVTHSWKDINAECLCPIKVPMPLLARVLNLARV 532
             *..*:*:*** *:: .*:.**  *::**: ::***:* *.* *: ***.:::**::::*.

EGVS (1)     IHVIYADFSDGYTRSDKAIRGYITSLLVDPIPL- 565
ADGDS (19)   LYVIYQD-EDGYTHPGTKVENFVTSVLIDSMPIN 565
             ::*** * .****:... :..::**:*:*.:*:
```

FIGURE 5B

```
EGVS (1)    MSLNVLSTSGSAPTTKSSEITRRSANYHPSLWGDKFLEYSSPDHLKNDSFTEKKHEQLKE 60
VGDS (20)   MSVQSSVVLLAPSKNLSPEVGRRCANFHPSIWGDHFLSYAS-EFTNTDDHLKQHVQQLKE 59
            **::   .  :.... *.*: **.**:***:***:**.*:* :. :.*.. ::: :****

EGVS (1)    EVKKMLVETVQKPQQQLNLINEIQRLGLSYLFEPEIEAALQEISVTYDEFCCSTDADDLH 120
VGDS (20)   EVRKMLMAADDDSAQKLLLIDAIQRLGVAYHFESEIDEVLKHM---FDGSVVS-AEEDVY 115
            **:***: : :.. *:* **: *****::* **.**: .*:.:   :*    *   :*::

EGVS (1)    NVALSFRILREHGHNVSSDVFQKFMDSNGKLKDYLVNDARGLLSLYEATHFRVHNDDKLE 180
VGDS (20)   TASLRFRLLRQQGYHVSCDLFNNFKDNEGNFKESLSSDVRGMLSLYEATHFRVHGEDILD 175
            ..:* **:**::*::**.*:*::* *.:*::*: * .*.**:************.:* *:

EGVS (1)    ELLSVTTSRLEHLKSHVKYPLEDEISRALKHPLHKELNRLGARYYISIYEKFDSHNKLLL 240
VGDS (20)   EALAFTTTHLQSATKHSSNPLAEQVVHALKQPIRKGLPRLEARHYFSVYQADDSHNKALL 235
            * *:.**::*:  ..* . ** ::: :***:*::* * ** **:*:*:*:  ***** **

EGVS (1)    EFAKLDFNRLQKMYQHELAHLTRWWKDLDFTNKLPFARDRIVEGYFWILGMYFEPERKDV 300
VGDS (20)   KLAKLDFNLLQKLHQKELSDISAWWKDLDFAHKLPFARDRVVECYFWILGVYFEPQFFFA 295
            ::****** ***::*:**:.:: *******::********:** ******:****:

EGVS (1)    REFLNRVFALITVVDDTYDVYGTFKELLLFTDAIERWGTSDLDQLPGYMRIIYQALMDVY 360
VGDS (20)   RRILTKVIAMTSIIDDIYDVYGTLEELELFTEAVERWDISAIDQLPEYMRVCYQALLYVY 355
            *.:*.:*:*: :::** ******::** ***:*:***. * :**** ***: ****: **

EGVS (1)    NQMEEKLSMKADCPTYRLEFAIETVKAMFRSYLEEARWSKEHYIPSMEEYMTVALVSVGY 420
VGDS (20)   SEIEEEMAKEG--RSYRLYYAKEAMKNQVRAYYEEAKWLQVQQIPTMEEYMPVALVTSAY 413
            .::**::: :.   :*** :* *::*  .*:* ***:* : : **:*****.****: .*

EGVS (1)    KTILTNSFVGMGDIATREVFEWVFNSPLIIRASDLIARLGDDIGGHEEEQKKGDAATAIE 480
VGDS (20)   SMLATTSFVGMGDAVTKESFDWIFSKPKIVRASAIVCRLMDDMVSHKFEQKRGHVASAVE 473
            . : *.******* .*:* *:*:*..* *:*** ::.** **: .*: ***:*..*:*:*

EGVS (1)    CYIKENHVTKHEAYDEFQKQIDNAWKDLNKEALRPFPVPMTFITRVVHFTRAIHVIYADF 540
VGDS (20)   CYMKQHGASEQETHNEFHKQVRDAWKDINEECLIPTAVPMPILMRVLNLARVIDVIYKN- 532
            **:*:: .:::*:::**:**: :****:*:*.* * .***.:: **::::*.*.*** :

EGVS (1)    SDGYTRSDKAIRGYITSLLVDPIPL 565
VGDS (20)   EDGYTHSGTVLKDFVTSMLIDPVPI 557
            .****:*...::.::**:*:**:*:
```

FIGURE 5C

```
EGVS (1)    MSLNVLSTSGSAPTTKSSEITRRSANYHPSLWGDKFLEYSSPDHLKNDSFTEKKHEQLKE 60
SMSS (21)   MENQKMPISSVPNLKDLNMISRPIANFPPSIWGDRFINYTCEDEN-DQTQKERQVEELKE 59
            *. : :. *. .   .. . *:*  **: **:***:*::*:. *.  ::: .*:: *:***

EGVS (1)    EVKKMLVETVQKPQQQLNLINEIQRLGLSYLFEPEIEAALQEISV-TYDEFCCSTDADDL 119
SMSS (21)   QVRRELAATVDKPLQQLNIIDATQRLGIAYLFENEIEESLKHIYLHTYVENNCFEGSDDL 119
            :*:: *. **:** ****:*:  ****::**** *** :*:.* : ** *  *  .:***

EGVS (1)    HNVALSFRILREHGHNVSSDVFQKFMDSNGKLKDYLVNDARGLLSLYEATHFRVHNDDKL 179
SMSS (21)   YSVALWFRLLRQNGYKVSCDVFNKFRDNEGNFKNNLMEDAKGLLELYEATHVSIHGEEML 179
            :.*** **:**::*::**.***:** *.:*::*: *::**:***.******. :*.:: *

EGVS (1)    EELLSVTTSRLEHLKSHVKYPLEDEISRALKHPLHKELNRLGARYYISIYEKFDSHNKLL 239
SMSS (21)   DDALEFTKTRLESVVSHLNYPLAEQVRHALYQPLHRGLPRLEAVYFFRIYEAHASHNKAL 239
            :: *..*.:*** : **::*** ::: :** :***: * ** * *:: *** . **** *

EGVS (1)    LEFAKLDFNRLQKMYQHELAHLTRWWKDLDFTNKLPFARDRIVEGYFWILGMYFEPERKD 299
SMSS (21)   LKLAKLDFNLLQSFHKKELSDIARWWKSLDFAAKFPFARDRLVEGYFWVLGVYFEPQYSL 299
            *::****** **.::::**:.::****.***: *:******:******:**:****: .

EGVS (1)    VREFLNRVFALITVVDDTYDVYGTFKELLLFTDAIERWGTSDLDQLPGYMRIIYQALMDV 359
SMSS (21)   ARKIIIKVFTMISTIDDIYDAYGTLDELKLFTKAMQRWDVGSLDQLPEYMKPCYKSILDV 359
            .*::: :**::*:.:** **.***:.** ***.*::**...***** **:  *::::**

EGVS (1)    YNQMEEKLSMKADCPTYRLEFAIETVKAMFRSYLEEARWSKEHYIPSMEEYMTVALVSVG 419
SMSS (21)   YNEIEEEMANQG--SLFRMHYAKEVMKTIVEGYMDEAKWCHEKYVPTFQEYMSVALVTSG 417
            **::**::: :.   . :*:.:* *.:*::...*::**:*.:*:*:*:::***:****: *

EGVS (1)    YKTILTNSFVGMGDIATREVFEWVFNSPLIIRASDLIARLGDDIGGHEEEQKKGDAATAI 479
SMSS (21)   YTFLTTISYLGMGEIASKEAFDWLFSHPPVIEASESVGRLMDDMRSHKFEQERGHVASGI 477
            *. : * *::***:**::*.*:*:*. * :*.**: :.** **: .*: **::*..*:.*

EGVS (1)    ECYIKENHVTKHEAYDEFQKQIDNAWKDLNKEALRPFPVPMTFITRVVHFTRAIHVIYAD 539
SMSS (21)   ECYMKQYGVTEEEAHDEFRKRLVKAWKDINEECLRPYRVPKPLLTRILNLTRVIDVIYKN 537
            ***:*:  **:.**:***:*:: :****:*:*.***: ** .::**:::**.*.*** :

EGVS (1)    FSDGYTRSDKAIRGYITSLLVDPIPL 565
SMSS (21)   -EDGYTHVKKAMKDNIASLLIDPVIV 562
             .****: .**::. *:***:**: :
```

FIGURE 5D

```
EGVS (1)    MSLNVLSTSGSAPTTKSSEITRRSANYHPSLWGDKFLEYSSPDHLKNDSFTEKKHEQLKE 60
RCDCS (22)  MSAQTLAISNLKPNT-----TRHLASFHPNIWGDRFLSCAAESTDIEDDM-EQQVERLKE 54
             ** :.*: *.  *.*      **: *.:**.:***:**. :: .    :*.: *:: *:***

EGVS (1)    EVKKMLVETVQKPQQQLNLINEIQRLGLSYLFEPEIEAALQEISVTYDEFCCSTDADDLH 120
RCDCS (22)  EVKKMIAS-ADEPSQILNLIDLLQRLGVSYHFEKEIEEALQQVLNMNSD---SDKDDDLH 110
            *****:.. .::*.* ****: :****:** ** *** ***::     .:    * . ****

EGVS (1)    NVALSFRILREHGHNVSSDVFQKFMDSNGKLKDYLVNDARGLLSLYEATHFRVHNDDKLE 180
RCDCS (22)  SVALRFRLLREQGLNVSCDVFNKFRDRNGHFIQTLKTDLQGMLSLYEAAHFRVHGEGILD 170
             .*** **:***:* ***.***:** * **:: : * .* :*:******:*****.:. *:

EGVS (1)    ELLSVTTSRLEHLKSHVKYPLEDEISRALKHPLHKELNRLGARYYISIYEKFDSHNKLLL 240
RCDCS (22)  DALAFTTTYLESIVPNLSPPLAAQISRTLRQPLRKSLARVEARHFISIYQEDTSHNEVLL 230
            : *:.**: ** : .::. **  :***:*::**:*.* *: **::****::  ***::**

EGVS (1)    EFAKLDFNRLQKMYQHELAHLTRWWKDLDFTNKLPFARDRIVEGYFWILGMYFEPERKDV 300
RCDCS (22)  TFAKLDFNLLQKLHQKELKYISLWWKDLDFVNKLPFTRDRVVEGYFWILGVYFEPQYHRA 290
             ******* ***::*:** ::: *******.*****:***:*********:****: : .

EGVS (1)    REFLNRVFALITVVDDTYDVYGTFKELLLFTDAIERWGTSDLDQLPGYMRIIYQALMDVY 360
RCDCS (22)  RKFVTKVINVVSVIDDIYDAYGTLEELVVFTDAINRWDIDCIDQLPEYMKVCYKALLNVY 350
            *:*:.:*: :::*:** **.***::**::*****:**. . :**** **:: *:**::**

EGVS (1)    NQMEEKLSMKADCPTYRLEFAIETVKAMFRSYLEEARWSKEHYIPSMEEYMTVALVSVGY 420
RCDCS (22)  EEIERALSEQG--RSYRLHYAKEAMKKLVQAYLVEANWMNKNYVPTMDEYMSIALVSCAY 408
            :::*. ** :.   :***.:* *::* :.::** **.* :::*:*:*:***::**** .*

EGVS (1)    KTILTNSFVGMGDIATREVFEWVFNSPLIIRASDLIARLGDDIGGHEEEQKKGDAATAIE 480
RCDCS (22)  PLLTVTSFVGMGDIATKEVFDWASNDPKIVRVASIICRLMDDIVSHEFEQKRGHIASSVE 468
              : ..**********:***:*. *.* *:*.:.:*.** *** .** ***:*. *:::*

EGVS (1)    CYIKENHVTKHEAYDEFQKQIDNAWKDLNKEALRPFPVPMTFITRVVHFTRAIHVIYADF 540
RCDCS (22)  CYMKQNGVSEEATRDEFNKQIVDAWKDINEEHLQPNYVPMPFRTRVVNSARIMDYLYKD- 527
            **:*:* *::. : ***:*** :****:*:* *:*  ***.* ****: :* :. :* *

EGVS (1)    SDGYTRSDKAIRGYITSLLVDPIPL 565
RCDCS (22)  DDEYTHVGELMKGSVAALLIDPA-- 550
            .* **: .: ::* :::**:**
```

FIGURE 5E

```
EGVS (1)    MSLNVLSTSGSAPTTKSSEITRRSANYHPSLWGDKFLEYSSPDHLKNDSFTEKKHEQLKE 60
CDCS (23)   MSLEVSASPAKVIQNAGKDSTRRSANYHPSIWGDHFLQYTC-DTQETDDGSNVKHLELKK 59
            ***:* ::....  . ..: **********:***:**:*:. *  :.*. :: ** :**:

EGVS (1)    EVKKMLVETVQKPQQQLNLINEIQRLGLSYLFEPEIEAALQEIS-VTYDEFCCSTDADDL 119
CDCS (23)   EIRRMLKADN-KPSRTLQLIDAIQRLGVSYHFESEIDEILGKMHKASQDSDLCDNENDEL 118
            *:::**      **.: *:**: *****:** **.**:  * ::   .: *.  *..: *:*

EGVS (1)    HNVALSFRILREHGHNVSSDVFQKFMDSNGKLKDYLVNDARGLLSLYEATHFRVHNDDKL 179
CDCS (23)   YYISLHFRLLRQNGYKISADVFKKFKDTDGNFKTSLAKDVRGMLSLYEATHLGVHEEDIL 178
            : ::* **:**::*:::*:***:** *::*::*  *.:*.**:********: **::* *

EGVS (1)    EELLSVTTSRLEHLKSH-VKYPLEDEISRALKHPLHKELNRLGARYYISIYEKFDSHNKL 238
CDCS (23)   DEALAFTTSHLESIATHQIRSPLVEQVKHALVQPIHRGFQRLEARQYIPIYQEESPHNEA 238
            :* *:.***:** : :* :: ** :::.:** :*:*: ::** ** **.**:: ..**:

EGVS (1)    LLEFAKLDFNRLQKMYQHELAHLTRWWKDLDFTNKLPFARDRIVEGYFWILGMYFEPERK 298
CDCS (23)   LLTFAKLDFNKLQKPHQKELGDISRWWKELDFAHKLPFIRDRVAECYFWILGVYFEPQYS 298
            ** *******:*** :*:**..::****:***::**** ***:.* ******:****: .

EGVS (1)    DVREFLNRVFALITVVDDTYDVYGTFKELLLFTDAIERWGTSDLDQLPGYMRIIYQALMD 358
CDCS (23)   FARRILTKVISMTSVIDDIYDVYGKIEELELFTSAIERWDISAIDQLPEYMKLCYRALLD 358
             .*.:*.:*::: :*:** *****.::** ***.*****. * :**** **:: *:**:*

EGVS (1)    VYNQMEEKLSMKADCPTYRLEFAIETVKAMFRSYLEEARWSKEHYIPSMEEYMTVALVSV 418
CDCS (23)   VFSEAEKDLAPQGKS--YRLYYAKEAMKNMVKNYFYEAKWCLQNYVPTVDEYMTVALVTS 416
            *:.: *:.*: :...   *** :* *::* *.:.*: **:*. ::*:*:::********:

EGVS (1)    GYKTILTNSFVGMGDIATREVFEWVFNSPLIIRASDLIARLGDDIGGHEEEQKKGDAATA 478
CDCS (23)   GSPMLSTTSFVGMGDIVTKESFEWLFSNPRFIRASSIVCRLMDDIVSHKFEQSRGHVASS 476
            *   : *.********.*:* ***:*..* :****.::.** *** .*: **.:*..*::

EGVS (1)    IECYIKENHVTKHEAYDEFQKQIDNAWKDLNKEALRPFPVPMTFITRVVHFTRAIHVIYA 538
CDCS (23)   VECYMKQHGATEEEACNEFRKQVSNAWKDINEDCLRPTVVPMPLLMRILNLTRVIDVIYK 536
            :***:*:: .*:.** :**:**:.*****:*::.***  ***.:: *::::**.*.***

EGVS (1)    DFSDGYTRSDKAIRGYITSLLVDPIPL 565
CDCS (23)   -YEDGYTHSAVVLKDFVASLFINPVPI 562
             :.****:*  .::.:::**:::*:*:
```

FIGURE 5F

```
EGVS (1)    MSLNVLSTSGSAPTTKSSEITRRSANYHPSLWGDKFLEYSSPDHLKNDSFTEKKHEQLKE 60
TEAS (24)   -------MASAAVANYEEEIVRPVADFSPSLWGDQFLSFSIKNQVAEK--YAKEIEALKE 51
                   :.:* :. ..**.*  *:: ******:**.:*  ::: :.     *: * ***

EGVS (1)    EVKKMLVETVQKPQQQLNLINEIQRLGLSYLFEPEIEAALQEISVTYDEFCCSTDADDLH 120
TEAS (24)   QTRNMLLATGMKLADTLNLIDTIERLGISYHFEKEIDDILDQIYNQ------NSNCNDLC 105
            :.::**: *  *  : ****: *:***:** ** **:  *::*         .::.:**

EGVS (1)    NVALSFRILREHGHNVSSDVFQKFMDSNGKLKDYLVNDARGLLSLYEATHFRVHNDDKLE 180
TEAS (24)   TSALQFRLLRQHGFNISPEIFSKFQDENGKFKESLASDVLGLLNLYEASHVRTHADDILE 165
            . **.**:**:**.*:*.::*.** *.***:*: *..*. ***.****:*.*.* ** **

EGVS (1)    ELLSVTTSRLEHLKSHVKYPLEDEISRALKHPLHKELNRLGARYYIS-IYEKFDSHNKLL 239
TEAS (24)   DALAFSTIHLESAAPHLKSPLREQVTHALEQCLHKGVPRVETRFFISSIYDKEQSKNNVL 225
            : *:.:* :**    .*:* **.:::::**:: *** : *: :*::** **:* :*:*::*

EGVS (1)    LEFAKLDFNRLQKMYQHELAHLTRWWKDLDFTNKLPFARDRIVEGYFWILGMYFEPERKD 299
TEAS (24)   LRFAKLDFNLLQMLHKQELAQVSRWWKDLDFVTTLPYARDRVVECYFWALGVYFEPQYSQ 285
            *.******* ** ::::***::********...**:****:** *** **:****: .:

EGVS (1)    VREFLNRVFALITVVDDTYDVYGTFKELLLFTDAIERWGTSDLDQLPGYMRIIYQALMDV 359
TEAS (24)   ARVMLVKTISMISIVDDTFDAYGTVKELEAYTDAIQRWDINEIDRLPDYMKISYKAILDL 345
            .* :* :.:::*::****:*.***.***   :****:**. .::*:**.**:* *:*::*:

EGVS (1)    YNQMEEKLSMKADCPTYRLEFAIETVKAMFRSYLEEARWSKEHYIPSMEEYMTVALVSVG 419
TEAS (24)   YKDYEKELSSAG--RSHIVCHAIERMKEVVRNYNVESTWFIEGYTPPVSEYLSNALATTT 403
            *:: *::**   .    :: : .*** :* :.*.*  *: *  * * *.:.**:: **.:.

EGVS (1)    YKTILTNSFVGMGDIATREVFEWVFNSPLIIRASDLIARLGDDIGGHEEEQKKGDAATAI 479
TEAS (24)   YYYLATTSYLGM-KSATEQDFEWLSKNPKILEASVIICRVIDDTATYEVEKSRGQIATGI 462
            *  : *.*::** . **.: ***: :.* *:.** :*.*: **  . :* *:.:*: **.*

EGVS (1)    ECYIKENHVTKHEAYDEFQKQIDNAWKDLNKEALRPFPVPMTFITRVVHFTRAIHVIYAD 539
TEAS (24)   ECCMRDYGISTKEAMAKFQNMAETAWKDINEGLLRPTPVSTEFLTPILNLARIVEVTYIH 522
            ** :::  ::.:**  :**:  :.****:*:  *** **.  *:* ::::* :.* * .

EGVS (1)    FSDGYTRSDKAIRGYITSLLVDPIPL 565
TEAS (24)   NLDGYTHPEKVLKPHIINLLVDSIKI 548
              ****:.:*.:: :* .****.* :
```

FIGURE 5G

```
EGVS (1)    MSLNVLSTSGSAPTTKSSEITRRSANYHPSLWGDKFLEYSSPDHLKNDSFTEKKHEQLKE 60
HPS (25)    ---------------VDNQVAEKYA---------------------------QEIETLKE 18
                           ..::::.: *                           :: * ***

EGVS (1)    EVKKMLVETVQKPQ-QQLNLINEIQRLGLSYLFEPEIEAALQEISVTYDEFCCSTDADDL 119
HPS (25)    QTSTMLSAACGTTLTEKLNLIDIIERLGIAYHFEKQIEDMLDHIYR-ADPYFEAHEYNDL 77
            :...**  :  ..  ::****: *:***::* ** :**  *:.*    * :  : : :**

EGVS (1)    HNVALSFRILREHGHNVSSDVFQKFMDSNGKLKDYLVNDARGLLSLYEATHFRVHNDDKL 179
HPS (25)    NTSSVQFRLLRQHGYNVSPNIFSRFQDANGKFKESLRSDIRGLLNLYEASHVRTHKEDIL 137
            :. ::.**:**:**:***.::*.:* *:***:*: * .* ****.****:*.*.*::* *

EGVS (1)    EELLSVTTSRLEHLKSHVKYPLEDEISRALKHPLHKELNRLGARYYISIYEKFDSHNKLL 239
HPS (25)    EEALVFSVGHLESAAPHLKSPLSKQVTHALEQSLHKSIPRVEIRYFISIYEEEEFKNDLL 197
            ** * .:..:**   .*:* **..::::**::.***.: *:  **:*****: : :*.**

EGVS (1)    LEFAKLDFNRLQKMYQHELAHLTRWWKDLDFTNKLPFARDRIVEGYFWILGMYFEPERKD 299
HPS (25)    LRFAKLDYNLLQMLHKHELSEVSRWWKDLDFVTTLPYARDRAVECYFWTMGVYAEPQYSQ 257
            *.*****:* ** :::***:.::********...**:**** ** *** :*:* **: .:

EGVS (1)    VREFLNRVFALITVVDDTYDVYGTFKELLLFTDAIERWGTSDLDQLPGYMRIIYQALMDV 359
HPS (25)    ARVMLAKTIAMISIVDDTFDAYGIVKELEVYTDAIQRWDISQIDRLPEYMKISYKALLDL 317
            .* :* :.:*:*::****:*.** .*** ::****:**. *::*:** **:* *:**:*:

EGVS (1)    YNQMEEKLSMKADCPTYRLEFAIETVKAMFRSYLEEARWSKEHYIPSMEEYMTVALVSVG 419
HPS (25)    YDDYEKELSK--DGRSDVVHYAKERMKEIVGNYFIEGKWFIEGYMPSVSEYLSNALATST 375
            *:: *::**   *  :  :.:* * :* :. .*: *.:*  * *:**:.**:: **.:

EGVS (1)    YKTILTNSFVGMGDIATREVFEWVFNSPLIIRASDLIARLGDDIGGHEEEQKKGDAATAI 479
HPS (25)    YYLLTTTSYLGM-KSATKEHFEWLATNPKILEANATLCRVVDDIATYEVEKGRGQIATGI 434
            *  : *.*::** . **:* ***: ..* *:.*.  :.*: ***. :* *: :*: **.*

EGVS (1)    ECYIKENHVTKHEAYDEFQKQIDNAWKDLNKEALRPFPVPMTFITRVVHFTRAIHVIYAD 539
HPS (25)    ECYMRDYGVSTEVAMEKFQEMADIAWKDVNEEILRPTPVSSEILTRILNLARIIDVTYKH 494
            ***:::  *:.. * ::**:  * ****:*:* *** **.  ::**::::* *.* * .

EGVS (1)    FSDGYTRSDKAIRGYITSLLVDPIPL 565
HPS (25)    NQDGYTHPEKVLKPHIIALVVDSIDI 520
             .****:.:*.:: :* :*:**.* :
```

FIGURE 5H

```
EGVS (1)    MSLNVLSTSGSAPTTKSSEITRRSANYHPSLWGDKFLEYSSPDHLKNDSFTEKKHEQLKE 60
CGDS (45)   -----MSVEG-------------SANFHPSIWGDHFLQYTRDFQETGD--RSVKHLELKK 40
                 :*..*             ***:***:***:**:*:   : ..*   . ** :**:

EGVS (1)    EVKKMLVETVQKPQQQLNLINEIQRLGLSYLFEPEIEAALQEISVTY-DEFCCSTDADDL 119
CGDS (45)   EIRRMLKA-VNKTSHTLELIDAIQRLGVSYHFESEIDEILGKMHKTYRDCDLCDNENDEL 99
            *:::**   *:*..: *:**: *****:** **.**:  * ::  ** *   *..: *:*

EGVS (1)    HNVALSFRILREHGHNVSSDVFQKFMDSNGKLKDYLVNDARGLLSLYEATHFRVHNDDKL 179
CGDS (45)   YYISLQFRLFRQNGYRISADVFNTFKGSDGKFKASLAKDVRGMLSLYEATHLRVHGENIL 159
            : ::*.**::*::*:.:*:***:.* .*:**:*  *.:*.**:********:***.:: *

EGVS (1)    EELLSVTTSRLEHLKSHVKYPLEDEISRALKHPLHKELNRLGARYYISIYEKFDSHNKLL 239
CGDS (45)   DEALAFTTSHLESVAKQVCSPLVEQVKHALVQPIHKGLERLEARHYIPIYQGESSHNEAL 219
            :* *:.***:** : .:*  ** :::.:** :*:** *:** **:**.**:  .***: *

EGVS (1)    LEFAKLDFNRLQKMYQHELAHLTRWWKDLDFTNKLPFARDRIVEGYFWILGMYFEPERKD 299
CGDS (45)   LTFAKLGFNGLQKLHQKELGDISRWWKELDFAHKLPFVRDRIAEVYFWAVGVHFEPQYSF 279
            * ****.** ***::*:**..::****:***::****.****.* *** :*::***: .

EGVS (1)    VREFLNRVFALITVVDDTYDVYGTFKELLLFTDAIERWGTSDLDQLPGYMRIIYQALMDV 359
CGDS (45)   TRKLFTKVIYMTSIIDDIYDVYGKIEELDLFTSAIERWDINAIDQLPEYMKLCIRALINV 339
            .*:::.:*: : :::** *****.::** ***.*****. . :**** **::  :**::*

EGVS (1)    YNQMEEKLSMKADCPTYRLEFAIETVKAMFRSYLEEARWSKEHYIPSMEEYMTVALVSVG 419
CGDS (45)   YSEVEKDLVSQG--KLYRLHYAKEAMKNQVKHYFFEAKWCHQNYVPTVDEYMTVALISSG 397
            *.::*:.*  :.    ***.:* *::*  .: *: **:*.:::*:*:::*******:* *

EGVS (1)    YKTILTNSFVGMGDIATREVFEWVFNSPLIIRASDLIARLGDDIGGHEEEQKKGDAATAI 479
CGDS (45)   HPNLSTISFVGLGDIVTKESFEWLFSNPRSIRASCAVGRLMNDMVSHKFEQSRGHVASSV 457
            : .: * ****:***.*:* ***:*..*  ****  :.** :*: .*: **.:*..*:::

EGVS (1)    ECYIKENHVTKHEAYDEFQKQIDNAWKDLNKEALRPFPVPMTFITRVVHFTRAIHVIYAD 539
CGDS (45)   ECYINQYGATEEEAYSEFRKQVSNAWKDINEECLRPTVVPVPLLMRILNLTRAADVIYK- 516
            ****::  .*:.***.**:**:.*****:*:*.***  **:.:: *::::*** .***

EGVS (1)    FSDGYTRSDKAIRGYITSLLVDPIPL 565
CGDS (45)   YKDGYTYS-EELKDFIVSLLINPVPI 541
            :.**** * : ::.:*.***::*:*:
```

FIGURE 5I

```
V277 (31)    MSTQVSASSLAQIPQPKNRPVANFHPNIWGDQFITYTPEDK-VTRACKEEQIEALKEEVR 59
CVS  (14)    MSSGE-----------TFRPTADFHPSLWRNHFLKGASDFKTVDHTATQERHEALKEEVR 49
             **:             . **.*:***.:* ::*:. :.: * * ::..:*: ********

V277 (31)    RMILATGRKPIQKLRLIDEVQRLGVAYHFEKEIEDMLDHIYRADPYFEAHEYNDLHTVSL 119
CVS  (14)    RMITDAEDKPVQKLRLIDEVQRLGVAYHFEKEIEDAIQKLC---PIYIDSNRADLHTVSL 106
             ***  :  **:************************ ::::    * :  . :  *******

V277 (31)    HFRLLRQQGIKISCDVFEQFKDDEGRFKSSLINDVQGMLSLYEAAYMAVRGEHILDEAIA 179
CVS  (14)    HFRLLRQQGIKISCDVFEKFKDDEGRFKSSLINDVQGMLSLYEAAYMAVRGEHILDEAIA 166
             ******************:*****************************************

V277 (31)    FTTTHLQS--AAPHLKSPLAEQINHALYRPLRKTLPRLEARYIMSVY--QDEAFHNKTLL 235
CVS  (14)    FTTTHLKSLVAQDHVTPKLAEQINHALYRPLRKTLPRLEARYFMSMINSTSDHLYNKTLL 226
             ******:*  *  *:.. ************************:**:  . .: ::*****

V277 (31)    NFAKLDFNILLDLHKEELNELTKWWQDLDFTTKLPYARDRLVELYFWDLGTYFESQYAFG 295
CVS  (14)    NFAKLDFNILLELHKEELNELTKWWKDLDFTTKLPYARDRLVELYFWDLGTYFEPQYAFG 286
             ***********:*************:****************************.*****

V277 (31)    RKIMTKLNYILSIIDDTYDAYGTLEECTMFSEAVARWNIEAVDMLPDYMRIIYRTLLDTF 355
CVS  (14)    RKIMTQLNYILSIIDDTYDAYGTLEELSLFTEAVQRWNIEAVDMLPEYMKLIYRTLLDAF 346
             *****:******************** ::*:*** ***********:**::*******:*

V277 (31)    NEIEEDMAKQRRSHCVRYAKEEIQKVIGAYYVQAKWFSEGYVPTIEEYMPIALTSCAYRF 415
CVS  (14)    NEIEEDMAKQGRSHCVRYAKEENQKVIGAYSVQAKWFSEGYVPTIEEYMPIALTSCAYTF 406
             ********** *********** ******* *************************** *

V277 (31)    VITNSFLGMGDFATKEVFEWISGNPKVVKSASVICRLMDDMQGHEFEQKRGHVASAIECY 475
CVS  (14)    VITNSFLGMGDFATKEVFEWISNNPKVVKAASVICRLMDDMQGHEFEQKRGHVASAIECY 466
             **********************.******:******************************

V277 (31)    TKQHGVSKEEAIKMFEEDVANAWKDINEELMMKPPVVARPLLGTILNLARAIDFIYKEDD 535
CVS  (14)    TKQHGVSKEEAIKMFEEEVANAWKDINEELMMKPTVVARPLLGTILNLARAIDFIYKEDD 526
             *****************:****************.*************************

V277 (31)    GYTHSYLIKEQIASVLGDHVPF 557
CVS  (14)    GYTHSYLIKDQIASVLGDHVPF 548
             *********:************
```

FIGURE 5J

SEQUENCE LISTING

<160> NUMBER OF SEQ ID NOS: 45

<210> SEQ ID NO 1
<211> LENGTH: 565
<212> TYPE: PRT
<213> ORGANISM: Eryngium glaciale
<220> FEATURE:
<223> OTHER INFORMATION: valencene synthase protein

<400> SEQUENCE: 1

Met Ser Leu Asn Val Leu Ser Thr Ser Gly Ser Ala Pro Thr Thr Lys
1               5                   10                  15

Ser Ser Glu Ile Thr Arg Arg Ser Ala Asn Tyr His Pro Ser Leu Trp
            20                  25                  30

Gly Asp Lys Phe Leu Glu Tyr Ser Ser Pro Asp His Leu Lys Asn Asp
        35                  40                  45

-continued

```
Ser Phe Thr Glu Lys Lys His Glu Gln Leu Lys Glu Glu Val Lys Lys
    50                  55                  60

Met Leu Val Glu Thr Val Gln Lys Pro Gln Gln Gln Leu Asn Leu Ile
65                  70                  75                  80

Asn Glu Ile Gln Arg Leu Gly Leu Ser Tyr Leu Phe Glu Pro Glu Ile
                85                  90                  95

Glu Ala Ala Leu Gln Glu Ile Ser Val Thr Tyr Asp Glu Phe Cys Cys
            100                 105                 110

Ser Thr Asp Ala Asp Asp Leu His Asn Val Ala Leu Ser Phe Arg Ile
        115                 120                 125

Leu Arg Glu His Gly His Asn Val Ser Ser Asp Val Phe Gln Lys Phe
    130                 135                 140

Met Asp Ser Asn Gly Lys Leu Lys Asp Tyr Leu Val Asn Asp Ala Arg
145                 150                 155                 160

Gly Leu Leu Ser Leu Tyr Glu Ala Thr His Phe Arg Val His Asn Asp
                165                 170                 175

Asp Lys Leu Glu Glu Leu Leu Ser Val Thr Thr Ser Arg Leu Glu His
            180                 185                 190

Leu Lys Ser His Val Lys Tyr Pro Leu Glu Asp Glu Ile Ser Arg Ala
        195                 200                 205

Leu Lys His Pro Leu His Lys Glu Leu Asn Arg Leu Gly Ala Arg Tyr
    210                 215                 220

Tyr Ile Ser Ile Tyr Glu Lys Phe Asp Ser His Asn Lys Leu Leu Leu
225                 230                 235                 240

Glu Phe Ala Lys Leu Asp Phe Asn Arg Leu Gln Lys Met Tyr Gln His
                245                 250                 255

Glu Leu Ala His Leu Thr Arg Trp Trp Lys Asp Leu Asp Phe Thr Asn
            260                 265                 270

Lys Leu Pro Phe Ala Arg Asp Arg Ile Val Glu Gly Tyr Phe Trp Ile
        275                 280                 285

Leu Gly Met Tyr Phe Glu Pro Glu Arg Lys Asp Val Arg Glu Phe Leu
    290                 295                 300

Asn Arg Val Phe Ala Leu Ile Thr Val Val Asp Asp Thr Tyr Asp Val
305                 310                 315                 320

Tyr Gly Thr Phe Lys Glu Leu Leu Leu Phe Thr Asp Ala Ile Glu Arg
                325                 330                 335

Trp Gly Thr Ser Asp Leu Asp Gln Leu Pro Gly Tyr Met Arg Ile Ile
            340                 345                 350

Tyr Gln Ala Leu Met Asp Val Tyr Asn Gln Met Glu Glu Lys Leu Ser
        355                 360                 365

Met Lys Ala Asp Cys Pro Thr Tyr Arg Leu Glu Phe Ala Ile Glu Thr
    370                 375                 380

Val Lys Ala Met Phe Arg Ser Tyr Leu Glu Glu Ala Arg Trp Ser Lys
385                 390                 395                 400

Glu His Tyr Ile Pro Ser Met Glu Glu Tyr Met Thr Val Ala Leu Val
                405                 410                 415

Ser Val Gly Tyr Lys Thr Ile Leu Thr Asn Ser Phe Val Gly Met Gly
            420                 425                 430

Asp Ile Ala Thr Arg Glu Val Phe Glu Trp Val Phe Asn Ser Pro Leu
        435                 440                 445

Ile Ile Arg Ala Ser Asp Leu Ile Ala Arg Leu Gly Asp Asp Ile Gly
    450                 455                 460
```

-continued

Gly His Glu Glu Glu Gln Lys Lys Gly Asp Ala Ala Thr Ala Ile Glu
465 470 475 480

Cys Tyr Ile Lys Glu Asn His Val Thr Lys His Glu Ala Tyr Asp Glu
485 490 495

Phe Gln Lys Gln Ile Asp Asn Ala Trp Lys Asp Leu Asn Lys Glu Ala
500 505 510

Leu Arg Pro Phe Pro Val Pro Met Thr Phe Ile Thr Arg Val Val His
515 520 525

Phe Thr Arg Ala Ile His Val Ile Tyr Ala Asp Phe Ser Asp Gly Tyr
530 535 540

Thr Arg Ser Asp Lys Ala Ile Arg Gly Tyr Ile Thr Ser Leu Leu Val
545 550 555 560

Asp Pro Ile Pro Leu
565

<210> SEQ ID NO 2
<211> LENGTH: 1698
<212> TYPE: DNA
<213> ORGANISM: Eryngium glaciale
<220> FEATURE:
<223> OTHER INFORMATION: Valencene synthase DNA WT

<400> SEQUENCE: 2
atgtctctta atgtacttag tacgtcaggt tcagctccaa caaccaaatc atctgagatt 60
actcgtaggt ccgctaatta tcatcctagt ttatggggag acaagttcct cgaatattcg 120
agcccagatc acctgaaaaa tgattcattc acagaaaaga aacatgaaca actcaaagaa 180
gaggtgaaga agatgctagt agaaacggtt caaaagcctc aacaacagct gaatctgatc 240
aacgaaatac aacgactagg tttatcatac ctttttgaac ccgaaattga ggctgcattg 300
caggaaatca gtgttaccta tgatgaattt tgttgtagta cagacgctga tgaccttcac 360
aatgttgctc tctctttccg aatacttaga gaacatggac ataatgtatc ttctgatgtg 420
tttcagaaat tcatggatag caatgggaag ttgaaagact acttggttaa tgatgctaga 480
ggactgttaa gcttgtacga agcaacacat tttcgggttc ataatgatga taaacttgaa 540
gagttgctgt cagtaacaac ctctcgtctt gagcatctca aatcccacgt gaagtaccct 600
cttgaggacg aaatcagtag agcacttaag catcccctcc ataaagaact aaatcgacta 660
ggagcgagat attacatatc catttacgaa aaatttgatt cacacaataa attgcttttg 720
gagtttgcaa aactagattt taaccgactg cagaaaatgt atcaacatga gctagcccac 780
cttacaaggt ggtggaaaga tttagatttt acaaacaaac ttccatttgc aagagataga 840
attgttgagg gttacttttg gatcttagga atgtactttg agccagaacg taaggatgtc 900
agggaattct tgaacagagt atttgcactt attacagtag ttgatgacac gtatgatgtg 960
tatggtacct tcaaagaact tctactgttc actgatgcaa ttgaaagatg gggaactagt 1020
gatttggatc agctaccggg atatatgaga attatttatc aagctctcat ggatgtttat 1080
aatcaaatgg aggaaaagtt gtcaatgaaa gctgattgtc caacataccg tcttgagttt 1140
gcaatagaaa cagttaaagc catgttcaga tcatacctcg aagaagctag atggtccaaa 1200
gaacattata tcccatcgat ggaagagtat atgaccgtgg cactggtatc ggttggctac 1260
aaaaccatat taactaattc ctttgttgga atgggggata ttgcaacacg ggaagttttt 1320
gagtgggtgt tcaatagtcc attgattatt agagcttccg acttaattgc cagattggga 1380
gatgatattg gaggccatga ggaggagcag aagaaaggag acgcagccac tgctatcgag 1440

-continued tgttacataa aagagaatca tgtaacaaag catgaagctt atgatgaatt tcagaaacaa 1500
attgataatg cttggaagga tttgaataag gaagctctac gtccatttcc tgttccaatg 1560
actttcatca caagagttgt tcattttacg cgcgccatac atgttattta tgccgacttt 1620
agtgatggtt acacacgttc agacaaggcg atcagaggtt acataacttc actgctcgtg 1680
gatcctattc ctttgtaa 1698

<210> SEQ ID NO 3
<211> LENGTH: 1698
<212> TYPE: DNA
<213> ORGANISM: Eryngium glaciale
<220> FEATURE:
<223> OTHER INFORMATION: Valencene synthase DNA c969a

<400> SEQUENCE: 3
atgtctctta atgtacttag tacgtcaggt tcagctccaa caaccaaatc atctgagatt 60
actcgtaggt ccgctaatta tcatcctagt ttatggggag acaagttcct cgaatattcg 120
agcccagatc acctgaaaaa tgattcattc acagaaaaga aacatgaaca actcaaagaa 180
gaggtgaaga agatgctagt agaaacggtt caaaagcctc aacaacagct gaatctgatc 240
aacgaaatac aacgactagg tttatcatac ctttttgaac ccgaaattga ggctgcattg 300
caggaaatca gtgttaccta tgatgaattt tgttgtagta cagacgctga tgaccttcac 360
aatgttgctc tctctttccg aatacttaga gaacatggac ataatgtatc ttctgatgtg 420
tttcagaaat tcatggatag caatgggaag ttgaaagact acttggttaa tgatgctaga 480
ggactgttaa gcttgtacga agcaacacat tttcgggttc ataatgatga taaacttgaa 540
gagttgctgt cagtaacaac ctctcgtctt gagcatctca aatcccacgt gaagtaccct 600
cttgaggacg aaatcagtag agcacttaag catcccctcc ataaagaact aaatcgacta 660
ggagcgagat attacatatc catttacgaa aaatttgatt cacacaataa attgcttttg 720
gagtttgcaa aactagattt taaccgactg cagaaaatgt atcaacatga gctagcccac 780
cttacaaggt ggtggaaaga tttagatttt acaaacaaac ttccatttgc aagagataga 840
attgttgagg gttacttttg gatcttagga atgtactttg agccagaacg taaggatgtc 900
agggaattct tgaacagagt atttgcactt attacagtag ttgatgacac gtatgatgtg 960
tatggtacat tcaaagaact tctactgttc actgatgcaa ttgaaagatg ggaactagt 1020 gatttggatc agctaccggg atatatgaga attatttatc aagctctcat ggatgtttat 1080
aatcaaatgg aggaaaagtt gtcaatgaaa gctgattgtc caacataccg tcttgagttt 1140
gcaatagaaa cagttaaagc catgttcaga tcatacctcg aagaagctag atggtccaaa 1200
gaacattata tcccatcgat ggaagagtat atgaccgtgg cactggtatc ggttggctac 1260
aaaaccatat taactaattc ctttgttgga atgggggata ttgcaacacg ggaagttttt 1320
gagtgggtgt tcaatagtcc attgattatt agagcttccg acttaattgc cagattggga 1380
gatgatattg gaggccatga ggaggagcag aagaaaggag acgcagccac tgctatcgag 1440
tgttacataa aagagaatca tgtaacaaag catgaagctt atgatgaatt tcagaaacaa 1500
attgataatg cttggaagga tttgaataag gaagctctac gtccatttcc tgttccaatg 1560
actttcatca caagagttgt tcattttacg cgcgccatac atgttattta tgccgacttt 1620
agtgatggtt acacacgttc agacaaggcg atcagaggtt acataacttc actgctcgtg 1680
gatcctattc ctttgtaa 1698

-continued

<210> SEQ ID NO 4
<211> LENGTH: 847
<212> TYPE: DNA
<213> ORGANISM: Eryngium glaciale
<220> FEATURE:
<223> OTHER INFORMATION: contig sequence containing partial EGVS

<400> SEQUENCE: 4

```
tgtaataagt gcaaatactc tgttcaagaa ttccctgaca tccttacgtt ctggctcaaa     60

gtacattcct aagatccaaa agtaaccctc aacaattcta tctcttgcaa atggaagttt    120

gtttgtaaaa tctaaatctt tccaccacct tgtaaggtgg gctagctcat gttgatacat    180

tttctgcagt cggttaaaat ctagttttgc aaactccaaa agcaatttat tgtgtgaatc    240

aaatttttcg taaatggata tgtaatatct cgctcctagt cgatttagtt ctttatggag    300

gggatgctta agtgctctac tgatttcgtc ctcaagaggg tacttcacgt gggatttgag    360

atgctcaaga cgagaggttg ttactgacag caactcttca agtttatcat cattatgaac    420

ccgaaaatgt gttgcttcgt acaagcttaa cagtcctcta gcatcattaa ccaagtagtc    480

tttcaacttc ccattgctat ccatgaattt ctgaaacaca tcagaagata cattatgtcc    540

atgttctcta agtattcgga aagagagagc aacattgtga aggtcatcag cgtctgtact    600

acaacaaaat tcatcatagg taacactgat ttcctgcaat gcagcctcaa tttcgggttc    660

aaaaaggtat gataaaccta gtcgttgtat ttcgttgatc agattcagct gttgttgagg    720

cttttgaacc gtttctacta gcatcttctt cacctcttct ttgagttgtt catgtttctt    780

ttctgtgaat gaatcatttt tcaggtgatc tgggctcgaa tattcgagga acttgtctcc    840

ccataaa                                                              847
```

<210> SEQ ID NO 5
<211> LENGTH: 32
<212> TYPE: DNA
<213> ORGANISM: Artificial Sequence
<220> FEATURE:
<223> OTHER INFORMATION: 63-1-2-Fwd2 RACE primer

<400> SEQUENCE: 5

```
gctagctcat gttgatacat tttctgcagt cg                                   32
```

<210> SEQ ID NO 6
<211> LENGTH: 29
<212> TYPE: DNA
<213> ORGANISM: Artificial Sequence
<220> FEATURE:
<223> OTHER INFORMATION: 63-1-2-Rev2 RACE primer

<400> SEQUENCE: 6

```
gctgtcagta acaacctctc gtcttgagc                                       29
```

<210> SEQ ID NO 7
<211> LENGTH: 33
<212> TYPE: DNA
<213> ORGANISM: Artificial Sequence
<220> FEATURE:
<223> OTHER INFORMATION: 63-1-2-NestFwd2 RACE primer

<400> SEQUENCE: 7

```
cggttaaaat ctagttttgc aaactccaaa agc                                  33
```

<210> SEQ ID NO 8
<211> LENGTH: 27
<212> TYPE: DNA

<213> ORGANISM: Artificial Sequence
<220> FEATURE:
<223> OTHER INFORMATION: 63-1-2-NestRev2 RACE primer

<400> SEQUENCE: 8
cccacgtgaa gtaccctctt gaggacg 27

<210> SEQ ID NO 9
<211> LENGTH: 60
<212> TYPE: DNA
<213> ORGANISM: Artificial Sequence
<220> FEATURE:
<223> OTHER INFORMATION: 63-52-EG2FwdPart1 Gibson assembly primer

<400> SEQUENCE: 9
gctgaattcg agctcggtac cattaaaaaa aatgtctctt aatgtactta gtacgtcagg 60

<210> SEQ ID NO 10
<211> LENGTH: 33
<212> TYPE: DNA
<213> ORGANISM: Artificial Sequence
<220> FEATURE:
<223> OTHER INFORMATION: 63-52-EG2RevPart1 Gibson assembly primer

<400> SEQUENCE: 10
gaagttcttt gaatgtacca tacacatcat acg 33

<210> SEQ ID NO 11
<211> LENGTH: 40
<212> TYPE: DNA
<213> ORGANISM: Artificial Sequence
<220> FEATURE:
<223> OTHER INFORMATION: 63-52-EG2FwdPart2 Gibson assembly primer

<400> SEQUENCE: 11
gatgtgtatg gtacattcaa agaacttcta ctgttcactg 40

<210> SEQ ID NO 12
<211> LENGTH: 56
<212> TYPE: DNA
<213> ORGANISM: Artificial Sequence
<220> FEATURE:
<223> OTHER INFORMATION: 63-52-EG2RevPart2

<400> SEQUENCE: 12
tacgcgcaca aaagcagaga ttctagatta caaaggaata ggatccacga gcagtg 56

<210> SEQ ID NO 13
<211> LENGTH: 1647
<212> TYPE: DNA
<213> ORGANISM: Citrus sinensis
<220> FEATURE:
<223> OTHER INFORMATION: Citrus valencene synthase DNA
<300> PUBLICATION INFORMATION:
<308> DATABASE ACCESSION NUMBER: GenBank GQ988384.1
<309> DATABASE ENTRY DATE: 2009-10-20

<400> SEQUENCE: 13
atgtcgtctg gagaaacatt tcgtcctact gcagatttcc atcctagttt atggagaaac 60
catttcctca aaggtgcttc tgatttcaag acagttgatc atactgcaac tcaagaacga 120
cacgaggcac tgaaagaaga ggtaaggaga atgataacag atgctgaaga taagcctgtt 180
cagaagttac gcttgattga tgaagtacaa cgcctggggg tggcttatca ctttgagaaa 240
gaaatagaag atgcaataca aaaattatgt ccaatctata ttgacagtaa tagagctgat 300

-continued

```
ctccacaccg tttcccttca ttttcgattg cttaggcagc aaggaatcaa gatttcatgt    360

gatgtgtttg agaagttcaa agatgatgag ggtagattca agtcatcgtt gataaacgat    420

gttcaaggga tgttaagttt gtacgaggca gcatacatgg cagttcgcgg agaacatata    480

ttagatgaag ccattgcttt cactaccact cacctgaagt cattggtagc tcaggatcat    540

gtaaccccta agcttgcgga acagataaat catgctttat accgtcctct tcgtaaaacc    600

ctaccaagat tagaggcgag gtattttatg tccatgatca attcaacaag tgatcattta    660

tacaataaaa ctctgctgaa ttttgcaaag ttagatttta acatattgct agagctgcac    720

aaggaggaac tcaatgaatt aacaaagtgg tggaaagatt tagacttcac tacaaaacta    780

ccttatgcaa gagacagatt agtggagtta tatttttggg atttagggac atacttcgag    840

cctcaatatg catttgggag aaagataatg acccaattaa attacatatt atccatcata    900

gatgatactt atgatgcgta tggtacactt gaagaactca gcctctttac tgaagcagtt    960

caaagatgga atattgaggc cgtagatatg cttccagaat acatgaaatt gatttacagg   1020

acactcttag atgcttttaa tgaaattgag gaagatatgg ccaagcaagg aagatcacac   1080

tgcgtacgtt atgcaaaaga ggagaatcaa aaagtaattg gagcatactc tgttcaagcc   1140

aaatggttca gtgaaggtta cgttccaaca attgaggagt atatgcctat tgcactaaca   1200

agttgtgctt acacattcgt cataacaaat tccttccttg gcatgggtga ttttgcaact   1260

aaagaggttt ttgaatggat ctccaataac cctaaggttg taaaagcagc atcagttatc   1320

tgcagactca tggatgacat gcaaggtcat gagtttgagc agaagagagg acatgttgcg   1380

tcagctattg aatgttacac gaagcagcat ggtgtctcta aggaagaggc aattaaaatg   1440

tttgaagaag aagttgcaaa tgcatggaaa gatattaacg aggagttgat gatgaagcca   1500

accgtcgttg cccgaccact gctcgggacg attcttaatc ttgctcgtgc aattgatttt   1560

atttacaaag aggacgacgg ctatacgcat tcttacctaa ttaaagatca aattgcttct   1620

gtgctaggag accacgttcc attttga                                       1647
```

```
<210> SEQ ID NO 14
<211> LENGTH: 548
<212> TYPE: PRT
<213> ORGANISM: Citrus sinensis
<220> FEATURE:
<223> OTHER INFORMATION: Citrus valencene synthase protein

<400> SEQUENCE: 14

Met Ser Ser Gly Glu Thr Phe Arg Pro Thr Ala Asp Phe His Pro Ser
 1               5                  10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60

Leu Ile Asp Glu Val Gln Arg Leu Gly Val Ala Tyr His Phe Glu Lys
65                  70                  75                  80

Glu Ile Glu Asp Ala Ile Gln Lys Leu Cys Pro Ile Tyr Ile Asp Ser
                85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125
```

-continued

```
Asp Glu Gly Arg Phe Lys Ser Ser Leu Ile Asn Asp Val Gln Gly Met
    130                 135                 140

Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
        195                 200                 205

Phe Met Ser Met Ile Asn Ser Thr Ser Asp His Leu Tyr Asn Lys Thr
    210                 215                 220

Leu Leu Asn Phe Ala Lys Leu Asp Phe Asn Ile Leu Leu Glu Leu His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270

Trp Asp Leu Gly Thr Tyr Phe Glu Pro Gln Tyr Ala Phe Gly Arg Lys
        275                 280                 285

Ile Met Thr Gln Leu Asn Tyr Ile Leu Ser Ile Ile Asp Asp Thr Tyr
    290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335

Leu Ile Tyr Arg Thr Leu Leu Asp Ala Phe Asn Glu Ile Glu Glu Asp
            340                 345                 350

Met Ala Lys Gln Gly Arg Ser His Cys Val Arg Tyr Ala Lys Glu Glu
        355                 360                 365

Asn Gln Lys Val Ile Gly Ala Tyr Ser Val Gln Ala Lys Trp Phe Ser
    370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
                405                 410                 415

Asp Phe Ala Thr Lys Glu Val Phe Glu Trp Ile Ser Asn Asn Pro Lys
            420                 425                 430

Val Val Lys Ala Ala Ser Val Ile Cys Arg Leu Met Asp Asp Met Gln
        435                 440                 445

Gly His Glu Phe Glu Gln Lys Arg Gly His Val Ala Ser Ala Ile Glu
    450                 455                 460

Cys Tyr Thr Lys Gln His Gly Val Ser Lys Glu Glu Ala Ile Lys Met
465                 470                 475                 480

Phe Glu Glu Glu Val Ala Asn Ala Trp Lys Asp Ile Asn Glu Glu Leu
                485                 490                 495

Met Met Lys Pro Thr Val Val Ala Arg Pro Leu Leu Gly Thr Ile Leu
            500                 505                 510

Asn Leu Ala Arg Ala Ile Asp Phe Ile Tyr Lys Glu Asp Asp Gly Tyr
        515                 520                 525

Thr His Ser Tyr Leu Ile Lys Asp Gln Ile Ala Ser Val Leu Gly Asp
    530                 535                 540
```

His Val Pro Phe
545

<210> SEQ ID NO 15
<211> LENGTH: 548
<212> TYPE: PRT
<213> ORGANISM: Citrus x paradisi
<220> FEATURE:
<223> OTHER INFORMATION: Citrus valencene synthase protein AAM00426
<300> PUBLICATION INFORMATION:
<308> DATABASE ACCESSION NUMBER: Genbank AAM00426
<309> DATABASE ENTRY DATE: 2002-04-02

<400> SEQUENCE: 15

Met Ser Ser Gly Glu Thr Phe Arg Pro Thr Ala Asp Phe His Pro Ser
1 5 10 15

Leu Trp Arg Asn His Phe Leu Lys Gly Ala Ser Asp Phe Lys Thr Val
20 25 30

Asp His Thr Ala Thr Gln Glu Arg His Glu Ala Leu Lys Glu Glu Val
35 40 45

Arg Arg Met Ile Thr Asp Ala Glu Asp Lys Pro Val Gln Lys Leu Arg
50 55 60

Leu Ile Asp Glu Val Gln Arg Leu Gly Val Ala Tyr His Phe Glu Lys
65 70 75 80

Glu Ile Glu Asp Ala Ile Leu Lys Leu Cys Pro Ile Tyr Ile Asp Ser
85 90 95

Asn Arg Ala Asp Leu His Thr Val Ser Leu His Phe Arg Leu Leu Arg
100 105 110

Gln Gln Gly Ile Lys Ile Ser Cys Asp Val Phe Glu Lys Phe Lys Asp
115 120 125

Asp Glu Gly Arg Phe Lys Ser Ser Leu Ile Asn Asp Val Gln Gly Met
130 135 140

Leu Ser Leu Tyr Glu Ala Ala Tyr Met Ala Val Arg Gly Glu His Ile
145 150 155 160

Leu Asp Glu Ala Ile Ala Phe Thr Thr Thr His Leu Lys Ser Leu Val
165 170 175

Ala Gln Asp His Val Thr Pro Lys Leu Ala Glu Gln Ile Asn His Ala
180 185 190

Leu Tyr Arg Pro Leu Arg Lys Thr Leu Pro Arg Leu Glu Ala Arg Tyr
195 200 205

Phe Met Ser Met Ile Asn Ser Thr Ser Asp His Leu Tyr Asn Lys Thr
210 215 220

Leu Leu Asn Phe Ala Lys Leu Asp Phe Asn Ile Leu Leu Glu Pro His
225 230 235 240

Lys Glu Glu Leu Asn Glu Leu Thr Lys Trp Trp Lys Asp Leu Asp Phe
245 250 255

Thr Thr Lys Leu Pro Tyr Ala Arg Asp Arg Leu Val Glu Leu Tyr Phe
260 265 270

Trp Asp Leu Gly Thr Tyr Phe Glu Pro Gln Tyr Ala Phe Gly Arg Lys
275 280 285

Ile Met Thr Gln Leu Asn Tyr Ile Leu Ser Ile Ile Asp Asp Thr Tyr
290 295 300

Asp Ala Tyr Gly Thr Leu Glu Glu Leu Ser Leu Phe Thr Glu Ala Val
305 310 315 320

Gln Arg Trp Asn Ile Glu Ala Val Asp Met Leu Pro Glu Tyr Met Lys
325 330 335

```
Leu Ile Tyr Arg Thr Leu Leu Asp Ala Phe Asn Glu Ile Glu Glu Asp
            340                 345                 350

Met Ala Lys Gln Gly Arg Ser His Cys Val Arg Tyr Ala Lys Glu Glu
        355                 360                 365

Asn Gln Lys Val Ile Gly Ala Tyr Ser Val Gln Ala Lys Trp Phe Ser
    370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
                405                 410                 415

Asp Phe Ala Thr Lys Glu Val Phe Glu Trp Ile Ser Asn Asn Pro Lys
            420                 425                 430

Val Val Lys Ala Ala Ser Val Ile Cys Arg Leu Met Asp Asp Met Gln
        435                 440                 445

Gly His Glu Phe Glu Gln Lys Arg Gly His Val Ala Ser Ala Ile Glu
    450                 455                 460

Cys Tyr Thr Lys Gln His Gly Val Ser Lys Glu Glu Ala Ile Lys Met
465                 470                 475                 480

Phe Glu Glu Glu Val Ala Asn Ala Trp Lys Asp Ile Asp Glu Glu Leu
                485                 490                 495

Met Met Lys Pro Thr Val Val Ala Arg Pro Leu Leu Gly Thr Ile Leu
            500                 505                 510

Asn Leu Ala Arg Ala Ile Asp Phe Ile Tyr Lys Glu Asp Asp Gly Tyr
        515                 520                 525

Thr His Ser Tyr Leu Ile Lys Asp Gln Ile Ala Ser Val Leu Gly Asp
    530                 535                 540

His Val Pro Phe
545


<210> SEQ ID NO 16
<211> LENGTH: 556
<212> TYPE: PRT
<213> ORGANISM: Vitis vinifera
<220> FEATURE:
<223> OTHER INFORMATION: Valencene Synthase protein
<300> PUBLICATION INFORMATION:
<308> DATABASE ACCESSION NUMBER: Uniprot C1JXK7
<309> DATABASE ENTRY DATE: 2011-09-21

<400> SEQUENCE: 16

Met Ser Thr Gln Val Ser Ala Ser Ser Leu Ala Gln Ile Pro Gln Pro
 1               5                  10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125
```

-continued

```
Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met His Gly Val Tyr Phe
        275                 280                 285

Glu Pro Gln Tyr Leu Arg Gly Arg Arg Ile Leu Thr Lys Val Ile Ala
    290                 295                 300

Met Thr Ser Ile Leu Asp Asp Ile His Asp Ala Tyr Gly Thr Pro Glu
305                 310                 315                 320

Glu Leu Lys Leu Phe Ile Glu Ala Ile Glu Arg Trp Asp Ile Asn Ser
                325                 330                 335

Ile Asn Gln Leu Pro Glu Tyr Met Lys Leu Cys Tyr Val Ala Leu Leu
            340                 345                 350

Asp Val Tyr Lys Glu Ile Glu Glu Glu Met Glu Lys Glu Gly Asn Gln
        355                 360                 365

Tyr Arg Val His Tyr Ala Lys Glu Val Met Lys Asn Gln Val Arg Ala
    370                 375                 380

Tyr Phe Ala Glu Ala Lys Trp Leu His Glu Glu His Val Pro Ala Phe
385                 390                 395                 400

Glu Glu Tyr Met Arg Val Ala Leu Ala Ser Ser Gly Tyr Cys Leu Leu
                405                 410                 415

Ala Thr Thr Ser Phe Val Gly Met Gly Glu Ile Ala Thr Lys Glu Ala
            420                 425                 430

Phe Asp Trp Val Thr Ser Asp Pro Lys Ile Met Ser Ser Ser Asn Phe
        435                 440                 445

Ile Thr Arg Leu Met Asp Asp Ile Lys Ser His Lys Phe Glu Gln Lys
    450                 455                 460

Arg Gly His Val Ala Ser Ala Val Glu Cys Tyr Met Lys Gln Tyr Gly
465                 470                 475                 480

Val Ser Glu Glu Gln Val Tyr Ser Glu Phe Gln Lys Gln Ile Glu Asn
                485                 490                 495

Ala Trp Leu Asp Ile Asn Gln Glu Cys Leu Lys Pro Thr Ala Val Ser
            500                 505                 510

Met Pro Leu Leu Ala Arg Leu Leu Asn Leu Thr Arg Thr Met Asp Val
        515                 520                 525

Ile Tyr Lys Glu Gln Asp Ser Tyr Thr His Val Gly Lys Val Met Arg
    530                 535                 540

Asp Asn Ile Ala Ser Val Phe Ile Asn Ala Val Ile
```

-continued 545 550 555

<210> SEQ ID NO 17
<211> LENGTH: 573
<212> TYPE: PRT
<213> ORGANISM: Chamaecyparis nootkatensis
<220> FEATURE:
<223> OTHER INFORMATION: Valencene synthase protein

<400> SEQUENCE: 17

```
Met Pro Val Lys Asp Ala Leu Arg Arg Thr Gly Asn His His Pro Asn
 1               5                  10                  15

Leu Trp Thr Asp Asp Phe Ile Gln Ser Leu Asn Ser Pro Tyr Ser Asp
            20                  25                  30

Ser Ser Tyr His Lys His Arg Glu Ile Leu Ile Asp Glu Ile Arg Asp
        35                  40                  45

Met Phe Ser Asn Gly Glu Gly Asp Glu Phe Gly Val Leu Glu Asn Ile
    50                  55                  60

Trp Phe Val Asp Val Val Gln Arg Leu Gly Ile Asp Arg His Phe Gln
65                  70                  75                  80

Glu Glu Ile Lys Thr Ala Leu Asp Tyr Ile Tyr Lys Phe Trp Asn His
                85                  90                  95

Asp Ser Ile Phe Gly Asp Leu Asn Met Val Ala Leu Gly Phe Arg Ile
            100                 105                 110

Leu Arg Leu Asn Arg Tyr Val Ala Ser Ser Asp Val Phe Lys Lys Phe
        115                 120                 125

Lys Gly Glu Glu Gly Gln Phe Ser Gly Phe Glu Ser Ser Asp Gln Asp
    130                 135                 140

Ala Lys Leu Glu Met Met Leu Asn Leu Tyr Lys Ala Ser Glu Leu Asp
145                 150                 155                 160

Phe Pro Asp Glu Asp Ile Leu Lys Glu Ala Arg Ala Phe Ala Ser Met
                165                 170                 175

Tyr Leu Lys His Val Ile Lys Glu Tyr Gly Asp Ile Gln Glu Ser Lys
            180                 185                 190

Asn Pro Leu Leu Met Glu Ile Glu Tyr Thr Phe Lys Tyr Pro Trp Arg
        195                 200                 205

Cys Arg Leu Pro Arg Leu Glu Ala Trp Asn Phe Ile His Ile Met Arg
    210                 215                 220

Gln Gln Asp Cys Asn Ile Ser Leu Ala Asn Asn Leu Tyr Lys Ile Pro
225                 230                 235                 240

Lys Ile Tyr Met Lys Lys Ile Leu Glu Leu Ala Ile Leu Asp Phe Asn
                245                 250                 255

Ile Leu Gln Ser Gln His Gln His Glu Met Lys Leu Ile Ser Thr Trp
            260                 265                 270

Trp Lys Asn Ser Ser Ala Ile Gln Leu Asp Phe Phe Arg His Arg His
        275                 280                 285

Ile Glu Ser Tyr Phe Trp Trp Ala Ser Pro Leu Phe Glu Pro Glu Phe
    290                 295                 300

Ser Thr Cys Arg Ile Asn Cys Thr Lys Leu Ser Thr Lys Met Phe Leu
305                 310                 315                 320

Leu Asp Asp Ile Tyr Asp Thr Tyr Gly Thr Val Glu Glu Leu Lys Pro
                325                 330                 335

Phe Thr Thr Thr Leu Thr Arg Trp Asp Val Ser Thr Val Asp Asn His
            340                 345                 350

Pro Asp Tyr Met Lys Ile Ala Phe Asn Phe Ser Tyr Glu Ile Tyr Lys
```

```
        355                 360                 365

Glu Ile Ala Ser Glu Ala Glu Arg Lys His Gly Pro Phe Val Tyr Lys
    370                 375                 380

Tyr Leu Gln Ser Cys Trp Lys Ser Tyr Ile Glu Ala Tyr Met Gln Glu
385                 390                 395                 400

Ala Glu Trp Ile Ala Ser Asn His Ile Pro Gly Phe Asp Glu Tyr Leu
                405                 410                 415

Met Asn Gly Val Lys Ser Ser Gly Met Arg Ile Leu Met Ile His Ala
            420                 425                 430

Leu Ile Leu Met Asp Thr Pro Leu Ser Asp Glu Ile Leu Glu Gln Leu
        435                 440                 445

Asp Ile Pro Ser Ser Lys Ser Gln Ala Leu Leu Ser Leu Ile Thr Arg
    450                 455                 460

Leu Val Asp Asp Val Lys Asp Phe Glu Asp Glu Gln Ala His Gly Glu
465                 470                 475                 480

Met Ala Ser Ser Ile Glu Cys Tyr Met Lys Asp Asn His Gly Ser Thr
                485                 490                 495

Arg Glu Asp Ala Leu Asn Tyr Leu Lys Ile Arg Ile Glu Ser Cys Val
            500                 505                 510

Gln Glu Leu Asn Lys Glu Leu Leu Glu Pro Ser Asn Met His Gly Ser
        515                 520                 525

Phe Arg Asn Leu Tyr Leu Asn Val Gly Met Arg Val Ile Phe Phe Met
    530                 535                 540

Leu Asn Asp Gly Asp Leu Phe Thr His Ser Asn Arg Lys Glu Ile Gln
545                 550                 555                 560

Asp Ala Ile Thr Lys Phe Phe Val Glu Pro Ile Ile Pro
                565                 570


<210> SEQ ID NO 18
<211> LENGTH: 556
<212> TYPE: PRT
<213> ORGANISM: Eleutherococcus trifoliatus
<220> FEATURE:
<223> OTHER INFORMATION: alpha-copaene synthase protein
<300> PUBLICATION INFORMATION:
<308> DATABASE ACCESSION NUMBER: GenBank ADK94034.1
<309> DATABASE ENTRY DATE: 2012-04-01

<400> SEQUENCE: 18

Met Ala Thr Tyr Leu Gln Ala Ser Ser Gly Pro Cys Ser Thr Ile Val
 1               5                  10                  15

Pro Glu Ile Thr Arg Arg Ser Ala Asn Tyr His Pro Asn Ile Trp Gly
            20                  25                  30

Asp Gln Phe Leu Lys Tyr Asn Ser Phe Asp Leu Ser Lys Thr Asp Ala
        35                  40                  45

Asn Thr Lys Glu His Phe Arg Gln Leu Lys Glu Glu Val Lys Lys Met
    50                  55                  60

Leu Val Asp Ala Gly Pro Asn Gln Gln Leu Asn Leu Ile Asp Asp Ile
65                  70                  75                  80

Gln Arg Leu Gly Val Ala Tyr Gln Phe Glu Ala Glu Ile Asp Ala Ala
                85                  90                  95

Leu Gln Arg Met Asn Val Ile Phe Gln Gly Asn Asp Asp Asp Leu His
            100                 105                 110

Thr Ile Ser Leu Arg Phe Arg Leu Leu Arg Gln His Gly Tyr Asn Val
        115                 120                 125

Ser Ser Asp Val Phe Arg Lys Phe Met Asp Asn Asn Gly Lys Phe Lys
```

```
    130                 135                 140

Glu Cys Leu Ile Ser Asp Leu Arg Gly Val Leu Ser Leu Tyr Glu Ala
145                 150                 155                 160

Thr His Phe Arg Val His Gly Glu Asp Ile Leu Glu Asp Ala Leu Glu
                165                 170                 175

Phe Thr Thr Ser His Leu Glu Arg Leu Lys Ser His Leu Lys Asn Pro
            180                 185                 190

Leu Ala Ala Gln Val Ile Arg Ala Leu Lys Cys Pro Ile His Lys Gly
        195                 200                 205

Leu Asn Arg Leu Glu Ala Lys His Tyr Ile Ser Ile Tyr Gln Gln Glu
    210                 215                 220

Asp Asp Ser His Asn Lys Val Leu Leu Asn Phe Ala Lys Leu Asp Phe
225                 230                 235                 240

Asn Leu Leu Gln Lys Met His Gln Gly Glu Leu Ser His Ile Thr Arg
                245                 250                 255

Trp Trp Lys Glu Leu Asn Phe Ala Lys Lys Leu Pro Phe Ala Arg Asp
            260                 265                 270

Arg Val Val Glu Cys Tyr Phe Trp Ile Leu Gly Val Tyr Phe Glu Pro
        275                 280                 285

Gln Tyr Leu Ile Ala Arg Arg Phe Leu Thr Lys Ile Ile Ala Met Ala
    290                 295                 300

Ser Val Ala Asp Asp Ile Tyr Asp Val Tyr Gly Thr Leu Glu Glu Leu
305                 310                 315                 320

Val Ile Leu Thr Asp Ala Ile Glu Arg Trp Asp Met Gly Ala Leu Asp
                325                 330                 335

Gln Ile Pro Glu Cys Met Arg Val Tyr His Arg Ala Leu Leu Asp Val
            340                 345                 350

Tyr Thr Glu Met Glu Glu Glu Met Ala Lys Thr Gly Arg Pro Ser Tyr
        355                 360                 365

Arg Val His Tyr Ala Lys Glu Ala Tyr Lys Glu Leu Val Arg Gln Tyr
    370                 375                 380

Leu Ala Glu Ala Lys Trp Phe Gln Glu Asp Tyr Asp Pro Thr Leu Glu
385                 390                 395                 400

Glu Tyr Leu Pro Val Ala Leu Ile Ser Gly Gly Tyr Lys Met Leu Ala
                405                 410                 415

Thr His Ser Phe Val Gly Met Gly Asp Leu Ala Thr Lys Glu Ala Phe
            420                 425                 430

Asp Trp Val Ser Asn Asn Pro Leu Ile Val Lys Ala Ser Ser Val Ile
        435                 440                 445

Cys Arg Leu Ser Asp Asp Met Val Gly His Glu Val Glu His Glu Arg
    450                 455                 460

Gly Asp Val Ala Ser Ala Val Glu Cys Tyr Met Lys Gln Tyr Gly Val
465                 470                 475                 480

Thr Lys Gln Glu Val Tyr Ile Glu Phe Gln Lys Gln Ile Ser Asn Ala
                485                 490                 495

Trp Lys Asp Met Asn Gln Glu Cys Leu His Pro Thr Thr Val Thr Met
            500                 505                 510

Pro Leu Leu Thr Val Ile Phe Asn Met Thr Arg Val Ile Asn Leu Leu
        515                 520                 525

Tyr Asp Glu Glu Asp Gly Tyr Thr Asn Ser Asn Thr Arg Thr Lys Asp
    530                 535                 540

Phe Ile Thr Ser Val Leu Ile Asp Pro Val Gln Ile
545                 550                 555
```

<210> SEQ ID NO 19
<211> LENGTH: 565
<212> TYPE: PRT
<213> ORGANISM: Actinidia deliciosa
<220> FEATURE:
<223> OTHER INFORMATION: germacrene-D synthase protein
<300> PUBLICATION INFORMATION:
<308> DATABASE ACCESSION NUMBER: GenBank AAX16121.1
<309> DATABASE ENTRY DATE: 2005-11-01
<310> PATENT DOCUMENT NUMBER: US7312323
<311> PATENT FILING DATE: 2007-12-25

<400> SEQUENCE: 19

```
Met Gln Leu Pro Cys Ala Gln Ala Leu Pro Ile Pro Thr Val Thr Thr
1               5                   10                  15

Thr Thr Ser Ile Glu Pro Pro His Val Thr Arg Arg Ser Ala Asn Tyr
            20                  25                  30

His Pro Ser Ile Trp Gly Asp His Phe Leu Ala Tyr Ser Ser Asp Ala
        35                  40                  45

Met Glu Glu Glu Val Ile Asn Met Glu Gln Gln Gln Arg Leu His His
    50                  55                  60

Leu Lys Gln Lys Val Arg Lys Met Leu Glu Ala Ala Ala Glu Gln Ser
65                  70                  75                  80

Ser Gln Met Leu Asn Leu Val Asp Lys Ile Gln Arg Leu Gly Val Ser
                85                  90                  95

Tyr His Phe Glu Thr Glu Ile Glu Thr Ala Leu Arg His Ile Tyr Lys
            100                 105                 110

Thr Cys Asp Tyr His Phe Asp Asp Leu His Thr Ala Ala Leu Ser Phe
        115                 120                 125

Arg Leu Leu Arg Gln Gln Gly Tyr Pro Val Ser Cys Asp Met Phe Asp
    130                 135                 140

Lys Phe Lys Asn Ser Lys Gly Glu Phe Gln Glu Ser Ile Ile Ser Asp
145                 150                 155                 160

Val Gln Gly Met Leu Ser Leu Tyr Glu Ala Thr Cys Leu Arg Ile His
                165                 170                 175

Gly Glu Asp Ile Leu Asp Glu Ala Leu Ala Phe Thr Ile Thr Gln Leu
            180                 185                 190

Arg Ser Ala Leu Pro Asn Leu Ser Thr Pro Phe Lys Glu Gln Ile Ile
        195                 200                 205

His Ala Leu Asn Gln Pro Ile His Lys Gly Leu Thr Arg Leu Asn Ala
    210                 215                 220

Arg Ser His Ile Leu Phe Phe Glu Gln Asn Asp Cys His Ser Lys Asp
225                 230                 235                 240

Leu Leu Asn Phe Ala Lys Leu Asp Phe Asn Leu Leu Gln Lys Leu His
                245                 250                 255

Gln Arg Glu Leu Cys Glu Ile Thr Arg Trp Trp Lys Asp Leu Asn Phe
            260                 265                 270

Ala Lys Thr Leu Pro Phe Ala Arg Asp Arg Met Val Glu Cys Tyr Phe
        275                 280                 285

Trp Ile Leu Gly Val Tyr Phe Glu Pro Gln Tyr Leu Leu Ala Arg Arg
    290                 295                 300

Met Leu Thr Lys Val Ile Ala Met Ile Ser Ile Ile Asp Asp Ile Tyr
305                 310                 315                 320

Asp Val Tyr Gly Thr Leu Glu Glu Leu Val Leu Phe Thr Asp Ala Ile
                325                 330                 335
```

```
Glu Arg Trp Glu Ile Ser Ala Leu Asp Gln Leu Pro Glu Tyr Met Lys
            340                 345                 350

Leu Cys Tyr Gln Ala Leu Leu Asp Val Tyr Ser Met Ile Asp Glu Glu
        355                 360                 365

Met Ala Lys Gln Gly Arg Ser Tyr Cys Val Asp Tyr Ala Lys Ser Ser
    370                 375                 380

Met Lys Ile Leu Val Arg Ala Tyr Phe Glu Glu Ala Lys Trp Phe His
385                 390                 395                 400

Gln Gly Tyr Val Pro Thr Met Glu Glu Tyr Met Gln Val Ala Leu Val
                405                 410                 415

Thr Ala Gly Tyr Lys Met Leu Ala Thr Ser Ser Phe Val Gly Met Gly
            420                 425                 430

Asp Leu Ala Thr Lys Glu Ala Phe Asp Trp Val Ser Asn Asp Pro Leu
        435                 440                 445

Ile Val Gln Ala Ala Ser Val Ile Gly Arg Leu Lys Asp Asp Ile Val
    450                 455                 460

Gly His Lys Phe Glu Gln Lys Arg Gly His Val Ala Ser Ala Val Glu
465                 470                 475                 480

Cys Tyr Ser Lys Gln His Gly Thr Thr Glu Glu Glu Ala Ile Ile Glu
                485                 490                 495

Leu Asp Lys Gln Val Thr His Ser Trp Lys Asp Ile Asn Ala Glu Cys
            500                 505                 510

Leu Cys Pro Ile Lys Val Pro Met Pro Leu Leu Ala Arg Val Leu Asn
        515                 520                 525

Leu Ala Arg Val Leu Tyr Val Ile Tyr Gln Asp Glu Asp Gly Tyr Thr
    530                 535                 540

His Pro Gly Thr Lys Val Glu Asn Phe Val Thr Ser Val Leu Ile Asp
545                 550                 555                 560

Ser Met Pro Ile Asn
                565


<210> SEQ ID NO 20
<211> LENGTH: 557
<212> TYPE: PRT
<213> ORGANISM: Vitis vinifera
<220> FEATURE:
<223> OTHER INFORMATION: (-)-germacrene D synthase protein
<300> PUBLICATION INFORMATION:
<308> DATABASE ACCESSION NUMBER: NCBI XP_003634696.1
<309> DATABASE ENTRY DATE: 2011-12-07

<400> SEQUENCE: 20

Met Ser Val Gln Ser Ser Val Val Leu Leu Ala Pro Ser Lys Asn Leu
 1               5                  10                  15

Ser Pro Glu Val Gly Arg Arg Cys Ala Asn Phe His Pro Ser Ile Trp
            20                  25                  30

Gly Asp His Phe Leu Ser Tyr Ala Ser Glu Phe Thr Asn Thr Asp Asp
        35                  40                  45

His Leu Lys Gln His Val Gln Gln Leu Lys Glu Glu Val Arg Lys Met
    50                  55                  60

Leu Met Ala Ala Asp Asp Asp Ser Ala Gln Lys Leu Leu Leu Ile Asp
65                  70                  75                  80

Ala Ile Gln Arg Leu Gly Val Ala Tyr His Phe Glu Ser Glu Ile Asp
                85                  90                  95

Glu Val Leu Lys His Met Phe Asp Gly Ser Val Val Ser Ala Glu Glu
            100                 105                 110
```

-continued

```
Asp Val Tyr Thr Ala Ser Leu Arg Phe Arg Leu Leu Arg Gln Gln Gly
        115                 120                 125

Tyr His Val Ser Cys Asp Leu Phe Asn Asn Phe Lys Asp Asn Glu Gly
    130                 135                 140

Asn Phe Lys Glu Ser Leu Ser Ser Asp Val Arg Gly Met Leu Ser Leu
145                 150                 155                 160

Tyr Glu Ala Thr His Phe Arg Val His Gly Glu Asp Ile Leu Asp Glu
                165                 170                 175

Ala Leu Ala Phe Thr Thr Thr His Leu Gln Ser Ala Thr Lys His Ser
            180                 185                 190

Ser Asn Pro Leu Ala Glu Gln Val Val His Ala Leu Lys Gln Pro Ile
        195                 200                 205

Arg Lys Gly Leu Pro Arg Leu Glu Ala Arg His Tyr Phe Ser Val Tyr
    210                 215                 220

Gln Ala Asp Asp Ser His Asn Lys Ala Leu Leu Lys Leu Ala Lys Leu
225                 230                 235                 240

Asp Phe Asn Leu Leu Gln Lys Leu His Gln Lys Glu Leu Ser Asp Ile
                245                 250                 255

Ser Ala Trp Trp Lys Asp Leu Asp Phe Ala His Lys Leu Pro Phe Ala
            260                 265                 270

Arg Asp Arg Val Val Glu Cys Tyr Phe Trp Ile Leu Gly Val Tyr Phe
        275                 280                 285

Glu Pro Gln Phe Phe Phe Ala Arg Arg Ile Leu Thr Lys Val Ile Ala
    290                 295                 300

Met Thr Ser Ile Ile Asp Asp Ile Tyr Asp Val Tyr Gly Thr Leu Glu
305                 310                 315                 320

Glu Leu Glu Leu Phe Thr Glu Ala Val Glu Arg Trp Asp Ile Ser Ala
                325                 330                 335

Ile Asp Gln Leu Pro Glu Tyr Met Arg Val Cys Tyr Gln Ala Leu Leu
            340                 345                 350

Tyr Val Tyr Ser Glu Ile Glu Glu Glu Met Ala Lys Glu Gly Arg Ser
        355                 360                 365

Tyr Arg Leu Tyr Tyr Ala Lys Glu Ala Met Lys Asn Gln Val Arg Ala
    370                 375                 380

Tyr Tyr Glu Glu Ala Lys Trp Leu Gln Val Gln Gln Ile Pro Thr Met
385                 390                 395                 400

Glu Glu Tyr Met Pro Val Ala Leu Val Thr Ser Ala Tyr Ser Met Leu
                405                 410                 415

Ala Thr Thr Ser Phe Val Gly Met Gly Asp Ala Val Thr Lys Glu Ser
            420                 425                 430

Phe Asp Trp Ile Phe Ser Lys Pro Lys Ile Val Arg Ala Ser Ala Ile
        435                 440                 445

Val Cys Arg Leu Met Asp Asp Met Val Ser His Lys Phe Glu Gln Lys
    450                 455                 460

Arg Gly His Val Ala Ser Ala Val Glu Cys Tyr Met Lys Gln His Gly
465                 470                 475                 480

Ala Ser Glu Gln Glu Thr His Asn Glu Phe His Lys Gln Val Arg Asp
                485                 490                 495

Ala Trp Lys Asp Ile Asn Glu Glu Cys Leu Ile Pro Thr Ala Val Pro
            500                 505                 510

Met Pro Ile Leu Met Arg Val Leu Asn Leu Ala Arg Val Ile Asp Val
        515                 520                 525

Ile Tyr Lys Asn Glu Asp Gly Tyr Thr His Ser Gly Thr Val Leu Lys
```

```
    530                 535                 540

Asp Phe Val Thr Ser Met Leu Ile Asp Pro Val Pro Ile
545                 550                 555
```

```
<210> SEQ ID NO 21
<211> LENGTH: 562
<212> TYPE: PRT
<213> ORGANISM: Santalum murrayanum
<220> FEATURE:
<223> OTHER INFORMATION: sesquiterpene synthase protein
<300> PUBLICATION INFORMATION:
<308> DATABASE ACCESSION NUMBER: Uniprot F6M8H7.1
<309> DATABASE ENTRY DATE: 2012-10-03

<400> SEQUENCE: 21

Met Glu Asn Gln Lys Met Pro Ile Ser Ser Val Pro Asn Leu Lys Asp
 1               5                  10                  15

Leu Asn Met Ile Ser Arg Pro Ile Ala Asn Phe Pro Pro Ser Ile Trp
            20                  25                  30

Gly Asp Arg Phe Ile Asn Tyr Thr Cys Glu Asp Glu Asn Asp Gln Thr
        35                  40                  45

Gln Lys Glu Arg Gln Val Glu Glu Leu Lys Glu Gln Val Arg Arg Glu
    50                  55                  60

Leu Ala Ala Thr Val Asp Lys Pro Leu Gln Gln Leu Asn Ile Ile Asp
65                  70                  75                  80

Ala Thr Gln Arg Leu Gly Ile Ala Tyr Leu Phe Glu Asn Glu Ile Glu
                85                  90                  95

Glu Ser Leu Lys His Ile Tyr Leu His Thr Tyr Val Glu Asn Asn Cys
            100                 105                 110

Phe Glu Gly Ser Asp Asp Leu Tyr Ser Val Ala Leu Trp Phe Arg Leu
        115                 120                 125

Leu Arg Gln Asn Gly Tyr Lys Val Ser Cys Asp Val Phe Asn Lys Phe
    130                 135                 140

Arg Asp Asn Glu Gly Asn Phe Lys Asn Asn Leu Met Glu Asp Ala Lys
145                 150                 155                 160

Gly Leu Leu Glu Leu Tyr Glu Ala Thr His Val Ser Ile His Gly Glu
                165                 170                 175

Glu Met Leu Asp Asp Ala Leu Glu Phe Thr Lys Thr Arg Leu Glu Ser
            180                 185                 190

Val Val Ser His Leu Asn Tyr Pro Leu Ala Glu Gln Val Arg His Ala
        195                 200                 205

Leu Tyr Gln Pro Leu His Arg Gly Leu Pro Arg Leu Glu Ala Val Tyr
    210                 215                 220

Phe Phe Arg Ile Tyr Glu Ala His Ala Ser His Asn Lys Ala Leu Leu
225                 230                 235                 240

Lys Leu Ala Lys Leu Asp Phe Asn Leu Leu Gln Ser Phe His Lys Lys
                245                 250                 255

Glu Leu Ser Asp Ile Ala Arg Trp Trp Lys Ser Leu Asp Phe Ala Ala
            260                 265                 270

Lys Phe Pro Phe Ala Arg Asp Arg Leu Val Glu Gly Tyr Phe Trp Val
        275                 280                 285

Leu Gly Val Tyr Phe Glu Pro Gln Tyr Ser Leu Ala Arg Lys Ile Ile
    290                 295                 300

Ile Lys Val Phe Thr Met Ile Ser Thr Ile Asp Asp Ile Tyr Asp Ala
305                 310                 315                 320

Tyr Gly Thr Leu Asp Glu Leu Lys Leu Phe Thr Lys Ala Met Gln Arg
```

```
                325                 330                 335

Trp Asp Val Gly Ser Leu Asp Gln Leu Pro Glu Tyr Met Lys Pro Cys
            340                 345                 350

Tyr Lys Ser Ile Leu Asp Val Tyr Asn Glu Ile Glu Glu Glu Met Ala
        355                 360                 365

Asn Gln Gly Ser Leu Phe Arg Met His Tyr Ala Lys Glu Val Met Lys
    370                 375                 380

Thr Ile Val Glu Gly Tyr Met Asp Glu Ala Lys Trp Cys His Glu Lys
385                 390                 395                 400

Tyr Val Pro Thr Phe Gln Glu Tyr Met Ser Val Ala Leu Val Thr Ser
                405                 410                 415

Gly Tyr Thr Phe Leu Thr Thr Ile Ser Tyr Leu Gly Met Gly Glu Ile
            420                 425                 430

Ala Ser Lys Glu Ala Phe Asp Trp Leu Phe Ser His Pro Pro Val Ile
        435                 440                 445

Glu Ala Ser Glu Ser Val Gly Arg Leu Met Asp Asp Met Arg Ser His
    450                 455                 460

Lys Phe Glu Gln Glu Arg Gly His Val Ala Ser Gly Ile Glu Cys Tyr
465                 470                 475                 480

Met Lys Gln Tyr Gly Val Thr Glu Glu Glu Ala His Asp Glu Phe Arg
                485                 490                 495

Lys Arg Leu Val Lys Ala Trp Lys Asp Ile Asn Glu Glu Cys Leu Arg
            500                 505                 510

Pro Tyr Arg Val Pro Lys Pro Leu Leu Thr Arg Ile Leu Asn Leu Thr
        515                 520                 525

Arg Val Ile Asp Val Ile Tyr Lys Asn Glu Asp Gly Tyr Thr His Val
    530                 535                 540

Lys Lys Ala Met Lys Asp Asn Ile Ala Ser Leu Leu Ile Asp Pro Val
545                 550                 555                 560

Ile Val


<210> SEQ ID NO 22
<211> LENGTH: 550
<212> TYPE: PRT
<213> ORGANISM: Ricinus communis
<220> FEATURE:
<223> OTHER INFORMATION: (+)-delta-cadinene synthase protein
<300> PUBLICATION INFORMATION:
<308> DATABASE ACCESSION NUMBER: GenBank EEF38721.1
<309> DATABASE ENTRY DATE: 2009-02-12

<400> SEQUENCE: 22

Met Ser Ala Gln Thr Leu Ala Ile Ser Asn Leu Lys Pro Asn Thr Thr
 1               5                  10                  15

Arg His Leu Ala Ser Phe His Pro Asn Ile Trp Gly Asp Arg Phe Leu
            20                  25                  30

Ser Cys Ala Ala Glu Ser Thr Asp Ile Glu Asp Asp Met Glu Gln Gln
        35                  40                  45

Val Glu Arg Leu Lys Glu Glu Val Lys Lys Met Ile Ala Ser Ala Asp
    50                  55                  60

Glu Pro Ser Gln Ile Leu Asn Leu Ile Asp Leu Leu Gln Arg Leu Gly
65                  70                  75                  80

Val Ser Tyr His Phe Glu Lys Glu Ile Glu Glu Ala Leu Gln Gln Val
                85                  90                  95

Leu Asn Met Asn Ser Asp Ser Asp Lys Asp Asp Asp Leu His Ser Val
            100                 105                 110
```

```
Ala Leu Arg Phe Arg Leu Leu Arg Glu Gln Gly Leu Asn Val Ser Cys
        115                 120                 125

Asp Val Phe Asn Lys Phe Arg Asp Arg Asn Gly His Phe Ile Gln Thr
    130                 135                 140

Leu Lys Thr Asp Leu Gln Gly Met Leu Ser Leu Tyr Glu Ala Ala His
145                 150                 155                 160

Phe Arg Val His Gly Glu Gly Ile Leu Asp Asp Ala Leu Ala Phe Thr
                165                 170                 175

Thr Thr Tyr Leu Glu Ser Ile Val Pro Asn Leu Ser Pro Pro Leu Ala
            180                 185                 190

Ala Gln Ile Ser Arg Thr Leu Arg Gln Pro Leu Arg Lys Ser Leu Ala
        195                 200                 205

Arg Val Glu Ala Arg His Phe Ile Ser Ile Tyr Gln Glu Asp Thr Ser
    210                 215                 220

His Asn Glu Val Leu Leu Thr Phe Ala Lys Leu Asp Phe Asn Leu Leu
225                 230                 235                 240

Gln Lys Leu His Gln Lys Glu Leu Lys Tyr Ile Ser Leu Trp Trp Lys
                245                 250                 255

Asp Leu Asp Phe Val Asn Lys Leu Pro Phe Thr Arg Asp Arg Val Val
            260                 265                 270

Glu Gly Tyr Phe Trp Ile Leu Gly Val Tyr Phe Glu Pro Gln Tyr His
        275                 280                 285

Arg Ala Arg Lys Phe Val Thr Lys Val Ile Asn Val Val Ser Val Ile
    290                 295                 300

Asp Asp Ile Tyr Asp Ala Tyr Gly Thr Leu Glu Glu Leu Val Val Phe
305                 310                 315                 320

Thr Asp Ala Ile Asn Arg Trp Asp Ile Asp Cys Ile Asp Gln Leu Pro
                325                 330                 335

Glu Tyr Met Lys Val Cys Tyr Lys Ala Leu Leu Asn Val Tyr Glu Glu
            340                 345                 350

Ile Glu Arg Ala Leu Ser Glu Gln Gly Arg Ser Tyr Arg Leu His Tyr
        355                 360                 365

Ala Lys Glu Ala Met Lys Lys Leu Val Gln Ala Tyr Leu Val Glu Ala
    370                 375                 380

Asn Trp Met Asn Lys Asn Tyr Val Pro Thr Met Asp Glu Tyr Met Ser
385                 390                 395                 400

Ile Ala Leu Val Ser Cys Ala Tyr Pro Leu Leu Thr Val Thr Ser Phe
                405                 410                 415

Val Gly Met Gly Asp Ile Ala Thr Lys Glu Val Phe Asp Trp Ala Ser
            420                 425                 430

Asn Asp Pro Lys Ile Val Arg Val Ala Ser Ile Ile Cys Arg Leu Met
        435                 440                 445

Asp Asp Ile Val Ser His Glu Phe Glu Gln Lys Arg Gly His Ile Ala
    450                 455                 460

Ser Ser Val Glu Cys Tyr Met Lys Gln Asn Gly Val Ser Glu Glu Ala
465                 470                 475                 480

Thr Arg Asp Glu Phe Asn Lys Gln Ile Val Asp Ala Trp Lys Asp Ile
                485                 490                 495

Asn Glu Glu His Leu Gln Pro Asn Tyr Val Pro Met Pro Phe Arg Thr
            500                 505                 510

Arg Val Val Asn Ser Ala Arg Ile Met Asp Tyr Leu Tyr Lys Asp Asp
        515                 520                 525
```

```
Asp Glu Tyr Thr His Val Gly Glu Leu Met Lys Gly Ser Val Ala Ala
    530                 535                 540

Leu Leu Ile Asp Pro Ala
545                 550


<210> SEQ ID NO 23
<211> LENGTH: 562
<212> TYPE: PRT
<213> ORGANISM: Citrus x paradisi
<220> FEATURE:
<223> OTHER INFORMATION: delta-cadinene synthase protein
<300> PUBLICATION INFORMATION:
<310> PATENT DOCUMENT NUMBER: US7273735
<311> PATENT FILING DATE: 2007-09-25

<400> SEQUENCE: 23

Met Ser Leu Glu Val Ser Ala Ser Pro Ala Lys Val Ile Gln Asn Ala
 1               5                  10                  15

Gly Lys Asp Ser Thr Arg Arg Ser Ala Asn Tyr His Pro Ser Ile Trp
            20                  25                  30

Gly Asp His Phe Leu Gln Tyr Thr Cys Asp Thr Gln Glu Thr Asp Asp
        35                  40                  45

Gly Ser Asn Val Lys His Leu Glu Leu Lys Lys Glu Ile Arg Arg Met
    50                  55                  60

Leu Lys Ala Asp Asn Lys Pro Ser Arg Thr Leu Gln Leu Ile Asp Ala
65                  70                  75                  80

Ile Gln Arg Leu Gly Val Ser Tyr His Phe Glu Ser Glu Ile Asp Glu
                85                  90                  95

Ile Leu Gly Lys Met His Lys Ala Ser Gln Asp Ser Asp Leu Cys Asp
            100                 105                 110

Asn Glu Asn Asp Glu Leu Tyr Tyr Ile Ser Leu His Phe Arg Leu Leu
        115                 120                 125

Arg Gln Asn Gly Tyr Lys Ile Ser Ala Asp Val Phe Lys Lys Phe Lys
    130                 135                 140

Asp Thr Asp Gly Asn Phe Lys Thr Ser Leu Ala Lys Asp Val Arg Gly
145                 150                 155                 160

Met Leu Ser Leu Tyr Glu Ala Thr His Leu Gly Val His Glu Glu Asp
                165                 170                 175

Ile Leu Asp Glu Ala Leu Ala Phe Thr Thr Ser His Leu Glu Ser Ile
            180                 185                 190

Ala Thr His Gln Ile Arg Ser Pro Leu Val Glu Gln Val Lys His Ala
        195                 200                 205

Leu Val Gln Pro Ile His Arg Gly Phe Gln Arg Leu Glu Ala Arg Gln
    210                 215                 220

Tyr Ile Pro Ile Tyr Gln Glu Glu Ser Pro His Asn Glu Ala Leu Leu
225                 230                 235                 240

Thr Phe Ala Lys Leu Asp Phe Asn Lys Leu Gln Lys Pro His Gln Lys
                245                 250                 255

Glu Leu Gly Asp Ile Ser Arg Trp Trp Lys Glu Leu Asp Phe Ala His
            260                 265                 270

Lys Leu Pro Phe Ile Arg Asp Arg Val Ala Glu Cys Tyr Phe Trp Ile
        275                 280                 285

Leu Gly Val Tyr Phe Glu Pro Gln Tyr Ser Phe Ala Arg Arg Ile Leu
    290                 295                 300

Thr Lys Val Ile Ser Met Thr Ser Val Ile Asp Asp Ile Tyr Asp Val
305                 310                 315                 320
```

```
Tyr Gly Lys Ile Glu Glu Leu Glu Leu Phe Thr Ser Ala Ile Glu Arg
                325                 330                 335

Trp Asp Ile Ser Ala Ile Asp Gln Leu Pro Glu Tyr Met Lys Leu Cys
            340                 345                 350

Tyr Arg Ala Leu Leu Asp Val Phe Ser Glu Ala Glu Lys Asp Leu Ala
        355                 360                 365

Pro Gln Gly Lys Ser Tyr Arg Leu Tyr Tyr Ala Lys Glu Ala Met Lys
    370                 375                 380

Asn Met Val Lys Asn Tyr Phe Tyr Glu Ala Lys Trp Cys Leu Gln Asn
385                 390                 395                 400

Tyr Val Pro Thr Val Asp Glu Tyr Met Thr Val Ala Leu Val Thr Ser
                405                 410                 415

Gly Ser Pro Met Leu Ser Thr Thr Ser Phe Val Gly Met Gly Asp Ile
            420                 425                 430

Val Thr Lys Glu Ser Phe Glu Trp Leu Phe Ser Asn Pro Arg Phe Ile
        435                 440                 445

Arg Ala Ser Ser Ile Val Cys Arg Leu Met Asp Asp Ile Val Ser His
    450                 455                 460

Lys Phe Glu Gln Ser Arg Gly His Val Ala Ser Ser Val Glu Cys Tyr
465                 470                 475                 480

Met Lys Gln His Gly Ala Thr Glu Glu Glu Ala Cys Asn Glu Phe Arg
                485                 490                 495

Lys Gln Val Ser Asn Ala Trp Lys Asp Ile Asn Glu Asp Cys Leu Arg
            500                 505                 510

Pro Thr Val Val Pro Met Pro Leu Leu Met Arg Ile Leu Asn Leu Thr
        515                 520                 525

Arg Val Ile Asp Val Ile Tyr Lys Tyr Glu Asp Gly Tyr Thr His Ser
    530                 535                 540

Ala Val Val Leu Lys Asp Phe Val Ala Ser Leu Phe Ile Asn Pro Val
545                 550                 555                 560

Pro Ile


<210> SEQ ID NO 24
<211> LENGTH: 548
<212> TYPE: PRT
<213> ORGANISM: Nicotiana tabacum
<220> FEATURE:
<223> OTHER INFORMATION: Tobacco 5-epi-aristolochene synthase protein
<300> PUBLICATION INFORMATION:
<308> DATABASE ACCESSION NUMBER: GenBank L04680.1
<309> DATABASE ENTRY DATE: 1994-06-27

<400> SEQUENCE: 24

Met Ala Ser Ala Ala Val Ala Asn Tyr Glu Glu Glu Ile Val Arg Pro
 1               5                  10                  15

Val Ala Asp Phe Ser Pro Ser Leu Trp Gly Asp Gln Phe Leu Ser Phe
            20                  25                  30

Ser Ile Lys Asn Gln Val Ala Glu Lys Tyr Ala Lys Glu Ile Glu Ala
        35                  40                  45

Leu Lys Glu Gln Thr Arg Asn Met Leu Leu Ala Thr Gly Met Lys Leu
    50                  55                  60

Ala Asp Thr Leu Asn Leu Ile Asp Thr Ile Glu Arg Leu Gly Ile Ser
65                  70                  75                  80

Tyr His Phe Glu Lys Glu Ile Asp Asp Ile Leu Asp Gln Ile Tyr Asn
                85                  90                  95

Gln Asn Ser Asn Cys Asn Asp Leu Cys Thr Ser Ala Leu Gln Phe Arg
```

-continued

```
            100                 105                 110

Leu Leu Arg Gln His Gly Phe Asn Ile Ser Pro Glu Ile Phe Ser Lys
        115                 120                 125

Phe Gln Asp Glu Asn Gly Lys Phe Lys Glu Ser Leu Ala Ser Asp Val
    130                 135                 140

Leu Gly Leu Leu Asn Leu Tyr Glu Ala Ser His Val Arg Thr His Ala
145                 150                 155                 160

Asp Asp Ile Leu Glu Asp Ala Leu Ala Phe Ser Thr Ile His Leu Glu
                165                 170                 175

Ser Ala Ala Pro His Leu Lys Ser Pro Leu Arg Glu Gln Val Thr His
            180                 185                 190

Ala Leu Glu Gln Cys Leu His Lys Gly Val Pro Arg Val Glu Thr Arg
        195                 200                 205

Phe Phe Ile Ser Ser Ile Tyr Asp Lys Glu Gln Ser Lys Asn Asn Val
    210                 215                 220

Leu Leu Arg Phe Ala Lys Leu Asp Phe Asn Leu Leu Gln Met Leu His
225                 230                 235                 240

Lys Gln Glu Leu Ala Gln Val Ser Arg Trp Trp Lys Asp Leu Asp Phe
                245                 250                 255

Val Thr Thr Leu Pro Tyr Ala Arg Asp Arg Val Val Glu Cys Tyr Phe
            260                 265                 270

Trp Ala Leu Gly Val Tyr Phe Glu Pro Gln Tyr Ser Gln Ala Arg Val
        275                 280                 285

Met Leu Val Lys Thr Ile Ser Met Ile Ser Ile Val Asp Asp Thr Phe
    290                 295                 300

Asp Ala Tyr Gly Thr Val Lys Glu Leu Glu Ala Tyr Thr Asp Ala Ile
305                 310                 315                 320

Gln Arg Trp Asp Ile Asn Glu Ile Asp Arg Leu Pro Asp Tyr Met Lys
                325                 330                 335

Ile Ser Tyr Lys Ala Ile Leu Asp Leu Tyr Lys Asp Tyr Glu Lys Glu
            340                 345                 350

Leu Ser Ser Ala Gly Arg Ser His Ile Val Cys His Ala Ile Glu Arg
        355                 360                 365

Met Lys Glu Val Val Arg Asn Tyr Asn Val Glu Ser Thr Trp Phe Ile
    370                 375                 380

Glu Gly Tyr Thr Pro Pro Val Ser Glu Tyr Leu Ser Asn Ala Leu Ala
385                 390                 395                 400

Thr Thr Thr Tyr Tyr Tyr Leu Ala Thr Thr Ser Tyr Leu Gly Met Lys
                405                 410                 415

Ser Ala Thr Glu Gln Asp Phe Glu Trp Leu Ser Lys Asn Pro Lys Ile
            420                 425                 430

Leu Glu Ala Ser Val Ile Ile Cys Arg Val Ile Asp Asp Thr Ala Thr
        435                 440                 445

Tyr Glu Val Glu Lys Ser Arg Gly Gln Ile Ala Thr Gly Ile Glu Cys
    450                 455                 460

Cys Met Arg Asp Tyr Gly Ile Ser Thr Lys Glu Ala Met Ala Lys Phe
465                 470                 475                 480

Gln Asn Met Ala Glu Thr Ala Trp Lys Asp Ile Asn Glu Gly Leu Leu
                485                 490                 495

Arg Pro Thr Pro Val Ser Thr Glu Phe Leu Thr Pro Ile Leu Asn Leu
            500                 505                 510

Ala Arg Ile Val Glu Val Thr Tyr Ile His Asn Leu Asp Gly Tyr Thr
        515                 520                 525
```

```
His Pro Glu Lys Val Leu Lys Pro His Ile Ile Asn Leu Leu Val Asp
    530                 535                 540

Ser Ile Lys Ile
545


<210> SEQ ID NO 25
<211> LENGTH: 520
<212> TYPE: PRT
<213> ORGANISM: Hyoscyamus muticus
<220> FEATURE:
<223> OTHER INFORMATION: premnaspirodiene synthase protein
<300> PUBLICATION INFORMATION:
<308> DATABASE ACCESSION NUMBER: GenBank: AAA86337.1
<309> DATABASE ENTRY DATE: 1996-01-30

<400> SEQUENCE: 25

Val Asp Asn Gln Val Ala Glu Lys Tyr Ala Gln Glu Ile Glu Thr Leu
 1               5                  10                  15

Lys Glu Gln Thr Ser Thr Met Leu Ser Ala Ala Cys Gly Thr Thr Leu
            20                  25                  30

Thr Glu Lys Leu Asn Leu Ile Asp Ile Ile Glu Arg Leu Gly Ile Ala
        35                  40                  45

Tyr His Phe Glu Lys Gln Ile Glu Asp Met Leu Asp His Ile Tyr Arg
    50                  55                  60

Ala Asp Pro Tyr Phe Glu Ala His Glu Tyr Asn Asp Leu Asn Thr Ser
65                  70                  75                  80

Ser Val Gln Phe Arg Leu Leu Arg Gln His Gly Tyr Asn Val Ser Pro
                85                  90                  95

Asn Ile Phe Ser Arg Phe Gln Asp Ala Asn Gly Lys Phe Lys Glu Ser
            100                 105                 110

Leu Arg Ser Asp Ile Arg Gly Leu Leu Asn Leu Tyr Glu Ala Ser His
        115                 120                 125

Val Arg Thr His Lys Glu Asp Ile Leu Glu Glu Ala Leu Val Phe Ser
    130                 135                 140

Val Gly His Leu Glu Ser Ala Ala Pro His Leu Lys Ser Pro Leu Ser
145                 150                 155                 160

Lys Gln Val Thr His Ala Leu Glu Gln Ser Leu His Lys Ser Ile Pro
                165                 170                 175

Arg Val Glu Ile Arg Tyr Phe Ile Ser Ile Tyr Glu Glu Glu Glu Phe
            180                 185                 190

Lys Asn Asp Leu Leu Leu Arg Phe Ala Lys Leu Asp Tyr Asn Leu Leu
        195                 200                 205

Gln Met Leu His Lys His Glu Leu Ser Glu Val Ser Arg Trp Trp Lys
    210                 215                 220

Asp Leu Asp Phe Val Thr Thr Leu Pro Tyr Ala Arg Asp Arg Ala Val
225                 230                 235                 240

Glu Cys Tyr Phe Trp Thr Met Gly Val Tyr Ala Glu Pro Gln Tyr Ser
                245                 250                 255

Gln Ala Arg Val Met Leu Ala Lys Thr Ile Ala Met Ile Ser Ile Val
            260                 265                 270

Asp Asp Thr Phe Asp Ala Tyr Gly Ile Val Lys Glu Leu Glu Val Tyr
        275                 280                 285

Thr Asp Ala Ile Gln Arg Trp Asp Ile Ser Gln Ile Asp Arg Leu Pro
    290                 295                 300

Glu Tyr Met Lys Ile Ser Tyr Lys Ala Leu Leu Asp Leu Tyr Asp Asp
305                 310                 315                 320
```

```
Tyr Glu Lys Glu Leu Ser Lys Asp Gly Arg Ser Asp Val Val His Tyr
                325                 330                 335

Ala Lys Glu Arg Met Lys Glu Ile Val Gly Asn Tyr Phe Ile Glu Gly
            340                 345                 350

Lys Trp Phe Ile Glu Gly Tyr Met Pro Ser Val Ser Glu Tyr Leu Ser
        355                 360                 365

Asn Ala Leu Ala Thr Ser Thr Tyr Tyr Leu Leu Thr Thr Thr Ser Tyr
    370                 375                 380

Leu Gly Met Lys Ser Ala Thr Lys Glu His Phe Glu Trp Leu Ala Thr
385                 390                 395                 400

Asn Pro Lys Ile Leu Glu Ala Asn Ala Thr Leu Cys Arg Val Val Asp
                405                 410                 415

Asp Ile Ala Thr Tyr Glu Val Glu Lys Gly Arg Gly Gln Ile Ala Thr
            420                 425                 430

Gly Ile Glu Cys Tyr Met Arg Asp Tyr Gly Val Ser Thr Glu Val Ala
        435                 440                 445

Met Glu Lys Phe Gln Glu Met Ala Asp Ile Ala Trp Lys Asp Val Asn
    450                 455                 460

Glu Glu Ile Leu Arg Pro Thr Pro Val Ser Ser Glu Ile Leu Thr Arg
465                 470                 475                 480

Ile Leu Asn Leu Ala Arg Ile Ile Asp Val Thr Tyr Lys His Asn Gln
                485                 490                 495

Asp Gly Tyr Thr His Pro Glu Lys Val Leu Lys Pro His Ile Ile Ala
            500                 505                 510

Leu Val Val Asp Ser Ile Asp Ile
        515                 520


<210> SEQ ID NO 26
<211> LENGTH: 548
<212> TYPE: PRT
<213> ORGANISM: Citrus x paradisi
<220> FEATURE:
<223> OTHER INFORMATION: Valencene synthase protein
<300> PUBLICATION INFORMATION:
<310> PATENT DOCUMENT NUMBER: US7273735
<311> PATENT FILING DATE: 2007-09-25

<400> SEQUENCE: 26

Met Ser Ser Gly Glu Thr Phe Arg Pro Thr Ala Asp Phe His Pro Ser
 1               5                  10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60

Leu Ile Asp Glu Val Gln Arg Leu Gly Val Ala Tyr His Phe Glu Lys
65                  70                  75                  80

Glu Ile Glu Asp Ala Ile Gln Lys Leu Cys Pro Asn Tyr Ile His Ser
                85                  90                  95

Asn Ser Pro Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125

Asp Glu Gly Arg Phe Lys Ser Ser Leu Ile Asn Asp Val Gln Gly Met
    130                 135                 140
```

-continued

```
Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
        195                 200                 205

Phe Met Ser Met Ile Asn Ser Thr Ser Asp His Leu Tyr Asn Lys Thr
    210                 215                 220

Leu Leu Asn Phe Ala Lys Leu Asp Phe Asn Ile Leu Leu Glu Leu His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270

Trp Asp Leu Gly Thr Tyr Phe Glu Pro Gln Tyr Ala Phe Gly Arg Lys
        275                 280                 285

Ile Met Thr Gln Leu Asn Tyr Ile Leu Ser Ile Ile Asp Asp Thr Tyr
    290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335

Leu Ile Tyr Arg Thr Leu Leu Asp Ala Phe Asn Glu Ile Glu Glu Asp
            340                 345                 350

Met Ala Lys Gln Gly Arg Ser His Cys Val Arg Tyr Ala Lys Glu Glu
        355                 360                 365

Asn Gln Lys Val Ile Gly Ala Tyr Ser Val Gln Ala Lys Trp Phe Ser
    370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
                405                 410                 415

Asp Phe Ala Thr Lys Glu Val Phe Glu Trp Ile Ser Asn Asn Pro Lys
            420                 425                 430

Val Val Lys Ala Ala Ser Val Ile Cys Arg Leu Met Asp Asp Met Gln
        435                 440                 445

Gly His Glu Phe Glu Gln Lys Arg Gly His Val Ala Ser Ala Ile Glu
    450                 455                 460

Cys Tyr Thr Lys Gln His Gly Val Ser Lys Glu Glu Ala Ile Lys Met
465                 470                 475                 480

Phe Glu Glu Glu Val Ala Asn Ala Trp Lys Asp Ile Asn Glu Glu Leu
                485                 490                 495

Met Met Lys Pro Thr Val Val Ala Arg Pro Leu Leu Gly Thr Ile Leu
            500                 505                 510

Asn Leu Ala Arg Ala Ile Asp Phe Ile Tyr Lys Glu Asp Asp Gly Tyr
        515                 520                 525

Thr His Ser Tyr Leu Ile Lys Asp Gln Ile Ala Ser Val Leu Gly Asp
    530                 535                 540

His Val Pro Phe
545
```

<210> SEQ ID NO 27
<211> LENGTH: 548
<212> TYPE: PRT
<213> ORGANISM: Citrus x paradisi
<220> FEATURE:
<223> OTHER INFORMATION: Valencene synthase protein
<300> PUBLICATION INFORMATION:
<310> PATENT DOCUMENT NUMBER: US7442785
<311> PATENT FILING DATE: 2008-10-28

<400> SEQUENCE: 27

```
Met Ser Ser Gly Glu Thr Phe Arg Pro Thr Ala Asp Phe His Pro Ser
 1              5                   10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60

Leu Ile Asp Glu Val Gln Arg Leu Gly Val Ala Tyr His Phe Glu Lys
65                  70                  75                  80

Glu Ile Glu Asp Ala Ile Leu Lys Leu Cys Pro Ile Tyr Ile Asp Ser
                85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125

Asp Glu Gly Arg Phe Lys Ser Ser Leu Ile Asn Asp Val Gln Gly Met
    130                 135                 140

Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
        195                 200                 205

Phe Met Ser Met Ile Asn Ser Thr Ser Asp His Leu Tyr Asn Lys Thr
    210                 215                 220

Leu Leu Asn Phe Ala Lys Leu Asp Phe Asn Ile Leu Leu Glu Pro His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270

Trp Asp Leu Gly Thr Tyr Phe Glu Pro Gln Tyr Ala Phe Gly Arg Lys
        275                 280                 285

Ile Met Thr Gln Leu Asn Tyr Ile Leu Ser Ile Ile Asp Asp Thr Tyr
    290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335

Leu Ile Tyr Arg Thr Leu Leu Asp Ala Phe Asn Glu Ile Glu Glu Asp
            340                 345                 350
```

```
Met Ala Lys Gln Gly Arg Ser His Cys Val Arg Tyr Ala Lys Glu Glu
        355                 360                 365

Asn Gln Lys Val Ile Gly Ala Tyr Ser Val Gln Ala Lys Trp Phe Ser
    370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
                405                 410                 415

Asp Phe Ala Thr Lys Glu Val Phe Glu Trp Ile Ser Asn Asn Pro Lys
            420                 425                 430

Val Val Lys Ala Ala Ser Val Ile Cys Arg Leu Met Asp Asp Met Gln
        435                 440                 445

Gly His Glu Phe Glu Gln Lys Arg Gly His Val Ala Ser Ala Ile Glu
    450                 455                 460

Cys Tyr Thr Lys Gln His Gly Val Ser Lys Glu Glu Ala Ile Lys Met
465                 470                 475                 480

Phe Glu Glu Glu Val Ala Asn Ala Trp Lys Asp Ile Asn Glu Glu Leu
                485                 490                 495

Met Met Lys Pro Thr Val Val Ala Arg Pro Leu Leu Gly Thr Ile Leu
            500                 505                 510

Asn Leu Ala Arg Ala Ile Asp Phe Ile Tyr Lys Glu Asp Asp Gly Tyr
        515                 520                 525

Thr His Ser Tyr Leu Ile Lys Asp Gln Ile Ala Ser Val Leu Gly Asp
    530                 535                 540

His Val Pro Phe
545


<210> SEQ ID NO 28
<211> LENGTH: 556
<212> TYPE: PRT
<213> ORGANISM: Vitis vinifera
<220> FEATURE:
<223> OTHER INFORMATION: Valencene synthase protein
<300> PUBLICATION INFORMATION:
<308> DATABASE ACCESSION NUMBER: Uniprot Q6Q3H2
<309> DATABASE ENTRY DATE: 2011-09-21

<400> SEQUENCE: 28

Met Ser Thr Gln Val Ser Ala Ser Ser Leu Ala Gln Ile Pro Gln Pro
 1               5                  10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140
```

-continued

```
Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met His Gly Val Tyr Phe
        275                 280                 285

Glu Pro Gln Tyr Leu Arg Gly Arg Arg Ile Leu Thr Lys Val Ile Ala
    290                 295                 300

Met Thr Ser Ile Leu Asp Asp Ile His Asp Ala Tyr Gly Thr Pro Glu
305                 310                 315                 320

Glu Leu Lys Leu Phe Ile Glu Ala Ile Glu Arg Trp Asp Ile Asn Ser
                325                 330                 335

Ile Asn Gln Leu Pro Glu Tyr Met Lys Leu Cys Tyr Val Ala Leu Leu
            340                 345                 350

Asp Val Tyr Lys Glu Ile Glu Glu Glu Met Glu Lys Glu Gly Asn Gln
        355                 360                 365

Tyr Arg Val His Tyr Ala Lys Glu Val Met Lys Asn Gln Val Arg Ala
    370                 375                 380

Tyr Phe Ala Glu Ala Lys Trp Leu His Glu Glu His Val Pro Ala Phe
385                 390                 395                 400

Glu Glu Tyr Met Arg Val Ala Leu Ala Ser Ser Gly Tyr Cys Leu Leu
                405                 410                 415

Ala Thr Thr Ser Phe Val Gly Met Gly Glu Ile Ala Thr Lys Glu Ala
            420                 425                 430

Phe Asp Trp Val Thr Ser Asp Pro Lys Ile Met Ser Ser Ser Asn Phe
        435                 440                 445

Ile Thr Arg Leu Met Asp Asp Ile Lys Ser His Lys Phe Glu Gln Lys
    450                 455                 460

Arg Gly His Val Thr Ser Ala Val Glu Cys Tyr Met Lys Gln Tyr Gly
465                 470                 475                 480

Val Ser Glu Glu Gln Val Tyr Ser Glu Phe Gln Lys Gln Ile Glu Asn
                485                 490                 495

Ala Trp Leu Asp Ile Asn Gln Glu Cys Leu Lys Pro Thr Ala Val Ser
            500                 505                 510

Met Pro Leu Leu Ala Arg Leu Leu Asn Phe Thr Arg Thr Met Asp Val
        515                 520                 525

Ile Tyr Lys Glu Gln Asp Ser Tyr Thr His Val Gly Lys Val Met Arg
    530                 535                 540

Asp Asn Ile Ala Ser Val Phe Ile Asn Ala Val Ile
545                 550                 555
```

<210> SEQ ID NO 29
<211> LENGTH: 589
<212> TYPE: PRT
<213> ORGANISM: Chamaecyparis nootkatensis
<220> FEATURE:
<223> OTHER INFORMATION: Valencene synthase protein

<400> SEQUENCE: 29

```
Met Ala Glu Met Phe Asn Gly Asn Ser Ser Asn Asp Gly Ser Ser Cys
 1               5                  10                  15

Met Pro Val Lys Asp Ala Leu Arg Arg Thr Gly Asn His His Pro Asn
            20                  25                  30

Leu Trp Thr Asp Asp Phe Ile Gln Ser Leu Asn Ser Pro Tyr Ser Asp
        35                  40                  45

Ser Ser Tyr His Lys His Arg Glu Ile Leu Ile Asp Glu Ile Arg Asp
    50                  55                  60

Met Phe Ser Asn Gly Glu Gly Asp Glu Phe Gly Val Leu Glu Asn Ile
65                  70                  75                  80

Trp Phe Val Asp Val Val Gln Arg Leu Gly Ile Asp Arg His Phe Gln
                85                  90                  95

Glu Glu Ile Lys Thr Ala Leu Asp Tyr Ile Tyr Lys Phe Trp Asn His
            100                 105                 110

Asp Ser Ile Phe Gly Asp Leu Asn Met Val Ala Leu Gly Phe Arg Ile
        115                 120                 125

Leu Arg Leu Asn Arg Tyr Val Ala Ser Ser Asp Val Phe Lys Lys Phe
    130                 135                 140

Lys Gly Glu Glu Gly Gln Phe Ser Gly Phe Glu Ser Ser Asp Gln Asp
145                 150                 155                 160

Ala Lys Leu Glu Met Met Leu Asn Leu Tyr Lys Ala Ser Glu Leu Asp
                165                 170                 175

Phe Pro Asp Glu Asp Ile Leu Lys Glu Ala Arg Ala Phe Ala Ser Met
            180                 185                 190

Tyr Leu Lys His Val Ile Lys Glu Tyr Gly Asp Ile Gln Glu Ser Lys
        195                 200                 205

Asn Pro Leu Leu Met Glu Ile Glu Tyr Thr Phe Lys Tyr Pro Trp Arg
    210                 215                 220

Cys Arg Leu Pro Arg Leu Glu Ala Trp Asn Phe Ile His Ile Met Arg
225                 230                 235                 240

Gln Gln Asp Cys Asn Ile Ser Leu Ala Asn Asn Leu Tyr Lys Ile Pro
                245                 250                 255

Lys Ile Tyr Met Lys Lys Ile Leu Glu Leu Ala Ile Leu Asp Phe Asn
            260                 265                 270

Ile Leu Gln Ser Gln His Gln His Glu Met Lys Leu Ile Ser Thr Trp
        275                 280                 285

Trp Lys Asn Ser Ser Ala Ile Gln Leu Asp Phe Phe Arg His Arg His
    290                 295                 300

Ile Glu Ser Tyr Phe Trp Trp Ala Ser Pro Leu Phe Glu Pro Glu Phe
305                 310                 315                 320

Ser Thr Cys Arg Ile Asn Cys Thr Lys Leu Ser Thr Lys Met Phe Leu
                325                 330                 335

Leu Asp Asp Ile Tyr Asp Thr Tyr Gly Thr Val Glu Glu Leu Lys Pro
            340                 345                 350

Phe Thr Thr Thr Leu Thr Arg Trp Asp Val Ser Thr Val Asp Asn His
        355                 360                 365

Pro Asp Tyr Met Lys Ile Ala Phe Asn Phe Ser Tyr Glu Ile Tyr Lys
```

```
    370                 375                 380

Glu Ile Ala Ser Glu Ala Glu Arg Lys His Gly Pro Phe Val Tyr Lys
385                 390                 395                 400

Tyr Leu Gln Ser Cys Trp Lys Ser Tyr Ile Glu Ala Tyr Met Gln Glu
                405                 410                 415

Ala Glu Trp Ile Ala Ser Asn His Ile Pro Gly Phe Asp Glu Tyr Leu
            420                 425                 430

Met Asn Gly Val Lys Ser Ser Gly Met Arg Ile Leu Met Ile His Ala
        435                 440                 445

Leu Ile Leu Met Asp Thr Pro Leu Ser Asp Glu Ile Leu Glu Gln Leu
    450                 455                 460

Asp Ile Pro Ser Ser Lys Ser Gln Ala Leu Leu Ser Leu Ile Thr Arg
465                 470                 475                 480

Leu Val Asp Asp Val Lys Asp Phe Glu Asp Glu Gln Ala His Gly Glu
                485                 490                 495

Met Ala Ser Ser Ile Glu Cys Tyr Met Lys Asp Asn His Gly Ser Thr
            500                 505                 510

Arg Glu Asp Ala Leu Asn Tyr Leu Lys Ile Arg Ile Glu Ser Cys Val
        515                 520                 525

Gln Glu Leu Asn Lys Glu Leu Leu Glu Pro Ser Asn Met His Gly Ser
    530                 535                 540

Phe Arg Asn Leu Tyr Leu Asn Val Gly Met Arg Val Ile Phe Phe Met
545                 550                 555                 560

Leu Asn Asp Gly Asp Leu Phe Thr His Ser Asn Arg Lys Glu Ile Gln
                565                 570                 575

Asp Ala Ile Thr Lys Phe Phe Val Glu Pro Ile Ile Pro
            580                 585
```

<210> SEQ ID NO 30
<211> LENGTH: 1674
<212> TYPE: DNA
<213> ORGANISM: Artificial Sequence
<220> FEATURE:
<223> OTHER INFORMATION: Citrus valencene synthase V277 DNA
<300> PUBLICATION INFORMATION:
<310> PATENT DOCUMENT NUMBER: US20120246767
<311> PATENT FILING DATE: 2012-09-27

<400> SEQUENCE: 30

```
atgtctactc aagtctcagc atcttctcta gcccagattc cccaacccaa aaatcgtcct      60

gtggcaaact ttcaccccaa catttggggt gaccaattta tcacctacac tcctgaagac     120

aaggttactc gtgcctgcaa agaggagcag attgaagctt tgaaggaaga agttagaaga     180

atgattttag caaccggaag gaaaccaatt caaaaattga gattgattga tgaagttcaa     240

agattgggtg ttgcttacca ttttgaaaaa gaaattgaag atatgttgga tcacatttac     300

agagctgatc cttattttga ggctcatgaa tacaatgatt tgcatactgt ttctttgcat     360

ttcagattgt tgagacaaca aggtattaag atttcttgtg atgttttcga acaatttaag     420

gatgatgaag gtagattcaa aagttctttg attaatgatg ttcaaggcat gttgtctttg     480

tatgaagctg cttatatggc tgttagaggt gaacatattt tggatgaagc tattgcattt     540

actactactc atttgcaatc tgcagctcca catttgaagt cacctttggc tgaacaaatt     600

aaccatgctt tgtatagacc attgagaaaa actttgccaa gattggaagc aagatacatt     660

atgtcagtct accaagatga agctttccat aacaagactt tgttaaattt cgctaagttg     720

gatttcaata ttttgttgga tttgcataaa gaagaattga acgaattgac taaatggtgg     780
```

```
caagatttgg attttactac taaattgcca tatgctagag atagattggt tgaactgtac    840

ttttgggatt tggggactta ttttgaatca caatacgctt ttggtagaaa aatcatgact    900

aaattgaact acattttgtc cattattgat gatacctacg atgcttacgg tactttggaa    960

gaatgcacga tgttcagtga agctgttgct cgttggaaca ttgaagctgt tgatatgttg   1020

ccagattata tgcgaattat ctacagaact ttgttggata cattcaacga aatagaagag   1080

gatatggcta aacaacggag atctcattgt gtaagatacg ctaaagaaga aattcaaaag   1140

gttattggtg cttattacgt tcaagctaag tggttttctg aaggttatgt ccctactatt   1200

gaagaataca tgccaattgc tttgacttct tgcgcttaca gatttgttat taccaattct   1260

tttttgggta tgggtgattt cgctacaaag gaagtattcg aatggatttc tggtaatcca   1320

aaagttgtta aatctgcttc tgttatttgt agattgatgg acgatatgca aggacacgaa   1380

tttgaacaaa aaagaggtca cgttgcatct gcaattgaat gctatactaa acaacatggt   1440

gtttccaagg aagaggctat caagatgttc gaggaagatg ttgctaacgc ttggaaggat   1500

atcaatgaag aattaatgat gaaaccacca gttgttgcta gaccattgtt aggtactatt   1560

ttgaatttgg ctagagctat cgattttatc tataaagaag atgacggtta cactcattct   1620

tatttgatta aggaacaaat cgcatctgtt ttgggtgatc atgttccatt ttaa         1674
```

<210> SEQ ID NO 31
<211> LENGTH: 557
<212> TYPE: PRT
<213> ORGANISM: Artificial Sequence
<220> FEATURE:
<223> OTHER INFORMATION: Citrus valencene synthase V277 protein
<300> PUBLICATION INFORMATION:
<310> PATENT DOCUMENT NUMBER: US20120246767
<311> PATENT FILING DATE: 2012-09-27

<400> SEQUENCE: 31

```
Met Ser Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Ala Leu Lys Glu Glu Val Arg Arg Met Ile Leu Ala
    50                  55                  60

Thr Gly Arg Lys Pro Ile Gln Lys Leu Arg Leu Ile Asp Glu Val Gln
65                  70                  75                  80

Arg Leu Gly Val Ala Tyr His Phe Glu Lys Glu Ile Glu Asp Met Leu
                85                  90                  95

Asp His Ile Tyr Arg Ala Asp Pro Tyr Phe Glu Ala His Glu Tyr Asn
            100                 105                 110

Asp Leu His Thr Val Ser Leu His Phe Arg Leu Leu Arg Gln Gln Gly
        115                 120                 125

Ile Lys Ile Ser Cys Asp Val Phe Glu Gln Phe Lys Asp Asp Glu Gly
    130                 135                 140

Arg Phe Lys Ser Ser Leu Ile Asn Asp Val Gln Gly Met Leu Ser Leu
145                 150                 155                 160

Tyr Glu Ala Ala Tyr Met Ala Val Arg Gly Glu His Ile Leu Asp Glu
                165                 170                 175

Ala Ile Ala Phe Thr Thr Thr His Leu Gln Ser Ala Ala Pro His Leu
            180                 185                 190
```

```
Lys Ser Pro Leu Ala Glu Gln Ile Asn His Ala Leu Tyr Arg Pro Leu
        195                 200                 205

Arg Lys Thr Leu Pro Arg Leu Glu Ala Arg Tyr Ile Met Ser Val Tyr
    210                 215                 220

Gln Asp Glu Ala Phe His Asn Lys Thr Leu Leu Asn Phe Ala Lys Leu
225                 230                 235                 240

Asp Phe Asn Ile Leu Leu Asp Leu His Lys Glu Glu Leu Asn Glu Leu
                245                 250                 255

Thr Lys Trp Trp Gln Asp Leu Asp Phe Thr Thr Lys Leu Pro Tyr Ala
            260                 265                 270

Arg Asp Arg Leu Val Glu Leu Tyr Phe Trp Asp Leu Gly Thr Tyr Phe
        275                 280                 285

Glu Ser Gln Tyr Ala Phe Gly Arg Lys Ile Met Thr Lys Leu Asn Tyr
    290                 295                 300

Ile Leu Ser Ile Ile Asp Asp Thr Tyr Asp Ala Tyr Gly Thr Leu Glu
305                 310                 315                 320

Glu Cys Thr Met Phe Ser Glu Ala Val Ala Arg Trp Asn Ile Glu Ala
                325                 330                 335

Val Asp Met Leu Pro Asp Tyr Met Arg Ile Ile Tyr Arg Thr Leu Leu
            340                 345                 350

Asp Thr Phe Asn Glu Ile Glu Glu Asp Met Ala Lys Gln Arg Arg Ser
        355                 360                 365

His Cys Val Arg Tyr Ala Lys Glu Glu Ile Gln Lys Val Ile Gly Ala
    370                 375                 380

Tyr Tyr Val Gln Ala Lys Trp Phe Ser Glu Gly Tyr Val Pro Thr Ile
385                 390                 395                 400

Glu Glu Tyr Met Pro Ile Ala Leu Thr Ser Cys Ala Tyr Arg Phe Val
                405                 410                 415

Ile Thr Asn Ser Phe Leu Gly Met Gly Asp Phe Ala Thr Lys Glu Val
            420                 425                 430

Phe Glu Trp Ile Ser Gly Asn Pro Lys Val Val Lys Ser Ala Ser Val
        435                 440                 445

Ile Cys Arg Leu Met Asp Asp Met Gln Gly His Glu Phe Glu Gln Lys
    450                 455                 460

Arg Gly His Val Ala Ser Ala Ile Glu Cys Tyr Thr Lys Gln His Gly
465                 470                 475                 480

Val Ser Lys Glu Glu Ala Ile Lys Met Phe Glu Glu Asp Val Ala Asn
                485                 490                 495

Ala Trp Lys Asp Ile Asn Glu Glu Leu Met Met Lys Pro Pro Val Val
            500                 505                 510

Ala Arg Pro Leu Leu Gly Thr Ile Leu Asn Leu Ala Arg Ala Ile Asp
        515                 520                 525

Phe Ile Tyr Lys Glu Asp Asp Gly Tyr Thr His Ser Tyr Leu Ile Lys
    530                 535                 540

Glu Gln Ile Ala Ser Val Leu Gly Asp His Val Pro Phe
545                 550                 555
```

<210> SEQ ID NO 32
<211> LENGTH: 7927
<212> TYPE: DNA
<213> ORGANISM: Artificial Sequence
<220> FEATURE:
<223> OTHER INFORMATION: pALx31-108.2 expression vector DNA

<400> SEQUENCE: 32

-continued

```
cgcggccgcg tggaatattt cggatatcct tttgttgttt ccgggtgtac aatatggact     60
tcctcttttc tggcaaccaa acccatacat cgggattcct ataatacctt cgttggtctc    120
cctaacatgt aggtggcgga ggggagatat acaatagaac agataccaga caagacataa    180
tgggctaaac aagactacac caattacact gcctcattga tggtggtaca taacgaacta    240
atactgtagc cctagacttg atagccatca tcatatcgaa gtttcactac cctttttcca    300
tttgccatct attgaagtaa taataggcgc atgcaacttc ttttcttttt ttttcttttc    360
tctctccccc gttgttgtct caccatatcc gcaatgacaa aaaaatgatg gaagacacta    420
aaggaaaaaa ttaacgacaa agacagcacc aacagatgtc gttgttccag agctgatgag    480
gggtatctcg aagcacacga aactttttcc ttccttcatt cacgcacact actctctaat    540
gagcaacggt atacggcctt ccttccagtt acttgaattt gaaataaaaa aaagtttgct    600
gtcttgctat caagtataaa tagacctgca attattaatc ttttgtttcc tcgtcattgt    660
tctcgttccc tttcttcctt gtttcttttt ctgcacaata tttcaagcta taccaagcat    720
acaatcaact ccaagctgaa ttcgagctcg gtacccatca acaagtttgt acaaaaaagc    780
aggctatggc cccagctata gtgatgagta actacgaaga ggaggagatt gttcgccctg    840
ttgcagattt ttctccaagt ctttggggtg atcgtttcca ttcattctca gttgacaatc    900
aggttgcgga aaagtatgct caagagattg aaactttgaa ggaacaaaca agtactatgt    960
tgtctgctgc ttgtggaaca acattgactg agaaattgaa tttgatagat attattgagc   1020
gccttggaat agcttatcat ttcgagaaac aaatagaaga tatgttggat cacatttaca   1080
gagctgatcc ttattttgag gctcatgaat acaatgattt aaacacttca tccgttcaat   1140
ttcgactact cagacaacat ggttacaacg tctctccaaa tatatttagc agattccaag   1200
atgcaaatgg caaattcaag gagtctctta gaagcgacat caggggccta ctgaacttat   1260
acgaagcttc acatgtaagg actcataaag aggatatttt ggaagaagca cttgtttttt   1320
ctgttggtca tcttgaatct gcagctccac atttgaagtc acctctgagt aagcaagtga   1380
cacatgccct cgaacaatct ctccataaga gcattccaag agtcgagata cggtacttca   1440
tctccatcta cgaagaggag gaatttaaga atgatttgtt gcttcgattt gctaaattgg   1500
attacaactt acttcagatg ttgcacaagc atgaactcag tgaagtatca aggtggtgga   1560
aagatttgga tttcgtgaca acacttccat atgctaggga cagagcagtt gagtgctact   1620
tttggacgat gggggtgtat gctgaacctc aatactccca ggctcgtgtc atgcttgcta   1680
agactatagc aatgatttcc atagtagatg acacattcga tgcttatggc atcgtaaaag   1740
aacttgaagt ctacacagat gccatacaga ggtgggatat tagtcaaatt gatcgactcc   1800
cggaatatat gaaaatcagt tataaggctc ttttggatct ctatgacgat tatgaaaagg   1860
agttgtcaaa ggatggtaga tccgatgttg tccactatgc aaaagaaaga atgaaggaga   1920
ttgtgagaaa ctattttatt gaagcaaaat ggtttattga gggatatatg ccatctgttt   1980
ccgagtacct tagcaatgca ctagctacta gcacatatta cttgctaact acgacatcct   2040
acttgggaat gaaatcagca accaaggaac attttgaatg gttggctacg aaccctaaaa   2100
ttctggaagc taatgctaca ttatgccgag ttgttgatga catagccacg tatgaggttg   2160
agaagggtag gggtcaaatt gcaacaggaa ttgagtgtta tatgagggat tacggtgtat   2220
ccacagaagt agcaatggag aaattccaag aaatggctga catagcatgg aaggatgtaa   2280
atgaagaaat tcttcgacca acacctgtct cttcagaaat tcttactcgt attctcaacc   2340
```

```
tcgctcgaat tatagatgtc acttacaagc ataatcaaga tggatacact catcctgaaa   2400
aagtactaaa acctcacatc atcgccttgg tggtggattc tattgatatt tgaacccagc   2460
tttcttgtac aaagtggttg atggctcttc tagaatctct gcttttgtgc gcgtatgttt   2520
atgtatgtac ctctctctct atttctattt ttaaaccacc ctctcaataa aataaaaata   2580
ataaagtatt tttaaggaaa agacgtgttt aagcactgac tttatctact ttttgtacgt   2640
tttcattgat ataatgtgtt ttgtctctcc cttttctacg aaaatttcaa aaattgacca   2700
aaaaaaggaa tatatatacg aaaaactatt atatttatat atcatagtgt tgataaaaaa   2760
tgtttatcca ttggaccgtg tatcagggcc cggatcctct aggcttggca ctggccgtcg   2820
ttttacaacg tcgtgactgg gaaaaccctg gcgttaccca acttaatcgc cttgcagcac   2880
atccccctttt cgccagctgg cgtaatagcg aagaggcccg caccgatcgc ccttcccaac   2940
agttgcgcag cctgaatggc gaatggcgcc tgatgcggta ttttctcctt acgcatctgt   3000
gcggtatttc acaccgcata gggtaataac tgatataatt aaattgaagc tctaatttgt   3060
gagtttagta tacatgcatt tacttataat acagtttttt agttttgctg gccgcatctt   3120
ctcaaatatg cttcccagcc tgcttttctg taacgttcac cctctacctt agcatccctt   3180
ccctttgcaa atagtcctct tccaacaata ataatgtcag atcctgtaga gaccacatca   3240
tccacggttc tatactgttg acccaatgcg tctcccttgt catctaaacc cacaccgggt   3300
gtcataatca accaatcgta accttcatct cttccaccca tgtctctttg agcaataaag   3360
ccgataacaa aatctttgtc gctcttcgca atgtcaacag taccettagt atattctcca   3420
gtagataggg agcccttgca tgacaattct gctaacatca aaaggcctct aggttccttt   3480
gttacttctt ctgccgcctg cttcaaaccg ctaacaatac ctgggcccac cacaccgtgt   3540
gcattcgtaa tgtctgccca ttctgctatt ctgtatacac ccgcagagta ctgcaatttg   3600
actgtattac caatgtcagc aaattttctg tcttcgaaga gtaaaaaatt gtacttggcg   3660
gataatgcct ttagcggctt aactgtgccc tccatggaaa aatcagtcaa gatatccaca   3720
tgtgttttta gtaaacaaat tttgggacct aatgcttcaa ctaactccag taattccttg   3780
gtggtacgaa catccaatga agcacacaag tttgtttgct ttcgtgcat gatattaaat   3840
agcttggcag caacaggact aggatgagta gcagcacgtt ccttatatgt agctttcgac   3900
atgatttatc ttcgtttcgg tttttgttct gtgcagttgg gttaagaata ctgggcaatt   3960
tcatgtttct tcaacactac atatgcgtat atataccaat ctaagtctgt gctccttcct   4020
tcgttcttcc ttctgttcgg agattaccga atcaaaaaaa tttcaaggaa accgaaatca   4080
aaaaaaagaa taaaaaaaaa atgatgaatt gaaaagcact tgttacccat cattgaattt   4140
tgaacatccg aacctgggag ttttccctga aacagatagt atatttgaac ctgtataata   4200
atatatagtc tagcgcttta cggaagacaa tgtatgtatt tcggttcctg gagaaactat   4260
tgcatctatt gcataggtaa tcttgcacgt cgcatccccg gttcattttc tgcgtttcca   4320
tcttgcactt caatagcata tctttgttaa cgaagcatct gtgcttcatt ttgtaaaaca   4380
aaaatgcaac gcgagagcgc taatttttca aacaaagaat ctgagctgca tttttacaga   4440
acagaaatgc aacgcgaaag cgctatttta ccaacgaaga atctgtgctt catttttgta   4500
aaacaaaaat gcaacgcgag agcgctaatt tttcaaacaa agaatctgag ctgcattttt   4560
acagaacaga aatgcaacgc gagagcgcta ttttaccaac aaagaatcta tacttctttt   4620
ttgttctaca aaaatgcatc ccgagagcgc tatttttcta acaaagcatc ttagattact   4680
ttttttctcc tttgtgcgct ctataatgca gtctcttgat aactttttgc actgtaggtc   4740
```

-continued

```
cgttaaggtt agaagaaggc tactttggtg tctattttct cttccataaa aaaagcctga   4800
ctccacttcc cgcgtttact gattactagc gaagctgcgg gtgcattttt tcaagataaa   4860
ggcatccccg attatattct ataccgatgt ggattgcgca tactttgtga acagaaagtg   4920
atagcgttga tgattcttca ttggtcagaa aattatgaac ggtttcttct attttgtctc   4980
tatatactac gtataggaaa tgtttacatt ttcgtattgt tttcgattca ctctatgaat   5040
agttcttact acaatttttt tgtctaaaga gtaatactag agataaacat aaaaaatgta   5100
gaggtcgagt ttagatgcaa gttcaaggag cgaaaggtgg atgggtaggt tatataggga   5160
tatagcacag agatatatag caaagagata cttttgagca atgtttgtgg aagcggtatt   5220
cgcaatattt tagtagctcg ttacagtccg gtgcgttttt ggttttttga aagtgcgtct   5280
tcagagcgct tttggttttc aaaagcgctc tgaagttcct atactttcta gctagagaat   5340
aggaacttcg gaataggaac ttcaaagcgt ttccgaaaac gagcgcttcc gaaaatgcaa   5400
cgcgagctgc gcacatacag ctcactgttc acgtcgcacc tatatctgcg tgttgcctgt   5460
atatatatat acatgagaag aacggcatag tgcgtgttta tgcttaaatg cgttatggtg   5520
cactctcagt acaatctgct ctgatgccgc atagttaagc cagccccgac acccgccaac   5580
acccgctgac gcgccctgac gggcttgtct gctcccggca tccgcttaca gacaagctgt   5640
gaccgtctcc gggagctgca tgtgtcagag gttttcaccg tcatcaccga aacgcgcgag   5700
acgaaagggc ctcgtgatac gcctattttt ataggttaat gtcatgataa taatggtttc   5760
ttagacgtca ggtggcactt ttcggggaaa tgtgcgcgga acccctattt gtttattttt   5820
ctaaatacat tcaaatatgt atccgctcat gagacaataa ccctgataaa tgcttcaata   5880
atattgaaaa aggaagagta tgagtattca acatttccgt gtcgccctta ttcccttttt   5940
tgcggcattt tgccttcctg tttttgctca cccagaaacg ctggtgaaag taaaagatgc   6000
tgaagatcag ttgggtgcac gagtgggtta catcgaactg gatctcaaca gcggtaagat   6060
ccttgagagt tttcgccccg aagaacgttt tccaatgatg agcactttta aagttctgct   6120
atgtggcgcg gtattatccc gtattgacgc cgggcaagag caactcggtc gccgcataca   6180
ctattctcag aatgacttgg ttgagtactc accagtcaca gaaaagcatc ttacggatgg   6240
catgacagta agagaattat gcagtgctgc cataaccatg agtgataaca ctgcggccaa   6300
cttacttctg acaacgatcg gaggaccgaa ggagctaacc gcttttttgc acaacatggg   6360
ggatcatgta actcgccttg atcgttggga accggagctg aatgaagcca taccaaacga   6420
cgagcgtgac accacgatgc ctgtagcaat ggcaacaacg ttgcgcaaac tattaactgg   6480
cgaactactt actctagctt cccggcaaca attaatagac tggatggagg cggataaagt   6540
tgcaggacca cttctgcgct cggcccttcc ggctggctgg tttattgctg ataaatctgg   6600
agccggtgag cgtgggtctc gcggtatcat tgcagcactg gggccagatg gtaagccctc   6660
ccgtatcgta gttatctaca cgacggggag tcaggcaact atggatgaac gaaatagaca   6720
gatcgctgag ataggtgcct cactgattaa gcattggtaa ctgtcagacc aagtttactc   6780
atatatactt tagattgatt taaaacttca tttttaattt aaaaggatct aggtgaagat   6840
cctttttgat aatctcatga ccaaaatccc ttaacgtgag ttttcgttcc actgagcgtc   6900
agaccccgta gaaaagatca aaggatcttc ttgagatcct ttttttctgc gcgtaatctg   6960
ctgcttgcaa acaaaaaaac caccgctacc agcggtggtt tgtttgccgg atcaagagct   7020
accaactctt tttccgaagg taactggctt cagcagagcg cagataccaa atactgttct   7080
```

tctagtgtag ccgtagttag gccaccactt caagaactct gtagcaccgc ctacatacca 7140
cgctctgcta atcctgttac cagtggctgc tgccagtggc gataagtcgt gtcttaccgg 7200
gttggactca agacgatagt taccggataa ggcgcagcgg tcgggctgaa cggggggttc 7260
gtgcacacag cccagcttgg agcgaacgac ctacaccgaa ctgagatacc tacagcgtga 7320
gctatgagaa agcgccacgc ttcccgaagg gagaaaggcg gacaggtatc cggtaagcgg 7380
cagggtcgga acaggagagc gcacgaggga gcttccaggg ggaaacgcct ggtatcttta 7440
tagtcctgtc gggtttcgcc acctctgact tgagcgtcga tttttgtgat gctcgtcagg 7500
ggggcggagc ctatggaaaa acgccagcaa cgcggccttt ttacggttcc tggccttttg 7560
ctggcctttt gctcacatgt tctttcctgc gttatcccct gattctgtgg ataaccgtat 7620
taccgccttt gagtgagctg ataccgctcg ccgcagccga acgaccgagc gcagcgagtc 7680
agtgagcgag gaagcggaag agcgcccaat acgcaaaccg cctctccccg cgcgttggcc 7740
gattcattaa tgcagctggc acgacaggtt tcccgactgg aaagcgggca gtgacgcaac 7800
gcaattaatg tgagttagct cactcattag gcaccccagg ctttacactt tatgcttccg 7860
gctcgtatgt tgtgtggaat tgtgagcgga taacaatttc acacaggaaa cagctatgac 7920
atgatta 7927

<210> SEQ ID NO 33
<211> LENGTH: 7902
<212> TYPE: DNA
<213> ORGANISM: Artificial Sequence
<220> FEATURE:
<223> OTHER INFORMATION: pALX63-71 expression construct DNA

<400> SEQUENCE: 33
cgcggccgcg tggaatattt cggatatcct tttgttgttt ccgggtgtac aatatggact 60
tcctcttttc tggcaaccaa acccatacat cgggattcct ataatacctt cgttggtctc 120
cctaacatgt aggtggcgga ggggagatat acaatagaac agataccaga caagacataa 180
tgggctaaac aagactacac caattacact gcctcattga tggtggtaca taacgaacta 240
atactgtagc cctagacttg atagccatca tcatatcgaa gtttcactac cctttttcca 300
tttgccatct attgaagtaa taataggcgc atgcaacttc ttttcttttt ttttcttttc 360
tctctccccc gttgttgtct caccatatcc gcaatgacaa aaaaatgatg gaagacacta 420
aaggaaaaaa ttaacgacaa agacagcacc aacagatgtc gttgttccag agctgatgag 480
gggtatctcg aagcacacga aactttttcc ttccttcatt cacgcacact actctctaat 540
gagcaacggt atacggcctt ccttccagtt acttgaattt gaaataaaaa aaagtttgct 600
gtcttgctat caagtataaa tagacctgca attattaatc ttttgtttcc tcgtcattgt 660
tctcgttccc tttcttcctt gtttcttttt ctgcacaata tttcaagcta taccaagcat 720
acaatcaact ccaagctgaa ttcgagctcg gtaccattaa aaaaaatgtc tcttaatgta 780
cttagtacgt caggttcagc tccaacaacc aaatcatctg agattactcg taggtccgct 840
aattatcatc ctagtttatg gggagacaag ttcctcgaat attcgagccc agatcacctg 900
aaaaatgatt cattcacaga aaagaaacat gaacaactca aagaagaggt gaagaagatg 960
ctagtagaaa cggttcaaaa gcctcaacaa cagctgaatc tgatcaacga aatacaacga 1020
ctaggtttat catacctttt tgaacccgaa attgaggctg cattgcagga aatcagtgtt 1080
acctatgatg aattttgttg tagtacagac gctgatgacc ttcacaatgt tgctctctct 1140
ttccgaatac ttagagaaca tggacataat gtatcttctg atgtgtttca gaaattcatg 1200

-continued

```
gatagcaatg ggaagttgaa agactacttg gttaatgatg ctagaggact gttaagcttg   1260
tacgaagcaa cacattttcg ggttcataat gatgataaac ttgaagagtt gctgtcagta   1320
acaacctctc gtcttgagca tctcaaatcc cacgtgaagt accctcttga ggacgaaatc   1380
agtagagcac ttaagcatcc cctccataaa gaactaaatc gactaggagc gagatattac   1440
atatccattt acgaaaaatt tgattcacac aataaattgc ttttggagtt tgcaaaacta   1500
gattttaacc gactgcagaa aatgtatcaa catgagctag cccaccttac aaggtggtgg   1560
aaagatttag attttacaaa caaacttcca tttgcaagag atagaattgt tgagggttac   1620
ttttggatct taggaatgta ctttgagcca gaacgtaagg atgtcaggga attcttgaac   1680
agagtatttg cacttattac agtagttgat gacacgtatg atgtgtatgg tacattcaaa   1740
gaacttctac tgttcactga tgcaattgaa agatggggaa ctagtgattt ggatcagcta   1800
ccgggatata tgagaattat ttatcaagct ctcatggatg tttataatca aatggaggaa   1860
aagttgtcaa tgaaagctga ttgtccaaca taccgtcttg agtttgcaat agaaacagtt   1920
aaagccatgt tcagatcata cctcgaagaa gctagatggt ccaaagaaca ttatatccca   1980
tcgatggaag agtatatgac cgtggcactg gtatcggttg gctacaaaac catattaact   2040
aattcctttg ttggaatggg ggatattgca acacgggaag tttttgagtg ggtgttcaat   2100
agtccattga ttattagagc ttccgactta attgccagat tgggagatga tattggaggc   2160
catgaggagg agcagaagaa aggagacgca gccactgcta tcgagtgtta cataaaagag   2220
aatcatgtaa caaagcatga agcttatgat gaatttcaga aacaaattga taatgcttgg   2280
aaggatttga ataaggaagc tctacgtcca tttcctgttc caatgacttt catcacaaga   2340
gttgttcatt ttacgcgcgc catacatgtt atttatgccg actttagtga tggttacaca   2400
cgttcagaca aggcgatcag aggttacata acttcactgc tcgtggatcc tattcctttg   2460
taatctagaa tctctgcttt tgtgcgcgta tgtttatgta tgtacctctc tctctatttc   2520
tatttttaaa ccaccctctc aataaaataa aaataataaa gtatttttaa ggaaaagacg   2580
tgtttaagca ctgactttat ctactttttg tacgttttca ttgatataat gtgttttgtc   2640
tctccctttt ctacgaaaat ttcaaaaatt gaccaaaaaa aggaatatat atacgaaaaa   2700
ctattatatt tatatatcat agtgttgata aaaaatgttt atccattgga ccgtgtatca   2760
gggcccggat cctctaggct tggcactggc cgtcgtttta caacgtcgtg actgggaaaa   2820
ccctggcgtt acccaactta atcgccttgc agcacatccc cctttcgcca gctggcgtaa   2880
tagcgaagag gcccgcaccg atcgcccttc ccaacagttg cgcagcctga atggcgaatg   2940
gcgcctgatg cggtattttc tccttacgca tctgtgcggt atttcacacc gcatagggta   3000
ataactgata taattaaatt gaagctctaa tttgtgagtt tagtatacat gcatttactt   3060
ataatacagt tttttagttt tgctggccgc atcttctcaa atatgcttcc cagcctgctt   3120
ttctgtaacg ttcaccctct accttagcat cccttccctt tgcaaatagt cctcttccaa   3180
caataataat gtcagatcct gtagagacca catcatccac ggttctatac tgttgaccca   3240
atgcgtctcc cttgtcatct aaacccacac cgggtgtcat aatcaaccaa tcgtaacctt   3300
catctcttcc acccatgtct ctttgagcaa taaagccgat aacaaaatct ttgtcgctct   3360
tcgcaatgtc aacagtaccc ttagtatatt ctccagtaga tagggagccc ttgcatgaca   3420
attctgctaa catcaaaagg cctctaggtt cctttgttac ttcttctgcc gcctgcttca   3480
aaccgctaac aatacctggg cccaccacac cgtgtgcatt cgtaatgtct gcccattctg   3540
```

-continued

```
ctattctgta tacacccgca gagtactgca atttgactgt attaccaatg tcagcaaatt   3600
ttctgtcttc gaagagtaaa aaattgtact tggcggataa tgcctttagc ggcttaactg   3660
tgccctccat ggaaaaatca gtcaagatat ccacatgtgt ttttagtaaa caaattttgg   3720
gacctaatgc ttcaactaac tccagtaatt ccttggtggt acgaacatcc aatgaagcac   3780
acaagtttgt ttgcttttcg tgcatgatat taaatagctt ggcagcaaca ggactaggat   3840
gagtagcagc acgttcctta tatgtagctt tcgacatgat ttatcttcgt ttcggttttt   3900
gttctgtgca gttgggttaa gaatactggg caatttcatg tttcttcaac actacatatg   3960
cgtatatata ccaatctaag tctgtgctcc ttccttcgtt cttccttctg ttcggagatt   4020
accgaatcaa aaaaatttca aggaaaccga aatcaaaaaa aagaataaaa aaaaaatgat   4080
gaattgaaaa gcacttgtta cccatcattg aattttgaac atccgaacct gggagttttc   4140
cctgaaacag atagtatatt tgaacctgta taataatata tagtctagcg ctttacggaa   4200
gacaatgtat gtatttcggt tcctggagaa actattgcat ctattgcata ggtaatcttg   4260
cacgtcgcat ccccggttca ttttctgcgt ttccatcttg cacttcaata gcatatcttt   4320
gttaacgaag catctgtgct tcattttgta aaacaaaaat gcaacgcgag agcgctaatt   4380
tttcaaacaa agaatctgag ctgcattttt acagaacaga aatgcaacgc gaaagcgcta   4440
ttttaccaac gaagaatctg tgcttcattt ttgtaaaaca aaaatgcaac gcgagagcgc   4500
taatttttca aacaaagaat ctgagctgca tttttacaga acagaaatgc aacgcgagag   4560
cgctatttta ccaacaaaga atctatactt cttttttgtt ctacaaaaat gcatcccgag   4620
agcgctattt ttctaacaaa gcatcttaga ttactttttt tctcctttgt gcgctctata   4680
atgcagtctc ttgataactt tttgcactgt aggtccgtta aggttagaag aaggctactt   4740
tggtgtctat tttctcttcc ataaaaaaag cctgactcca cttcccgcgt ttactgatta   4800
ctagcgaagc tgcgggtgca ttttttcaag ataaaggcat ccccgattat attctatacc   4860
gatgtggatt gcgcatactt tgtgaacaga aagtgatagc gttgatgatt cttcattggt   4920
cagaaaatta tgaacggttt cttctatttt gtctctatat actacgtata ggaaatgttt   4980
acattttcgt attgttttcg attcactcta tgaatagttc ttactacaat ttttttgtct   5040
aaagagtaat actagagata aacataaaaa atgtagaggt cgagtttaga tgcaagttca   5100
aggagcgaaa ggtggatggg taggttatat agggatatag cacagagata tatagcaaag   5160
agatactttt gagcaatgtt tgtggaagcg gtattcgcaa tattttagta gctcgttaca   5220
gtccggtgcg tttttggttt tttgaaagtg cgtcttcaga gcgcttttgg ttttcaaaag   5280
cgctctgaag ttcctatact ttctagctag agaataggaa cttcggaata ggaacttcaa   5340
agcgtttccg aaaacgagcg cttccgaaaa tgcaacgcga gctgcgcaca tacagctcac   5400
tgttcacgtc gcacctatat ctgcgtgttg cctgtatata tatatacatg agaagaacgg   5460
catagtgcgt gtttatgctt aaatgcgtta tggtgcactc tcagtacaat ctgctctgat   5520
gccgcatagt taagccagcc ccgacacccg ccaacacccg ctgacgcgcc ctgacgggct   5580
tgtctgctcc cggcatccgc ttacagacaa gctgtgaccg tctccgggag ctgcatgtgt   5640
cagaggtttt caccgtcatc accgaaacgc gcgagacgaa agggcctcgt gatacgccta   5700
tttttatagg ttaatgtcat gataataatg gtttcttaga cgtcaggtgg cacttttcgg   5760
ggaaatgtgc gcggaacccc tatttgttta tttttctaaa tacattcaaa tatgtatccg   5820
ctcatgagac aataaccctg ataaatgctt caataatatt gaaaaaggaa gagtatgagt   5880
attcaacatt tccgtgtcgc ccttattccc ttttttgcgg cattttgcct tcctgttttt   5940
```

```
gctcacccag aaacgctggt gaaagtaaaa gatgctgaag atcagttggg tgcacgagtg   6000

ggttacatcg aactggatct caacagcggt aagatccttg agagttttcg ccccgaagaa   6060

cgttttccaa tgatgagcac ttttaaagtt ctgctatgtg gcgcggtatt atcccgtatt   6120

gacgccgggc aagagcaact cggtcgccgc atacactatt ctcagaatga cttggttgag   6180

tactcaccag tcacagaaaa gcatcttacg gatggcatga cagtaagaga attatgcagt   6240

gctgccataa ccatgagtga taacactgcg gccaacttac ttctgacaac gatcggagga   6300

ccgaaggagc taaccgcttt tttgcacaac atgggggatc atgtaactcg ccttgatcgt   6360

tgggaaccgg agctgaatga agccatacca aacgacgagc gtgacaccac gatgcctgta   6420

gcaatggcaa caacgttgcg caaactatta actggcgaac tacttactct agcttcccgg   6480

caacaattaa tagactggat ggaggcggat aaagttgcag gaccacttct gcgctcggcc   6540

cttccggctg gctggtttat tgctgataaa tctggagccg gtgagcgtgg gtctcgcggt   6600

atcattgcag cactggggcc agatggtaag ccctcccgta tcgtagttat ctacacgacg   6660

gggagtcagg caactatgga tgaacgaaat agacagatcg ctgagatagg tgcctcactg   6720

attaagcatt ggtaactgtc agaccaagtt tactcatata tactttagat tgatttaaaa   6780

cttcattttt aatttaaaag gatctaggtg aagatccttt ttgataatct catgaccaaa   6840

atcccttaac gtgagttttc gttccactga gcgtcagacc ccgtagaaaa gatcaaagga   6900

tcttcttgag atcctttttt tctgcgcgta atctgctgct tgcaaacaaa aaaaccaccg   6960

ctaccagcgg tggtttgttt gccggatcaa gagctaccaa ctctttttcc gaaggtaact   7020

ggcttcagca gagcgcagat accaaatact gttcttctag tgtagccgta gttaggccac   7080

cacttcaaga actctgtagc accgcctaca tacctcgctc tgctaatcct gttaccagtg   7140

gctgctgcca gtggcgataa gtcgtgtctt accgggttgg actcaagacg atagttaccg   7200

gataaggcgc agcggtcggg ctgaacgggg ggttcgtgca cacagcccag cttggagcga   7260

acgacctaca ccgaactgag atacctacag cgtgagctat gagaaagcgc cacgcttccc   7320

gaagggagaa aggcggacag gtatccggta agcggcaggg tcggaacagg agagcgcacg   7380

agggagcttc cagggggaaa cgcctggtat ctttatagtc ctgtcgggtt tcgccacctc   7440

tgacttgagc gtcgattttt gtgatgctcg tcaggggggc ggagcctatg gaaaaacgcc   7500

agcaacgcgg cctttttacg gttcctggcc ttttgctggc cttttgctca catgttcttt   7560

cctgcgttat cccctgattc tgtggataac cgtattaccg cctttgagtg agctgatacc   7620

gctcgccgca gccgaacgac cgagcgcagc gagtcagtga gcgaggaagc ggaagagcgc   7680

ccaatacgca aaccgcctct ccccgcgcgt tggccgattc attaatgcag ctggcacgac   7740

aggtttcccg actggaaagc gggcagtgac gcaacgcaat taatgtgagt tagctcactc   7800

attaggcacc ccaggcttta cactttatgc ttccggctcg tatgttgtgt ggaattgtga   7860

gcggataaca atttcacaca ggaaacagct atgacatgat ta                      7902
```

<210> SEQ ID NO 34
<211> LENGTH: 548
<212> TYPE: PRT
<213> ORGANISM: Citrus sinensis
<220> FEATURE:
<223> OTHER INFORMATION: Citrus valencene synthase protein
<300> PUBLICATION INFORMATION:
<308> DATABASE ACCESSION NUMBER: Genbank AAQ04608
<309> DATABASE ENTRY DATE: 2004-01-12

<400> SEQUENCE: 34

```
Met Ser Ser Gly Glu Thr Phe Arg Pro Thr Ala Asp Phe His Pro Ser
 1               5                  10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60

Leu Ile Asp Glu Val Gln Arg Leu Gly Val Ala Tyr His Phe Glu Lys
65                  70                  75                  80

Glu Ile Gly Asp Ala Ile Gln Lys Leu Cys Pro Ile Tyr Ile Asp Ser
                85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125

Asp Glu Gly Arg Phe Lys Ser Ser Leu Ile Asn Asp Val Gln Gly Met
    130                 135                 140

Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
        195                 200                 205

Phe Met Ser Met Ile Asn Ser Thr Ser Asp His Leu Cys Asn Lys Thr
    210                 215                 220

Leu Leu Asn Phe Ala Lys Leu Asp Phe Asn Ile Leu Leu Glu Leu His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270

Trp Asp Leu Gly Thr Tyr Phe Glu Pro Gln Tyr Ala Phe Gly Arg Lys
        275                 280                 285

Ile Met Thr Gln Leu Asn Tyr Ile Leu Ser Ile Ile Asp Asp Thr Tyr
    290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335

Leu Ile Tyr Arg Thr Leu Leu Asp Ala Phe Asn Glu Ile Glu Glu Asp
            340                 345                 350

Met Ala Lys Gln Gly Arg Ser His Cys Val Arg Tyr Ala Lys Glu Glu
        355                 360                 365

Asn Gln Lys Val Ile Gly Ala Tyr Ser Val Gln Ala Lys Trp Phe Ser
    370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
                405                 410                 415
```

-continued

```
Asp Phe Ala Thr Lys Glu Val Phe Glu Trp Ile Ser Asn Asn Pro Lys
            420                 425                 430

Val Val Lys Ala Ala Ser Val Ile Cys Arg Leu Met Asp Asp Met Gln
        435                 440                 445

Gly His Glu Phe Glu Gln Lys Arg Gly His Val Ala Ser Ala Ile Glu
    450                 455                 460

Cys Tyr Thr Lys Gln His Gly Val Ser Lys Glu Glu Ala Ile Lys Met
465                 470                 475                 480

Phe Glu Glu Glu Val Ala Asn Ala Trp Lys Asp Ile Asn Glu Glu Leu
                485                 490                 495

Met Met Lys Pro Thr Val Val Ala Arg Pro Leu Leu Gly Thr Ile Leu
            500                 505                 510

Asn Leu Ala Arg Ala Ile Asp Phe Ile Tyr Lys Glu Asp Asp Gly Tyr
        515                 520                 525

Thr His Ser Tyr Leu Ile Lys Asp Gln Ile Ala Ser Val Leu Gly Asp
    530                 535                 540

His Val Pro Phe
545


<210> SEQ ID NO 35
<211> LENGTH: 5
<212> TYPE: PRT
<213> ORGANISM: Artificial Sequence
<220> FEATURE:
<223> OTHER INFORMATION: aspartate rich region 1 motif
<220> FEATURE:
<221> NAME/KEY: VARIANT
<222> LOCATION: 3, 4
<223> OTHER INFORMATION: Xaa = Any Amino Acid

<400> SEQUENCE: 35

Asp Asp Xaa Xaa Asp
 1               5


<210> SEQ ID NO 36
<211> LENGTH: 9
<212> TYPE: PRT
<213> ORGANISM: Artificial Sequence
<220> FEATURE:
<223> OTHER INFORMATION: NSD/DTE motif
<220> FEATURE:
<221> NAME/KEY: VARIANT
<222> LOCATION: 1
<223> OTHER INFORMATION: Xaa = Asn or Asp
<220> FEATURE:
<221> NAME/KEY: VARIANT
<222> LOCATION: 2, 3, 4, 6, 7, 8
<223> OTHER INFORMATION: Xaa = Any Amino Acid
<220> FEATURE:
<221> NAME/KEY: VARIANT
<222> LOCATION: 5
<223> OTHER INFORMATION: Xaa = Ser or Thr

<400> SEQUENCE: 36

Xaa Xaa Xaa Xaa Xaa Xaa Xaa Xaa Glu
 1               5


<210> SEQ ID NO 37
<211> LENGTH: 548
<212> TYPE: PRT
<213> ORGANISM: Citrus sinensis
<220> FEATURE:
<223> OTHER INFORMATION: Valencene synthase A517I, I518V
<300> PUBLICATION INFORMATION:
<308> DATABASE ACCESSION NUMBER: GenBank AAQ04608.1
<309> DATABASE ENTRY DATE: 2004-01-12
```

<400> SEQUENCE: 37

```
Met Ser Ser Gly Glu Thr Phe Arg Pro Thr Ala Asp Phe His Pro Ser
1               5                   10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60

Leu Ile Asp Glu Val Gln Arg Leu Gly Val Ala Tyr His Phe Glu Lys
65                  70                  75                  80

Glu Ile Gly Asp Ala Ile Gln Lys Leu Cys Pro Ile Tyr Ile Asp Ser
                85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125

Asp Glu Gly Arg Phe Lys Ser Ser Leu Ile Asn Asp Val Gln Gly Met
    130                 135                 140

Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
        195                 200                 205

Phe Met Ser Met Ile Asn Ser Thr Ser Asp His Leu Cys Asn Lys Thr
    210                 215                 220

Leu Leu Asn Phe Ala Lys Leu Asp Phe Asn Ile Leu Leu Glu Leu His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270

Trp Asp Leu Gly Thr Tyr Phe Glu Pro Gln Tyr Ala Phe Gly Arg Lys
        275                 280                 285

Ile Met Thr Gln Leu Asn Tyr Ile Leu Ser Ile Ile Asp Asp Thr Tyr
    290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335

Leu Ile Tyr Arg Thr Leu Leu Asp Ala Phe Asn Glu Ile Glu Glu Asp
            340                 345                 350

Met Ala Lys Gln Gly Arg Ser His Cys Val Arg Tyr Ala Lys Glu Glu
        355                 360                 365

Asn Gln Lys Val Ile Gly Ala Tyr Ser Val Gln Ala Lys Trp Phe Ser
    370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
```

```
                405                 410                 415

Asp Phe Ala Thr Lys Glu Val Phe Glu Trp Ile Ser Asn Asn Pro Lys
            420                 425                 430

Val Val Lys Ala Ala Ser Val Ile Cys Arg Leu Met Asp Asp Met Gln
        435                 440                 445

Gly His Glu Phe Glu Gln Lys Arg Gly His Val Ala Ser Ala Ile Glu
    450                 455                 460

Cys Tyr Thr Lys Gln His Gly Val Ser Lys Glu Glu Ala Ile Lys Met
465                 470                 475                 480

Phe Glu Glu Glu Val Ala Asn Ala Trp Lys Asp Ile Asn Glu Glu Leu
                485                 490                 495

Met Met Lys Pro Thr Val Val Ala Arg Pro Leu Leu Gly Thr Ile Leu
            500                 505                 510

Asn Leu Ala Arg Ile Val Asp Phe Ile Tyr Lys Glu Asp Asp Gly Tyr
        515                 520                 525

Thr His Ser Tyr Leu Ile Lys Asp Gln Ile Ala Ser Val Leu Gly Asp
    530                 535                 540

His Val Pro Phe
545


<210> SEQ ID NO 38
<211> LENGTH: 550
<212> TYPE: PRT
<213> ORGANISM: Perilla frutescens var. frutescens
<220> FEATURE:
<223> OTHER INFORMATION: Valencene synthase protein
<300> PUBLICATION INFORMATION:
<308> DATABASE ACCESSION NUMBER: GenBank AAX16077.1
<309> DATABASE ENTRY DATE: 2005-03-01

<400> SEQUENCE: 38

Met Ala Ser Glu Gln Ala Gln Asn His Arg Pro Val Ala Asp Phe Ser
 1               5                  10                  15

Pro Ser Leu Trp Gly Asp Gln Phe Val Lys Tyr Asp Ser Cys Pro Gln
            20                  25                  30

Val Gln Lys Lys Tyr Ser Asn Thr Val Asp Val Leu Lys Lys Glu Val
        35                  40                  45

Lys Gly Met Ile Thr Ala Pro Gly Thr Lys Met Val Asp Thr Met Glu
    50                  55                  60

Leu Ile Asp Thr Ile Glu Arg Leu Gly Val Ser Phe His Phe Gln Asp
65                  70                  75                  80

Glu Ile Glu Gln Lys Leu Gln Gln Phe Phe Asp Leu Lys Thr Asp Tyr
                85                  90                  95

Cys Asn Asp Gly Asp Asp Ala Tyr Asp Leu Tyr Thr Val Ala Leu His
            100                 105                 110

Phe Arg Leu Phe Arg Gln His Gly Tyr Arg Ile Ser Cys Asp Ile Phe
        115                 120                 125

Gly Arg Trp Ile Asp Gly Asn Gly Lys Phe Lys Glu Gly Leu Lys Ser
    130                 135                 140

Asp Gly Lys Ser Leu Leu Ser Leu Tyr Glu Ala Ser Tyr Leu Arg Thr
145                 150                 155                 160

Arg Gly Glu Thr Ile Leu Asp Glu Ala Leu Asp Phe Ala Ala Ala Ser
                165                 170                 175

Leu Lys Ser Ile Ala Pro His Leu Gln Ser Pro Leu Gly Lys Gln Val
            180                 185                 190

Val His Ala Leu Val Gln Pro Leu His Phe Gly Asn Pro Arg Ile Glu
```

-continued

```
        195                 200                 205

Ala Arg Asn Phe Ile Ser Ile Tyr Glu Glu Tyr Glu Gly Met Asn Glu
    210                 215                 220

Ala Leu Leu Arg Leu Ala Lys Leu Asp Tyr Asn Leu Leu Gln Met Leu
225                 230                 235                 240

His Lys Glu Glu Leu His Gln Val Ser Arg Trp Trp Lys Asp Leu Asp
                245                 250                 255

Leu Ile Thr Lys Leu Pro Tyr Ala Arg Asp Arg Val Val Glu Cys Phe
            260                 265                 270

Phe Trp Ala Val Gly Val Tyr His Glu Pro Gln Tyr Ser Arg Ala Arg
        275                 280                 285

Val Met Leu Thr Lys Thr Ile Val Met Thr Ser Ile Ile Asp Asp Thr
    290                 295                 300

Tyr Asp Ala Tyr Gly Thr Ile Glu Glu Leu Asp Ile Phe Thr Glu Ala
305                 310                 315                 320

Ile Glu Arg Trp Asn Val Glu Glu Thr Lys Arg Leu Pro Glu Tyr Met
                325                 330                 335

Lys Pro Leu Tyr Lys Ala Leu Leu Glu Leu Tyr Lys Gln Phe Glu Gln
            340                 345                 350

Glu Leu Glu Lys Glu Gly Arg Ser Tyr Val Ala Tyr Tyr Ala Ile Glu
        355                 360                 365

Ser Leu Lys Glu Leu Val Arg Ser Tyr Arg Ile Glu Ala Lys Trp Phe
    370                 375                 380

Ile Gln Gly Tyr Leu Pro Pro Tyr Glu Glu Tyr Leu Lys Asn Ala Leu
385                 390                 395                 400

Ile Thr Cys Thr Tyr Cys Tyr His Thr Thr Thr Ser Leu Leu Gly Val
                405                 410                 415

Glu Ser Ala Ile Lys Glu Asn Phe Glu Trp Leu Ser Asn Lys Pro Lys
            420                 425                 430

Met Leu Val Ala Gly Leu Leu Ile Cys Arg Leu Ile Asp Asp Ile Ala
        435                 440                 445

Thr Tyr Ile Leu Glu Arg Gly Arg Gly Gln Val Ala Thr Gly Ile Glu
    450                 455                 460

Ser Tyr Met Lys Asp Asn Gly Ala Thr Gln Glu Glu Pro Ile Ala Lys
465                 470                 475                 480

Ile Phe Glu Ile Ala Thr Asp Ala Trp Lys Asp Ile Asn Asp Glu Cys
                485                 490                 495

Leu Arg Pro Ser Leu Tyr Asn Ser Arg Asp Val Leu Met Arg Ile Phe
            500                 505                 510

Asn Leu Glu Arg Ile Ile Asp Val Thr Tyr Lys Gly Asn Gln Asp Arg
        515                 520                 525

Tyr Thr Gln Pro Glu Lys Val Leu Lys Pro His Ile Ile Val Phe Phe
    530                 535                 540

Phe Asp Pro Ile Leu Ile
545                 550
```

<210> SEQ ID NO 39
<211> LENGTH: 1653
<212> TYPE: DNA
<213> ORGANISM: Perilla frutescens var. frutescens
<220> FEATURE:
<223> OTHER INFORMATION: Valencene synthase DNA
<300> PUBLICATION INFORMATION:
<308> DATABASE ACCESSION NUMBER: GenBank AY917195.1
<309> DATABASE ENTRY DATE: 2005-03-01

<400> SEQUENCE: 39
atggcttcag aacaagcaca aaatcatcgc cccgtcgccg atttctcccc cagcttgtgg 60
ggcgatcagt tcgtcaaata tgattcttgt ccacaggttc agaagaagta ttcgaacacg 120
gttgatgttt tgaagaagga agttaagggt atgataactg ctcctggaac caaaatggtc 180
gacacgatgg agctgattga cacgatcgaa cgtctaggcg tgtcgtttca ctttcaagat 240
gagattgaac aaaaattgca gcagtttttt gatctcaaaa cagattattg caacgatggt 300
gatgacgcct atgatttgta cactgttgct cttcatttcc gattattcag gcaacatggc 360
taccgtatat cttgtgacat ttttggtaga tggatcgatg ggaatgggaa attcaaggag 420
ggactgaaga gtgatgggaa gagtttgcta agtctgtacg aggcgtcgta tctgagaaca 480
cgtggcgaaa ccatactcga cgaggcgctc gactttgctg cggctagtct gaagtcgata 540
gcgccacacc tccaatcacc ccttgggaaa caagttgtgc acgccctagt gcagcctttg 600
cactttggca atccaagaat cgaagcgcgt aatttcatct ccatctatga ggaatatgaa 660
ggcatgaatg aagctctctt gaggttagct aaattagact ataatctatt gcaaatgcta 720
cataaggagg aacttcatca agtctcgagg tggtggaaag atttggatct gatcacgaaa 780
cttccatatg caagagatag agtggtggag tgtttctttt gggcagtcgg agtataccat 840
gagccacaat attctcgtgc tcgtgtaatg cttactaaaa ccatcgttat gacctctata 900
atagatgata cttatgatgc ttatggtacc attgaagaac ttgatatttt cactgaagca 960
atagagaggt ggaatgttga agagactaaa aggctccccg agtacatgaa accattgtat 1020
aaagctcttc tggaactcta caagcagttt gaacaagaac tagaaaagga aggaagatcc 1080
tacgtggcat actatgccat cgaatctctt aaggaattgg tgagaagcta tcgcattgag 1140
gcaaagtggt ttatacaagg atatttacca ccttacgaag aatacctaaa gaatgcactg 1200
atcacctgca cttactgtta ccacacaacg acgtcgttgt tgggggttga atcagccatc 1260
aaggaaaact tcgaatggct aagcaacaaa cctaaaatgc ttgtagctgg cctcctaata 1320
tgtcgactca ttgatgacat agctacttat atcctggaga ggggtagggg tcaggttgct 1380
actggcatcg agtcctacat gaaggataat ggcgcaacac aagaagaacc catagctaaa 1440
attttcgaaa tagctacaga tgcatggaag gatataaatg acgaatgctt gagacctagc 1500
ctttacaact cgagggatgt tttgatgcga atatttaacc ttgaacgtat aatagacgtt 1560
acttacaaag gcaaccaaga tcgatacact caaccagaaa aggttttgaa gcctcacatc 1620
attgtcttct tcttcgatcc cattctcatt taa 1653

<210> SEQ ID NO 40
<211> LENGTH: 1647
<212> TYPE: DNA
<213> ORGANISM: Citrus sinensis
<220> FEATURE:
<223> OTHER INFORMATION: Citrus valencene synthase DNA
<300> PUBLICATION INFORMATION:
<308> DATABASE ACCESSION NUMBER: GenBank AF441124.1
<309> DATABASE ENTRY DATE: 2004-01-12

<400> SEQUENCE: 40
atgtcgtctg gagaaacatt tcgtcctact gcagatttcc atcctagttt atggagaaac 60
catttcctca aaggtgcttc tgatttcaag acagttgatc atactgcaac tcaagaacga 120
cacgaggcac tgaaagaaga ggtaaggaga atgataacag atgctgaaga taagcctgtt 180
cagaagttac gcttgattga tgaagtacaa cgcctggggg tggcttatca ctttgagaaa 240
gaaataggag atgcaataca aaaattatgt ccaatctata ttgacagtaa tagagctgat 300
ctccacaccg tttcccttca ttttcggttg cttaggcagc aaggaatcaa gatttcatgt 360
gatgtgtttg agaagttcaa agatgatgag ggtagattca agtcatcgtt gataaacgat 420
gttcaaggga tgttaagttt gtacgaggca gcatacatgg cagttcgcgg agaacatata 480
ttagatgaag ccattgcttt cactaccact cacctgaagt cattggtagc tcaggatcat 540
gtaaccccta agcttgcgga acagataaat catgctttat accgtcctct tcgtaaaacc 600
ctaccaagat tagaggcgag gtattttatg tccatgatca attcaacaag tgatcattta 660
tgcaataaaa ctctgctgaa ttttgcaaag ttagatttta acatattgct agagctgcac 720
aaggaggaac tcaatgaatt aacaaagtgg tggaaagatt tagacttcac tacaaaacta 780
ccttatgcaa gagacagatt agtggagtta tatttttggg atttagggac atacttcgag 840
cctcaatatg catttgggag aaagataatg acccaattaa attacatatt atccatcata 900
gatgatactt atgatgcgta tggtacactt gaagaactca gcctctttac tgaagcagtt 960
caaagatgga atattgaggc cgtagatatg cttccagaat acatgaaatt gatttacagg 1020
acactcttag atgcttttaa tgaaattgag gaagatatgg ccaagcaagg aagatcacac 1080
tgcgtacgtt atgcaaaaga ggagaatcaa aaagtaattg gagcatactc tgttcaagcc 1140
aaatggttca gtgaaggtta cgttccaaca attgaggagt atatgcctat tgcactaaca 1200
agttgtgctt acacattcgt cataacaaat tccttccttg gcatgggtga ttttgcaact 1260
aaagaggttt ttgaatggat ctccaataac cctaaggttg taaaagcagc atcagttatc 1320
tgcagactca tggatgacat gcaaggtcat gagtttgagc agaagagagg acatgttgcg 1380
tcagctattg aatgttacac gaagcagcat ggtgtctcta aggaagaggc aattaaaatg 1440
tttgaagaag aagttgcaaa tgcatggaaa gatattaacg aggagttgat gatgaagcca 1500
accgtcgttg cccgaccact gctcgggacg attcttaatc ttgctcgtgc aattgatttt 1560
atttacaaag aggacgacgg ctatacgcat tcttacctaa ttaaagatca aattgcttct 1620
gtgctaggag accacgttcc attttga 1647

<210> SEQ ID NO 41
<211> LENGTH: 1750
<212> TYPE: DNA
<213> ORGANISM: Hyoscyamus muticus
<220> FEATURE:
<223> OTHER INFORMATION: premnaspirodiene synthase DNA
<300> PUBLICATION INFORMATION:
<308> DATABASE ACCESSION NUMBER: GenBank U20188.1
<309> DATABASE ENTRY DATE: 1996-01-31

<400> SEQUENCE: 41
gttgacaatc aggttgcgga aaagtatgct caagagattg aaactttgaa ggaacaaaca 60
agtactatgt tgtctgctgc ttgtggaaca acattgactg agaaattgaa tttgatagat 120
attattgagc gccttggaat agcttatcat ttcgagaaac aaatagaaga tatgttggat 180
cacatttaca gagctgatcc ttattttgag gctcatgaat acaatgattt aaacacttca 240
tccgttcaat ttcgactact cagacaacat ggttacaacg tctctccaaa tatatttagc 300
agattccaag atgcaaatgg caaattcaag gagtctctta gaagcgacat caggggccta 360
ctgaacttat acgaagcttc acatgtaagg actcataaag aggatatttt ggaagaagca 420
cttgtttttt ctgttggtca tcttgaatct gcagctccac atttgaagtc acctctgagt 480
aagcaagtga cacatgccct cgaacaatct ctccataaga gcattccaag agtcgagata 540
cggtacttca tctccatcta cgaagaggag gaatttaaga atgatttgtt gcttcgattt 600
gctaaattgg attacaactt acttcagatg ttgcacaagc atgaactcag tgaagtatca 660
aggtggtgga aagatttgga tttcgtgaca acacttccat atgctaggga cagagcagtt 720
gagtgctact tttggacgat gggggtgtat gctgaacctc aatactccca ggctcgtgtc 780
atgcttgcta agactatagc aatgatttcc atagtagatg acacattcga tgcttatggc 840
atcgtaaaag aacttgaagt ctacacagat gccatacaga ggtgggatat tagtcaaatt 900
gatcgactcc cggaatatat gaaaatcagt tataaggctc ttttggatct ctatgacgat 960
tatgaaaagg agttgtcaaa ggatggtaga tccgatgttg tccactatgc aaaagaaaga 1020
atgaaggaga ttgtgggaaa ctattttatt gaaggaaaat ggtttattga gggatatatg 1080
ccatctgttt ccgagtacct tagcaatgca ctagctacta gcacatatta cttgctaact 1140
acgacatcct acttgggaat gaaatcagca accaaggaac attttgaatg gttggctacg 1200
aaccctaaaa ttctggaagc taatgctaca ttatgccgag ttgttgatga catagccacg 1260
tatgaggttg agaagggtag ggtcaaatt gcaacaggaa ttgagtgtta tatgagggat 1320
tacggtgtat ccacagaagt agcaatggag aaattccaag aaatggctga catagcatgg 1380
aaggatgtaa atgaagaaat tcttcgacca acacctgtct cttcagaaat tcttactcgt 1440
attctcaacc tggctcgaat tatagatgtc acttacaagc ataatcaaga tggatacact 1500
catcctgaaa aagtactaaa acctcacatc atcgccttgg tggtggattc tattgatatt 1560
tgaatcacca attgttgtgt acacctggga gcacttggtt cccacccccct caaataagtt 1620 tttgacagac acttgatgga tggtatctct gttgctaggt atacatgttg taatcgtgca 1680
gtgaagttac gtccttaatt cttttgtatg attatttaca tttgaaatat aataattctg 1740
ctttttaact 1750

<210> SEQ ID NO 42
<211> LENGTH: 1839
<212> TYPE: DNA
<213> ORGANISM: Citrus hystrix
<220> FEATURE:
<223> OTHER INFORMATION: germacrene D synthase DNA
<300> PUBLICATION INFORMATION:
<308> DATABASE ACCESSION NUMBER: GenBank HQ652871.1
<309> DATABASE ENTRY DATE: 2011-06-28

<400> SEQUENCE: 42
atgtctgttg aaggttctgc aaattttcat ccaagcattt ggggtgatca tttccttcaa 60
tatactcgtg acttccagga aactggtgat cgaagtgtaa agcatctaga gctgaagaaa 120
gaaattagaa gaatgctaaa agctgtaaac aagacttcac atacactcga attgatagat 180
gcaattcagc ggttaggagt gtcttaccat tttgaaagtg agattgatga aatcttggga 240
aagatgcaca agacttatcg agactgtgat ctttgtgata atgaaaatga tgagctttat 300
tatatctctc ttcagtttcg attgttcaga caaaatggct atagaatttc cgctgatgtt 360
ttcaatacgt tcaagggcag cgatgggaaa tttaaggcat ctcttgcaaa agatgttcga 420
ggaatgttaa gcttgtatga agctacacat ctgagggttc atggagaaaa tatacttgat 480
gaggcgcttg ctttcaccac tagtcacctt gagtcagtag caaaacaagt ctgttctcca 540
ctagttgaac aagtcaagca cgccttagtt cagcctatcc acaagggctt agaaaggctt 600
gaggcaagac actacattcc tatctatcaa ggagaatctt cccacaatga agctctgtta 660
acctttgcaa agttaggttt taatggattg caaaagcttc accagaagga actcggtgat 720

-continued

```
atttcaaggt ggtggaaaga attagacttt gcgcataagc taccccttcgt aagagataga    780

attgcagagg tctacttttg ggcagtagga gttcatttcg agccccaata ttcgtttact    840

agaaaactat ttacgaaagt gatttatatg acatctatca ttgatgacat ctatgatgtg    900

tatggcaaaa ttgaagaact tgatcttttt acttcagcta ttgaaaggtg ggatatcaat    960

gccatagatc aacttcctga gtatatgaaa ctgtgtatta gggcgcttat caatgtttac   1020

agtgaagtag agaaagattt ggtctcccag gggaagttat accgactcca ttatgcgaaa   1080

gaagcaatga agaatcaagt taagcattac ttctttgaag ctaaatggtg tcatcagaat   1140

tatgttccga cggtggatga gtacatgacg gttgcattaa ttagctctgg ccacccaaat   1200

ttgtcaacca tatcttttgt tggcctggga gacattgtaa ctaaagaatc ttttgaatgg   1260

ttattcagca atcctagatc gattagggct tcttgtgcag ttggcagact aatgaatgac   1320

atggtgtcac acaagtttga acaaagcaga gggcacgttg cctcaagcgt tgagtgttac   1380

atcaaccaat atggagcaac agaagaggaa gcatacagtg agttccggaa acaagtttca   1440

aatgcatgga aggatataaa tgaggaatgc ctgcgcccaa ctgttgtgcc agtgccactt   1500

cttatgcgaa ttctcaatct tacacgagct gcagatgtca tttacaagta taaagatggc   1560

tacacttact ccgaagagct gaaagatttt attgtttctc tgcttattaa tcctgtgccg   1620

atatgagcat gatattaagc ttatgtttca acaccctgct ggaaaataat tagtccattg   1680

ccgtttcagc ttggatgctt tttaaaaata aattgaaggg tggtgatccc cgttgtaatc   1740

agagtgcact caaatagaca agtggtaata aagttttata gctctattta attaaattat   1800

ccagcagttt gcacgattaa aaaaaaaaaa aaaaaaaaa                          1839
```

<210> SEQ ID NO 43
<211> LENGTH: 1722
<212> TYPE: DNA
<213> ORGANISM: Chamaecyparis nootkatensis
<220> FEATURE:
<223> OTHER INFORMATION: Valencene synthase DNA
<300> PUBLICATION INFORMATION:
<310> PATENT DOCUMENT NUMBER: WO 2011/074954
<311> PATENT FILING DATE: 2010-12-15

<400> SEQUENCE: 43

```
atgcccgtga aggacgccct tcgtcggact ggaaatcatc atcctaactt gtggactgat     60

gatttcatac agtccctcaa ttctccatat tcggattctt cataccataa acatagggaa    120

atactaattg atgagattcg tgatatgttt tctaatggag aaggcgatga gttcggtgta    180

cttgaaaata tttggtttgt tgatgttgta caacgtttgg gaatagatcg acattttcaa    240

gaggaaatca aaactgcact tgattatatc tacaagttct ggaatcatga tagtattttt    300

ggcgatctca acatggtggc tctaggattt cggatactac gactgaatag atatgtcgct    360

tcttcagatg tttttaaaaa gttcaaaggt gaagaaggac aattctctgg ttttgaatct    420

agcgatcaag atgcaaaatt agaaatgatg ttaaatttat ataaagcttc agaattagat    480

tttcctgatg aagatatctt aaaagaagca agagcgtttg cttctatgta cctgaaacat    540

gttatcaaag aatatggtga catacaagaa tcaaaaaatc cacttctaat ggagatagag    600

tacactttta aatatccttg gagatgtagg cttccaaggt tggaggcttg gaactttatt    660

catataatga gacaacaaga ttgcaatata tcacttgcca ataaccttta taaaattcca    720

aaaatatata tgaaaaagat attggaacta gcaatactgg acttcaatat tttgcagtca    780

caacatcaac atgaaatgaa attaatatcc acatggtgga aaaattcaag tgcaattcaa    840
```

ttggatttct ttcggcatcg tcacatagaa agttattttt ggtgggctag tccattattt 900
gaacctgagt tcagtacatg tagaattaat tgtaccaaat tatctacaaa aatgttcctc 960
cttgacgata tttatgacac atatgggact gttgaggaat tgaaaccatt cacaacaaca 1020
ttaacaagat gggatgtttc cacagttgat aatcatccag actacatgaa aattgctttc 1080
aatttttcat atgagatata taaggaaatt gcaagtgaag ccgaaagaaa gcatggtccc 1140
tttgtttaca aataccttca atcttgctgg aagagttata tcgaggctta tatgcaagaa 1200
gcagaatgga tagcttctaa tcatatacca ggttttgatg aatacttgat gaatggagta 1260
aaaagtagcg gcatgcgaat tctaatgata catgcactaa tactaatgga tactccttta 1320
tctgatgaaa ttttggagca acttgatatc ccatcatcca agtcgcaagc tcttctatca 1380
ttaattactc gactagtgga tgatgtcaaa gactttgagg atgaacaagc tcatggggag 1440
atggcatcaa gtatagagtg ctacatgaaa gacaaccatg gttctacaag ggaagatgct 1500
ttgaattatc tcaaaattcg tatagagagt tgtgtgcaag agttaaataa ggagcttctc 1560
gagccttcaa atatgcatgg atcttttaga aacctatatc tcaatgttgg catgcgagta 1620
atatttttta tgctcaatga tggtgatctc tttacacact ccaatagaaa agagatacaa 1680
gatgcaataa caaaattttt tgtggaacca atcattccat ag 1722

<210> SEQ ID NO 44
<211> LENGTH: 1770
<212> TYPE: DNA
<213> ORGANISM: Chamaecyparis nootkatensis
<220> FEATURE:
<223> OTHER INFORMATION: Valencene synthase DNA
<300> PUBLICATION INFORMATION:
<310> PATENT DOCUMENT NUMBER: WO 2011/074954
<311> PATENT FILING DATE: 2010-12-15

<400> SEQUENCE: 44
atggctgaaa tgtttaatgg aaattccagc aatgatggaa gttcttgcat gcccgtgaag 60
gacgcccttc gtcggactgg aaatcatcat cctaacttgt ggactgatga tttcatacag 120
tccctcaatt ctccatattc ggattcttca taccataaac atagggaaat actaattgat 180
gagattcgtg atatgttttc taatggagaa ggcgatgagt tcggtgtact tgaaaatatt 240
tggtttgttg atgttgtaca acgtttggga atagatcgac attttcaaga ggaaatcaaa 300
actgcacttg attatatcta caagttctgg aatcatgata gtatttttgg cgatctcaac 360
atggtggctc taggatttcg gatactacga ctgaatagat atgtcgcttc ttcagatgtt 420
tttaaaaagt tcaaaggtga agaaggacaa ttctctggtt ttgaatctag cgatcaagat 480
gcaaaattag aaatgatgtt aaatttatat aaagcttcag aattagattt tcctgatgaa 540
gatatcttaa aagaagcaag agcgtttgct tctatgtacc tgaaacatgt tatcaaagaa 600
tatggtgaca tacaagaatc aaaaaatcca cttctaatgg agatagagta cacttttaaa 660
tatccttgga gatgtaggct tccaaggttg gaggcttgga actttattca tataatgaga 720
caacaagatt gcaatatatc acttgccaat aacctttata aaattccaaa aatatatatg 780
aaaaagatat tggaactagc aatactggac ttcaatattt tgcagtcaca acatcaacat 840
gaaatgaaat taatatccac atggtggaaa aattcaagtg caattcaatt ggatttcttt 900
cggcatcgtc acatagaaag ttatttttgg tgggctagtc cattatttga acctgagttc 960
agtacatgta gaattaattg taccaaatta tctacaaaaa tgttcctcct tgacgatatt 1020
tatgacacat atgggactgt tgaggaattg aaaccattca caacaacatt aacaagatgg 1080

```
gatgtttcca cagttgataa tcatccagac tacatgaaaa ttgctttcaa tttttcatat   1140

gagatatata aggaaattgc aagtgaagcc gaaagaaagc atggtccctt tgtttacaaa   1200

taccttcaat cttgctggaa gagttatatc gaggcttata tgcaagaagc agaatggata   1260

gcttctaatc atataccagg ttttgatgaa tacttgatga atggagtaaa aagtagcggc   1320

atgcgaattc taatgataca tgcactaata ctaatggata ctcctttatc tgatgaaatt   1380

ttggagcaac ttgatatccc atcatccaag tcgcaagctc ttctatcatt aattactcga   1440

ctagtggatg atgtcaaaga ctttgaggat gaacaagctc atggggagat ggcatcaagt   1500

atagagtgct acatgaaaga caaccatggt tctacaaggg aagatgcttt gaattatctc   1560

aaaattcgta tagagagttg tgtgcaagag ttaaataagg agcttctcga gccttcaaat   1620

atgcatggat cttttagaaa cctatatctc aatgttggca tgcgagtaat attttttatg   1680

ctcaatgatg gtgatctctt tacacactcc aatagaaaag agatacaaga tgcaataaca   1740

aaatttttg tggaaccaat cattccatag                                      1770
```

```
<210> SEQ ID NO 45
<211> LENGTH: 541
<212> TYPE: PRT
<213> ORGANISM: Citrus hystrix
<220> FEATURE:
<223> OTHER INFORMATION: germacrene D synthase protein
<300> PUBLICATION INFORMATION:
<308> DATABASE ACCESSION NUMBER: GenBank ADX01384.1
<309> DATABASE ENTRY DATE: 2011-06-28

<400> SEQUENCE: 45

Met Ser Val Glu Gly Ser Ala Asn Phe His Pro Ser Ile Trp Gly Asp
1               5                   10                  15

His Phe Leu Gln Tyr Thr Arg Asp Phe Gln Glu Thr Gly Asp Arg Ser
            20                  25                  30

Val Lys His Leu Glu Leu Lys Lys Glu Ile Arg Arg Met Leu Lys Ala
        35                  40                  45

Val Asn Lys Thr Ser His Thr Leu Glu Leu Ile Asp Ala Ile Gln Arg
    50                  55                  60

Leu Gly Val Ser Tyr His Phe Glu Ser Glu Ile Asp Glu Ile Leu Gly
65                  70                  75                  80

Lys Met His Lys Thr Tyr Arg Asp Cys Asp Leu Cys Asp Asn Glu Asn
                85                  90                  95

Asp Glu Leu Tyr Tyr Ile Ser Leu Gln Phe Arg Leu Phe Arg Gln Asn
            100                 105                 110

Gly Tyr Arg Ile Ser Ala Asp Val Phe Asn Thr Phe Lys Gly Ser Asp
        115                 120                 125

Gly Lys Phe Lys Ala Ser Leu Ala Lys Asp Val Arg Gly Met Leu Ser
    130                 135                 140

Leu Tyr Glu Ala Thr His Leu Arg Val His Gly Glu Asn Ile Leu Asp
145                 150                 155                 160

Glu Ala Leu Ala Phe Thr Thr Ser His Leu Glu Ser Val Ala Lys Gln
                165                 170                 175

Val Cys Ser Pro Leu Val Glu Gln Val Lys His Ala Leu Val Gln Pro
            180                 185                 190

Ile His Lys Gly Leu Glu Arg Leu Glu Ala Arg His Tyr Ile Pro Ile
        195                 200                 205

Tyr Gln Gly Glu Ser Ser His Asn Glu Ala Leu Leu Thr Phe Ala Lys
    210                 215                 220
```

-continued

```
Leu Gly Phe Asn Gly Leu Gln Lys Leu His Gln Lys Glu Leu Gly Asp
225                 230                 235                 240

Ile Ser Arg Trp Trp Lys Glu Leu Asp Phe Ala His Lys Leu Pro Phe
                245                 250                 255

Val Arg Asp Arg Ile Ala Glu Val Tyr Phe Trp Ala Val Gly Val His
            260                 265                 270

Phe Glu Pro Gln Tyr Ser Phe Thr Arg Lys Leu Phe Thr Lys Val Ile
        275                 280                 285

Tyr Met Thr Ser Ile Ile Asp Asp Ile Tyr Asp Val Tyr Gly Lys Ile
    290                 295                 300

Glu Glu Leu Asp Leu Phe Thr Ser Ala Ile Glu Arg Trp Asp Ile Asn
305                 310                 315                 320

Ala Ile Asp Gln Leu Pro Glu Tyr Met Lys Leu Cys Ile Arg Ala Leu
                325                 330                 335

Ile Asn Val Tyr Ser Glu Val Glu Lys Asp Leu Val Ser Gln Gly Lys
            340                 345                 350

Leu Tyr Arg Leu His Tyr Ala Lys Glu Ala Met Lys Asn Gln Val Lys
        355                 360                 365

His Tyr Phe Phe Glu Ala Lys Trp Cys His Gln Asn Tyr Val Pro Thr
    370                 375                 380

Val Asp Glu Tyr Met Thr Val Ala Leu Ile Ser Ser Gly His Pro Asn
385                 390                 395                 400

Leu Ser Thr Ile Ser Phe Val Gly Leu Gly Asp Ile Val Thr Lys Glu
                405                 410                 415

Ser Phe Glu Trp Leu Phe Ser Asn Pro Arg Ser Ile Arg Ala Ser Cys
            420                 425                 430

Ala Val Gly Arg Leu Met Asn Asp Met Val Ser His Lys Phe Glu Gln
        435                 440                 445

Ser Arg Gly His Val Ala Ser Ser Val Glu Cys Tyr Ile Asn Gln Tyr
    450                 455                 460

Gly Ala Thr Glu Glu Glu Ala Tyr Ser Glu Phe Arg Lys Gln Val Ser
465                 470                 475                 480

Asn Ala Trp Lys Asp Ile Asn Glu Glu Cys Leu Arg Pro Thr Val Val
                485                 490                 495

Pro Val Pro Leu Leu Met Arg Ile Leu Asn Leu Thr Arg Ala Ala Asp
            500                 505                 510

Val Ile Tyr Lys Tyr Lys Asp Gly Tyr Thr Tyr Ser Glu Glu Leu Lys
        515                 520                 525

Asp Phe Ile Val Ser Leu Leu Ile Asn Pro Val Pro Ile
    530                 535                 540
```

VALENCENE SYNTHASE POLYPEPTIDES, ENCODING NUCLEIC ACID MOLECULES AND USES THEREOF

RELATED APPLICATIONS

Benefit of priority is claimed to U.S. Provisional Application Ser. No. 61/852,462, filed Mar. 14, 2013, entitled "VALENCENE SYNTHASE POLYPEPTIDES, ENCODING NUCLEIC ACID MOLECULES AND USES THEREOF." The subject matter of the above-noted application is incorporated by reference in its entirety.

This application is related to International PCT Application No. PCT/US2014/23759, filed the same day herewith, entitled "VALENCENE SYNTHASE POLYPEPTIDES, ENCODING NUCLEIC ACID MOLECULES AND USES THEREOF," which also claims priority to U.S. Provisional Application Ser. No. 61/852,462.

The subject matter of each of the above-noted applications is incorporated by reference in its entirety.

INCORPORATION BY REFERENCE OF SEQUENCE LISTING PROVIDED ELECTRONICALLY

An electronic version on compact disc (CD-R) of the Sequence Listing is filed herewith in duplicate (labeled Copy 1 and Copy 2), the contents of which are incorporated by reference in their entirety. The computer-readable file on each of the aforementioned compact discs, created on Mar. 11, 2014, is identical, 148 kilobytes in size, and titled 237seq.001.txt.

FIELD OF THE INVENTION

Provided are valencene synthase polypeptides, nucleic acid molecules encoding the valencene synthases, host cells containing the nucleic acids and methods for producing products whose production is catalyzed by the polypeptides. Also provided are methods for producing valencene and nootkatone.

BACKGROUND

Valencene and nootkatone are sesquiterpenes that occur in essential oils, such as citrus oils, including orange and grapefruit. Valencene is produced by cyclization of the acyclic pyrophosphate terpene precursor farnesyl diphosphate (FPP), and oxidation of valencene results in the formation of nootkatone. Valencene and nootkatone are both used in the perfume and flavor industry.

Valencene originally was extracted from the peel of the Valencia orange and nootkatone is extracted from grapefruit peels or produced by oxidation of extracted valencene. Although chemical approaches to generate valencene and nootkatone have been attempted, the highly complex structures of these compounds have rendered economically viable synthetic processes for their preparation in large quantities unattainable. Valencene has been produced in host cells catalyzed by nucleic acid encoding a citrus valencene synthase (see, e.g., U.S. Pat. No. 7,442,785). Improvements in production and alternative means of production and production of valencene and other terpenes are sought.

Thus, among the objects herein, is the provision of valencene synthase polypeptides and methods for production of terpene products whose production is catalyzed by the polypeptides.

SUMMARY

Provided are *Eryngium* valencene synthases (EgVSs). Provided are isolated valencene synthase polypeptides that have a sequence of amino acids that has at least 55%, such as at least 58% or at least 85%, sequence identity to the valencene synthase polypeptide whose sequence is set forth in SEQ ID NO:1. The exemplified *Eryngium glaciale* synthase has the sequence of amino acids set forth in SEQ ID NO:1. The valencene synthases provided herein catalyze production of valencene and other products from an acyclic pyrophosphate terpene precursor, such as, but not limited to, farnesyl diphosphate. Production can be effected in vitro by contacting the isolated synthase with an acyclic pyrophosphate terpene precursor, or in vivo in a suitable host cell that encodes the synthase. Suitable host cells produce or are modified to produce an acyclic pyrophosphate precursor. If the cells are human in origin, they are isolated or cultured cells or a cell culture. Cells, such as yeast cells, particularly cells that express an acyclic pyrophosphate terpene precursor, that express the EgVS produce very high amounts of valencene compared to the same cells that express the citrus (*Citrus sinensis*) valencene synthase (CVS) and variants thereof that are optimized and/or modified to express high levels of valencene.

Also provided are nucleic acid molecules that encode any of the valencene synthases provided herein. The nucleic acid molecules include isolated nucleic acid molecules and also cDNA. For example, nucleic acid molecules provided herein are those that encode the sequence of amino acids set forth in SEQ ID NO:1, and also any that encode a sequence of amino acids that has at least 58%, 60%, 65%, 70%, 75%, 80%, 85%, 86%, 87%, 88%, 89%, 90%, 91%, 92%, 93%, 94%, 95%, 96%, 97%, 98% or 99% sequence identity to a valencene synthase polypeptide whose sequence is set forth in SEQ ID NO:1 or a catalytically active fragment thereof, where the encoded polypeptide catalyzes production of valencene from an acyclic pyrophosphate terpene precursor. For example, the isolated nucleic acid molecule is selected from among nucleic acid molecules that contain: (a) the sequence of nucleic acids set forth in SEQ ID NO:2; (b) a sequence of nucleic acids having at least 85% sequence identity to a sequence of nucleic acids set forth in SEQ ID NO:2; and (c) degenerates of (a) and (b). Also provided are the isolated polypeptides and catalytically active fragments encoded by the nucleic acid molecules provided herein. The encoded polypeptides can be produced by expression in any host cell, including eukaryotic and prokaryotic cells, such as mammalian cells, yeast cells and bacterial cells. In examples where the host cell is a mammalian cell that is a human cell, the cell is an isolated cell or a cell in culture, such as in a cell culture.

Also provided are vectors that contain the nucleic acid molecules provided herein. Vectors include prokaryotic and eukaryotic vectors, including viral vectors and yeast vectors, such as *Saccharomyces* vectors.

Also provided are cells that contain the vectors and nucleic acid molecules encoding an EgVS. The cells include prokaryotic cells and eukaryotic cells, including, but not limited to bacteria, yeast, insect, plant and mammalian cells. In examples where the host cell is a mammalian cell that is a human cell, the cell is an isolated cell or a cultured cell. In some examples, the nucleic acid is heterologous to the cell. Yeast cells provided herein include, but are not limited to, *Saccharomyces* genus cells and *Pichia* genus cells. Bacterial cells provided herein include *Escherichia coli* cells. Plant cells provided herein include protoplasts. The cells can produce the acyclic precursor, such as farnesyl diphosphate, natively, or can be modified to produce it or to produce more than an unmodified cell. Among the cells provided herein are those that encode a valencene synthase polypeptide, where: the host cell produces an acyclic pyrophosphate terpene precursor; the valencene synthase polypeptide is heterologous to the host; and the valencene synthase catalyzes production of valencene from the acyclic pyrophosphate terpene precursor, such as farnesyl diphosphate. Also provided are transgenic plants that encode the valencene synthase polypeptides provided herein. They can include nucleic acid encoding the valencene synthase polypeptide or a suitable vector encoding it. Exemplary transgenic plants include tobacco plants.

Provided herein are methods for producing a valencene synthase polypeptide. The methods include the steps of introducing a nucleic acid molecule that encodes the valencene synthase polypeptides, or catalytically active fragments thereof, provided herein or a vector that encodes the valencene synthase polypeptide, or catalytically active fragments thereof, into a cell, for example, by transfection or transformation; culturing the cell in vitro or in vivo under conditions suitable for expression of the valencene synthase polypeptide or catalytically active fragment thereof; and, optionally isolating the valencene synthase polypeptide. Cells for use in the methods include eukaryotic and prokaryotic host cells, including, but not limited to, bacteria, yeast, insect, plant and mammalian cells. Yeast cells for use in the methods include, but are not limited to, *Saccharomyces* genus cells and *Pichia* genus cells.

Also provided are methods for producing valencene. The methods involve contacting an acyclic pyrophosphate terpene precursor with a valencene synthase polypeptide or catalytically active fragment thereof, provided herein, in vitro or in vivo, under conditions suitable for the formation of valencene from the acyclic pyrophosphate terpene precursor, such as farnesyl diphosphate. In some examples, the valencene is isolated or purified. In the provided methods, the step of contacting the acyclic pyrophosphate terpene precursor with the valencene synthase polypeptide or catalytically active fragment thereof can be effected in vitro or in vivo in a suitable host cell provided herein. When effected in vivo, the nucleic acids or vectors can be introduced into the cells as described herein, such that the encoded valencene synthase polypeptide or catalytic fragment thereof is heterologous to the cells, and the cells cultured under conditions in which the encoded valencene synthase is expressed. The cells for use in such methods can be modified to produce the acyclic precursor or to produce more of the acyclic precursor than the unmodified cells. Exemplary cells and methods for selecting such cells include those described in issued U.S. Pat. No. 8,609,371 (U.S. Pub. No. 2010-0151555) and U.S. Pat. No. 8,481,286 (U.S. Pub. No. 2010-0151519). The valencene can be converted to nootkatone, such as by oxidation, which can be performed by known methods, including biosynthetic and chemical methods.

Thus, also provided herein are methods of producing nootkatone. Such methods involve producing valencene using the steps set forth in any of the methods provided herein for producing valencene; isolating the valencene product; oxidizing the valencene to produce nootkatone; and isolating the nootkatone. The valencene can be oxidized chemically or biosynthetically.

In any of the provided methods, any method known to the skilled artisan can be used for isolating valencene and/or nootkatone, as well as any other products of the reaction(s), including aristolochene, which is the peak 2 compound in FIG. 3A. Such methods of isolation include, but are not limited to, extraction with an organic solvent and/or column chromatography.

BRIEF DESCRIPTION OF THE FIGURES

FIG. 2A depicts the gas chromatogram of the *Eryngium glaciale* plant oil extract. Valencene (peak 1) is detected at 10.18 minutes. FIG. 2B depicts the mass spectrum of the peak at 10.18 minutes, which corresponds to valencene.

FIG. 3A depicts the gas chromatogram of an exemplary yeast strain designated ALX7-95 strain transformed with a gene encoding *Eryngium glaciale* valencene synthase. Valencene (peak 1) is observed at 12.46 minutes. An additional compound (designated Peak 2) is observed at 12.37 minutes. FIG. 3B depicts the mass spectrum of the peak at 12.46, which corresponds to valencene.

FIGS. 4A-G depicts exemplary alignments of *Eryngium glaciale* valencene synthase (EGVS) with other valencene synthases. A "*" means that the residues or nucleotides in that column are identical in all sequences in the alignment, a ":" means that conserved substitutions have been observed, and a "." means that semi-conserved substitutions are observed. For example, FIG. 4A depicts the alignment of *Eryngium glaciale* valencene synthase set forth in SEQ ID NO:1 with *Citrus sinensis* valencene synthase (CVS) set forth in SEQ ID NO:14. FIG. 4B depicts the alignment of *Eryngium glaciale* valencene synthase set forth in SEQ ID NO:1 with *Citrus*×*paradisi* valencene synthase (CVS) set forth in SEQ ID NO:15. FIG. 4C depicts the alignment of *Eryngium glaciale* valencene synthase set forth in SEQ ID NO:1 with *Vitis vinifera* valencene synthase (VVS) set forth in SEQ ID NO:16. FIG. 4D depicts the alignment of *Eryngium glaciale* valencene synthase set forth in SEQ ID NO:1 with *Chamaecyparis nootkatensis* valencene synthase (CNVS) set forth in SEQ ID NO:17. FIG. 4E depicts the alignment of *Eryngium glaciale* valencene synthase set forth in SEQ ID NO:1 with a modified CVS valencene synthase designated V277 (described in copending U.S. Publication Serial No. 2012-0246767), whose sequence is set forth in SEQ ID NO:31. FIG. 4F depicts the alignment of *Eryngium glaciale* valencene synthase set forth in SEQ ID NO:1 with *Chamaecyparis nootkatensis* valencene synthase (CNVS) set forth in SEQ ID NO:29. FIG. 4G depicts the alignment of *Eryngium glaciale* valencene synthase set forth in SEQ ID NO:1 with *Perilla frutescens* valencene synthase (PFVS) set forth in SEQ ID NO:38.

FIGS. 5A-J depicts exemplary alignments of *Eryngium glaciale* valencene synthase (EGVS) with other terpene synthases. A "*" means that the residues or nucleotides in that column are identical in all sequences in the alignment, a ":" means that conserved substitutions have been observed, and a "." means that semi-conserved substitutions are observed. For example, FIG. 5A depicts the alignment of *Eryngium glaciale* valencene synthase set forth in SEQ ID NO:1 with *Eleutherococcus trifoliatus* alpha-copaene synthase (ETACS) set forth in SEQ ID NO:18. FIG. 5B depicts the alignment of *Eryngium glaciale* valencene synthase set forth in SEQ ID NO:1 with *Actinidia deliciosa* germacrene-D synthase (ADGDS) set forth in SEQ ID NO:19. FIG. 5C depicts the alignment of *Eryngium glaciale* valencene synthase set forth in SEQ ID NO:1 with *Vitis vinifera* (−)-germacrene-D synthase (VGDS) set forth in SEQ ID NO:20. FIG. 5D depicts the alignment of *Eryngium glaciale* valencene synthase set forth in SEQ ID NO:1 with *Santalum murrayanum* sesquiterpene synthase (SMSS) set forth in SEQ ID NO:21. FIG. 5E depicts the alignment of *Eryngium glaciale* valencene synthase set forth in SEQ ID NO:1 with *Ricinus communis* (+)-delta-cadinene synthase (RCDCS) set forth in SEQ ID NO:22. FIG. 5F depicts the alignment of *Eryngium glaciale* valencene synthase set forth in SEQ ID NO:1 with *Citrus*×*paradisi* delta-cadinene synthase (CDCS) set forth in SEQ ID NO:23. FIG. 5G depicts the alignment of *Eryngium glaciale* valencene synthase set forth in SEQ ID NO:1 with *Nicotiana tabacum* 5-epi-aristolochene synthase (TEAS) set forth in SEQ ID NO:24. FIG. 5H depicts the alignment of *Eryngium glaciale* valencene synthase set forth in SEQ ID NO:1 with *Hyoscyamus muticus* premnaspirodiene synthase (HPS) set forth in SEQ ID NO:25. FIG. 5I depicts an alignment of *Eryngium glaciale* valencene synthase set forth in SEQ ID NO:1 with *Citrus hystrix* germacrene D synthase (CGDS) set forth in SEQ ID NO:45. FIG. 5J depicts an alignment of V277 set forth in SEQ ID NO:31 and citrus valencene synthase (CVS) set forth in SEQ ID NO:14.

DETAILED DESCRIPTION

Outline

Figure 1:
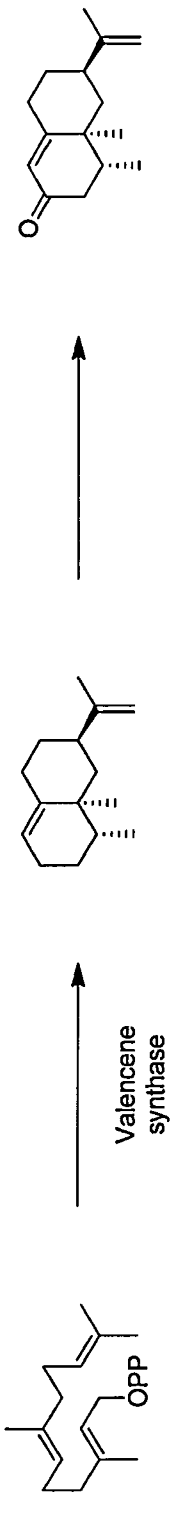
FIG. 1 is the reaction scheme for the production of valencene and nootkatone. Valencene synthases are class 1 plant terpene cyclases or synthases that convert farnesyl diphosphate (FPP) into the sesquiterpene valencene. Valencene then can be oxidized to form nootkatone.

A. Definitions
B. Overview
  1. Valencene structure and uses
  2. Nootkatone
  3. Valencene synthases
    a. Structure
    b. Activities
  4. Assays for detecting the enzymatic activity of valencene synthase polypeptides
C. Nucleic acid molecules encoding *Eryngium glaciale* valencene synthase and encoded polypeptides
  1. Isolation of nucleic acid encoding valencene synthases
    a. Generation of modified nucleic acid
  2. Vectors and cells for expression of valencene synthase polypeptides
  3. Expression systems
    a. Prokaryotic cells
    b. Yeast cells
    c. Plants and plant cells
    d. Insects and insect cells
    e. Mammalian cells
  4. Purification
D. Valencene synthase polypeptides
  1. *Eryngium glaciale* valencene synthase polypeptides
  2. Modifications of *Eryngium glaciale* valencene synthase polypeptides
    a. Truncated polypeptides
    b. Polypeptides with altered activities or properties
    c. Domain swaps
    d. Additional variants
    e. Fusion proteins
E. Methods for producing terpenes and methods for detecting such products and the acitivity of valencene synthase polypeptides
  1. Production of terpenes catalyzed by *Eryngium glaciale* valencene synthase
    a. Exemplary cells
    b. Culture of cells
    c. Isolation and assessment of products
  2. Production of Nootkatone
F. Examples

A. DEFINITIONS

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the interne. Reference thereto evidences the availability and public dissemination of such information.

As used herein, an acyclic pyrophosphate terpene precursor is any acyclic pyrophosphate compound that is a precursor to the production of at least one terpene, including, but not limited, farnesyl-pyrophosphate (FPP), to geranyl-pyrophosphate (GPP), and geranylgeranyl-pyrophosphate (GGPP). Acyclic pyrophosphate terpene precursors are thus substrates for terpene synthases.

As used herein, a terpene is an unsaturated hydrocarbon based on the isoprene unit ($C_5H_8$), and having a general formula $C_{5x}H_{8x}$, such as $C_{10}H_{16}$. Reference to a terpene includes acyclic, monocyclic and polycyclic terpenes. Terpenes include, but are not limited to, monoterpenes, which contain 10 carbon atoms; sesquiterpenes, which contain 15 carbon atoms; diterpenes, which contain 20 carbon atoms, and triterpenes, which contain 30 carbon atoms. Reference to a terpene also includes stereoisomers of the terpene.

As used herein, a terpene synthase is a polypeptide capable of catalyzing the formation of one or more terpenes from an acyclic pyrophosphate terpene precursor, for example, FPP, GPP or GGPP.

As used herein, valencene is a sesquiterpene having the following structure:

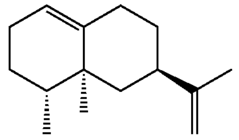

Reference to valencene includes reference to any isomer thereof, including, but not limited to (+)-valencene.

As used herein, nootkatone is a sesquiterpenoid having the following structure:

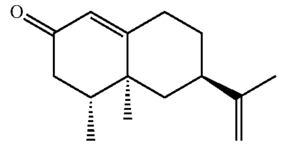

Reference to nootkatone includes reference to any isomer thereof.

As used herein, a "valencene synthase" or "valencene synthase polypeptide" is a polypeptide capable of catalyzing the formation of valencene from an acyclic pyrophosphate terpene precursor, such as farnesyl diphosphate (FPP). Included among the valencene synthase polypeptides herein are any that have greater than or greater than about or 63%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity with the valencene synthase set forth in SEQ ID NO:1, when aligned along its full length, or a catalytically active fragment thereof. These polypeptides catalyze the production of valencene as the only product or one among a mixture of products formed from the reaction of an acyclic pyrophosphate-terpene precursor with a valencene synthase. Typically valencene is the most prevalent product or among several prevalent products. For example, the amount of valencene produced from the reaction of a valencene synthase with an acyclic pyrophosphate terpene precursor typically is at least or at least about 1%, 5%, 10%, 20%, 30%, 40%, 50%, 60%, 70%, 80%, 90% or more of the total amount of terpene produced in the reaction. In some instances, valencene is the predominant terpene produced (i.e. present in greater amounts than any other single terpene produced from the reaction of an acyclic pyrophosphate terpene precursor with a valencene synthase).

Reference to a valencene synthase includes any polypeptide that catalyzes production of valencene, including, but not limited to, a recombinantly produced polypeptide, a synthetically produced polypeptide and a valencene synthase polypeptide extracted or isolated from cells and plant matter from which valencene has been isolated, including, but not limited to, the thistle species as provided herein. Other exemplary valencene synthase polypeptides include those isolated from citrus fruit, grapevine flowers (e.g. *Vitis vinifera* L. cv. Gewürztraminer and *Vitis vinifera* L. cv. Cabernet Sauvignon (see, Lucker et al., (2004) *Phytochemistry* 65(19):2649-2659 and Martin et al., (2009) *Proc. Natl. Acad. Sci, USA* 106:7245-7250) and perilla (green shiso). Citrus valencene synthases (CVS), include, but are not limited to, valencene synthase from *Citrus sinensis* (Sweet orange) (SEQ ID NOS:14, and 34) and *Citrus×paradisi* (Grapefruit) (SEQ ID NOS:15, 26 and 27). Other exemplary valencene synthase polypeptides include valencene synthase isolated from grapevine flowers, including *Vitis vinifera* L. cv. Gewürztraminer and *Vitis vinifera* L. cv. Cabernet Sauvignon (SEQ ID NOS:16 and 28), valencene synthases isolated from *Chamaecyparis nootkatensis pendula* (SEQ ID NO:17 and 29) and *Perilla frutescens* valencene synthase (SEQ ID NO:38). Reference to valencene synthase includes valencene synthase from any genus or species, and included allelic or species variants, variants encoded by splice variants, and other variants thereof, including polypeptides that have at least or at least about 40%, 45%, 50%, 55%, 60%, 65%, 70%, 75%, 80%, 85%, 90%, 95%, 96%, 97%, 98%, 99% or more sequence identity to the valencene synthase set forth in SEQ ID NO:1. Valencene synthase also includes fragments thereof that retain valencene synthase activity.

As used herein, catalytically active fragments of the valencene synthase polypeptides are truncated synthase polypeptides that retain the ability to catalyze the formation of valencene from an acyclic pyrophosphate terpene precursor. One of skill in the art readily can identify a fragment of a synthase that retains catalytic activity by testing it in any suitable assay, such as any described herein, and detecting formation of valencene from the precursor.

As used herein, "valencene synthase activity" (also referred to herein as catalytic activity) refers to the ability to catalyze the formation of valencene from an acyclic pyrophosphate terpene precursor, such as farnesyl diphosphate (FPP). Methods to assess valencene formation from the reaction of a synthase with an acyclic pyrophosphate terpene precursor, such as FPP, are well known in the art and described herein. For example, the synthase can be expressed in a host cell, such as a yeast cell, that also produces FPP. The production of valencene then can be assessed and quantified using, for example, gas chromatography-mass spectrometry (GC-MS) (see Examples below). A synthase is considered to exhibit valencene synthase activity or the ability to catalyze the formation of valencene from an acyclic pyrophosphate terpene precursor such as FPP if the amount of valencene produced from the reaction is at least or at least about 1%, 5%, 10%, 20%, 30%, 40%, 50%, 60%, 70%, 80%, 90% or more of the total amount of terpenes produced in the reaction.

As used herein, "increased catalytic activity" with reference to the activity of a valencene synthase means that the ability to catalyze the formation of valencene from an acyclic pyrophosphate terpene precursor, such as farnesyl diphosphate (FPP), is increased thereby resulting in increased formation of valencene. For purposes herein, a valencene synthase exhibits increased catalytic activity if the amount of valencene produced from FPP by the modified valencene synthase is 10% to 500%, 10% to 250%, 50% to 250%, 100% to 500% or is 100% to 250% greater than the amount of valencene produced from FPP by the valencene synthase set forth in SEQ ID NO:1, such as 10%, 20%, 30%, 40%, 50%, 60%, 70%, 80%, 90%, 100%, 110%, 120%, 130%, 140%, 150%, 160%, 170%, 180%, 190%, 200%, 250%, 300%, 350%, 400%, 500% or more greater than the amount of valencene produced from FPP by the valencene synthase set forth in SEQ ID NO:1. For example, a valencene synthase exhibits increased catalytic activity if the amount of valencene produced from FPP by the modified valencene synthase is at least or about at least 110%, 115%, 120%, 125%, 130%, 135%, 140%, 145%, 150%, 160%, 170%, 180%, 200%, 250%, 300%, 350%, 400%, 500%, 1500%, 2000%, 3000%, 4000%, 5000% of the amount of valencene produced from FPP by wild-type valencene synthase set forth in SEQ ID NO:1 under the same conditions.

As used herein, "wild-type" or "native" with reference to valencene synthase refers to a valencene synthase polypeptide encoded by a native or naturally occurring valencene synthase gene, including allelic variants, that is present in an organism, including a plant, in nature. Reference to wild-type valencene synthase without reference to a species is intended to encompass any species of a wild-type valencene synthase. The amino acid sequence of exemplary valencene synthases are set forth in SEQ ID NO:1 (isolated from *Eryngium glaciale*), SEQ ID NO: 14 (isolated from *Citrus sinensis* cv. Valencia, *Citrus sinensis* cv. Cara Cara and *Citrus×paradisi*), SEQ ID NO:34 (isolated from *Citrus sinensis* cv. Valencia), SEQ ED NO:27 (isolated from *Citrus×paradisi*), SEQ ID NO:26 (isolated from *Citrus×paradisi*), SEQ ID NOS:16 and 28 (isolated from *Vitis vinifera*), SEQ ID NO:29 (isolated from *Chamaecyparis nootkatensis pendula*) and SEQ ID NO:38 (isolated from *Perilla frutescens*).

As used herein, species variants refer to variants in polypeptides among different species.

As used herein, allelic variants refer to variations in encoded proteins among members of the same species.

As used herein, a splice variant refers to a variant produced by differential processing of a primary transcript of genomic DNA that results in more than one type of mRNA.

As used herein, "modified valencene synthase polypeptide" refers to a valencene synthase polypeptide that has one or more amino acid differences compared to an unmodified or wild-type valencene synthase polypeptide. The one or more amino acid differences can be amino acid mutations such as one or more amino acid replacements (substitutions), insertions or deletions, or can be insertions or deletions of entire domains, and any combinations thereof. Typically, a modified valencene synthase polypeptide has one or more modifications in primary sequence compared to an unmodified or wild-type valencene synthase polypeptide. For example, a modified valencene synthase polypeptide provided herein can have at least 1, 5, 10, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120, 125, 130, 135 or more amino acid differences compared to an unmodified valencene synthase polypeptide. Any modification is contemplated as long as the resulting polypeptide exhibits at least one valencene synthase activity associated with a wild-type valencene synthase polypeptide, such as, for example, catalytic activity, the ability to bind FPP, and/or the ability to catalyze the formation of valencene from FPP.

As used herein, reference to a modified valencene synthase polypeptide producing valencene from FPP in an amount that is greater than the amount of valencene produced from FPP by a reference valencene synthase, such as a wild-type valencene synthase, indicates that the modified valencene synthase produces at least or about 10% more valencene from FPP than the reference valencene synthase produces. For example, such a modified valencene synthase polypeptide can produce at least or at least about 10%, 11%, 12%, 13%, 14%, 15%, 20%, 30%, 40%, 50%, 60%, 70%, 80%, 90%, 100%, 110%, 120%, 130%, 140%, 150%, 160%, 170%, 180%, 190%, 200%, 250%, 300%, 350%, 400%, 500%, 600%, 700%, 800%, 900%, 1000%, 2000%, 5000% or more valencene from FPP compared to the amount of valencene produced from FPP by a reference valencene synthase. The amount of valencene produced from FPP by a valencene synthase can be assessed by any method known in the art. When comparing the amount of valencene produced from FPP by two valencene synthases, such as a modified valencene synthase and a reference valencene synthase, such as a wild-type valencene synthase, it is understood that the assay is performed under the same conditions for each synthase. In one example, the amount of valencene produced from FPP by two valencene synthases, such as a modified valencene synthase and a reference valencene synthase, is assessed by expressing the modified valencene synthase and the reference valencene synthase separately in a yeast cell of the same strain (wherein expression is from the same expression vector) that also produces FPP, and culturing the cells under the same conditions such that valencene is produced. The amount of valencene produced in the cell culture expressing the modified valencene synthase is compared to the amount of valencene produced in the cell culture expressing the reference valencene synthase, using methods of quantification well known in the art, such as GC-MS.

As used herein, corresponding residues refers to residues that occur at aligned loci. Related or variant polypeptides are aligned by any method known to those of skill in the art. Such methods typically maximize matches, and include methods such as using manual alignments and by using the numerous alignment programs available (for example, BLASTP) and others known to those of skill in the art. By aligning the sequences of polypeptides, one skilled in the art can identify corresponding residues, using conserved and identical amino acid residues as guides. Corresponding positions also can be based on structural alignments, for example by using computer simulated alignments of protein structure. For example, as shown in FIG. 4A, Asp315 of *E. glaciale* valencene synthase set forth in SEQ ID NO:1 corresponds to Asp301 of *C. sinensis* valencene synthase set forth in SEQ ID NO:14.

As used herein, domain or region (typically a sequence of three or more, generally 5 or 7 or more amino acids) refers to a portion of a molecule, such as a protein or the encoding nucleic acids, that is structurally and/or functionally distinct from other portions of the molecule and is identifiable. A protein can have one, or more than one, distinct domains. For example, a domain can be identified, defined or distinguished by homology of the sequence therein to related family members, such as other terpene synthases. A domain can be a linear sequence of amino acids or a non-linear sequence of amino acids. Many polypeptides contain a plurality of domains. Such domains are known, and can be identified by those of skill in the art. For exemplification herein, definitions are provided, but it is understood that it is well within the skill in the art to recognize particular domains by name. If needed, appropriate software can be employed to identify domains. For example, as discussed above, corresponding domains in different terpene synthases can be identified by sequence alignments, such as using tools and algorithms well known in the art (for example, BLASTP).

As used herein, a functional domain refers to those portions of a polypeptide that are recognized by virtue of a functional activity, such as catalytic activity. A functional domain can be distinguished by its function, such as by catalytic activity, or an ability to interact with a biomolecule, such as substrate binding or metal binding. In some examples, a domain independently can exhibit a biological function or property such that the domain independently, or fused to another molecule, can perform an activity, such as, for example catalytic activity or substrate binding.

As used herein, a structural domain refers to those portions of a polypeptide chain that can form an independently folded structure within a protein made up of one or more structural motifs.

As used herein, "heterologous" with respect to an amino acid or nucleic acid sequence refers to portions of a sequence that are not present in the native polypeptide or encoded by the native polynucleotide. For example, a portion of amino acids of a polypeptide, such as a domain or region or portion thereof, for a valencene synthase is heterologous thereto if such amino acids are not present in a native or wild-type valencene synthase (e.g. as set forth in SEQ ID NO:1), or encoded by the polynucleotide encoding a native or wild-type valencene synthase. Polypeptides containing such heterologous amino acids or polynucleotides encoding therefor are referred to as "chimeric polypeptides" or "chimeric polynucleotides," respectively.

As used herein, the phrase "a property of the modified terpene synthase is improved compared to the first terpene synthase" refers to a desirable change in a property of a modified terpene synthase compared to a terpene synthase that does not contain the modification(s). Typically, the property or properties are improved such that the amount of a desired terpene produced from the reaction of a substrate with the modified terpene synthase is increased compared to the amount of the desired terpene produced from the reaction of a substrate with a terpene synthase that is not so modified. Exemplary properties that can be improved in a modified terpene synthase include, for example, terpene production, catalytic activity, product distribution; substrate specificity; regioselectivity and stereoselectivity. One or more of the properties can be assessed using methods well-known in the art to determine whether the property had been improved (i.e. has been altered to be more desirable for the production of a desired terpene or terpenes).

As used herein, terpene production (also referred to as terpene yield) refers to the amount (in weight or weight/volume) of terpene produced from the reaction of an acyclic pyrophosphate terpene precursor with a terpene synthase. Reference to total terpene production refers to the total amount of all terpenes produced from the reaction, while reference to specific terpene production refers to the amount of a specific terpene (e.g. valencene), produced from the reaction.

As used herein, an improved terpene production refers to an increase in the total amount of terpene (i.e. improved total terpene production) or an increase in the specific amount of terpene (i.e. improved specific terpene production) produced from the reaction of an acyclic pyrophosphate terpene precursor with a modified terpene synthase compared to the amount produced from the reaction of the same acyclic pyrophosphate terpene precursor with a terpene synthase that is not so modified. The amount of terpene (total or specific) produced from the reaction of an acyclic pyrophosphate terpene precursor with a modified terpene synthase can be increased by at least or at least about 5%, 10%, 15%, 20%, 30%, 40%, 50%, 60%, 70%, 80%, 90%, 100% or more compared to the amount of terpene produced from the reaction of the same acyclic pyrophosphate terpene precursor under the same conditions with a terpene synthase that is not so modified.

As used herein, substrate specificity refers to the preference of a valencene synthase for one target substrate over another, such as one acyclic pyrophosphate terpene precursor (e.g. farnesyl-pyrophosphate (FPP), geranyl-pyrophosphate (GPP), or geranylgeranyl-pyrophosphate (GGPP)) over another. Substrate specificity can be assessed using methods well known in the art, such as those that calculate $k_{cat}/K_m$. For example, the substrate specificity can be assessed by comparing the relative $k_{cat}/K_m$, which is a measure of catalytic efficiency, of the enzyme against various substrates (e.g. GPP, FPP, GGPP).

As used herein, altered specificity refers to a change in substrate specificity of a modified terpene synthase polypeptide (such as a modified valencene synthase polypeptide) compared to a terpene synthase that is not so modified (such as, for example, a wild-type valencene synthase). The specificity (e.g. $k_{cat}/K_m$) of a modified terpene synthase polypeptide for a substrate, such as FPP, GPP or GGPP, can be altered by at least or at least about 10%, 15%, 20%, 30%, 40%, 50%, 60%, 70%, 80%, 90%, 100% or more compared to the specificity of a starting valencene synthase for the same substrate.

As used herein, improved substrate specificity refers to a change or alteration in the substrate specificity to a more desired specificity. For example, improved substrate specificity can include an increase in substrate specificity of a modified terpene synthase polypeptide for a desired substrate, such as FPP, GPP or GGPP. The specificity (e.g. $k_{cat}/K_m$) of a modified terpene synthase polypeptide for a substrate, such as FPP, GPP or GGPP, can be increased by at least or at least about 10%, 15%, 20%, 30%, 40%, 50%, 60%, 70%, 80%, 90%, 100% or more compared to the specificity of a terpene synthase that is not so modified.

As used herein, "product distribution" refers to the relative amounts of different terpenes produced from the reaction between an acyclic pyrophosphate terpene precursor, such as FPP, and a terpene synthase, including the modified valencene synthase polypeptides provided herein. The amount of a produced terpene can be depicted as a percentage of the total products produced by the terpene synthase. For example, the product distribution resulting from reaction of FPP with a valencene synthase can be 90% (weight/volume) valencene and 10% (weight/volume) β-elemene. Methods for assessing the type and amount of a terpene in a solution are well known in the art and described herein, and include, for example, gas chromatography-mass spectrometry (GC-MS) (see Examples below).

As used herein, an altered product distribution refers to a change in the relative amount of individual terpenes produced from the reaction between an acyclic pyrophosphate terpene precursor, such as FPP, and a terpene synthase, such as valencene synthase. Typically, the change is assessed by determining the relative amount of individual terpenes produced from the acyclic pyrophosphate terpene precursor using a first synthase (e.g. wild-type synthase) and then comparing it to the relative amount of individual terpenes produced using a second synthase (e.g. a modified synthase). An altered product distribution is considered to occur if the relative amount of any one or more terpenes is increased or decreased by at least or by at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more.

As used herein, an improved product distribution refers to a change in the product distribution to one that is more desirable, i.e. contains more desirable relative amounts of terpenes. For example, an improved product distribution can contain an increased amount of a desired terpene and a decreased amount of a terpene that is not so desired. The amount of desired terpene in an improved production distribution can be increased by at least or by at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more. The amount of a terpene that is not desired in an improved production distribution can be decreased by at least or by at least about 0.5%, 1%, 2%, 3%, 4%, 5%, 6%, 7%, 8%, 9%, 10%, 15%, 20%, 25%, 30%, 35%, 40%, 50%, 60%, 70%, 80% or more.

As used herein, nucleic acids or nucleic acid molecules include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleotides long.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated “nt”) or base pairs (abbreviated “bp”). The term nucleotide is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule cannot be paired. Such unpaired ends will, in general, not exceed 20 nucleotides in length.

As used herein, heterologous nucleic acid is nucleic acid that is not normally produced in vivo by the cell in which it is expressed or that is produced by the cell but is at a different locus or expressed differently or that mediates or encodes mediators that alter expression of endogenous nucleic acid, such as DNA, by affecting transcription, translation, or other regulatable biochemical processes. Heterologous nucleic acid is generally not endogenous to the cell into which it is introduced, but has been obtained from another cell or prepared synthetically. Heterologous nucleic acid can be endogenous, but is nucleic acid that is expressed from a different locus or altered in its expression. Generally, although not necessarily, such nucleic acid encodes RNA and proteins that are not normally produced by the cell or in the same way in the cell in which it is expressed. Heterologous nucleic acid, such as DNA, also can be referred to as foreign nucleic acid, such as DNA. Thus, heterologous nucleic acid or foreign nucleic acid includes a nucleic acid molecule not present in the exact orientation or position as the counterpart nucleic acid molecule, such as DNA, found in a genome. It also can refer to a nucleic acid molecule from another organism or species (i.e., exogenous).

Any nucleic acid, such as DNA, that one of skill in the art would recognize or consider as heterologous or foreign to the cell in which the nucleic acid is expressed is herein encompassed by heterologous nucleic acid; heterologous nucleic acid includes exogenously added nucleic acid that also is expressed endogenously. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and nucleic acid, such as DNA, that encodes other types of proteins, such as antibodies. Antibodies that are encoded by heterologous nucleic acid can be secreted or expressed on the surface of the cell in which the heterologous nucleic acid has been introduced.

As used herein, a peptide refers to a polypeptide that is from 2 to 40 amino acids in length.

As used herein, the amino acids that occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an “amino acid” is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

In keeping with standard polypeptide nomenclature described in *J. Biol. Chem.,* 243: 3557-3559 (1968), and adopted 37 C.F.R. § § 1.821-1.822, abbreviations for the amino acid residues are shown in Table 1:

TABLE 1

Table of Correspondence

| SYMBOL 1-Letter | SYMBOL 3-Letter | AMINO ACID |
|---|---|---|
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

All amino acid residue sequences represented herein by formulae have a left to right orientation in the conventional direction of amino-terminus to carboxyl-terminus. In addition, the phrase “amino acid residue” is broadly defined to include the amino acids listed in the Table of Correspondence (Table 1) and modified and unusual amino acids, such as those referred to in 37 C.F.R. § § 1.821-1.822, and incorporated herein by reference. Furthermore, a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, "non-natural amino acid" refers to an organic compound containing an amino group and a carboxylic acid group that is not one of the naturally-occurring amino acids listed in Table 1. Non-naturally occurring amino acids thus include, for example, amino acids or analogs of amino acids other than the 20 naturally-occurring amino acids and include, but are not limited to, the D-stereoisomers of amino acids. Exemplary non-natural amino acids are known to those of skill in the art and can be included in any of the modified valencene synthase polypeptides provided herein.

As used herein, modification is in reference to modification of a sequence of amino acids of a polypeptide or a sequence of nucleotides in a nucleic acid molecule and includes deletions, insertions, and replacements of amino acids and nucleotides, respectively. For purposes herein, amino acid replacements (or substitutions), deletions and/or insertions, can be made in any of the valencene synthases provided herein. Modifications can be made by making conservative amino acid replacements and also non-conservative amino acid substitutions. For example, amino acid replacements that desirably or advantageously alter properties of the valencene synthase can be made. For example, amino acid replacements can be made to the valencene synthase such that the resulting modified valencene synthase can produce more valencene from FPP compared to an unmodified valencene synthase.

Amino acid replacements or substitutions contemplated include conservative substitutions, including, but not limited to, those set forth in Table 2. Suitable conservative substitutions of amino acids are known to those of skill in the art and can be made generally without altering the conformation or activity of the polypeptide. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224). Conservative amino acid substitutions are made, for example, in accordance with those set forth in Table 2 as follows:

TABLE 2

| Original residue | Conservative substitution |
|---|---|
| Ala (A) | Gly; Ser; Abu |
| Arg (R) | Lys; Orn |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Ornithine | Lys; Arg |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu; Met |

Other conservative substitutions also are permissible and can be determined empirically or in accord with known conservative substitutions. The effects of such substitutions can be calculated using substitution score matrices such PAM120, PAM-200, and PAM-250 as discussed in Altschul (*J. Mol. Biol.* 219:555-565 (1991)).

As used herein, "primary sequence" refers to the sequence of amino acid residues in a polypeptide.

As used herein, "similarity" between two proteins or nucleic acids refers to the relatedness between the sequence of amino acids of the proteins or the nucleotide sequences of the nucleic acids. Similarity can be based on the degree of identity and/or homology of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

As used herein, the terms "homology" and "identity" are used are used to describe relatedness between and among polypeptides (or encoding nucleic acid molecules). Identity refers to identical sequences; homology can include conservative amino acid changes. In general to identify corresponding positions the sequences of amino acids are aligned so that the highest order match is obtained (see, e.g.: *Computational Molecular Biology*, Lesk, A. M., ed., Oxford University Press, New York, 1988*; Biocomputing: Informatics and Genome Projects*, Smith, D. W., ed., Academic Press, New York, 1993*; Computer Analysis of Sequence Data, Part* I, Griffin, A. M., and Griffin, H. G., eds., Humana Press, New Jersey, 1994*; Sequence Analysis in Molecular Biology*, von Heinje, G., Academic Press, 1987; and *Sequence Analysis Primer*, Gribskov, M. and Devereux, J., eds., M Stockton Press, New York, 1991; Carrillo et al. (1988) *SIAM J Applied Math* 48:1073).

As used herein, "sequence identity" refers to the number of identical or similar amino acids or nucleotide bases in a comparison between a test and a reference polypeptide or polynucleotide. Sequence identity can be determined by sequence alignment of nucleic acid or protein sequences to identify regions of similarity or identity. For purposes herein, sequence identity is generally determined by alignment to identify identical residues. Alignment can be local or global, but for purposes herein is generally a global alignment where the full-length of each sequence is compared. Matches, mismatches and gaps can be identified between compared sequences. Gaps are null amino acids or nucleotides inserted between the residues of aligned sequences so that identical or similar characters are aligned. Generally, there can be internal and terminal gaps. Sequence identity can be determined by taking into account gaps as the number of identical residues/length of the shortest sequence×100. When using gap penalties, sequence identity can be determined with no penalty for end gaps (e.g., terminal gaps are not penalized). Alternatively, sequence identity can be determined without taking into account gaps as the number of identical positions/length of the total aligned sequence×100.

As used herein, a "global alignment" is an alignment that aligns two sequences from beginning to end, aligning each letter in each sequence only once. An alignment is produced, regardless of whether or not there is similarity or identity between the sequences. For example, 50% sequence identity based on "global alignment" means that in an alignment of the full sequence of two compared sequences each of 100 nucleotides in length, 50% of the residues are the same. It is understood that global alignment also can be used in determining sequence identity even when the length of the aligned sequences is not the same. The differences in the terminal ends of the sequences will be taken into account in determining sequence identity, unless the "no penalty for end gaps" is selected. Generally, a global alignment is used on sequences that share significant similarity over most of their length. Exemplary algorithms for performing global alignment include the Needleman-Wunsch algorithm (Needleman et al. *J. Mol. Biol.* 48: 443 (1970). Exemplary programs for performing global alignment are publicly available and include the Global Sequence Alignment Tool available at the National Center for Biotechnology Information (NCBI) website (ncbi.nlm.nih.gov/), and the program available at deepc2.psi.iastate.edu/aat/align/align.html.

As used herein, a "local alignment" is an alignment that aligns two sequences, but only aligns those portions of the sequences that share similarity or identity. Hence, a local alignment determines if sub-segments of one sequence are present in another sequence. If there is no similarity, no alignment will be returned. Local alignment algorithms include BLAST® or Smith-Waterman algorithm (*Adv. Appl. Math.* 2: 482 (1981)). For example, 50% sequence identity based on "local alignment" means that in an alignment of the full sequence of two compared sequences of any length, a region of similarity or identity of 100 nucleotides in length has 50% of the residues that are the same in the region of similarity or identity.

For purposes herein, sequence identity can be determined by standard alignment algorithm programs used with default gap penalties established by each supplier. Default parameters for the GAP program can include: (1) a unary comparison matrix (containing a value of 1 for identities and 0 for non identities) and the weighted comparison matrix of Gribskov et al. *Nucl. Acids Res.* 14: 6745 (1986), as described by Schwartz and Dayhoff, eds., *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps. Whether any two nucleic acid molecules have nucleotide sequences or any two polypeptides have amino acid sequences that are at least 80%, 85%, 90%, 95%, 96%, 97%, 98% or 99% "identical," or other similar variations reciting a percent identity, can be determined using known computer algorithms based on local or global alignment (see e.g., wikipedia.org/wiki/Sequence_alignment_software, providing links to dozens of known and publicly available alignment databases and programs). Generally, for purposes herein sequence identity is determined using computer algorithms based on global alignment, such as the Needleman-Wunsch Global Sequence Alignment tool available from NCBI/BLAST® (blast.ncbi.nlm.nih.gov/Blast.cgi?CMD=Web&Page TYPE=BlastHome); LAlign (William Pearson implementing the Huang and Miller algorithm (*Adv. Appl. Math.* (1991) 12:337-357)); and program from Xiaoqui Huang available at deepc2.psi.iastate.edu/aat/align/align.html. Generally, when comparing nucleotide sequences herein, an alignment with penalty for end gaps is used. Local alignment also can be used when the sequences being compared are substantially the same length.

Therefore, as used herein, the term "identity" represents a comparison or alignment between a test and a reference polypeptide or polynucleotide. In one non-limiting example, "at least 90% identical to" refers to percent identities from 90 to 100% relative to the reference polypeptide or polynucleotide. Identity at a level of 90% or more is indicative of the fact that, assuming for exemplification purposes a test and reference polypeptide or polynucleotide length of 100 amino acids or nucleotides are compared, no more than 10% (i.e., 10 out of 100) of amino acids or nucleotides in the test polypeptide or polynucleotide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences also can be due to deletions or truncations of amino acid residues. Differences are defined as nucleic acid or amino acid substitutions, insertions or deletions. Depending on the length of the compared sequences, at the level of homologies or identities above about 85-90%, the result can be independent of the program and gap parameters set; such high levels of identity can be assessed readily, often without relying on software.

As used herein, it also is understood that the terms "substantially identical" or "similar" varies with the context as understood by those skilled in the relevant art, but that those of skill can assess such.

As used herein, an aligned sequence refers to the use of homology (similarity and/or identity) to align corresponding positions in a sequence of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, isolated or purified polypeptide or protein or biologically-active portion thereof is substantially free of cellular material or other contaminating proteins from the cell of tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as proteolytic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

The term substantially free of cellular material includes preparations of valencene synthase and terpene products in which the valencene synthase or terpene product is separated from cellular components of the cells from which it is isolated or produced. In one embodiment, the term substantially free of cellular material includes preparations of valencene synthase or terpene products having less than about 30%, 20%, 10%, 5% or less (by dry weight) of non-valencene synthase or terpene proteins or products, including cell culture medium.

As used herein, production by recombinant methods by using recombinant DNA methods refers to the use of the well known methods of molecular biology for expressing proteins encoded by cloned DNA.

As used herein, vector (or plasmid) refers to discrete DNA elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as bacterial artificial chromosomes, yeast artificial chromosomes and mammalian artificial chromosomes. Selection and use of such vehicles are well known to those of skill in the art.

As used herein, expression refers to the process by which nucleic acid is transcribed into mRNA and translated into peptides, polypeptides, or proteins. If the nucleic acid is derived from genomic DNA, expression can, if an appropriate eukaryotic host cell or organism is selected, include processing, such as splicing of the mRNA.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells.

As used herein, an adenovirus refers to any of a group of DNA-containing viruses that cause conjunctivitis and upper respiratory tract infections in humans.

As used herein, naked DNA refers to histone-free DNA that can be used for vaccines and gene therapy. Naked DNA is the genetic material that is passed from cell to cell during a gene transfer process called transformation or transfection. In transformation or transfection, purified or naked DNA that is taken up by the recipient cell will give the recipient cell a new characteristic or phenotype.

As used herein, operably or operatively linked when referring to DNA segments means that the segments are arranged so that they function in concert for their intended purposes, e.g., transcription initiates in the promoter and proceeds through the coding segment to the terminator.

As used herein, a "chimeric protein" or "fusion protein" refers to a polypeptide operatively-linked to a different polypeptide. A chimeric or fusion protein provided herein can include one or more valencene synthase polypeptides, or a portion thereof, and one or more other polypeptides for any one or more of a transcriptional/translational control signals, signal sequences, a tag for localization, a tag for purification, part of a domain of an immunoglobulin G, and/or a targeting agent. A chimeric valencene synthase polypeptide also includes those having their endogenous domains or regions of the polypeptide exchanged with another polypeptide. These chimeric or fusion proteins include those produced by recombinant means as fusion proteins, those produced by chemical means, such as by chemical coupling, through, for example, coupling to sulfhydryl groups, and those produced by any other method whereby at least one polypeptide (i.e. valencene synthase), or a portion thereof, is linked, directly or indirectly via linker(s) to another polypeptide.

As used herein, recitation that a polypeptide "consists essentially" of a recited sequence of amino acids means that only the recited portion, or a fragment thereof, of the full-length polypeptide is present. The polypeptide optionally, and generally will, include additional amino acids from another source or can be inserted into another polypeptide.

As used herein, the singular forms "a," "an" and "the" include plural referents unless the context clearly dictates otherwise. Thus, for example, reference to a polypeptide, comprising "an amino acid replacement" includes polypeptides with one or a plurality of amino acid replacements.

As used herein, ranges and amounts can be expressed as "about" a particular value or range. About also includes the exact amount. Hence "about 5%" means "about 5%" and also "5%."

As used herein, "optional" or "optionally" means that the subsequently described event or circumstance does or does not occur, and that the description includes instances where said event or circumstance occurs and instances where it does not. For example, an optional step of isolating valencene means that the valencene is isolated or is not isolated.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

B. OVERVIEW

Provided herein are valencene synthases from *Eryngium glaciale*, and variants and catalytically active fragments thereof, that catalyze production of terpenes from an acyclic pyrophosphate terpene precursor. The terpenes include valencene and optionally other sesquiterpenes. Such valencene synthases catalyze the biosynthetic production of valencene from an acyclic pyrophosphate precursor, such as farnesyl pyrophosphate. Also provided herein are methods for producing valencene and other sesquiterpenes from such precursor, such as, but not limited to, farnesyl pyrophosphate. Also provided herein are methods for making nootkatone from the resulting valencene and from the acyclic precursor, such as farnesyl pyrophosphate. The provided *Eryngium glaciale* valencene synthases (EgVSs) provide for production of valuable terpene products, including valencene, in commercially useful quantities and in a cost effective and energy efficient manner. In particular the EgVSs catalyze production of very high levels of valencene compared to other valencene synthases, including CVS.

1. Valencene Structure and Uses

Valencene (1,2,3,5,6,7,8,8a-octahydro-7-isopropenyl-1, 8a-dimethyl-naphthalene; (1) is a sesquiterpene found in citrus oils, such as orange and grapefruit. To date, valencene has been identified in various plants including citrus fruit (*Citrus* sp.), grapevine flowers (*Vitis vinifera*), celery (*Apium graveolens*), mango (*Mangifera indica*), olives (*Olea europea*) and coral. Valencene is used as an orange flavor/fragrance in perfumes, beverages and chewing gums, and is used as a starting material for the production of nootkatone.

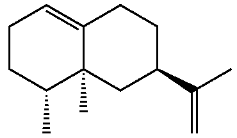

Valencene (1)

Valencene is generated in plants by the terpene synthase valencene synthase, which catalyzes the reaction of the acyclic pyrophosphate terpene precursor farnesyl pyrophosphate (FPP) into valencene (see FIG. 1).

2. Nootkatone

Nootkatone (4,4a,5,6,7,8-hexahydro-6-isopropenyl-4,4-a-dimethyl-2(3H)-naphthalenone; (2), is a sesquiterpenoid found in grapefruit oil which provides the dominant grapefruit aroma. Typically, nootkatone is isolated by extraction from grapefruit. Nootkatone has also been identified in various other plants including, for example, Alaska yellow cedar trees (*Cupressus nootkatensis*), vetiver grass (*Chrysopogon zizanioides*) and *Alpinia oxyphylla* Miguel.

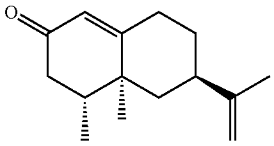 [SMILES: C=C(C)[C@@H]1CCC2=CC(=O)C[C@@H](C)[C@]2(C)C1]

Nootkatone (2)

Nootkatone is an oxidized product of valencene. Valencene can undergo regioselective hydroxylation to form 2-hydroxy valencene, which is further oxidized to form nootkatone (as described in further detail in Section E below). Nootkatone is valued for its grapefruit taste and aroma and is widely used in the perfumery and flavor industries. In addition, nootkatone has been shown to be an effective repellent and insecticide against ticks and mosquitoes.

3. Valencene Synthases

Valencene synthases are class 1 plant terpene cyclases, or terpene synthases, isoprenoid synthases or terpenoid cyclases, which convert farnesyl diphosphate into the sesquiterpene valencene. To date, valencene synthases have been isolated from citrus fruit, grapevine flowers and perilla (green shiso). Citrus valencene synthase (CVS) has been identified in the flavedo (outer peel) of *Citrus sinensis* (Sweet orange; Valencia orange) (SEQ ID NOS:14 and 34) and *Citrus×paradisi* (Grapefruit) (SEQ ID NOS:15, 26 and 27) (see, Chappell (2004) *Trends Plant Sci.,* 9:266; Sharon-Asa et al., (2003) *The Plant Journal* 36:664-674; AF411120 and U.S. Pat. Nos. 7,273,735; 7,442,785; 7,790,426; and International PCT Appl. No. WO2005021705 and WO2003025193). A variant valencene synthase has been described containing amino acid replacements A517I/I518V (Eyal, E. Master's Thesis, Department of Plant Sciences, Weizmann Institute of Science, Rehovot, Israel; January, 2001; set forth in SEQ ID NO:37). A variety of modified citrus valencene synthases have been described in U.S. Pat. Appl. No. 2012-0246767. Valencene synthases also have been identified and isolated from grapevine flowers, including *Vitis vinifera* L. cv. Gewürztraminer and *Vitis vinifera* L. cv. Cabernet Sauvignon (see, Lucker et al., (2004) *Phytochemistry* 65(19):2649-2659 and Martin et al., (2009) *Proc. Natl. Acad. Sci, USA* 106:7245-7250) (SEQ ID NOS:16 and 28). Valencene synthases also have been isolated from *Chamaecyparis nootkatensis pendula* (see e.g. International PCT Appl. Nos. WO2011074954 and WO2012177129; SEQ ID NOS: 17 and 29). The EgVS synthase provided herein is shown herein to catalyze production of high levels of valencene compared to other valencene synthases, including others whose sequences have been modified to produce increased levels of valencene.

a. Structure

Class 1 plant terpene cyclases include a diverse group of monomeric terpene synthases that share a common alpha helical architecture termed the class 1 terpenoid cyclase fold (see, e.g., Christianson, D. W., (2008) *Curr Opin Chem Biol* 12(2):141-150 and Bohlmann et al., (1998) *Proc. Natl. Acad. Sci. USA* 95:4126-4133). Although relatively little overall sequence similarity exists, class 1 plant terpene cyclases have homologous structures and some highly conserved motifs and/or residues. In its catalytic site, each terpene cyclase provides a template that binds the flexible isoprenoid substrate with an orientation and conformation such that upon cyclization, a specific intramolecular carbon-carbon bond is formed. Thus, the structure of each enzyme's catalytic site dictates the resulting cyclic monoterpenes, diterpenes and sesquiterpenes.

X-ray crystal structures of tobacco 5-epi-aristolochene synthase and pentalenene synthase revealed that class 1 plant terpene cyclases are composed of alpha helices interconnected by short connecting loops and turns (see, e.g., Starks et al., (1997) *Science* 277:1815-1820 and Lesburg et al., (1997) *Science* 277:1820-1824). These enzymes contain two distinct structural domains, an N-terminal domain, whose structure resembles catalytic cores of glycosyl hydrolysases but whose function remains largely unknown, and a C-terminal catalytic domain. The catalytic domain contains two conserved metal binding motifs, i.e., aspartate-rich regions, which are responsible for enzyme catalytic activity. The catalytic site contains a large central cavity formed by mostly antiparallel alpha helices with the two aspartate-rich regions located on opposite walls. The aspartate-rich regions mediate binding of substrate diphosphates via bridging $Mg^{2+}$ ions. Subsequent binding of the substrate induces conformational changes such that the N-terminal region forms a cap over the catalytic core that closes the active site to solvent, thereby stabilizing the reactive carbocation intermediates.

Conserved alpha helices C, D, F, G and H make up the catalytic or active site of class 1 plant terpene synthases. The active site is a hydrophobic pocket lined by aromatic residues to accommodate the olefin chain of the substrate. The aromatic residues stabilize carbocation intermediates through π-cation interactions. An aspartate-rich region 1 is located on Helix D and is characterized by the conserved sequence DDxxD (SEQ ID NO:35), which also functions to bind $Mg^{2+}$ (see, e.g., Starks et al., (1997), *Science* 277:1815-1820). A second conserved metal-binding region is located on Helix H and is characterized by the conserved sequence [N/D]xxx[S/T]xxxE (SEQ ID NO:36), also referred to as the "NSE/DTE motif." These two conserved metal binding motifs coordinate the binding of three $Mg^{2+}$ ions to the isoprenoid diphosphate.

*Eryngium glaciale* valencene synthase, provided herein, contains an N-terminal domain (aa 1-280 of SEQ ID NO:1) and a C-terminal catalytic domain (aa 281-565 of SEQ ID NO:1). Within the C-terminal catalytic domain is the conserved metal binding site that contains aspartate-rich regions 1 and 2. Based on alignment with known valencene synthases, such as citrus valencene synthase, aspartate-rich region 1, containing the conserved DDxxD motif, corresponds to amino acids D315, D316, T317, Y318 and D319 of SEQ ID NO:1. Asp315 and Asp319 bind the diphosphate moieties of FPP through coordination with $Mg^{2+}$. The aspartate-rich region 2, containing the NSE/DTE motif, corresponds to amino acids D461, D462, I463, G464, G465, H466, E467, F468 and E469 of SEQ ID NO:1. This region binds an additional $Mg^{2+}$ ion through amino acids Asp461, Gly465 and Glu469.

b. Activities Valencene synthase catalyzes the formation of valencene from acyclic pyrophosphate precursors, such as the ubiquitous pyrophosphate intermediate farnesyl diphosphate (FPP), which is produced as part of the mevalonate-dependent isoprenoid biosynthetic pathway in fungi and animals and the non-mevalonate-dependent isoprenoid biosynthetic pathway in bacteria and higher plants. Additional terpene products that can be produced by valencene synthase from acyclic pyrophosphate terpene precursors such as, FPP include, but are not limited to, germacrene A, beta-elemene (beta-elemene is formed by spontaneous decomposition of germacrene A), β-selinene, τ-selinene,7-epi-α-selinene and an additional compound, aristolochene, (see, e.g., Peak 2 in FIG. 3).

In general, class 1 plant terpene cyclases, such as valencene synthase, are metal dependent cyclases that convert linear all-trans isoprenoid diphosphates, such as geranyl diphosphate, farnesyl diphosphate and geranyl-geranyl diphosphate, into cyclic monoterpenes, diterpenes and sesquiterpenes. Cyclization reactions proceed via electrophilic alkylation in which new carbon-carbon single bonds are formed through reaction of a highly reactive electron-deficient allylic carbocation and an electron-rich carbon-carbon double bond.

Terpene synthases contain divalent metal ions, typically $Mg^{2+}$ ions or sometimes $Mn^{2+}$, at the active center of the enzyme that are required for enzyme catalysis. More specifically, they are required for pyrophosphate departure. Generally, the enzymes contain two conserved metal binding motifs that line the catalytic site, including the aspartate-rich DDxxD motif (SEQ ID NO:35) that coordinates binding of two $Mg^{2+}$ ions and the NSE/DTE motif (SEQ ID NO:36) that coordinates a third $Mg^{2+}$ ion (see, Starks et al., (1997), *Science* 277:1815-1820 and Lesburg et al., (1997), *Science* 277:1820-1824). The aspartate-rich regions of the catalytic active site mediate binding of prenyl diphosphates via bridging $Mg^{2+}$ ions. Binding of $(Mg^{2+})_3$-$PP_i$ induces conformational changes such that the N-terminal region forms a cap over the catalytic core and therefore stabilizes the active site in a closed conformation that is free from bulk solvent. Loss of pyrophosphate ($PP_i$) from the enzyme-bound substrate results in a highly reactive allylic carbocation that electrophilically attacks an intramolecular double bond further down the terpene chain to effect ring closure. The $PP_i$ anion accepts hydrogen bonds from conserved basic residues when bound in the closed synthase conformation and a hydrophobic pocket lined by aromatic residues cradles the prenyl side chain and likely templates the cyclization reaction by enforcing particular substrate conformations and stabilizing carbocations through it-stacking interactions (Noel et al., (2010) *ACS Chemical Biology* 5(4):377-392).

4. Assays for Detecting the Enzymatic Activity of Valencene Synthase Polypeptides One of skill in the art is familiar with methods and assays to detect the enzymatic activity of valencene synthase polypeptides. Valencene synthase polypeptides can be overexpressed and purified as described in Section C below. Typically, the activity of a valencene synthase is determined by incubation of a valencene synthase with an acyclic pyrophosphate terpene precursor, such as farnesyl pyrophosphate (FPP), and identifying, measuring and/or quantifying the valencene and other reaction products.

For example, valencene synthase activity can be determined in vitro by incubation of a valencene synthase with an acyclic pyrophosphate terpene precursor, such as FPP, and identifying the reaction products. Reaction products, including ratios of the products, can be determined by any method known to one of skill in the art, including gas chromatography-mass spectrometry (GC-MS), GC-FID, liquid chromatography-mass spectrometry (LC-MS), comparison to known standards, and proton and carbon nuclear magnetic resonance (NMR).

Alternatively, valencene synthase activity can be determined in vivo by expression of a valencene synthase in a yeast strain that produces an acyclic pyrophosphate terpene precursor, such as FPP, whereby expression of the valencene synthase results in production of valencene and additional compounds/reaction products or byproducts. The valencene and additional compounds can be purified from the cell culture medium, for example, by extraction with an organic solvent whereby the valencene and other products partition into the aqueous phase, as described in Example 4, and the reaction products can be identified and quantified as described above. Exemplary yeast cells for expression of valencene synthases and methods for generating modified yeast cells that produce an acyclic pyrophosphate terpene precursor are described in further detail in Section E below.

The kinetics of valencene production can be determined by standard methods, such as by synthase assays in which radioactive isoprenoid substrates, such as $^{3}H$ FPP or $^{14}C$ FPP, are employed with varying concentrations of synthase. The products of the reaction are extracted into an organic layer and radioactivity is measured using a liquid scintillation counter. Kinetic constants are determined from direct fits of the Michaelis-Menton equation to the data.

C. NUCLEIC ACID MOLECULES ENCODING *ERYNGIUM GLACIALE* VALENCENE SYNTHASE (EGVS) AND ENCODED POLYPEPTIDES

Provided herein are nucleic acid molecules that encode a valencene synthase polypeptide, including cDNA molecules. Also provided herein are valencene synthase polypeptides, and catalytically active fragments thereof, encoded by the nucleic acid molecules provided herein. The valencene synthases encoded by nucleic acid molecules provided herein catalyze the formation of valencene from any suitable acyclic pyrophosphate terpene precursor, including farnesyl pyrophosphate (FPP), geranyl pyrophosphate (GPP) and geranyl-geranyl pyrophosphate (GGPP). Of interest herein is the production of valencene from FPP. In some examples, the nucleic acid molecules provided herein that encode the valencene synthase polypeptides are those that are the same as those that are isolated from the thistle *Eryngium glaciale*.

In other examples, the nucleic acid molecules and encoded valencene synthase polypeptides provided herein are variants of those isolated from the thistle *Eryngium glaciale*.

For example, provided herein is a nucleic acid molecule that has a sequence of nucleotides set forth in SEQ ID NO:2, and degenerates thereof, that encode a valencene synthase polypeptide having a sequence of amino acids set forth in SEQ ID NO:1. Also provided herein are nucleic acid molecules having at least 85% sequence identity to a sequence of nucleotides set forth in SEQ ID NO:2 that encode a valencene synthase polypeptide. For example, the nucleic acid molecules provided herein can exhibit at least or about at least 85%, 86%, 87%, 88%, 89%, 90%, 91%, 92%, 93%, 95%, 95%, 96%, 97%, 98% or 99% or more sequence identity to a sequence of nucleotides set forth in SEQ ID NO:2, so long as the encoded valencene synthase polypeptides exhibit valencene synthase activity (i.e., the ability to catalyze the formation of valencene). Percent identity can be determined by one skilled in the art using standard alignment programs. Also provided herein are degenerate sequences of the nucleotide sequence set forth in SEQ ID NO:2, encoding a valencene synthase having a sequence of amino acids set forth in SEQ ID NO:1. In some examples, the nucleic acid molecules that encode the valencene synthase polypeptides are isolated from the thistle *Eryngium glaciale*. In other examples, the nucleic acid molecules and encoded valencene synthase polypeptides are variants of those isolated from the thistle *Eryngium glaciale*.

Also provided herein are nucleic acid molecules that encode a modified valencene synthase polypeptide provided herein. The modifications can be made in any region of a gene encoding the valencene synthase provided the resulting encoded modified valencene synthase polypeptide at least retains valencene synthase activity (i.e. the ability to catalyze the formation of valencene from an acyclic pyrophosphate terpene precursor, typically FPP). The modifications can include codon optimization of the nucleic acids and/or changes that result in a single amino acid modification in the encoded valencene synthase polypeptide, such as single amino acid replacements (substitutions), insertions or deletions, or multiple amino acid modifications, such as multiple amino acid replacements, insertions or deletions, including swaps of regions or domains of the polypeptide.

Expression of the nucleic acid molecules provided herein in a suitable host, for example, a bacterial or yeast cell, results in expression of valencene synthase. Such cells can be used to produce the valencene synthase and/or to perform reactions in vivo to produce valencene. For example, valencene can be generated in a yeast cell from FPP, particularly a yeast cell that overproduces the acyclic pyrophosphate terpene precursor FPP.

In particular examples, the nucleic acid molecules provided herein can be codon optimized, for example, to increase expression levels of the encoded sequence. The particular codon usage is dependent on the host organism in which the modified polypeptide is expressed. One of skill in the art is familiar with optimal codons for expression in bacteria or yeast, including for example *E. coli* or *Saccharomyces cerevisiae*. For example, codon usage information is available from the Codon Usage Database available at kazusa.or.jp.codon (see Richmond (2000) *Genome Biology,* 1:241 for a description of the database). See also, Forsburg (2004) *Yeast,* 10:1045-1047; Brown et al. (1991) *Nucleic Acids Research,* 19:4298; Sharp et al. (1988) *Nucleic Acids Research,* 12:8207-8211; Sharp et al. (1991) *Yeast,* 657-678. In some examples, the nucleic acid molecules provided herein encoding a valencene synthase polypeptide are codon optimized for expression in bacteria or yeast. In particular examples, the nucleic acid molecules provided herein encoding a valencene synthase are codon optimized for expression based on codon usage in *Saccharomyces cerevisiae.*

Also provided herein are valencene synthase polypeptides encoded by any of the nucleic acid molecules provided herein. Valencene synthase polypeptides and active fragments thereof encoded by the nucleic acid molecules provided herein can be obtained by methods well known in the art for recombinant protein generation and expression. Such valencene synthase polypeptides can be used to produce valencene from a suitable acyclic pyrophosphate terpene precursor, such as FPP, in the host cell from which the synthase is expressed, or in vitro following purification of the synthase. Any method known to those of skill in the art for identification of nucleic acids that encode desired genes can be used to obtain the nucleic acid encoding a terpene synthase, such as a valencene synthase. For example, nucleic acid encoding valencene synthase polypeptides can be obtained using well known methods from a plant source, such as thistle. Modified valencene polypeptides then can be engineered using any method known in the art for introducing mutations into unmodified or wild type valencene synthase polypeptides, including any method described herein, such as random mutagenesis of the encoding nucleic acid by error-prone PCR, site-directed mutagenesis, overlap PCR, or other recombinant methods. The nucleic acids encoding the polypeptides then can be introduced into a host cell to be expressed heterologously.

1. Isolation of Nucleic Acid Encoding Valencene Synthases

Nucleic acids encoding valencene synthases can be cloned or isolated using any available methods known in the art for cloning and isolating nucleic acid molecules. Such methods include PCR amplification of nucleic acids and screening of libraries, including nucleic acid hybridization screening. In some examples, methods for amplification of nucleic acids can be used to isolate nucleic acid molecules encoding a valencene synthase polypeptide, including for example, polymerase chain reaction (PCR) methods. A nucleic acid containing material can be used as a starting material from which a valencene synthase-encoding nucleic acid molecule can be isolated. Nucleic acid libraries can be used as a source of starting material. Primers are designed to amplify a valencene synthase-encoding molecule. The molecules provided herein can be used as templates for primers or hybridization or comparison.

To isolate the nucleic acid provided here, DNA and mRNA preparations from thistle (*Eryngium* sp.), in this instance *Eryngium glaciale*, were prepared and screened with primers based on other valencene synthases employed for screening. For example, primers were designed based on known nucleic acid sequences encoding a terpene synthase, such as a valencene synthase, germacrene D synthase and vetispiradiene (premnaspirodiene) synthase, including those whose sequences are set forth in SEQ ID NOS: 39-44. Nucleic acid molecules generated by amplification can be sequenced and those that encode a valencene synthase polypeptide identified.

Additional nucleotide sequences can be joined to a valencene synthase-encoding nucleic acid molecule, including linker sequences containing restriction endonuclease sites for the purpose of cloning the synthetic gene into a vector, for example, a protein expression vector or a vector designed for the amplification of the core protein coding DNA sequences. Furthermore, additional nucleotide sequences specifying functional DNA elements can be operatively linked to a valencene synthase-encoding nucleic acid molecule. Still further, nucleic acid encoding other moieties or domains also can be included so that the resulting synthase is a fusion protein. For example, nucleic acids encoding other enzymes, such as FPP synthase, or protein purification tags, such as His or Flag tags.

a. Preparation of Modified Nucleic Acid

Nucleic acid encoding a modified valencene synthase (described in further detail in Section D below) can be prepared or generated using any method known in the art to effect modification, particularly amino acid insertions, deletions and replacements. Methods for modification of nucleic acid molecules include standard rational and/or random mutagenesis of encoding nucleic acid molecules (using e.g., error prone PCR, random site-directed saturation mutagenesis, DNA shuffling or rational site-directed mutagenesis, such as, for example, mutagenesis kits (e.g. QuikChange available from Stratagene), or solid phase synthesis methods). In addition, routine recombinant DNA techniques can be utilized to generate nucleic acids encoding polypeptides that contain heterologous amino acids. For example, nucleic acid encoding chimeric polypeptides or polypeptides containing heterologous amino acid sequence can be generated using a two-step PCR method, and/or using restriction enzymes and cloning methodologies for routine subcloning of the desired chimeric polypeptide components.

Once generated, the nucleic acid molecules can be expressed in cells to generate modified valencene synthase polypeptides using any method known in the art. The modified valencene synthase polypeptides then can be assessed by screening for a desired property or activity, for example, for the ability to produce a valencene from a suitable substrate, e.g., FPP, as described in Section E. In particular examples, modified valencene synthases with desired properties are generated by mutation and screened for a property in accord with the examples exemplified herein. Typically, the modified valencene synthase polypeptides produce valencene from FPP.

2. Vectors and Cells for Expression of Valencene Synthase Polypeptides

For recombinant expression of one or more of the valencene synthase polypeptides encoded by the nucleic acids provided herein, the nucleic acid containing all or a portion of the nucleotide sequence encoding the synthase can be inserted into an appropriate expression vector, i.e., a vector that contains the necessary elements for the transcription and translation of the inserted protein coding sequence. Depending upon the expression system used, the necessary transcriptional and translational signals also can be supplied by the native promoter for a valencene synthase gene, and/or their flanking regions. Thus, also provided herein are vectors that contain nucleic acid encoding any valencene synthase polypeptide provided herein. Exemplary vectors include pALX.63-71 set forth in SEQ ID NO:33 and described in Example 4 below.

Cells, including prokaryotic and eukaryotic cells, containing the vectors also are provided. Such cells include bacterial cells, yeast cells, fungal cells, Archea, plant cells, insect cells and animal cells. In particular examples, the cells are yeast, such as *Saccharomyces cerevisiae*, that express an acyclic pyrophosphate terpene precursor, such as FPP. The cells are used to produce a valencene synthase, by growing the above-described cells under conditions whereby the encoded valencene synthase is expressed by the cell. In some instances, the expressed synthase is purified. In other instances, the expressed valencene synthase converts FPP to one or more sesquiterpenes (e.g. valencene) in the host cell.

Any method known to those of skill in the art for the insertion of DNA fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding a valencene synthase polypeptide, or domains, derivatives, fragments or homologs thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes encoding a valencene synthase protein. Promoters that can be used include but are not limited to prokaryotic, yeast, mammalian and plant promoters. The type of promoter depends upon the expression system used, described in more detail below.

In a specific embodiment, a vector is used that contains a promoter operably linked to nucleic acids encoding a valencene synthase polypeptide, or a domain, fragment, derivative or homolog thereof, one or more origins of replication, and optionally, one or more selectable markers (e.g., an antibiotic resistance gene). Vectors and systems for expression of valencene synthase polypeptides are described.

3. Expression Systems

Valencene synthase polypeptides (modified and unmodified) can be produced by any methods known in the art for protein production including in vitro and in vivo methods such as, for example, the introduction of nucleic acid molecules encoding the valencene synthase into a host cell or host plant for in vivo production or expression from nucleic acid molecules encoding the valencene synthase in vitro. Valencene synthase polypeptides can be expressed in any organism suitable to produce the required amounts and forms of a synthase polypeptide. Expression hosts include prokaryotic and eukaryotic organisms such as *E. coli*, yeast, plants, insect cells, mammalian cells, including human cell lines and transgenic animals. Expression hosts can differ in their protein production levels as well as the types of post-translational modifications that are present on the expressed proteins. The choice of expression host can be made based on these and other factors, such as regulatory and safety considerations, production costs and the need and methods for purification.

Expression in eukaryotic hosts can include expression in yeast cells such as those from the *Saccharomyces* genus (e.g. *Saccharomyces cerevisiae*) and *Pichia* genus (e.g. *Pichia pastoris*), insect cells such as *Drosophila* cells and lepidopteran cells, plants and plant cells such as citrus, tobacco, corn, rice, algae, and lemna. Eukaryotic cells for expression also include mammalian cells lines such as Chinese hamster ovary (CHO) cells or baby hamster kidney (BHK) cells. Eukaryotic expression hosts also include production in transgenic animals, for example, including production in serum, milk and eggs.

Many expression vectors are available and known to those of skill in the art for the expression of a terpene synthase, such as valencene synthase. An exemplary expression vector is pALX31-108.2, set forth in SEQ ID NO:32, and described elsewhere herein. The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows for selection and maintenance of the transformed cells. In some cases, an origin of replication can be used to amplify the copy number of the vectors in the cells.

Methods of production of terpene synthase polypeptides, including valencene synthase polypeptides, can include co-expression of an acyclic pyrophosphate terpene precursor, such as FPP, in the host cell. In some instances, the host cell naturally expresses FPP. Such a cell can be modified to express greater quantities of FPP (see e.g. U.S. Pat. Nos. 6,531,303, 6,689,593, 7,838,279 and 7,842,497). In other instances, a host cell that does not naturally produce FPP is modified genetically to produce FPP.

a. Prokaryotic Cells

Prokaryotes, especially *E. coli*, provide a system for producing large amounts of valencene synthase polypeptides provided herein. Transformation of *E. coli* is a simple and rapid technique well known to those of skill in the art. Exemplary expression vectors for transformation of *E. coli* cells include, for example, the pGEM expression vectors, the pQE expression vectors, and the pET expression vectors (see, U.S. Pat. No. 4,952,496; available from Novagen, Madison, Wis.; see, also literature published by Novagen describing the system). Such plasmids include pET 11a, which contains the T7lac promoter, T7 terminator, the inducible *E. coli* lac operator, and the lac repressor gene; pET 12a-c, which contains the T7 promoter, T7 terminator, and the *E. coli* ompT secretion signal; and pET 15b and pET19b (Novagen, Madison, Wis.), which contain a His-Tag™ leader sequence for use in purification with a Ni column and a thrombin cleavage site that permits cleavage following purification over the column, the T7-lac promoter region and the T7 terminator.

Expression vectors for *E. coli* can contain inducible promoters that are useful for inducing high levels of protein expression and for expressing proteins that exhibit some toxicity to the host cells. Exemplary prokaryotic promoters include, for example, the β-lactamase promoter (Jay et al., (1981) *Proc. Natl. Acad. Sci. USA* 78:5543) and the tac promoter (DeBoer et al., (1983) *Proc. Natl. Acad. Sci. USA* 80:21-25); see also "Useful Proteins from Recombinant Bacteria": in Scientific American 242:74-94 (1980)). Examples of inducible promoters include the lac promoter, the trp promoter, the hybrid tac promoter, the T7 and SP6 RNA promoters and the temperature regulated $\lambda P_L$ promoter.

Valencene synthase polypeptides provided herein can be expressed in the cytoplasmic environment of *E. coli*. The cytoplasm is a reducing environment and for some molecules, this can result in the formation of insoluble inclusion bodies. Reducing agents such as dithiothreitol and β-mercaptoethanol and denaturants (e.g., such as guanidine-HCl and urea) can be used to resolubilize the proteins. An alternative approach is the expression of valencene synthases in the periplasmic space of bacteria which provides an oxidizing environment and chaperonin-like and disulfide isomerases leading to the production of soluble protein. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility. Typically, temperatures between 25° C. and 37° C. are used. Mutations also can be used to increase solubility of expressed proteins. Typically, bacteria produce aglycosylated proteins.

b. Yeast Cells

Yeast systems, such as, but not limited to, those from the *Saccharomyces* genus (e.g. *Saccharomyces cerevisiae*), *Schizosaccharomyces pombe, Yarrowia lipolytica, Kluyveromyces lactis*, and *Pichia pastoris* can be used to express the valencene synthase polypeptides provided herein. Yeast expression systems also can be used to produce terpenes, e.g., valencene, whose reactions are catalyzed by the synthases (e.g., valencene synthases). Yeast can be transformed with episomal replicating vectors or by stable chromosomal integration by homologous recombination. In some examples, inducible promoters are used to regulate gene expression. Exemplary promoter sequences for expression of valencene synthase polypeptides in yeast include, among others, promoters for metallothionine, 3-phosphoglycerate kinase (Hitzeman et al. (1980) *J. Biol. Chem.* 255:12073), or other glycolytic enzymes (Hess et al. (1968) *J. Adv. Enzyme Reg.* 7:149; and Holland et al. (1978) *Biochem.* 17:4900), such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other suitable vectors and promoters for use in yeast expression are further described in Hitzeman et al. (1980) *J. Biol. Chem.* 255:12073, EPA-73,657 or in Fleer et al. (1991) *Gene,* 107:285-195; and van den Berg et al. (1990) *Bio/Technology,* 8:135-139. Another alternative includes, but is not limited to, the glucose-repressible ADH2 promoter described by Russell et al. (*J. Biol. Chem.* 258:2674, 1982) and Beier et al. (*Nature* 300:724, 1982), or a modified ADH1 promoter. Shuttle vectors replicable in yeast and *E. coli* can be constructed by, for example, inserting DNA sequences from pBR322 for selection and replication in *E. coli* ($Amp^r$ gene and origin of replication) into the above-described yeast vectors.

Yeast expression vectors can include a selectable marker such as LEU2, TRP1, HIS3, and URA3 for selection and maintenance of the transformed DNA. Exemplary vectors include pALX31-108.2, described elsewhere herein, that contains a URA3 marker. Proteins expressed in yeast are often soluble and co-expression with chaperonins, such as Bip and protein disulfide isomerase, can improve expression levels and solubility. Additionally, proteins expressed in yeast can be directed for secretion using secretion signal peptide fusions such as the yeast mating type alpha-factor secretion signal from *Saccharomyces cerevisiae* and fusions with yeast cell surface proteins such as the Aga2p mating adhesion receptor or the *Arxula adeninivorans* glucoamylase. A protease cleavage site (e.g., the Kex-2 protease) can be engineered to remove the fused sequences from the polypeptides as they exit the secretion pathway.

Yeast naturally expresses the required proteins, including FPP synthase (ERG20 gene; which can produce FPP) for the mevalonate-dependent isoprenoid biosynthetic pathway. Thus, expression of the terpene synthases, including valencene synthase polypeptides provided herein, in yeast cells can result in the production of sesquiterpenes, such as valencene from FPP. Exemplary yeast cells for the expression of valencene synthase polypeptides include yeast modified to express increased levels of FPP. For example, yeast cells can be modified to produce less squalene synthase or less active squalene synthase (e.g. erg9 mutants; see e.g. U.S. Pat. Nos. 6,531,303 and 6,689,593 and U.S. Pat. Pub. Nos. 2010-0151519 and 2010-0151555). This results in accumulation of FPP in the host cell at higher levels compared to wild type yeast cells, which in turn can result in increased yields of sesquiterpenes (e.g. valencene).

In another example, yeast cells can be modified to produce more FPP synthase by introduction of a FPP synthase gene, such as FPPS from *A. annua* (see, e.g., Brodelius et al. (2002) *Eur. J. Biochem.* 269:3570-3579), FPP from *N. crassa*, and FPS1 and FPS2 from *A. thaliana*. In some examples, the native FPP gene in such yeast can be deleted. Other modifications that enable increased production of FPP in yeast include, for example, but are not limited to, modifications that increase production of acetyl CoA, inactivate genes that encode enzymes that use FPP and GPP as substrate and overexpress of HMG-CoA reductases, as described in U.S. Pat. No. 7,842,497. Exemplary modified yeast cells include, but are not limited to, modified *Saccharomyces cerevisiae* strains CALI5-1 (ura3, leu2, his3, trp1, Δerg9::HIS3, HMG2cat/TRP1::rDNA, dpp1, sue), ALX7-95 (ura3, his3, trp1, Δerg9::HIS3, HMG2cat/TRP1::rDNA, dpp1 sue), ALX11-30 (ura3, trp1, erg9$^{def}$25, HMG2cat/TRP1::rDNA, dpp1, sue), which are known and described in one or more of U.S. Pat. Nos. 6,531,303, 6,689,593, 7,838,279, 7,842,497, and published U.S. Pat. Application Nos. 2004-0249219 and 2011-0189717.

c. Plants and Plant Cells

Transgenic plant cells and plants can be used for the expression of valencene synthase polypeptides provided herein. Expression constructs are typically transferred to plants using direct DNA transfer such as microprojectile bombardment and PEG-mediated transfer into protoplasts, and with *agrobacterium*-mediated transformation. Expression vectors can include promoter and enhancer sequences, transcriptional termination elements, and translational control elements. Expression vectors and transformation techniques are usually divided between dicot hosts, such as *Arabidopsis* and tobacco, and monocot hosts, such as corn and rice. Examples of plant promoters used for expression include the cauliflower mosaic virus promoter, the nopaline synthase promoter, the ribose bisphosphate carboxylase promoter and the ubiquitin and UBQ3 promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce proteins (see, for example, Mayfield et al. (2003) *Proc Natl Acad Sci USA* 100:438-442). Transformed plants include, for example, plants selected from the genera *Nicotiana, Solanum, Sorghum, Arabidopsis, Medicago* (alfalfa), *Gossypium* (cotton) and *Brassica* (rape). In some examples, the plant belongs to the species of *Nicotiana tabacum*, and is transformed with vectors that overexpress valencene synthase and farnesyl diphosphate synthase, such as described in U.S. Pat. Pub. No. 2009-0123984 and U.S. Pat. No. 7,906,710.

d. Insects and Insect Cells

Insects and insect cells, particularly a baculovirus expression system, can be used for expressing valencene synthase polypeptides provided herein (see, for example, Muneta et al. (2003) *J. Vet. Med. Sci.* 65(2):219-223). Insect cells and insect larvae; including expression in the haemolymph, express high levels of protein and are capable of most of the post-translational modifications used by higher eukaryotes. Baculoviruses have a restrictive host range which improves the safety and reduces regulatory concerns of eukaryotic expression. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda, Pseudaletia unipuncta* (A7S) and *Danaus plexippus* (DpN1). For high level expression, the nucleotide sequence of the molecule to be expressed is fused immediately downstream of the polyhedrin initiation codon of the virus. Mammalian secretion signals are accurately processed in insect cells and can be used to secrete the expressed protein into the culture medium. In addition, the cell lines *Pseudaletia unipuncta* (A7S) and *Danaus plexippus* (DpN1) produce proteins with glycosylation patterns similar to mammalian cell systems.

An alternative expression system in insect cells is the use of stably transformed cells. Cell lines such as the Schnieder 2 (S2) and Kc cells (*Drosophila melanogaster*) and C7 cells (*Aedes albopictus*) can be used for expression. The *Drosophila* metallothionein promoter can be used to induce high levels of expression in the presence of heavy metal induction with cadmium or copper. Expression vectors are typically maintained by the use of selectable markers such as neomycin and hygromycin.

e. Mammalian Cells

Mammalian expression systems can be used to express valencene synthase polypeptides provided herein and also can be used to produce valencene and other terpenes whose formation are catalyzed by the valencene synthases. Expression constructs can be transferred to mammalian cells by standard methods, including, but not limited to, viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the SV40 promoter-enhancer, the human cytomegalovirus (CMV) promoter, or the long terminal repeat of Rous sarcoma virus (RSV) promoter. These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha-fetoprotein, alpha 1-antitrypsin, beta-globin, myelin basic protein, myosin light chain-2 and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase and thymidine kinase. Fusion with cell surface signaling molecules such as TCR-ζ and $Fc_{\epsilon}RI$-γ can direct expression of the proteins in an active state on the cell surface.

Many cell lines are available for mammalian expression including mouse, rat human, monkey, and chicken and hamster cells. Exemplary cell lines include, but are not limited to, BHK (i.e. BHK-21 cells), 293-F, CHO, CHO Express (CHOX; Excellgene), Balb/3T3, HeLa, MT2, mouse NS0 (non-secreting) and other myeloma cell lines, hybridoma and heterohybridoma cell lines, lymphocytes, fibroblasts, Sp2/0, COS, NIH3T3, HEK293, 293S, 293T, 2B8, and HKB cells. Cell lines also are available adapted to serum-free media which facilitates purification of secreted proteins from the cell culture media. One such example is the serum free EBNA-1 cell line (Pham et al. (2003) *Biotechnol. Bioeng.* 84:332-42).

4. Purification

Methods for purification of valencene synthase polypeptides from host cells depend on the chosen host cells and expression systems. For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary the proteins can be extracted and further purified using standard methods in the art.

Valencene synthases can be purified using standard protein purification techniques known in the art including but not limited to, SDS-PAGE, size fraction and size exclusion chromatography, ammonium sulfate precipitation, chelate chromatography and ionic exchange chromatography. Expression constructs also can be engineered to add an affinity tag such as a myc epitope, GST fusion or $His_6$ and affinity purified with myc antibody, glutathione resin, and Ni-resin, respectively, to a protein. Purity can be assessed by any method known in the art including gel electrophoresis and staining and spectrophotometric techniques.

D. VALENCENE SYNTHASE POLYPEPTIDES

Provided herein are valencene synthase polypeptides. In some examples, the valencene synthase polypeptides are encoded by nucleic acids isolated from the thistle *Eryngium glaciale*. In other examples, the valencene synthase polypeptides are variants or catalytically active fragments of those encoded by nucleic acids isolated from the thistle *Eryngium glaciale*. The valencene synthase polypeptides provided herein catalyze the formation of valencene from a suitable precursor, such as an acyclic pyrophosphate terpene precursor, e.g., farnesyl pyrophosphate (FPP).

Also provided herein are modified valencene synthase polypeptides. Modifications contemplated herein include, for example, amino acid replacements or substitutions, additions or deletions, truncations or combinations thereof. The modifications can be made in any region of a valencene synthase provided the resulting modified valencene synthase polypeptide at least retains valencene synthase activity (i.e. the ability to catalyze the formation of valencene synthase from an acyclic pyrophosphate terpene precursor, typically FPP). The valencene synthase polypeptides provided herein can contain other modifications, for example, modifications not in the primary sequence of the polypeptide, including, for example, post-translational modifications.

Also provided herein are catalytically active fragments of the valencene synthase polypeptides. For example, provided herein are active fragments of the valencene synthase polypeptide having a sequence of amino acids set forth in SEQ ID NO:1. The active fragments retain the ability to catalyze the formation of valencene from the acyclic pyrophosphate terpene precursor, such as farnesyl pyrophosphate (FPP). In particular examples the valencene synthase polypeptides are truncated at the N- or C-terminus as described in further detail below. In some examples, the active fragments of valencene synthase polypeptides are modified as described herein. Such fragments retain one or more properties of a full-length valencene synthase polypeptide. Typically, the active fragments exhibit valencene synthase activity (i.e., catalyze the formation of valencene).

Valencene synthase polypeptides provided herein can be generated by any method known to one of skill in the art. In some examples, the valencene synthase polypeptides provided herein are produced synthetically, such as using sold phase or solution phase peptide synthesis. Typically, the valencene synthase polypeptides provided herein are expressed in a host cell from a nucleic acid encoding the valencene synthase polypeptide, as described in Section C above. An exemplary host cell for the expression of a valencene synthase polypeptide is a yeast cell, e.g., a *S. cerevisiae* cell.

The valencene synthase polypeptides provided herein can be used catalyze production of valencene. Typically, the valencene synthase polypeptides provided herein catalyze the formation of valencene from FPP. Reactions can be performed in vivo, such as in a host cell into which a nucleic acid encoding the valencene synthase polypeptide has been introduced (as described in Section C above). At least one of the polypeptides, e.g., the valencene synthase polypeptide, will be heterologous to the host. Reactions also can be performed in vitro by contacting with valencene synthase polypeptide with the appropriate substrate, e.g., farnesyl diphosphate, under appropriate conditions for generation of valencene.

1. *Eryngium glaciale* Valencene Synthase Polypeptides

Provided herein is a valencene synthase polypeptide having a sequence of amino acids set forth in SEQ ID NO:1. Also provided herein are valencene synthase polypeptides that exhibit at least 50% amino acid sequence identity to a valencene synthase polypeptide set forth in SEQ ID NO:1. For example, the valencene synthase polypeptides provided herein can exhibit at least or at least about 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid sequence identity to a valencene synthase polypeptide set forth in SEQ ID NO:1, provided the resulting valencene synthase polypeptide at least retains valencene synthase activity (i.e. the ability to catalyze the formation of valencene from an acyclic pyrophosphate terpene precursor, typically FPP). Percent identity can be determined by one skilled in the art using standard alignment programs.

2. Modifications of *Eryngium glaciale* Valencene Synthase Polypeptides

Provided herein are modified *Eryngium glaciale* valencene synthase polypeptides. Also provided herein are nucleic acid molecules that encode any of the modified valencene synthase polypeptides provided herein. The modifications can be made in any region of a valencene synthase provided the resulting modified valencene synthase polypeptide at least retains valencene synthase activity (i.e., the ability to catalyze the formation of valencene from an acyclic pyrophosphate terpene precursor, typically FPP).

The modifications can be a single amino acid modification, such as single amino acid replacements (substitutions), insertions or deletions, or multiple amino acid modifications, such as multiple amino acid replacements, insertions or deletions. In some examples, entire or partial domains or regions, such as any domain or region described herein below, are exchanged with corresponding domains or regions or portions thereof from another terpene synthase. Exemplary modifications are amino acid replacements, including single or multiple amino acid replacements. Typically, the modification is an amino acid replacement, which can be a conservative substitution, such as set forth in Table 2, or a non-conservative substitution. For example, modified valencene synthase polypeptides provided herein can contain at least or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 105, 110, 115, 120 or more modified positions compared to the valencene synthase polypeptide not containing the modification.

The modifications described herein can be in any valencene synthase polypeptide. Typically, the modifications are made in a valencene synthase polypeptide provided herein. For example, the modifications described herein can be in a valencene synthase polypeptide as set forth in SEQ ID NO:1 or any variant thereof, including any that have at least 60%, 70%, 75%, 80%, 85%, 90%, 91%, 92%, 93%, 94%, 95%, 96%, 97%, 98%, or 99% sequence identity to a valencene synthase polypeptide set forth in SEQ ID NO:1.

In particular, the modified valencene synthase polypeptides provided herein contain amino acid replacements or substitutions, additions or deletions, truncations or combinations thereof with reference to the valencene synthase polypeptide set forth in SEQ ID NO:1. It is within the level of one of skill in the art to make such modifications in valencene synthase polypeptides, such as any set forth in SEQ ID NO:1 or any variant thereof. Exemplary methods for generating modified valencene synthase polypeptides are provided in Section C.1.a. above. It is within the level of one of skill in the art to generate a valencene synthase containing any one or more of the described mutations, and test each for valencene synthase activity as described herein.

Also, in some examples, provided herein are modified active fragments of valencene synthase polypeptides that contain any of the modifications provided herein. Such fragments retain one or more properties of a valencene synthase. Typically, the modified active fragments exhibit valencene synthase activity (i.e. the ability to catalyze the formation of valencene from an acyclic pyrophosphate terpene precursor, e.g., FPP).

Modifications in a valencene synthase polypeptide also can be made to a valencene polypeptide that also contains other modifications, including modifications of the primary sequence and modifications not in the primary sequence of the polypeptide. For example, modification described herein can be in a valencene synthase polypeptide that is a fusion polypeptide or chimeric polypeptide, including hybrids of different valencene synthase polypeptides or different terpene synthase polypeptides (e.g. contain one or more domains or regions from another terpene synthase) and also synthetic valencene synthase polypeptides prepared recombinantly or synthesized or constructed by other methods known in the art based upon the sequence of known polypeptides.

To retain valencene synthase activity, modifications typically are not made at those positions that are necessary for valencene synthase activity, i.e., in the active site DDxxD (SEQ ID NO:35) motif or NSE/DTE motif (SEQ ID NO:36). For example, generally modifications are not made at a position corresponding to position D315, D316 or D319 or at a position corresponding to position D461, G465 or E469, with reference to a sequence of amino acids set forth in SEQ ID NO:1.

The modified valencene synthase polypeptides can contain one or more amino acid substitutions, in any combination, with or without additional modifications. Generally, multiple modifications provided herein can be combined by one of skill in the art so long as the modified polypeptide retains the ability to catalyze the formation of valencene and/or other terpenes from any suitable acyclic pyrophosphate terpene precursor, including, but not limited to, FPP, GPP and GGPP. Typically, the modified valencene polypeptides catalyze the formation of valencene from FPP. In some examples, the resulting modified valencene synthase polypeptide exhibits similar or increased valencene production from FPP compared to the unmodified valencene synthase polypeptide. In some instances, the resulting modified valencene synthase polypeptide exhibits decreased valencene production from FPP compared to the unmodified valencene synthase polypeptide.

Also provided herein are nucleic acid molecules that encode any of the modified valencene synthase polypeptides provided herein. In particular examples, the nucleic acid sequence can be codon optimized, for example, to increase expression levels of the encoded sequence. In one example, nucleic acid sequences encoding modified valencene synthase polypeptides provided herein are codon optimized based on codon usage in *S. cerevisiae.*

The modified polypeptides and encoding nucleic acid molecules provided herein can be produced by standard recombinant DNA techniques known to one of skill in the art. Any method known in the art to effect mutation of any one or more amino acids in a target protein can be employed. Exemplary methods are provided in Section C above. In some examples, the modified valencene synthase polypeptides are produced synthetically, such as using solid phase or solutions phase peptide synthesis.

a. Truncated Polypeptides

Also provided herein are truncated valencene synthase polypeptides. The truncated valencene synthase polypeptides can be truncated at the N-terminus or the C-terminus, so long as the truncated valencene synthase polypeptides retain catalytic activity of a valencene synthase. Typically, the truncated valencene synthase polypeptides exhibit valencene synthase activity (i.e. the ability to catalyze the formation of valencene from an acyclic pyrophosphate terpene precursor, such as FPP). In some examples, the valencene synthase polypeptides provided herein are truncated at the N-terminus. In other examples, the valencene synthase polypeptides provided herein are truncated at the C-terminus. In yet other examples, the valencene synthase polypeptides provided herein are truncated at the N-terminus and C-terminus.

In some examples, the valencene synthase polypeptides are truncated at the N-terminus, C-terminus or both termini of a valencene synthase polypeptide provided herein, such as truncation of a sequence of amino acids set forth in SEQ ID NO:1. In other examples, any of the modified valencene synthases provided herein are truncated. In some examples, the valencene synthase polypeptides are truncated at their N-terminus. For example, any valencene synthase polypeptide provided herein can be truncated by at or about or at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more amino acid residues at the N-terminus, provided the valencene synthase polypeptide retains valencene synthase activity.

In other examples, any valencene synthase polypeptide provided herein can be truncated by at or about or at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or more amino acid residues at the C-terminus, provided the valencene synthase polypeptide retains valencene synthase activity.

b. Polypeptides with Altered Activities or Properties

The modified valencene synthase polypeptides provided herein can also exhibit changes in activities and/or properties. The modified valencene synthase can exhibit, for example, increased catalytic activity, increased substrate (e.g. FPP) binding, increased stability, increased expression in a host cell and/or altered product distribution (i.e. altered relative amounts and/or types of terpenes) compared to a wild-type valencene synthase polypeptide. Such altered activities and properties can result in increased valencene production from farnesyl pyrophosphate. Typically, the product distribution of terpenes produced by a wild-type valencene synthase includes valencene, as well as a number of other terpene products (e.g., terpene byproduct or products derived therefrom) including, for example, β-selinene, r-selinene, eremophilone, 7-epi-α-selinene, germacrene A, β-elemene and aristolochene (peak 2 in FIG. 3A).

In some examples, the modified valencene synthase polypeptides can catalyze the formation of other terpenes than valencene from any suitable substrate, such as, for example, FPP, GPP or GGPP. For example, the modified valencene synthases can produce one or more monoterpenes, sesquiterpenes or diterpenes other than valencene. Typically, the modified valencene synthase polypeptides produce more valencene than any other terpene. This can result in increased production of nootkatone. Modifications that result in increased production of valencene from FPP can be identified using the assays described herein and well known in the art, thus allowing for identification of modified valencene synthase polypeptides with improved ability to produce valencene from FPP.

c. Domain Swaps

Provided herein are modified valencene synthase polypeptides that are chimeric polypeptides containing a swap (deletion and insertion) by deletion of amino acid residues of one of more domains or regions therein or portions thereof and insertion of a heterologous sequence of amino acids. In some examples, the heterologous sequence is a randomized sequence of amino acids. In other examples, the heterologous sequence is a contiguous sequence of amino acids for the corresponding domain or region or portion thereof from another terpene synthase polypeptide. The heterologous sequence that is replaced or inserted generally includes at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more amino acids. In examples where the heterologous sequence is from a corresponding domain or a portion thereof of another terpene synthase, the heterologous sequence generally includes at least 50%, 60%, 70%, 80%, 90%, 95% or more contiguous amino acids of the corresponding domain or region or portion. In such an example, adjacent residues to the heterologous corresponding domain or region or portion thereof also can be included in a modified valencene synthase polypeptide provided herein.

In one example of swap mutants provided herein, at least one domain or region or portion thereof of a valencene synthase polypeptide is replaced with a contiguous sequence of amino acids for the corresponding domain or region or portions thereof from another terpene synthase polypeptide. In some examples, 2, 3, 4, 5, 6, 7, 8, 9, 10 or more domains or regions or portions thereof are replaced with a contiguous sequence of amino acids for the corresponding domain or region or portions thereof from another terpene synthase polypeptide.

Any domain or region or portion thereof of a valencene synthase polypeptide can be replaced with a heterologous sequence of amino acids, such as a heterologous sequence from the corresponding domain or region from another terpene. A domain or region can be a structural domain or a functional domain. One of skill in the art is familiar with domains or regions in terpene synthases. Functional domains include, for example, the N-terminal domain and the C-terminal catalytic domain or a portion thereof. A structural domain can include all or a portion of a loop, unstructured loop or alpha helical domain.

One of skill in the art is familiar with various terpene synthases and can identify corresponding domains or regions or portions of amino acids thereof. For example, exemplary domains and regions of citrus valencene synthase are described in U.S. Pat. App. No. 2012-0246767. Exemplary terpene synthases include, for example, sesquiterpene synthases. In particular examples herein, modified valencene synthase polypeptide domain swap mutants provided herein contain heterologous sequences from a corresponding domain or region or portion thereof of a terpene synthase polypeptide that is a *Citrus* sp. valencene synthase (SEQ ID NOS:14-15, 26-27, 34 or 37), *V. vinifera* valencene synthase (SEQ ID NOS:16 or 28), *P. frutescens* valencene synthase (SEQ ID NO:38) or a *C. nootkatensis* valencene synthase (SEQ ID NOS:17 or 29).

Typically, the resulting modified valencene synthase exhibits valencene synthase activity and the ability to produce valencene from FPP. For example, the modified valencene synthase polypeptides exhibit 50% to 5000%, such as 50% to 120%, 100% to 500% or 110% to 250% of the valencene production from FPP compared to the valencene synthase polypeptide not containing the modification (e.g. the amino acid replacement or swap of amino acid residues of a domain or region) and/or compared to wild type valencene synthase polypeptide set forth in SEQ ID NO:1. Typically, the modified valencene synthase polypeptides exhibit increased valencene production from FPP compared to the valencene synthase polypeptide not containing the modification, such as compared to wild type valencene synthase set forth in SEQ ID NO:1.

For example, the modified valencene synthase polypeptides can produce valencene from FPP in an amount that is at least or about 101%, 102%, 103%, 104%, 105%, 106%, 107%, 108%, 109%, 110%, 115%, 120%, 125%, 130%, 135%, 140%, 145%, 150%, 160%, 170%, 180%, 200%, 250%, 300%, 350%, 400%, 500%, 1500%, 2000%, 3000%, 4000%, 5000% of the amount of valencene produced from FPP by wild type valencene synthase not containing the modification under the same conditions. For example, the valencene production is increased at least 1.2-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold or more.

In other examples, the modified valencene synthase polypeptides exhibit decreased valencene production from FPP compared to the valencene synthase polypeptide not containing the modification, such as compared to wild type valencene synthase set forth in SEQ ID NO:1. For example, the modified valencene synthase polypeptides can produce valencene from FPP in an amount that is at most or about 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 15%, 10%, or less of the amount of valencene produced from FPP by wild type valencene synthase not containing the modification under the same conditions. For example, the valencene production is decreased such that the FPP production by a wild type valencene synthase not containing the modification under the same conditions is at least 1.2-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or more, greater than the amount of valencene produced from FPP by the modified valencene synthase polypeptide.

Any methods known in the art for generating chimeric polypeptides can be used to replace all or a contiguous portion of a domain of a first terpene synthase with all or a contiguous portion of the corresponding domain of a second synthase (see, U.S. Pat. Nos. 5,824,774, 6,072,045, 7,186,891 and 8,106,260, and U.S. Pat. Pub. No. 2011-0081703). Also, gene shuffling methods can be employed to generate chimeric polypeptides and/or polypeptides with domain or region swaps.

For example, corresponding domains or regions of any two terpene synthases can be exchanged using any suitable recombinant method known in the art, or by in vitro synthesis. An example of a recombinant method is a two stage overlapping PCR method, such as described herein. In such methods, primers that introduce mutations at a plurality of codon positions in the nucleic acids encoding the targeted domain or portion thereof in the first terpene synthase can be employed, wherein the mutations together form the heterologous region (i.e. the corresponding region from the second terpene synthase). Alternatively, for example, randomized amino acids can be used to replace specific domains or regions. It is understood that primer errors, PCR errors and/or other errors in the cloning or recombinant methods can result in errors such that the resulting swapped or replaced region or domain does not exhibit an amino acid sequence that is identical to the corresponding region from the second terpene synthase.

In an exemplary PCR-based method, the first stage PCR uses (i) a downstream primer that anneals downstream of the region that is being replaced with a mutagenic primer that includes approximately fifteen nucleotides (or an effective number to effect annealing, such as 5, 6, 7, 8, 9, 10, 11, 12, 13, 14, 15, 16, 17, 20, 25 nucleotides or more) of homologous sequence on each side of the domain or region to be exchanged or randomized flanking the region to be imported into the target gene, and (ii) an upstream primer that anneals upstream of the region that is being replaced together with an opposite strand mutagenic primer that also includes approximately fifteen nucleotides (or an effective number to effect annealing, such as 5, 6, 7, 8, 9, 10, 11, 12, 13, 14, 15, 16, 17, 20, 25 nucleotides or more) of homologous sequence on each side of the domain or region to be exchanged or randomized flanking the region to be imported into the target gene. If a replacement in which a domain or region of a first terpene synthase gene is replaced with the corresponding domain or region from a second terpene synthase is being performed, nucleotides in the mutagenic primers between the flanking regions from the first terpene synthase contain codons for the corresponding region of the second terpene synthase. In instances where the amino acids in a domain or region are to be randomized, nucleotides of the mutagenic primers between the flanking regions from the first terpene synthase contain random nucleotides. An overlapping PCR is then performed to join the two fragments, using the upstream and downstream elige oligos. The resulting PCR product then can be cloned into any suitable vector for expression of the modified terpene synthase.

Further, any of the modified valencene synthase polypeptides containing swap mutations herein can contain one or more further amino acid replacements.

d. Additional Variants

Valencene synthase polypeptides provided herein can be modified by any method known to one of skill in the art for generating protein variants, including, but not limited to, DNA or gene shuffling, error prone PCR, overlap PCR or other recombinant methods. In one example, nucleic acid molecules encoding any valencene synthase polypeptide or variant valencene synthase polypeptide provided herein can be modified by gene shuffling. Gene shuffling involves one or more cycles of random fragmentation and reassembly of at least two nucleotide sequences, followed by screening to select nucleotide sequences encoding polypeptides with desired properties. The recombination can be performed in vitro (see Stemmer et al. (1994) *Proc Natl Acad Sci USA* 91:10747-10751; Stemmer et al. (1994) *Nature* 370:389-391; Crameri et al. (1998) *Nature* 391:288-291; U.S. Pat. Nos. 5,605,793, 5,811,238, 5,830,721, 5,834,252 and 5,837,458) or in vivo (see, International Pat. Pub. No. WO199707205). The nucleic acid molecules encoding the polypeptides then can be introduced into a host cell to be expressed heterologously and tested for their valencene synthase activity by any method described in section E below.

e. Fusion Proteins

Valencene synthase polypeptides also can be utilized or expressed as protein fusions. For example, a fusion can be generated to add additional functionality to a polypeptide. Examples of fusion proteins include, but are not limited to, fusions of a signal sequence, a tag such as for localization, e.g. a $his_6$ tag or a myc tag, or a tag for purification, for example, a GST fusion, GFP fusion or CBP fusion, and a sequence for directing protein secretion and/or membrane association. In other examples, a sesquiterpene synthase, such as a valencene synthase polypeptide provided herein, can be fused to FPP synthase (see, e.g., Brodelius et al. (2002) *Eur. J. Biochem.* 269:3570-3577).

Fusion proteins containing a valencene synthase polypeptide and one or more other polypeptides also are provided. Linkage of a valencene synthase polypeptide with another polypeptide can be effected directly or indirectly via a linker. In one example, linkage can be by chemical linkage, such as via heterobifunctional agents or thiol linkages or other such linkages. Fusion also can be effected by recombinant means. Fusion of a terpene synthase, such as a valencene synthase polypeptide, to another polypeptide can be to the N- or C-terminus of the valencene synthase polypeptide.

A fusion protein can be produced by standard recombinant techniques. For example, DNA fragments coding for the different polypeptide sequences can be ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel et al. (eds.) Current Protocols in Molecular Biology, John Wiley & Sons, 1992). Moreover, many expression vectors are commercially available that already encode a fusion moiety (e.g., a GST polypeptide). For example, a valencene synthase polypeptide-encoding nucleic acid can be cloned into such an expression vector such that the fusion moiety is linked in-frame to the valencene synthase protein. The valencene synthase and the fusion moiety can be linked directly, without a linker, or alternatively, linked indirectly in-frame with a linker.

E. METHODS FOR PRODUCING TERPENES AND METHODS FOR DETECTING SUCH PRODUCTS AND THE ACTIVITY OF VALENCENE SYNTHASE POLYPEPTIDES

The valencene synthases provided herein can be used, and assessed for their ability, to produce terpenes, such as monoterpenes, sesquiterpenes and diterpenes, from any suitable acyclic pyrophosphate terpene precursor, including, but not limited to, geranyl diphosphate (GPP), farnesyl diphosphate (FPP) or geranyl-geranyl diphosphate (GGPP). Typically, the valencene synthase polypeptides provided herein catalyze the formation of the sesquiterpene valencene from FPP. The valencene synthase polypeptides provided herein also catalyze the formation of an additional compound, aristolochene, (designated peak 2; see FIG. 3A) from FPP.

Any method known to one of skill in the art can be used to produce terpenes, including valencene, with the valencene synthases provided herein. The ability of the valencene synthases provided herein to catalyze the formation of valencene or other terpenes from FPP can be assessed using these methods. In some examples, the amount of terpene, such as valencene, produced from FPP using the valencene synthases provided herein is compared to the amount of terpene, such as valencene, produced from the same substrate using a different valencene synthase, such as a valencene synthase from a different species, for example, a citrus valencene synthase, or any other valencene synthase known to one of skill in the art.

Other activities and properties of the valencene synthases, such as the valencene synthase polypeptides provided herein, also can be assessed using methods and assays well known in the art. In addition, the activity of the valencene synthases and their ability to catalyze the formation of terpenes, the kinetics of the reaction, modified regiochemistry or stereochemistry, altered substrate utilization and/or altered product distribution (i.e. altered amount of the different terpenes produced from FPP or another substrate) compared to the valencene synthases can be assessed using methods well known in the art. For example, the type and amount of various terpenes produced from FPP, GPP or GGPP by the valencene synthase polypeptides provided herein can be assessed by gas chromatography methods (e.g. GC-MS), such as those described below and in Example 4. In some examples, profiles of terpenes produced by the valencene synthase polypeptides from FPP include, but are not limited to, valencene, β-elemene, and aristolochene (peak 2) Also produced by the host cells are the acyclic terpene alcohols nerolidol and farnesol.

Provided below are methods for the production of terpenes, including valencene and nootkatone, from FPP using the valencene synthases provided herein.

1. Production of Terpenes Catalyzed by *Eryngium glaciale* Valencene Synthase The modified valencene synthase polypeptides can be used to catalyze the formation of valencene and other terpenes from an acyclic pyrophosphate terpene precursor, such as FPP. In some examples, the valencene synthases provided herein are expressed in cells that produce or overproduce FPP, such that valencene is produced by the pathway described above. In other examples, the valencene synthases provided herein are expressed and purified from any suitable host cell, such as described in Section C. The purified synthases are then combined in vitro with FPP to produce valencene.

In some examples, the valencene synthase provided herein is overexpressed and purified as described in Section C above. The valencene synthase is then incubated with the substrate farnesyl diphosphate and valencene is produced. The pH of the solution containing FPP and valencene synthase can impact the amount of valencene produced (see e.g. U.S. Pat. Pub. No. 2010-0216186). An organic solvent is added to partition the valencene into the organic phase for analysis. Production of valencene and quantification of the amount of product are then determined using any method provided herein, such as gas chromatography (e.g. GC-MS) using an internal standard. Alternatively, the valencene synthase is expressed in host cells that also produce FPP, resulting in production of valencene. The valencene then can be extracted from the cell culture medium with an organic solvent and subsequently isolated and purified by any known method, such as column chromatography or HPLC, and the amount and purity of the recovered valencene are assessed. In some examples, the valencene is converted by oxidation to nootkatone either before or after purification.

a. Exemplary Cells

Valencene can be produced by expressing a valencene synthase polypeptide provided herein in a cell line that produces FPP as part of the mevalonate-dependent isoprenoid biosynthetic pathway (e.g. fungi, including yeast cells and animal cells) or the mevalonate-independent isoprenoid biosynthetic pathway (e.g. bacteria and higher plants). In particular examples, valencene is produced by expressing a valencene synthase polypeptide provided herein in a cell line that has been modified to overproduce FPP. Examples of such cells are modified yeast cells. For example, yeast cells that have been modified to produce less squalene synthase or less active squalene synthase (e.g. erg9 mutants; see e.g. U.S. Pat. Nos. 6,531,303 and 6,689,593 and U.S. Pat. Pub. Nos. 2010-0151519 and 2010-0151555) are useful in the methods provided herein to produce valencene. Reduced squalene synthase activity results in accumulation of FPP in the host cell at higher levels compared to wild-type yeast cells, which in turn can result in increased yields of valencene production. Exemplary modified yeast cells include, but are not limited to, modified *Saccharomyces cerevisiae* strains CALI5-1 (ura3, leu2, his3, trp1, Δerg9::HIS3, HMG2cat/TRP1::rDNA, dpp1), ALX7-95 (ura3, his3, trp1, Δerg9::HIS3, HMG2cat/TRP1::rDNA, dpp1, sue), ALX11-30 (ura3, trp1, erg$9^{def}$25, HMG2cat/TRP1::rDNA, dpp1, sue) and those described in U.S. Pat. Nos. 6,531,303 and 6,689,593 and published U.S. Patent Appl. Nos. 2004-0249219, 2010-0151519 and 2010-0151555.

*Saccharomyces cerevisiae* strain CALI5-1 is a derivative of SW23B#74 (described in U.S. Pat. Nos. 6,531,303 and 6,689,593, and Takahashi et al. (2007) (*Biotechnol Bioeng.* 97(1): 170-181), which was derived from wild-type strain ATCC 28383 (MATa). CALI5-1 was generated to have a decreased activity of the DPP1 phosphatase (see e.g. U.S. Published Appl. No. 2004-0249219). *Saccharomyces cerevisiae* strain CALI5-1 contains, among other mutations, an erg9 mutation (the Δerg9::HIS3 allele) as well as a mutation supporting aerobic sterol uptake enhancement (sue). It also contains approximately 8 copies of the truncated HMG2 gene. The truncated form of HMG2 is driven by the GPD promoter and is therefore no longer under tight regulation, allowing for an increase in carbon flow to FPP. It also contains a deletion in the gene encoding diacylglycerol pyrophosphate (DGPP) phosphatase enzyme (dpp1), which limits dephosphorylation of FPP.

ALX7-95 and ALX11-30.1 are derivatives of CALI5-1. ALX7-95 was derived from CALI5-1 by correcting the Δleu2 deficiency of CALI5-1 with a functional LEU2 gene so that leucine is not required to be supplemented to the media (see e.g. US2010/0151519). ALX11-30 was constructed from CAL5-1 in several steps, described in Example 4, below.

b. Culture of Cells

In exemplary methods, a valencene synthase provided herein is expressed in a host cell line that has been modified to overproduce farnesyl diphosphate whereby upon expression of the valencene synthase, farnesyl diphosphate is converted to valencene. The host cell is cultured using any suitable method well known in the art. In some examples, such as for high throughput screening of cells expressing various valencene synthases, the cells expressing the valencene synthase are cultured in individual wells of a 96-well plate (see e.g. Example 4, below). In other examples where the host cell is yeast, the cell expressing the valencene synthase polypeptides and FPP is cultured using fermentation methods such as those described in the Examples below (see, e.g., Example 5).

A variety of fermentation methodologies can be utilized for the production of valencene from yeast cells expressing the valencene synthase polypeptides provided herein. For example, large scale production can be effected by either batch or continuous fermentation. Classical batch fermentation is a closed system where the composition of the medium is set at the beginning of the fermentation and not subject to artificial alterations during the fermentation. Thus, at the beginning of the fermentation the medium is inoculated with the desired microorganism or microorganisms and fermentation is permitted to occur without further addition of nutrients. Typically, the concentration of the carbon source in a batch fermentation is limited, and factors such as pH and oxygen concentration are controlled. In batch systems the metabolite and biomass compositions of the system change constantly up to the time the fermentation is stopped. Within batch cultures, cells typically modulate through a static lag phase to a high growth log phase and finally to a stationary phase where growth rate is diminished or halted. If untreated, cells in the stationary phase will eventually die.

A variation on the standard batch system is the Fed-Batch system, which is similar to a typical batch system with the exception that nutrients are added as the fermentation progresses. Fed-Batch systems are useful when catabolite repression tends to inhibit the metabolism of the cells and where it is desirable to have limiting amounts of substrate in the medium. Also, the ability to feed nutrients will often result in higher cell densities in Fed-Batch fermentation processes compared to Batch fermentation processes. Factors such as pH, dissolved oxygen, nutrient concentrations, and the partial pressure of waste gases such as $CO_2$ are generally measured and controlled in Fed-Batch fermentations.

Production of the valencene also can be accomplished with continuous fermentation. Continuous fermentation is an open system where a defined fermentation medium is added continuously to a bioreactor and an equal amount of conditioned medium is removed simultaneously for processing. This system generally maintains the cultures at a constant high density where cells are primarily in their log phase of growth. Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems aim to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art. Following cell culture, the cell culture medium then can be harvested to obtain the produced valencene.

In one exemplary method, the host cells expressing the valencene synthase polypeptides (e.g. *Saccharomyces cerevisiae* strain CALI5-1, ALX7-95 or ALX11-30) are grown in 3 L fermentation tank at 28° C., pH 4.5 for approximately 132 hours, maintaining glucose at between 0 and 1 g/L. Following fermentation, sodium sulfate is added to a final concentration of 10-15%. Soybean oil also is added and agitated, and the oil containing the valencene (and other terpenes) is recovered by centrifugation.

c. Isolation and Assessment of Products

The valencene produced using the methods above with the valencene synthase polypeptides provided herein can be isolated and assessed by any method known in the art. In one example, the cell culture medium is extracted with an organic solvent to partition valencene, and any other terpene produced, into the organic layer. Valencene production can be assessed and/or the valencene isolated from other products using any method known in the art, such as, for example, gas chromatography. For example, the organic layer can be analyzed by gas chromatography using cedrene and hexadecane as internal standards. This method is exemplified in Examples 3 and 4 below.

The quantity of valencene produced can be determined by any known standard chromatographic technique useful for separating and analyzing organic compounds. For example, valencene production can be assayed by any known chromatographic technique useful for the detection and quantification of hydrocarbons, such as valencene and other terpenes, including, but not limited to, gas chromatography coupled to mass spectrometry (GC-MS), gas chromatography using a flame ionization detector (GC-FID), capillary GC-MS, high performance liquid chromatography (HPLC) and column chromatography. Typically, these techniques are carried out in the presence of known internal standards, for example, cedrene or hexadecane, which are used to quantify the amount of the terpene produced.

For example, terpenes, including sesquiterpenes, such as valencene, can be identified by comparison of retention times and mass spectra to those of authentic standards in gas chromatography with mass spectrometry detection. Typical standards include, but are not limited to, cedrene and hexadecane. In other examples, quantification can be achieved by gas chromatography with flame ionization detection based upon calibration curves with known amounts of authentic standards and normalization to the peak area of an internal standard. These chromatographic techniques allow for the identification of any terpene present in the organic layer, including, for example, other terpenes produced by the modified valencene synthase, including, for example, β-elemene and aristolochene (peak 2) and other compounds produced by the cells, including nerolidol and farnesol (see e.g. Example 4).

In some examples, kinetics of valencene production can be determined by synthase assays in which radioactive isoprenoid substrates, such as $^{3}$H FPP or $^{14}$C FPP, are utilized with varying concentrations of synthase. The products are extracted into an organic layer and radioactivity is measured using a liquid scintillation counter. Kinetic constants are determined from direct fits of the Michaelis-Menton equation to the data.

2. Production of Nootkatone

Nootkatone, which is the dominant grapefruit aroma, is an oxidized product of valencene. The valencene synthases provided herein catalyze production of valencene, which then can be oxidized to nootkatone. Valencene can undergo regioselective hydroxylation to form 2-hydroxy valencene, which is further oxidized to form nootkatone. Oxidation of valencene can be carried out through chemical or biosynthetic means (see e.g. U.S. Pat. No. 5,847,226, Eur. Pat. No. EP1083233; Girhard et al., (2009) *Microb. Cell. Fact.* 8:36; Fraatz et al., (2009) *Appl Microbiol Biotechnol.* 83(1):35-41; Furusawa et al. (2005) *Chem Pharm. Bull.* 53:1513-1514; Salvador et al., (2002) *Green Chemistry,* 4, 352-356). Biochemical oxidation can be effected by a laccase, hydroxylase, or other oxidative enzyme. In some examples, valencene is converted to nootkatone using chromium trioxide or a silica phosphonate-immobilized chromium (III) catalyst (as described for example, in U.S. Pat. Pub. No. 2012-0246767). Nootkatone formation can be confirmed and/or quantified by any of the chromatographic techniques described herein.

F. EXAMPLES

The following examples are included for illustrative purposes only and are not intended to limit the scope of the invention.

Example 1

Extraction and Identification of Valencene from *Eryngium glaciale*

Figure 2A:
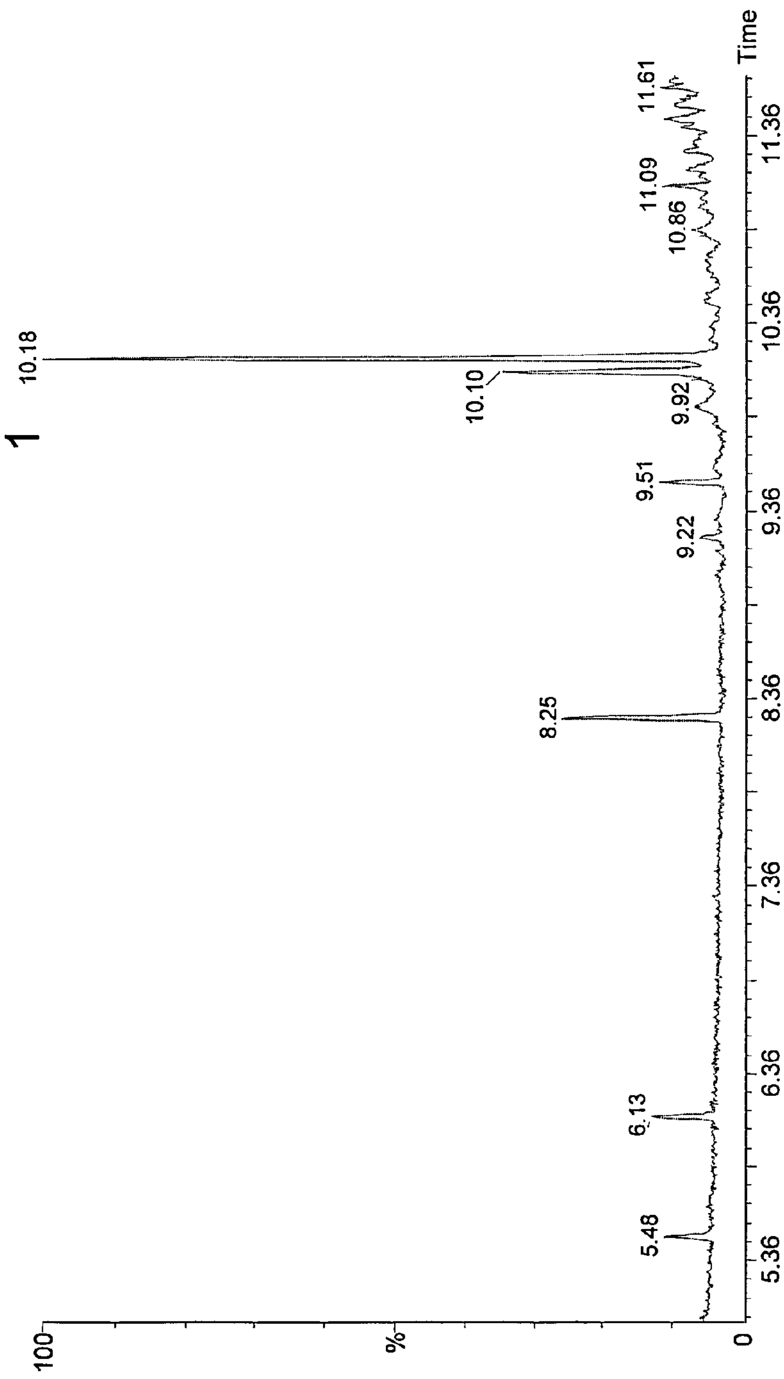
FIGS. 2A-B.
Figure 2B:
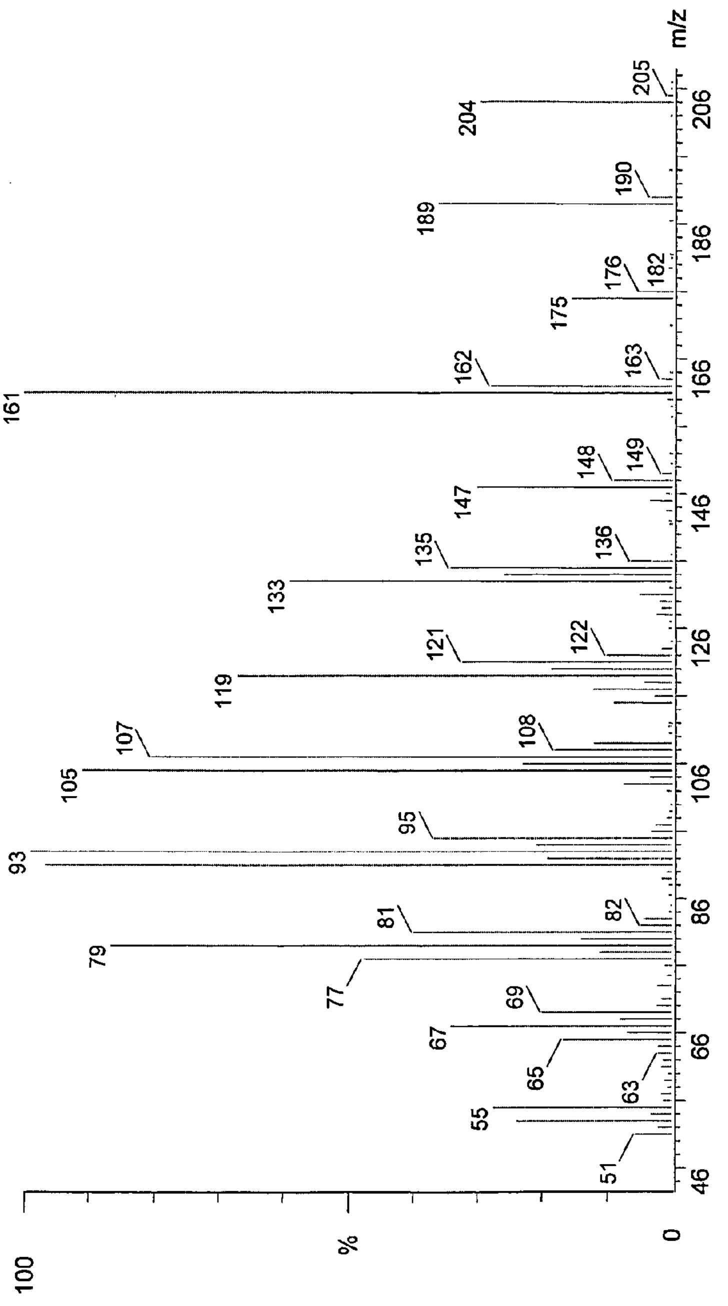

To confirm that *Eryngium glaciale* produces valencene, extracts of *Eryngium glaciale* leaves were tested for the presence of valencene. *Eryngium glaciale* leaves and branches were purchased from Wrightman alpine nursery (Ontario, Canada). Several leaves were dissected and submerged in ethyl acetate for several days. Plant oil in ethyl acetate was subsequently analyzed by gas chromatography-mass spectrometry (GC-MS). GC-MS analysis was performed with the PerkinElmer AutoSystem XL equipped with the TurboMass™ mass spectrometer. The gas chromatograph of the plant oil extract is shown in FIG. 2A. Valencene was detected around 10.18 minutes (Peak 1), and was the major peak. The mass spectrum of the peak at 10.18 minutes (valencene) is shown in FIG. 2B.

Example 2

Identification of the Valencene Synthase Encoding Nucleic Acid from *Eryngium* glaciale Valencene synthase from *Eryngium glaciale* was identified by sequencing the total transcriptome of *Eryngium glaciale* using 454 high-throughput pyrosequencing (Roche Diagnostics, Branford, Conn.) and searching for homology to known terpene synthases.

RNA Purification

RNA was isolated from one gram of plant material, flash frozen in liquid nitrogen and subsequently ground to a powder using mortar and pestle. The powdered sample was thawed in 10 mL of TRIzol® reagent (Invitrogen Corp., Carlsbad, Calif.) to extract RNA from the tissue, following the manufacturer's instruction with minor modifications. The powdered sample and TRIzol® mixture was centrifuged at 13,000 rpm for 10 minute at 4° C. to remove cell debris. Supernatant was transferred to new tubes, chloroform:isoamyl alcohol (24:1) was added, and the sample was vortexed. After further centrifugation, two volumes of isopropanol was added, and the mixture was incubated for 10 minute at room temperature. RNA was precipitated by centrifugation at 13,000 rpm for 10 minutes at 4° C. Precipitated RNA was washed once with 75% ethanol and resuspended in 20 μL RNAse-free water. RNA was further treated with DNase I (New England Biolabs, Ipswich, Mass.) to remove DNA, and was subsequently purified and concentrated using the Qiagen MinElute RNA cleanup kit (Qiagen, Hilden, Germany).

Sequencing of the Total Transcriptome

The total transcriptome of *Eryngium glaciale* was sequenced using 454 pyrosequencing. Extracted total RNA was submitted to the Advanced Genetic Technology Center (AGTC) at University of Kentucky (UK) for transcriptome sequencing analysis. Assembly of a total of 5512221 reads generated 15717 contigs, with an average contig size was 847 base pairs. The resulting database was searched by BLAST® against the sequences of several known terpene synthases. These synthases included: *Perilla frutescens* var. *frutescens* valencene synthase (SEQ ID NO:39; GenBank Accession No. AY917195.1); *Citrus sinensis* valencene synthase (SEQ ID NO:40; GenBank Accession No. AF441124.1); *Hyoscyamus muticus* vetispiradiene (or premnaspirodiene) synthase (SEQ ID NO:41; GenBank Accession No. U20188.1); *Citrus hystrix* germacrene D synthase (nucleic acid set forth in SEQ ID NO:42; GenBank Accession No. HQ652871.1; protein set forth in SEQ ID NO:45); and *Chamaecyparis nootkatensis* valencene synthase (SEQ ID NO:44). Homology among these ranged from about 35 to 50% identity at the nucleotide level. The generated BLAST® database was searched using all five sequences. Five different partial sequences encoding candidate terpene synthases were identified from the generated database for BLAST® searches Following amplification (described in Example 3 for the gene encoding the active synthase), DNA molecules encoding each of the five possible genes were produced. One gene, described in Example 3, encoded an active synthase that catalyzes production of valencene.

Example 3

Isolation of a Valencene Synthase-Encoding Gene from *Eryngium glaciale*

Based on the selected contig sequence (SEQ ID NO:4), primers for the amplification of 3' and 5' RACE fragments were designed such that there was about a 150 bp overlap between the 5' and 3' RACE fragments. Complementary DNA (cDNA) synthesis and PCR were performed as described in the protocols of the kit (SMARTer™ RACE cDNA Amplification Kit (Clontech, Mountain View, Calif., USA)) with some modifications of the PCR conditions. The 5' and 3' RACE PCR fragments were cloned in the TOPO-TA vector (Invitrogen, San Diego) and each amplification product was sequenced.

The following PCR conditions were used to amplify the 3' and 5' RACE fragments: 94° C. initial denaturation for 2 minutes, 10 cycles of 94° C. for 30 seconds, 61° C. annealing for 45 seconds, 72° C. extension for 1 minute 20 seconds, followed by 25 cycles of 94° C. for 30 seconds, 55° C. annealing for 40 seconds, 72° C. extension for 1 minute 20 seconds. The primers used for amplifying the gene encoding the active valencene synthase are set forth in Table 3 below and included forward primer 63-1-2-Fwd2 (SEQ ID NO:5) and reverse primer 63-1-2-Rev2 (SEQ ID NO:6). Forward nested primer 63-1-2-NestFwd2 (SEQ ID NO:7) and the reverse nested primer 63-1-2-NestRev2 (SEQ ID NO:8) were used to increase the specificity of amplification products in the PCR.

TABLE 3

Primers for RACE PCR

| Primer | Sequence | SEQ ID NO |
|---|---|---|
| 63-1-2-Fwd2 | GCTAGCTCATGTTGATACATTTTCTGCAGTCG | 5 |
| 63-1-2-Rev2 | GCTGTCAGTAACAACCTCTCGTCTTGAGC | 6 |
| 63-1-2-NestFwd2 | CGGTTAAAATCTAGTTTTGCAAACTCCAAAAGC | 7 |
| 63-1-2-NestRev2 | CCCACGTGAAGTACCCTCTTGAGGACG | 8 |

-

The full-length nucleotide sequence of the gene, designated EGVS and subsequently confirmed to encode a valencene synthase (see Example 3 below), is set forth in SEQ ID NO:2 and the encoded amino acid sequence is set forth in SEQ ID NO: 1.

Example 4

Cloning of EGVS into the pAlx31-108.2 Expression Vector

The isolated full-length EGVS gene was cloned into the pAlx31-108.2 expression vector (SEQ ID NO:32). The EGVS gene was amplified using two sets of primers (see Table 4 below) to remove the KpnI restriction site at position 964 of the coding sequence including forward primer 63-52-EG2FwdPart1 (SEQ ID NO:9) and reverse primer 63-52-EG2RevPart1 (SEQ ID NO:10); and forward primer 63-52-EG2FwdPart2 (SEQ ID NO:11) and reverse primer 63-52-EG2RevPart2 (SEQ ID NO:12).

TABLE 4

Primers

| Primer | Sequence | SEQ ID NO |
|---|---|---|
| 63-52-EG2FwdPart1 | GCTGAATTCGAGCTCGGTACCATTAAAAAAAATGTCTCT TAATGTACTTAGTACGTCAGG | 9 |
| 63-52-EG2RevPart1 | GAAGTTCTTTGAATGTACCATACACATCATACG | 10 |
| 63-52-EG2FwdPart2 | GATGTGTATGGTACATTCAAAGAACTTCTACTGTTCACTG | 11 |
| 63-52-EG2RevPart2 | TACGCGCACAAAAGCAGAGATTCTAGATTACAAAGGAAT AGGATCCACGAGCAGTG | 12 |

A KpnI restriction site beginning at position 964 of the coding sequence was removed, as KpnI and XbaI sites are frequently used to clone genes into the pAlx31-108.2 expression vector. The KpnI site was altered without affecting the amino acid sequence of EGVS, by replacing the C at position 969 of the wild-type EGVS gene with an A, thereby changing the ACC (encoding for threonine) codon to an ACA (encoding for threonine) (nucleotide sequence set forth in SEQ ID NO:3). The final EGVS expression vector, designated pAlx63-71 (SEQ ID NO:33) was constructed using the Gibson Assembly™ Master Mix (New England Biolabs) with PCR products amplified using the 63-52-EG2FwdPart1, 63-52-EG2RevPart1, 63-52-EG2FwdPart2, and 63-52-EG2RevPart2 primers (see Table 4 above).

Example 5

Expression of EGVS in Yeast and High Throughput Screening of Cells Expressing Valencene The pAlx63-71 expression vector encoding the EGVS was transformed into the modified *Saccharomyces cerevisiae* strains ALX7-95 (ura3, his3, trp1, Δerg9::HIS3, HMG2cat/TRP1::rDNA, dpp1, sue) and ALX11-30 (ura3, trp1, erg9def25, HMG2cat/TRP1::rDNA, dpp1, sue) for expression of valencene synthase and production of valencene using a high throughput screening assay.

A. Generation of Modified *Saccharomyces cerevisiae* Strains ALX7-95 and ALX7-95

As noted above, ALX7-95 and ALX11-30 were derived from *Saccharomyces cerevisiae* strain CALI5-1, which is a well-known and disseminated strain. (see, e.g., published U.S. Patent Appl. No. 2012-0246767). Strain CALI5-1 is a derivative of the strain designated SW23B#74 (described, for example, in U.S. Pat. Nos. 6,531,303 and 6,689,593; see, also Takahashi et al. (2007) *Biotechnol Bioeng.* 97(1):170-181), which is derived from wild-type strain MATa, deposited under accession number ATCC 28383. CALI5-1 was generated to have decreased activity of the DPP1 phosphatase (see e.g. U.S. Pat. Pub. No. 2004-0249219). *Saccharomyces cerevisiae* strain CALI5-1 contains, among other mutations, an erg9 mutation (the Δerg9::HIS3 allele) as well as a mutation supporting aerobic sterol uptake enhancement (sue). It also contains approximately 8 copies of the truncated HMG2 gene. The truncated form of HMG2 is driven by the GPD promoter and is therefore no longer under tight regulation, allowing for an increase in carbon flow to FPP. It also contains a deletion in the gene encoding diacylglycerol pyrophosphate (DGPP) phosphatase enzyme (dpp1), which limits dephosphorylation of FPP.

ALX7-95 was generated from CALI5-1 by correcting the Δleu2 deficiency of CALI5-1 with a functional LEU2 gene so that leucine supplementation is not required (see e.g. US2010/0151519). ALX11-30 was constructed from CALI5-1 in several steps from a strain designated ALX7-175.1 which as described in U.S. Pat. Pub. No. 2010-0151519.

Briefly, ALX7-175.1 was produced as follows. ALX7-95 HPS was obtained by transforming a plasmid containing the *Hyoscyamus muticus* premnaspirodiene synthase (HPS) into ALX7-95 strain. The YEp-HPS plasmid was obtained by cloning the gene for HPS into Yep-GW-URA to give YEp-HPS-ura (YEp-HPS). Then, an error prone PCR reaction of the ERG9 gene was performed, and the resulting DNA was transformed into ALX7-95 harboring YEpHPS. Transformants were plated on YP medium lacking ergosterol and screened for premnaspirodiene production. Those that produced high levels of premnaspirodiene were saved. One strain, ALX7-168.25 [ura3, trp1, his3, $erg9^{def}25$, HMG2cat/TRP1::rDNA, dpp1, sue, YEpHPS] was transformed with a PCR fragment of the complete HIS3 gene to create a functional HIS3 gene. Transformants were isolated that were able to grow in the absence of histidine in the medium. From this transformation, ALX7-175.1 was isolated [ura3, trp1, erg9def25, HMG2cat/TRP1::rDNA, dpp1, sue YEpHPS]. Finally, the plasmid YEpHPS was removed by growing ALX7-175.1 several generations in YPD (10 g/L yeast extract, 20 g/L peptone, 20 g/L glucose) and plating cells on YPD plates. Colonies were identified that were unable to grow on SD medium without uracil (0.67% Bacto yeast nitrogen base without amino acids, 2% glucose, 0.14% yeast synthetic drop-out medium without uracil). This strain was designated ALX11-30.

B. High Throughput Screening for Valencene Production

Eight colonies from each transformation of the pALx63-71 vector into ALX7-95 and ALX11-30 were analyzed for sesquiterpene production in deep well microtiter plates. Transformants were screened for valencene production by microculture analysis using 96 deep-well plates. Individual transformants were inoculated into individual wells of 96-well microtiter plates filled with 200 μL of synthetic defined medium (SD: 0.67% Bacto yeast nitrogen base without amino acids, 2% glucose, and 0.14% yeast synthetic drop-out medium supplement without histidine, leucine, tryptophan or uracil) for the ALX11-30 strains and synthetic defined media with ergosterol (SDE: 0.67% Bacto yeast nitrogen base without amino acids, 2% glucose, 0.14% yeast synthetic drop-out medium supplement without histidine, leucine, tryptophan or uracil, and 40 mg/L ergosterol) for the erg9 deficient ALX7-95 strains. The plates were incubated for two to three days at 28° C. After growth to saturation, 10 μL of the saturated culture from each well were used to inoculate a 96 deep-well plate containing 300 μL of medium suitable for growth and valencene production. The plate was sealed with Airpore tape (Qiagen) and incubated with shaking for 3 days.

Biosynthetic products were extracted first by the addition of 250 μL of acetone containing cedrene into each well, sealing with rubber plate sealer, vortexing, followed by addition of 500 μL of n-hexane containing hexadecane and additional vortexing. After phase separation, the plate was sealed with aluminum film and placed on the sample tray of a gas chromatography autosampler, which removed one microliter of the organic phase for each well for analysis of sesquiterpenes. The acetone and hexane used for extraction were each spiked with internal standards cedrene and hexadecane, respectively, to aid in quantitation of the samples. The extracted samples were analyzed by gas chromatography and the amount of valencene was calculated from the area under the peak representing valencene.

C. Results

Table 5 below provides the product distribution profiles and amount of valencene produced by *Eryngium glaciale* valencene synthase, as determined by gas chromatography, for the three highest valencene producers from ALX7-95 and the four highest valencene producers from ALX11-30, and their strain name designations. As indicated in Table 5, various additional compounds were observed in addition to valencene, including nerolidol, farnesol and the compound, aristolochene, at peak 2, which is aristolochene. The result demonstrates that this valencene synthase catalyzes production of product profile different from the citrus valencene synthase. Cedrene and hexadecane represent internal standards used to quantify the amount of valencene produced.

All seven of these strains were further analyzed in the shake flask assay described in Example 4.

TABLE 5

| Product distribution for microculture assay | | | | | | | | |
|---|---|---|---|---|---|---|---|---|
| Yeast | Peak Area | | | | | | mg/mL valen- | Strain |
| Strain | Cedrene | aristolochene | Valencene | nerolidol | Hexadecane | Farnesol | cene | name |
| 7-95 | 15794 | 23576 | 75056 | 6718 | 15085 | 7475 | 120.10 | Alx-63-70.1 |
| | 14916 | 18809 | 59731 | 6057 | 14930 | 7057 | 101.20 | Alx-63-70.2 |
| | 14443 | 19245 | 61326 | 5368 | 13706 | 6378 | 107.31 | Alx-63-70.3 |
| 11-30 | 14151 | 26590 | 80470 | | 15281 | | 143.71 | Alx-63-70.4 |
| | 14491 | 33936 | 107516 | | 16152 | | 187.51 | Alx-63-70.5 |
| | 14428 | 33512 | 105465 | | 15969 | | 184.73 | Alx-63-70.6 |
| | 16093 | 19851 | 60353 | | 17711 | | 94.78 | Alx-63-70.7 |

Example 6

Shake Flask Assay of Cells Expressing Valencene

Seed cultures were started in 250 mL flasks by inoculating 15 mL of SD or SDE medium (for ALX11-30 and ALX7-95 strains, respectively) with freshly growing colonies of the 7 strains shown in Table 5 above. The cultures were grown for 24 hours, and 2.5 mL of each culture were used to inoculate 50 mL of fermentation medium (2% ammonium sulfate, 2% potassium phosphate, 0.1% NaCl, 0.6% $MgSO_4.7H_2O$, 0.4% yeast extract, 1 mL mineral solution [$FeSO_4.7H_2O$ 0.028%, $ZnSO_4.7H_2O$ 0.029%, $CuSO_4.5H_2O$ 0.008%, $Na_2MoO_4.2H_2O$ 0.024%, $CoCl_2.6H_2O$ 0.024%, $MnSO_4.H_2O$ 0.017%, HCl 1 mL], 0.5 mL 50% glucose, 1.5 mL vitamin solution [biotin 0.001%, Ca-pantothenate 0.012%, inositol 0.06%, pyridoxine-HCl 0.012%, thiamine-HCl 0.012%], and 0.5 mL 10% $CaCl_2$) in a 250 mL baffled flask. The cultures were grown at 28° C. After 16 hours of incubation, the cultures were fed 3.6 mL of 50% glucose and 0.667 mL of 12.5% yeast extract. The cultures were fed every 24 after the initial feed. The pH of the cultures was adjusted to 4.5 every 24 hours with the addition of 30% NaOH. After approximately 88 hours of incubation, 0.1 mL of IGEPAL CA-630 were added and the culture was incubated with shaking to fully disperse the vegetable oil. After 30 minutes, a 2 mL culture sample was taken for analysis. The sample was extracted with 2 mL acetone/cedrene solution and then extracted with 4 mL hexane/hexadecane solution. An aliquot of the organic phase was analyzed by gas chromatography and the amount of valencene produced was quantified by calculating the area under the peak representing valencene. The product distribution profiles and valencene production for each of 2 EGVS containing strains were compared to a control citrus valencene synthases (CVS) and valencene synthase V277 (described in copending U.S. Publication Serial No. 2012-0246767) having a sequence of nucleotides set forth in SEQ ID NO:30 and a sequence of amino acid sequence set forth in SEQ ID NO:31. V277 has about 83% sequence identity with wild type CVS. Cells that express V277 produce more valencene than cells that express wild type CVS (amino acid sequence set forth in SEQ ID NO:14).

Table 6a below provides product distribution profiles including the amount of valencene produced from the shake flask assay, as determined by gas chromatography, of CVS 277 compared to two strains that produce EGVS in the ALX11-30 strain (as described in Example 3). As shown in Table 6, the *Eryngium glaciale* valencene synthase strains produced more valencene per mL as compared to the CVS V277 mutant, which in turn produces more valencene than the CVS wild type.

Figure 3A:
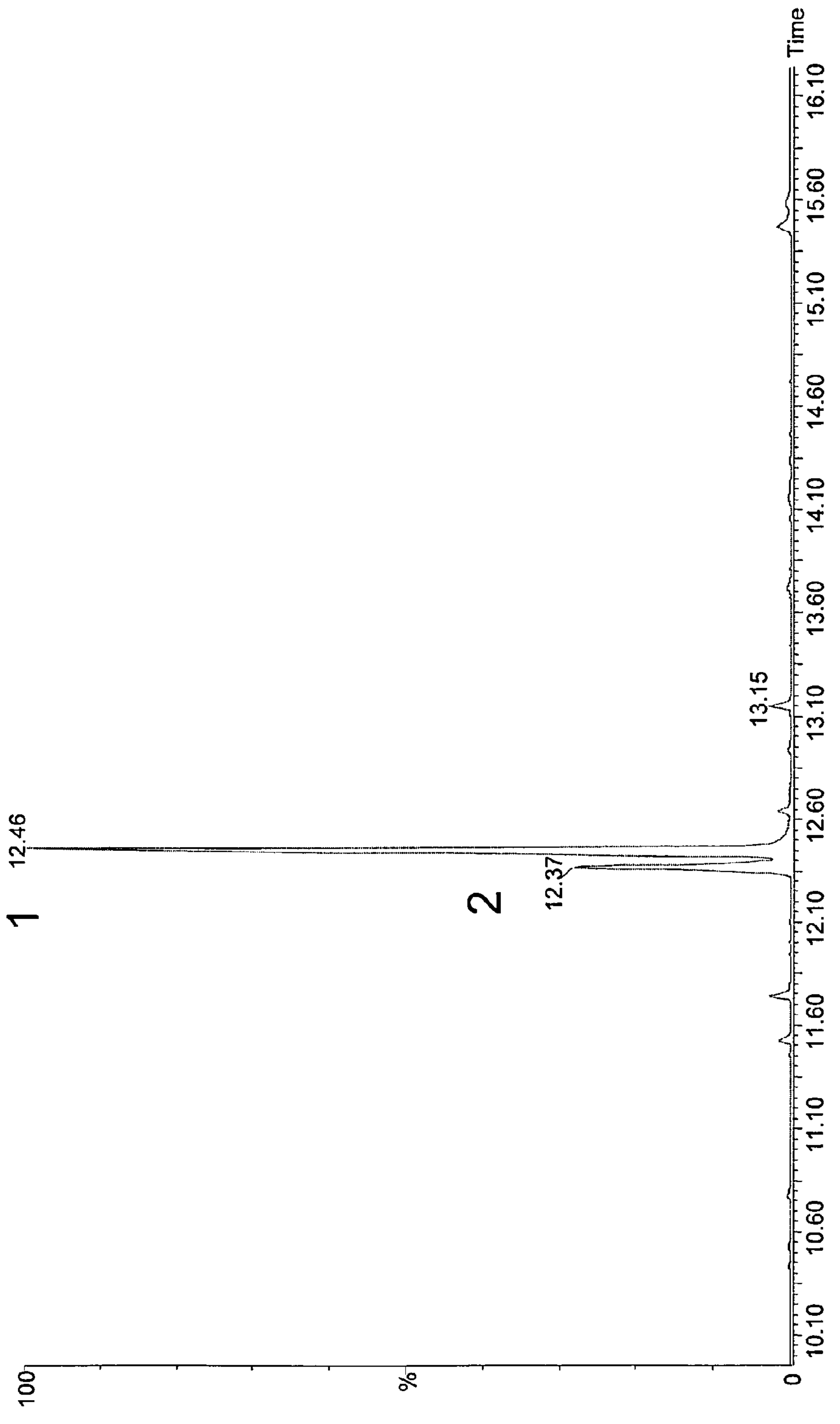
FIGS. 3A-B.
Figure 3B:
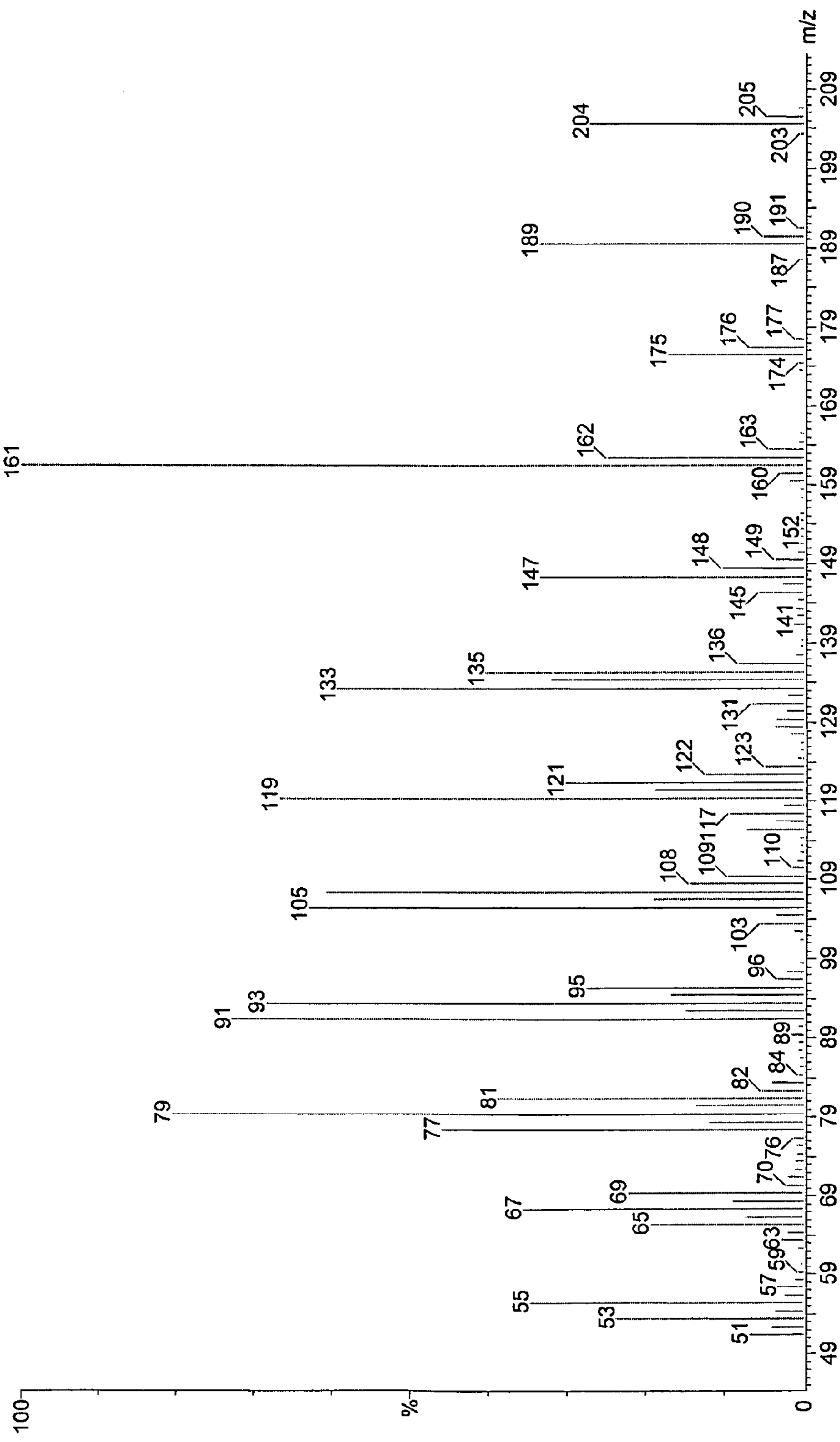
Figure 7:
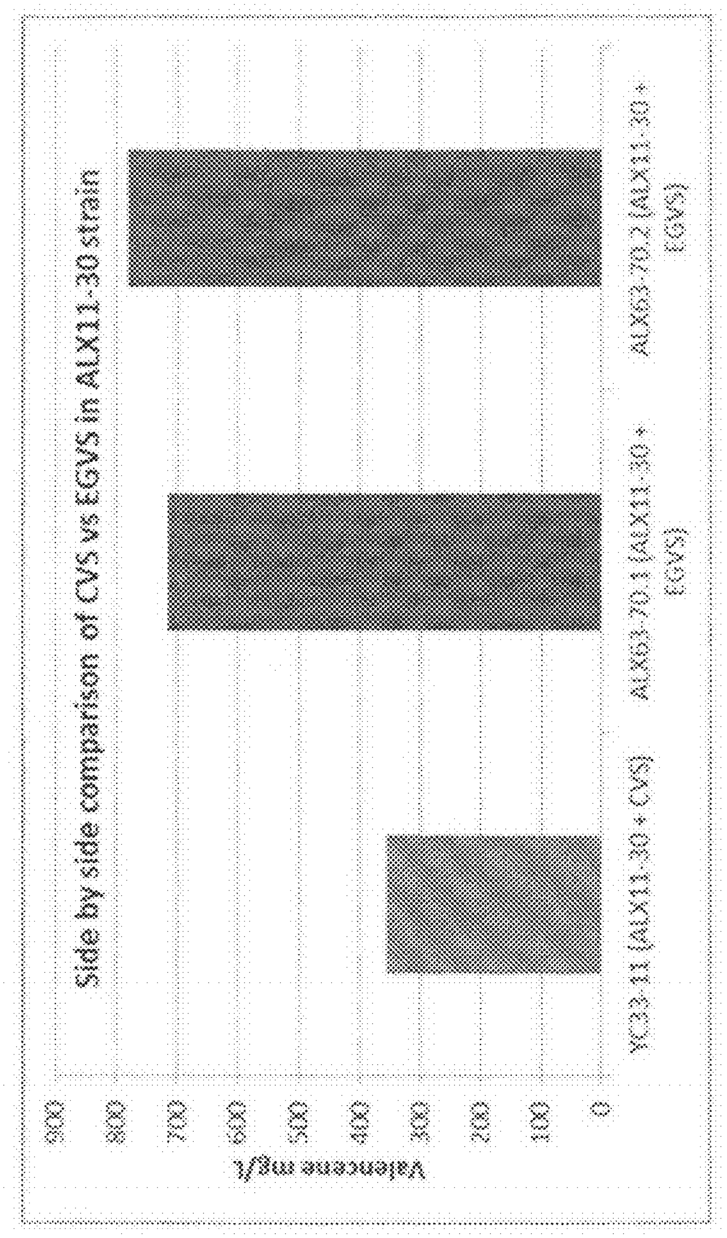
FIG. 7 demonstrates that valencene produced in yeast catalyzed by EVS is significantly greater than that produced in yeast catalyzed by CVS.

Cedrene and hexadecane represent internal standards used to quantify the amount of valencene produced. FIG. 3A shows an exemplary gas chromatogram of an exemplary ALX7-95 strain Alx-64.70.3, with valencene having a retention time of 12.46 min and FIG. 3B shows the mass spectrum of the valencene (peak at 12.46 min). FIG. 7 depicts the results graphically.

TABLE 6

| Product distribution for shake flask assay | | | | | |
|---|---|---|---|---|---|
| Yeast | Peak Area | | | mg/mL | |
| Strain | Cedrene | Valencene | Hexadecane | valencene | Strain name |
| ALX11-30 | 13743 | 2565260 | 15877 | 356.1 | YC33-11 |
| | 9770 | 378154 | 18747 | 714.2 | Alx-63-70.6 |
| | 11179 | 472779 | 19251 | 780.3 | Alx-63-70.7 |

FIG. 7 depicts the data in Table 6b and shows a comparison between production of valencene in cells that express the citrus valencene synthase with cells that express the *Eryngium glaciale* synthase. The EG synthase expressing cells produce more than twice the amount of valencene compared to the CVS synthase.

Example 7

Isolation of Valencene

The broths from two fermentations of ALX63-70.7 (2 L each) were vacuum filtered through a course filter funnel. The filter cake (soybean oil, cells, and cellular debris) was transferred to a 4 L flask and acetone (2 L each) was added to the filter cake and filtrate (soybean oil and cells), respectively and the solutions were stirred for 1 hr. The resulting heterogeneous mixtures were filtered and the solvent was removed under reduced pressure. The crude organic extract was then subjected to silica gel chromatography using hexanes as the only solvent. After removal of the solvent under reduced pressure, the light yellow oily material was dissolved in acetone and the phospholipids were precipitated at −20° C. The phospholipids were filtered and acetone in the filtrate was removed under reduced pressure to afford a clear oil (25 g). The clear oil was then further purified by falling film distillation (0.1 torr, 125° C.) to afford an enriched valencene fraction (3.13 g). Valencene was then purified from the enriched fraction by reversed phase (C18) HPLC using isocratic acetonitrile as solvent and a refractive index detector.

Proton ($^1H$) and Carbon-13 ($^{13}C$) nuclear magnetic resonance (NMR) of the purified sample showed the purified sample had identical chemical shifts as an authentic standard of valencene (see NMR data below). Furthermore, 1D-NOESY experiments where the quaternary methyl group (C11) was irradiated showed correlations with the methine on C9 and the C12 methyl group thus suggesting that the C11 and C12 methyl groups and the C9 methine are all on the same face of the molecule. The structure of valencene with carbon numbering assigned is shown below:

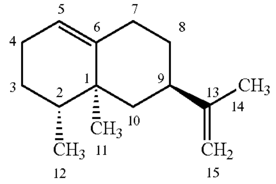

Finally, gas chromatography (GC-FID), chiral gas chromatography, and gas chromatography-mass spectrometry of the purified sample showed that the putative valencene peak had identical retention times and mass spectra as an authentic standard of valencene. These data together demonstrates that the structure of the isolated peak is (+)-valencene.

$^1H$ NMR (BENZENE-$d_6$) δ: 5.36 (dt, J=4.8, 2.6 Hz, 1H), 4.83 (s, 1H), 4.80 (s, 1H), 2.23-2.31 (m, 1H), 2.21 (s, 1H), 2.06 (ddd, J=13.9, 4.1, 2.6 Hz, 2H), 1.90-1.96 (m, 2H), 1.69 (d, J=0.9 Hz, 1H), 1.66 (s, 3H), 1.31-1.46 (m, 2H), 1.26 (d, J=4.4 Hz, 2H), 1.05 (t, J=12.7 Hz, 1H), 0.91 (s, 3H), 0.83 (d, J=6.6 Hz, 3H); $^{13}C$ NMR (BENZENE-$d_6$) δ: 150.8, 143.3, 120.9, 109.3, 45.7, 41.6, 41.7, 38.5, 33.8, 33.5, 27.9, 26.7, 21.3, 18.9, 16.2. GC-MS ($EI^+$, 70 eV); (%): 55(44), 67(38), 79(82), 91(80), 93(77), 105(75), 107(73), 119(66), 133(56), 147(33), 161(100), 175(17), 189(34), 204(29).

Example 8

Comparison of Kinetic Parameters of *E. Glaciale* Valencene Synthase (EgVS) and Valencene Synthase V277

In this example, the activity of *E. glaciale* valencene synthase (EgVS; SEQ ID NO:1) and of the citrus valencene synthase designated V277 (SEQ ID NO:31) were evaluated by steady state kinetic analysis. To compare the activities of these enzymes in vitro, the valencene synthases were Histidine-tagged at the C-terminus, expressed in *E. coli*, purified by nickel chelate chromatography, and evaluated for activity by steady state kinetic analysis. The reaction conditions were as follows: 50 nM EgVS or 250 nM valencene synthase V277, 50 mM Bis-Tris Propane (pH 7.5), 20 mM $MgCl_2$, 50 mM KCl. T=30C. Detection: GC/MS-SIM.

Figure 6:
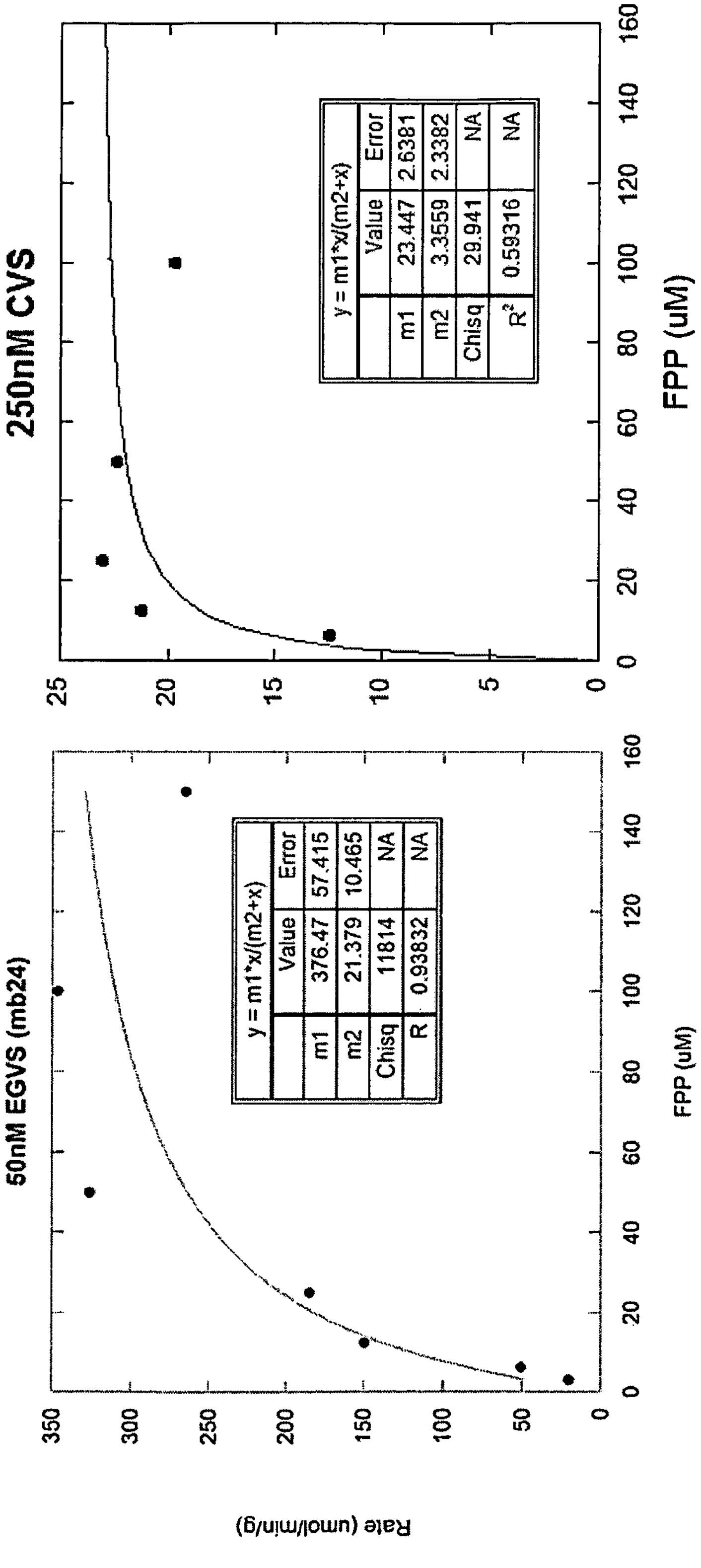
FIG. 6 depicts the steady state enzyme kinetic parameters for the *E. glaciale* valencene synthase (EgVS), whose sequence set forth in SEQ ID NO:1 (left) and the valencene synthase V277 (labeled CVS), whose sequence is set forth in SEQ ID NO:31 (right); FPP=farnesyl diphosphate.

As shown in FIG. 6 and Table 7 below, EgVS exhibits dramatically higher total and specific activity when compared side-by-side with the citrus valencene synthase designated V277. In addition to increased activity, EgVS also turned over significantly more times than valencene synthase V277.

TABLE 7

CVS and EgVS Steady State Kinetic parameters

| Enzyme (His-tag purified) | $K_{m, FPP}$ (μM) | $k_{cat}$ ($min^{-1}$) | $V_{max}$ (μmol (g protein)$^{-1}$ $min^{-1}$) |
|---|---|---|---|
| valencene synthase V277 | 7.8 | 1.5 | 23.4 |
| EgVS | 21.4 ± 10.5 | 25.2 ± 3.8 | 376 ± 57 |

The EgVS synthase provided herein, thus, not only produces a different terpene profile compared to other synthases, such as CVS, but also exhibits greater activity, even when compared to a CVS synthase that has been modified and optimized to exhibit increased activity.

Since modifications will be apparent to those of skill in this art, it is intended that this invention be limited only by the scope of the appended claims.

The invention claimed is:

1. A nucleic acid molecule encoding a valencene synthase polypeptide, wherein:

the valencene synthase polypeptide has at least 95% sequence identity to the sequence of amino acids set forth in SEQ ID NO: 1;

the encoded valencene synthase catalyzes the formation of valencene from an acyclic pyrophosphate terpene precursor;

the nucleic acid molecule has at least 95% identity to SEQ ID NO: 2; and the nucleic acid molecule is cDNA.

2. The nucleic acid molecule of claim 1, wherein: the encoded valencene synthase polypeptide comprises the sequence of amino acids set forth in SEQ ID NO:1.

3. A vector, comprising a nucleic acid molecule that encodes a valencene synthase polypeptide, wherein:

the valencene synthase polypeptide has at least 95% sequence identity to a valencene synthase polypeptide whose sequence is set forth in SEQ ID NO: 1;

the encoded valencene synthase catalyzes the formation of valencene from an acyclic pyrophosphate terpene precursor;

the nucleic acid molecule has at least 95% identity to SEQ ID NO: 2; and the nucleic acid molecule is cDNA.

4. The vector of claim 3, wherein the vector is a prokaryotic vector or a eukaryotic vector.

5. The vector of claim 3 that is a viral vector.

6. The vector of claim 3, wherein the vector is a yeast vector.

7. A host cell comprising the vector of claim 3.

8. The host cell of claim 7 that is a prokaryotic cell or a eukaryotic cell.

9. The host cell of claim 7 that is selected from among a bacteria, yeast, insect, plant or mammalian cell.

10. The host cell of claim 9 that is a yeast cell and is a *Saccharomyces* genus cell or a *Pichia* genus cell.

11. The cell of claim 7 that produces farnesyl diphosphate natively or is modified to produce more farnesyl diphosphate compared to an unmodified cell.

12. The cell of claim 7 that is a plant cell.

13. A transgenic plant, comprising the vector of claim 3.

14. A method for producing valencene, the method comprising:

culturing a yeast cell that contains the vector of claim 3 under conditions in which the encoded valencene synthase polypeptide is expressed and catalyzes production of valencene from an acyclic pyrophosphate terpene precursor, wherein:

the valencene synthase polypeptide is heterologous to the yeast cell; and the yeast cell produces the acyclic pyrophosphate terpene precursor.

15. The method of claim 14, wherein the acyclic pyrophosphate terpene precursor is farnesyl diphosphate.

16. The method of claim 14, wherein the yeast cell is a *Saccharomyces* genus cell of a *Pichia* genus cell.

17. The method of claim 14, wherein the cell is a *Saccharomyces cerevisiae* cell.

18. The method of claim 14, further comprising isolating the valencene.

19. The method of claim 14, further comprising oxidizing the valencene to nootkatone.

20. The method of claim 18, further comprising oxidizing the valencene to nootkatone.

21. A method for producing nootkatone, the method comprising:

culturing the cell of claim 7, wherein the cell is a yeast cell, under conditions in which the encoded valencene synthase polypeptide is expressed and catalyzes production of valencene from an acyclic pyrophosphate terpene precursor to produce valencene, wherein the yeast cell produces the acyclic pyrophosphate terpene precursor; and oxidizing the valencene to produce nootkatone.

22. The method of claim 21, wherein the acyclic pyrophosphate terpene precursor is farnesyl diphosphate.

23. The method of claim 21, wherein the yeast cell yeast cell that is a *Saccharomyces* genus cell or a *Pichia* genus cell.

24. The method of claim 21, wherein the yeast cell is a *Saccharomyces cerevisiae* cell.

25. The method of claim 21, further comprising isolating the valencene before oxidizing the valencene to nootkatone.

26. The method of claim 14, further comprising isolating aristolochene.

27. The nucleic acid molecule of claim 1 that is a nucleic acid sequence having the sequence set forth in SEQ ID NO: 3.

28. The nucleic acid molecule of claim 1, wherein the nucleic acid molecule contains at least one substitution modification relative to SEQ ID NO: 2.

29. The vector of claim 3, wherein the nucleic acid molecule contains at least one substitution modification relative to SEQ ID NO: 2.

* * * * *